(12) United States Patent
Santos et al.

(10) Patent No.: US 11,771,769 B2
(45) Date of Patent: Oct. 3, 2023

(54) OCULAR APPLICATIONS OF SILK-BASED PRODUCTS

(71) Applicant: Cocoon Biotech Inc., Mansfield, MA (US)

(72) Inventors: Michael Santos, Mansfield, MA (US); Scott Delisle, Mansfield, MA (US); Ailis Tweed-Kent, Mansfield, MA (US)

(73) Assignee: COCOON BIOTECH INC., Mansfield, MA (US)

( * ) Notice: Subject to any disclaimer, the term of this patent is extended or adjusted under 35 U.S.C. 154(b) by 0 days.

(21) Appl. No.: 17/838,566

(22) Filed: Jun. 13, 2022

(65) Prior Publication Data

US 2022/0323588 A1    Oct. 13, 2022

Related U.S. Application Data

(62) Division of application No. 16/762,544, filed as application No. PCT/US2018/059998 on Nov. 9, 2018, now abandoned.

(60) Provisional application No. 62/680,371, filed on Jun. 4, 2018, provisional application No. 62/659,209, filed on Apr. 18, 2018, provisional application No. 62/584,153, filed on Nov. 10, 2017.

(51) Int. Cl.
| | |
|---|---|
| A61K 47/42 | (2017.01) |
| A61K 9/00 | (2006.01) |
| A61K 45/06 | (2006.01) |
| A61K 47/10 | (2017.01) |
| A61K 47/26 | (2006.01) |

(52) U.S. Cl.
CPC ............ *A61K 47/42* (2013.01); *A61K 9/0019* (2013.01); *A61K 9/0051* (2013.01); *A61K 45/06* (2013.01); *A61K 47/10* (2013.01); *A61K 47/26* (2013.01)

(58) Field of Classification Search
CPC .... A61K 47/42; A61K 9/0019; A61K 9/0051; A61K 45/06; A61K 47/10; A61K 47/26
See application file for complete search history.

(56) References Cited

U.S. PATENT DOCUMENTS

| | | | |
|---|---|---|---|
| 4,806,355 | A | 2/1989 | Goosen |
| 5,015,476 | A | 5/1991 | Cochrum |
| 5,093,489 | A | 3/1992 | Diamantoglou |
| 5,263,992 | A | 11/1993 | Guire |
| 5,270,419 | A | 12/1993 | Domb |
| 5,576,881 | A | 11/1996 | Doerr |
| 5,902,800 | A | 5/1999 | Green |
| 6,127,143 | A | 10/2000 | Gunasekaran |
| 6,245,537 | B1 | 6/2001 | Williams |
| 6,267,776 | B1 | 7/2001 | O'Connell |
| 6,302,848 | B1 | 10/2001 | Larson |
| 6,310,188 | B1 | 10/2001 | Mukherjee |
| 6,325,810 | B1 | 12/2001 | Hamilton |
| 6,337,198 | B1 | 1/2002 | Levene |
| 6,372,244 | B1 | 4/2002 | Antanavich |
| 6,379,690 | B2 | 4/2002 | Blanchard |
| 6,395,734 | B1 | 5/2002 | Tang |
| 7,404,969 | B2 | 7/2008 | Chen |
| 7,575,897 | B2 | 8/2009 | Scheiflinger |
| 7,700,734 | B2 | 4/2010 | Lin |
| 7,888,067 | B2 | 2/2011 | Lin |
| 8,241,670 | B2 | 8/2012 | Ben-Sasson |
| 8,263,665 | B2 | 9/2012 | Sill |
| 9,763,777 | B2 | 9/2017 | Atlas |
| 9,802,374 | B2 | 10/2017 | Kaplan |
| 9,803,167 | B2 | 10/2017 | Choi |
| 9,808,557 | B2 | 11/2017 | Lovett |
| 9,815,874 | B2 | 11/2017 | Shoseyov |
| 9,826,723 | B2 | 11/2017 | Brigham |
| 9,827,709 | B2 | 11/2017 | Dhinojwala |
| 9,846,153 | B2 | 12/2017 | Hallisey |
| 9,848,871 | B2 | 12/2017 | Harris |
| 9,869,038 | B2 | 1/2018 | Haynie |
| 9,875,974 | B2 | 1/2018 | Rogers |
| RE46,716 | E | 2/2018 | Kennedy |
| 9,895,332 | B2 | 2/2018 | Zhang |
| 2003/0198659 | A1 | 10/2003 | Hoffmann |
| 2010/0003337 | A1 | 1/2010 | Hanes |
| 2010/0028451 | A1 | 2/2010 | Kaplan |
| 2010/0036115 | A1 | 2/2010 | Beigelman |
| 2010/0324120 | A1 | 12/2010 | Chen |

(Continued)

FOREIGN PATENT DOCUMENTS

| | | |
|---|---|---|
| EP | 2276514 | 1/2011 |
| EP | 2447055 | 5/2012 |

(Continued)

OTHER PUBLICATIONS

Wei G, et al., Three-dimensional Co-culture of Primary Hepatocytes and Stellate Cells in Silk Scaffold Improves Hepatic Morphology and Functionality in vitro, J Biomed Mater Res A. Apr. 1, 2018. doi: 10.1002/jbm.a.36421.
Wei Q, et al., The growth and pluripotency of mesenchymal stem cell on the biodegradable polyurethane synthesized with ferric catalyst, J Biomater Sci Polym Ed. Feb. 25, 2018:1-14.
Whittaker JL, et al., Structural evolution of photocrosslinked silk fibroin and silk fibroin-based hybrid hydrogels: A Small angle and ultra-small angle scattering investigation, Int J Biol Macromol. Mar. 12, 2018. pii: S0141-8130(17)35241-8.
Wu J, et al., Preparation of sulfonated silk fibroin for anti-coagulation material, J Biomater Sci Polym Ed. May 30, 2018:1-16.
Wu M, et al., Size-controllable dual drug-loaded silk fibroin nanospheres through a facile formation process, Journal of Mater Chem B., 6(8):1179-1186.

(Continued)

*Primary Examiner* — Sean M Basquill
(74) *Attorney, Agent, or Firm* — CANTOR COLBURN LLP

(57) ABSTRACT

The embodiments disclosed and embraced by the present invention include silk-based products useful in the treatment, diagnosis, palliation, and/or amelioration of ocular diseases or conditions of the eye including those of the structures of the eye and surrounding tissue. Such silk-based products may effect beneficial outcomes alone or in combination with therapeutic modalities, compounds or medicaments.

15 Claims, 6 Drawing Sheets

(56) References Cited

U.S. PATENT DOCUMENTS

| | | |
|---|---|---|
| 2011/0171239 A1 | 7/2011 | Kaplan |
| 2011/0200582 A1 | 8/2011 | Baryza |
| 2012/0121718 A1 | 5/2012 | Lai |
| 2012/0177724 A1 | 7/2012 | Irvine |
| 2012/0178702 A1 | 7/2012 | Huang |
| 2012/0189700 A1 | 7/2012 | Aguilar |
| 2014/0342905 A1 | 11/2014 | Bullis |
| 2015/0037422 A1* | 2/2015 | Kaplan ............ A61K 31/16 424/491 |
| 2015/0056294 A1* | 2/2015 | Kaplan ............ A61P 43/00 514/662 |
| 2015/0079012 A1 | 3/2015 | Bellas |
| 2015/0183841 A1 | 7/2015 | Lo et al. |
| 2017/0173161 A1 | 6/2017 | Kaplan |
| 2017/0258573 A1 | 9/2017 | Mortarino |
| 2017/0258889 A1 | 9/2017 | Kaplan |
| 2017/0296696 A1 | 10/2017 | Kaplan |
| 2017/0304498 A1 | 10/2017 | Kweon |
| 2017/0312387 A1 | 11/2017 | Alessandrino |
| 2017/0316487 A1 | 11/2017 | Mazed |
| 2017/0333351 A1 | 11/2017 | Kaplan |
| 2017/0340575 A1 | 11/2017 | Wu |
| 2017/0361201 A1 | 12/2017 | Briggs |
| 2017/0368236 A1 | 12/2017 | Jiang |
| 2017/0370709 A1 | 12/2017 | Mace |
| 2018/0000989 A1 | 1/2018 | Nazhat |
| 2018/0008522 A1 | 1/2018 | Altman |
| 2018/0008836 A1 | 1/2018 | George |
| 2018/0023246 A1 | 1/2018 | Edwards |
| 2018/0050109 A1 | 2/2018 | Kaplan |
| 2018/0051255 A1 | 2/2018 | Ong |
| 2018/0055971 A1 | 3/2018 | Yu |
| 2018/0057195 A1 | 3/2018 | Singer |
| 2018/0057228 A1 | 3/2018 | Singer |
| 2018/0071434 A1 | 3/2018 | Omenetto |

FOREIGN PATENT DOCUMENTS

| | | |
|---|---|---|
| EP | 2748359 | 7/2014 |
| EP | 2904134 | 8/2015 |
| EP | 2910675 | 8/2015 |
| EP | 2914308 | 9/2015 |
| EP | 3282042 | 2/2018 |
| EP | 3282043 | 2/2018 |
| EP | 3315147 | 5/2018 |
| WO | 1996023810 | 8/1996 |
| WO | 1996030540 | 10/1996 |
| WO | WO-0156626 A1 * | 8/2001 ............ A61L 15/32 |
| WO | 2005012606 | 2/2005 |
| WO | 2005123114 | 12/2005 |
| WO | 2008103276 | 8/2008 |
| WO | 2010036992 | 4/2010 |
| WO | 2010123945 | 10/2010 |
| WO | 2010129709 | 11/2010 |
| WO | 2011076807 | 6/2011 |
| WO | 2012006380 | 1/2012 |
| WO | 2012030901 | 3/2012 |
| WO | 2012031043 | 3/2012 |
| WO | 2012031046 | 3/2012 |
| WO | 2012082165 | 6/2012 |
| WO | 2012099755 | 7/2012 |
| WO | 2012099805 | 7/2012 |
| WO | 2012170655 | 12/2012 |
| WO | 2012170889 | 12/2012 |
| WO | 2013012476 | 1/2013 |
| WO | 2013102193 | 7/2013 |
| WO | 2013126799 | 8/2013 |
| WO | 2014145002 | 9/2014 |
| WO | 2014201044 | 12/2014 |
| WO | 2015013214 | 1/2015 |
| WO | 2015048805 | 4/2015 |
| WO | 2016059611 | 4/2016 |
| WO | 2016067189 | 5/2016 |
| WO | 2016072614 | 5/2016 |
| WO | 2016075473 | 5/2016 |
| WO | 2016077877 | 5/2016 |
| WO | 2016090055 | 6/2016 |
| WO | 2016110873 | 7/2016 |
| WO | 2016145281 | 9/2016 |
| WO | 2016176633 | 11/2016 |
| WO | 2017106631 | 6/2017 |
| WO | 2017123383 | 7/2017 |
| WO | 2017137611 A1 | 8/2017 |
| WO | 2017137937 | 8/2017 |
| WO | 2017165922 | 10/2017 |
| WO | 2017177281 A1 | 10/2017 |
| WO | 2017179069 A2 | 10/2017 |
| WO | 2017189832 | 11/2017 |
| WO | 2017192227 | 11/2017 |
| WO | 2017198655 | 11/2017 |
| WO | 2017200659 A2 | 11/2017 |
| WO | 2017210416 A1 | 12/2017 |
| WO | 2017210421 A1 | 12/2017 |
| WO | 2017212500 A1 | 12/2017 |
| WO | 2017213597 A1 | 12/2017 |
| WO | 2017214736 | 12/2017 |
| WO | 2017219305 | 12/2017 |
| WO | 2017223462 | 12/2017 |
| WO | 2018005848 | 1/2018 |
| WO | 2018006037 | 1/2018 |
| WO | 2018011732 | 1/2018 |
| WO | 2018013578 | 1/2018 |
| WO | 2018013612 | 1/2018 |
| WO | 2018017929 | 1/2018 |
| WO | 2018019595 | 2/2018 |
| WO | 2018022561 | 2/2018 |
| WO | 2018025186 | 2/2018 |
| WO | 2018026853 | 2/2018 |
| WO | 2018028224 | 2/2018 |
| WO | 2018031821 | 2/2018 |
| WO | 2018031973 | 2/2018 |
| WO | 2018039039 | 3/2018 |
| WO | 2018039496 | 3/2018 |
| WO | 2018053265 | 3/2018 |
| WO | 2018053524 | 3/2018 |
| WO | 2018054542 | 3/2018 |
| WO | 2018056937 | 3/2018 |
| WO | 2018081159 | 5/2018 |
| WO | 2018081554 | 5/2018 |
| WO | 2018081805 | 5/2018 |
| WO | 2018081815 | 5/2018 |
| WO | 2018089515 | 5/2018 |
| WO | 2018098299 | 5/2018 |
| WO | 2019094702 A1 | 5/2019 |

OTHER PUBLICATIONS

Wu Y, et al., Biosynthesis and characterization of recombinant silk-like polypeptides derived from the heavy chain of Silk fibroin, Polymers Dec. 3, 2017; 9(12): 669.

Wu YY, et al., Experimental Study on Effects of Adipose-Derived Stem Cell-Seeded Silk Fibroin Chitosan Film on Wound Healing of a Diabetic Rat Model, Ann Plast Surg. Feb. 13, 2018. doi: 10.1097/SAP.0000000000001355.

Xie QF, et al., Key Characteristics of a Novel Silk Yarn from Fresh Cocoons, Fiber Polym., 19 (1): 147-155.

Xie W, et al., Extreme mechanical behavior of nacre-mimetic graphene-oxide and silk nanocomposites, Nano Lett., 18 (2):987-993.

Xie X, et al., Silk Fibroin-Based Fibrous Anal Fistula Plug with Drug Delivery Function, Macromol Biosci. Feb. 7, 2018. doi: 10.1002/mabi.201700384.

Xu HL, et al., Silk fibroin nanoparticles dyeing indocyanine green for imaging-guided photo-thermal therapy of glioblastoma, Drug Deliv Jan. 25, 2018; 25(1):364-375.

Xu L, et al., Optimization Preparation of Silk Fibroin Nerve Scaffolds, J Biomat Tiss Eng., Jan. 8, 2018 (1): 117-123.

Xu LL, et al., Structural and Mechanical Roles for the C-Terminal Nonrepetitive Domain Become Apparent in Recombinant Spider Aciniform Silk, Biomacromolecules, Sep. 21, 2017. 18 (11): 3678-3686.

(56) References Cited

OTHER PUBLICATIONS

Yang M, et al.,Ice-templated protein nanoridges induce bone tissue formation, Adv Funct Mater., Oct. 2017; 27(44): 1703726.
Yang Y, et al., Sodium oleate induced rapid gelation of silk fibroin, J Biomater Sci Polym Ed. Mar. 20, 2018:1-13.
Ye P, et al., Application of silk fibroin/chitosan/nano-hydroxyapatite composite scaffold in the repair of rabbit radial pone defect, Exp Ther Med. Dec. 2017; 14(6):5547-5553.
Yi S, et al., Scalable fabrication of sulfated silk fibroin nanofibrous membranes for efficient lipase adsorption and recovery, Int J Biol Macromol. Jan. 12, 2018. pii: S0141-8130(17)34756-6.
Yin Y, et al,. A Tensile Constitutive Relationship and a Finite Element Model of Electrospun Nanofibrous Mats, Nanomaterials, 2018, 8(1): 29.
Yin Y, et al., Analysis of the comprehensive tensile relationship in electrospun silk fibroin/polycaprolactone nanofiber membranes, Membranes (Basel). Dec. 7, 2017;7(4). pii: E67.
Yin Y, et al., Effect of distribution of fiber orientation on the mechanical properties of silk fibroin/polycaprolactone nanofiber mats, J Eng Fibers Fabrics 2017; 12 (3): 17-28.
Yong J, et al., A silk fibroin bio-transient solution processable memristor, Sci Rep. Nov. 7, 2017;7(1):14731.
Yoshioka T, et al., Fabrication Scheme for Obtaining Transparent, Flexible, and Water-Insoluble Silk Films from Apparently Dissolved Silk-Gland Fibroin of Bombyx mori Silkworm, ACS Biomater. Sci. Eng., 2017, 3 (12), pp. 3207-3214.
Yun S, et al., Gastroprotective effect of mature silkworm, Bombyx mori against ethanol induced gastric mucosal injuries in rats, J Funct Food., Nov. 2, 2017 39: 279-286.
Zeng W, et al., BmYki is transcribed into four functional splicing isoforms in the silk glands of the silkworm Bombyx mori, Gene. Dec. 28, 2017. pii: S0378-1119(17)31107-1.
Zhang Y, et al., Distinctive Stress-Stiffening Responses of Regenerated Silk Fibroin Protein Polymers under Nanoscale Gap Geometries: Effect of Shear on Silk Fibroin-based Materials, Biomacromolecules. Feb. 26, 2018. doi: 10.1021/acs.biomac. 8b00070.
Zhao S, et al., Programmable Hydrogel Ionic Circuits for Biologically Matched Electronic Interfaces, Adv Mater. May 2, 2018:e1800598.
Zhao ZL, et al., Using of hydrated lime water as a novel degumming agent of silk and sericin recycling from wastewater, J Clean Prod., 172: 2090-2096.
Zheng Z, et al., 3D bioprinting of self-standing silk-based bioink, Adv Healthc Mater. Jan. 2, 2018; 1701026.
Zhou Q, et al., Preparation of a multifunctional fibroin-based biomaterial via laccase-assisted grafting of chitooligosaccharide, Int J Biol Macromol. Mar. 11, 2018. pii: S0141-8130(17)35036-5.
Zhou W, et al., Multifunctional bioreactor system for human intestine tissues, ACS Biomater Sci Eng. Jan. 8, 2018;4 (1):231-239.
Zhou Y, et al., Photopolymerized maleilated chitosan/methacrylated silk fibroin micro/nanocomposite hydrogels as potential scaffolds for cartilage tissue engineering, Int J Biol Macromol. Dec. 7, 2017;108:383-390.
Zhu C, Skin derived precursor Schwann cell-generated acellular matrix modified chitosan/silk scaffolds for bridging rat sciatic nerve gap, Neurosci Res. Dec. 27, 2017; pii: S0168-0102(17)30584-9.
Zhu ZH, et al., High-Strength, Durable All-Silk Fibroin Hydrogels with Versatile Processability toward Multifunctional Applications, Adv Funct Mater., 28(10): 1704757.
Zhou F, et al., Silk fibroin-chondroitin sulfate scaffold with immuno-inhibition property for articular cartilage repair, Acta Biomater. Nov. 2017; 63, 64-75.
Zhao L, et al., Temperature buffering capacity of silk hydrogel: A useful packaging material, Materials Letters. Jan. 2018; 110-113, 211.
Zou R and Zhou Q et al., Temperature Affects the Hydroxyapatite Crystal Arrangement on Silk Fibroin Surfaces, Polymers & Polymer Composites. 2017; 689-694, 25(9).

Zhang D and Peng H et al., High Water Content Silk Protein-based Hydrogels with Tunable Elasticity Fabricated via a Ru(II)Mediated Photochemical Cross-linking Method, Fbers and Polymers. 2017; 1831-1840, 18(10).
Zhang J, et al., Stablization of vaccines and antibiotics in silk and eliminating the cold chain, Proceedings of the National Academy of Sciences of the United States of America. Jul. 24, 2012; 11981-11986, 109(30).
Zhang H and Li L, et al., Preparaton and characterization of silk fibroin as a biomaterial with potential for drug delivery, Journal of Translational Medicine. 2012; 10(117).
Zhang M and Guo B, Electroactive 3D Scaffolds Based on Silk Fibroin and Water-Bome Polyaniline for Skeletal Muscle Tissue Engineering, Macromolecular Bioscience. 2017; 17(1700147).
Zhang C and Shao H et al., Structure and interaction of silk fibroin and graphene oxide in conentrated solution under shear, International Journal of Biological Macromolecules. Feb. 2017; 2590-2597, 107 Part B.
Wiesli M et al., High-Performance Polymers and Their Potential Application as Medical and Oral Implant Materials: A Review, Zurich Open Repository and Archive. 2015; 24(4).
Xie M, et al., Supercritical carbon dioxide-developed silk fibroin nanoplatform for smart colon cancer therapy, International Journal of Nanomedicine. Oct. 20, 2017; 7751-7761, 12.
Xu C, et al., Urethral Reconstruction with RNA Interference and Polycaprolactone/Silk Fibroin/Collagen Electrospun Fiber in Rabbits, Journal of Biomaterials and Tissue Engineering. 2017, 858-862, 7(9).
Yu E and Mi H-Y, et al. Development of Biomimetic Thermoplastic Polyurethane/Fibroin Small-Diameter Vascular Grafts via a Novel Electrospinning Approach, Journal of Biomedical Materials Research. Apr. 2018; 985-996, 106(4).
Yang Q, Silk fibroin/cartilage extracellular matrix scaffolds with sequential delivery of TGF-B3 for chondrogenic differentiation of adipose-derived stem cells, International Journal of Nanomedicine. Sep. 11, 2017; 12.
Qi Y, A Review of Structure Construction of Silk Fibroin Biomaterials from Single Structures to Multi-Level Structures, International Journal of Molecular Sciences. Mar. 3, 2017; 18, 237.
Xiong, R et al., Template-Guided Assembly of Silk Fibroin on Cellulose Nanofibers for Robust Nanostructures with Ultrafast Water Transport, ACS Nano. 2017; 12008-12019, 11(12).
Wang Y, et al., Evaluation of a series of silk fibroin protein-based nonwoven mats for use as an anti-adhesion patch for wound management in robotic surgery, Journal of Biomedical Materials Research. Jan. 2018; 221-230, 106(1).
Xiao D, et al. Adipose-derived stem cells-seeded bladder acellular matrix graft-silk fibroin enhances bladder reconstruction in a rat model, Oncotarget Sep. 23, 2017; 86471-86487, 8(49).
Jiang J, et al., Protein Bricks: 2D and 3D Bio-Nanostructures with Shape and Function on Demand, Adv Mater. Mar. 27, 2018:e1705919.
Joseph J, et al., Piezoelectric Micromachined Ultrasonic Transducer Using Silk Piezoelectric Thin Film, IEEE Electr Device L., 39 (5): 749-752.
Jung CS, et al., Development of Printable Natural Cartilage Matrix Bioink for 3D Printing of Irregular Tissue Shape, Tissue Eng Regen Med., Apr. 2018. 15 (2): 155-162.
Kang K, et al., Micro-and nanoscale topographies on silk regulate gene expression of human corneal epithelial cells, Invest Ophthalmol Vis Sci. Dec. 1, 2017; 58(14):6388-6398.
Kang YK, et al., Effect of a Fibroin Enzymatic Hydrolysate on Memory Improvement: A Placebo-Controlled, Double-Blind Study, Nutrients. Feb. 17, 2018;10(2). pii: E233.
Kheradvar SA, et al., Starch nanoparticle as a vitamin E-TPGS carrier loaded in silk fibroin-poly(vinyl alcohol)-Aloe vera nanofibrous dressing, Colloids Surface B., Mar. 2, 2018; 166:9-16.
Kim DK, et al., Functionalized silk fibroin film scaffold using B-Carotene for cornea endothelial cell regeneralion, Colloids Surf B Biointerfaces. Nov. 22, 2017; 164:340-346.
Kim SH, et al., Precisely printable and biocompatible silk fibroin bioinkfor digital light processing 3D printing, Nat Commun, Apr. 24, 2018, 9:1620.

(56) References Cited

OTHER PUBLICATIONS

Koh K, et al., Bone regeneration using silk hydroxyapatite hybrid composite in a rat alveolar defect model, Int J Med Sci., Jan. 1, 2018; 15 (1): 59-68.

Lee H, et al., Fabrication of micro/nanoporous collagen/dECM/silk-fibroin biocomposite scaffolds using a low temperature 3D printing process for bone tissue regeneration, Mater Sci Eng C Mater Biol Appl. Mar. 1, 2018;84:140-147.

Li CQ, et al., Refining cocoon to prepare (N, S, and Fe) ternary-doped porous carbon aerogel as efficient catalyst for the oxygen reduction reaction in alkaline medium, J Power Sources. Apr. 30, 2018, 384: 48-57.

Li DW, et al., Silk fibroin/chitosan thin film promotes osteogenic and adipogenic differentiation of rat bone marrow- derived mesenchymal stem cells, Biomater Appl. Jan. 1, 2018:885328218757767.

Li H, Fabrication of aqueous-based dual drug loaded silk fibroin electrospun nanofibers embedded with curcumin-loaded RSF nanospheres for drugs controlled release, RSC Advances 7(89):56550-56558.

Li X, et al., Soft freezing-induced self-assembly of silk fibroin for tunable gelation, Int J Biol Macromol. May 30, 2018. pii: S0141-8130(18)31255-8.

Li XF, et al., Tuning the structure and performance of silk biomaterials by combining mulberry and non-mulberry silk fibroin, Polym Degrad Stabil, Jan. 2018 147: 57-63.

Lin Y, et al., Electrochemically directed assembly of designer coiled-coil telechelic proteins, ACS Biomater Sci Eng., 3(12): 3195-3206.

Ling SJ, et al., Integration of Stiff Graphene and Tough Silk for the Design and Fabrication of Versatile Electronic Materials, Adv Funct Mater., 28 (9): 1705291.

Lintz ES, et al., Altering Silk Film Surface Properties through Lotus-Like Mechanisms, Macromol Mater Eng. Feb. 21, 2018. 303(4):1700637.

Liu C, et al., Toward large-scale fabrication of triboelectric nanogenerator (TENG) with silk-fibroin patches film via spray coating process, Nano Energy Sep. 25, 2017, 41: 359-366.

Liu HL, et al., Observation of luminescent gold nanoclusters using one-step syntheses from wool keratin and silk fibroin effect, Eur Polym J., Feb. 2018. 99: 1-8.

Liu K, et al., A silk cranial fixation system for neurosurgery, Adv Healthc Mater. Jan. 26, 2018; 1701359.

Liu Q, et al., Silk fibroin scavenges hydroxyl radicals produced from a long-term stored water-soluble fullerene system, J Mater Chem B. 6 (5): 769-780.

Liu ZK, et al., Silk fibroin-based woven endovascular prosthesis with heparin surface modification, J Mater Sci Mater Med. Apr. 12, 2018;29(4):46.

Luo J, et al., 3-D mineralized silk fibroin/polycaprolactone composite scaffold modified with polyglutamate conjugated with BMP-2 peptide for bone tissue engineering, Colloids Surf B Biointerfaces. Dec. 28, 2017;163:369-378.

Luo ZW, et al., Anticoagulation of Heparinized Silk Fibroin by N-2 Plasma and Carbodiimide Double Induction, J Biomater Tiss Eng., Nov. 2017. 7 (11): 1190-1198.

Ma L, et al., Ras-Raf-MAPK signaling promotes nuclear localization of FOXA transcription factor SGF1 via Ser91 phosphorylation, Biochim Biophys Acta. Jan. 17, 2018. pii: S0167-4889(18)30007-7.

Magri D, et al., Titanate fibroin nanocomposites: a novel approach for the removal of heavy-metal ions from water, ACS Appl Mater Interfaces. Dec. 22, 2017; 10:651-659.

Maleki H, et al., Compressible, thermally insulating and fire retardant aerogels through self-assembling the silk fibroin biopolymer inside the silica structure—An approach towards 3D printing of aerogels, ACS Appl Mater Interfaces. Jun. 4, 2018. doi: 10.1021/acsami.8b05856.

Maniglio D, et al., Silk fibroin porous scaffolds by N2O foaming, J Biomater Sci Polym Ed. Jan. 12, 2018; 3:1-27.

Mao B, et al., Cyclic cRGDfk peptide and Chlorin e6 functionalized silk fibroin nanoparticles for targeted drug delivery and photodynamic therapy, Biomaterials. Feb. 3, 2018;161:306-320.

Mehrabani MG, et al., Chitin/silk fibroin/TIO2 bio-nanocomposite as a biocompatible wound dressing bandage with strong antimicrobial activity, Int J Biol Macromol. May 18, 2018. pii: S0141-8130(18)30706-2.

Mehrabani MG, et al., Preparation of biocompatible and biodegradable silk fibroin/chitin/silver nanoparticles 3D scaffolds as a bandage for antimicrobial wound dressing, Int J Biol Macromol. Mar. 23, 2018. pii: S0141-8130(18)30569-5.

Midha S, et al., Differential Regulation of Hedgehog and Parathyroid Signaling in Mulberry and Nonmulberry Silk Fibroin Textile Braids, ACS Biomater Sci Eng, Feb. 2018. 4 (2): 595-607.

Mirmusavi MH, et al., Characterization of Silk/Poly 3-Hydroxybutyrate-chitosan-multi-walled Carbon Nanotube Micro-nano Scaffold: A New Hybrid Scaffold for Tissue Engineering Applications, Med Signals Sens. Jan.-Mar. 2018; 8 (1):46-52.

Moses JC, et al., Multifunctional Cell Instructive Silk-Bioactive Glass Composite Reinforced Scaffolds Toward Osteoinductive, Proangiogenic, and Resorbable Bone Grafts, Adv Healthc Mater. Feb. 14, 2018. doi: 10.1002/adhm.201701418.

Nadiger VG, et al., Antimicrobial treatment of silk with silver nanoparticles using acrylic binder, Indian J Fibre Text., Research Dec. 2017. 42 (4): 465-473.

Naito A, et al., Unusual Dynamics of Alanine Residues in Polyalanine Regions with Staggered Packing Structure of SamiaCynthia Ricini Silk Fiber in Dry and Hydrated States Studied by 13C Solid-State NMR and Molecular Dynamics Simulation, J Phys Chem B. Jun. 5, 2018. doi: 10.1021/acs.jpcb.8b03509.

Najjar R, et al., Biocompatible Silk/Polymer Energy Harvesters Using Stretched Poly (vinylidene fluoride-co- hexafluoropropylene) (PVDF-HFP) Nanofibers, Polymers, Sep. 30, 2017. 9(10): 479.

Nakazawa Y, et al., Evaluation of biocompatibility of silk fibroin and application to tissue engineered materials for cardiovascular system, Tissue Eng. Part A., Dec. 1, 2017; 23: S120-S120.

Naserzadeh P, et al., Evaluation of the toxicity effects of silk fibroin on human lymphocytes and monocytes, J Biochem Mol Toxicol. May 2, 2018:e22056.

Nisal A, et al., Silk fibroin micro-particle scaffolds with superior compression modulus and slow bioresorptionfor effective bone regeneration, Sci Rep., 8:7235.

Nishimura A, et al., Effect of Water on The Structure and Dynamics of Regenerated [3-13C] Ser, [3-13C] Tyr and [3-13C] Ala-Bombyx mori Silk Fibroin Studied with 13C Solid-State NMR, Biomacromolecules. Jan. 8, 2018. 19(2): 563-575.

Oktaviani NA, et al., Conformation and dynamics of soluble repetitive domain elucidates the initial B-sheet formation of spider silk, Nat Commun. May 29, 2018;9(1):2121.

Panico A, et al., Development of regenerative and flexible fibroin-based wound dressings, J Biomed Mater Res B Appl Biomater. Feb. 16, 2018. doi: 10.1002/jbm.b.34090.

Park YR, et al., NF-KB signaling is key in the wound healing processes of silk fibroin, Acta Biomater. Dec. 11, 2017. 67:183-195.

Peng ZC, et al., A Simple Method for the Cross-Section Area Determination of Single Profiled Fibers and Its Application, Microsc Microanal., Feb. 24, 2018 (1): 17-28.

Pereira RFP, et al., Silk fibroin separators: a step towards lithium ion batteries with enhanced sustainability, ACS Appl Mater Interfaces, 10(6): 5385-5394.

Pillai MM, et al., Tissue engineering of human knee meniscus using functionalized and reinforced Silk-PVA composite 3D scaffolds: Understanding the in vitro and in vivo behavior, J Biomed Mater Res A. Feb. 20, 2018. doi: 10.1002/jbm.a.36372.

Prajzler V, et al., The investigation of the waveguiding properties of silk fibroin from the visible to near-infrared Spectrum, Materials (Basel). Jan. 11, 2018; 11(1). pii: E112.

Prasad B, et al., Moisture responsive and CO2 selective biopolymer membrane containing silk fibroin as a green carrier for facilitated transport of CO2, J Membrane Sci., 550: 416-426.

Xiao Y, et al. Mechanical Testing of Hydrogels in Cartilage Tissue Engineering, Beyond the Compressive Modulus, Tissue Engineering. 2013; 403-412, 19(5).

(56) References Cited

OTHER PUBLICATIONS

Ran J, et al., Constructing Anisotropic Triple-Pass Tubular Framework within Lyophilized Porous Gelatin (GEL) Scaffold Using Dexamethasone (DEX)-Loaded Functionalized Whatman Paper (FP) to Reinforce Its Mechanical Strength and Promote Osteogenisis, Biomacromolecules. 2017; 3788-3801, 18(11).
Wu H and Fang Q, et al., Multi-tubule conduit-filler constructs loaded with gradient-distributed growth factors for neural issue engineering applications, accepted Oct. 23, 2017, Jan. 2018; 671-682, 7.
Wang Q and Cao, L et al., Evaluation of synergistic osteogenesis between icariin and BMP2 through a micro/meso hierarchical porous delivery system, International Journal of Nanomedicine. Oct. 19, 2017; 7721-7735, 12.
Varone A, et al., The potential of Antheraea pernyi silk for spinal cord repair, Scientific Reports. Oct. 23, 2017; 7 (13790).
Chantawong P, et al., Silk fibroin-Pellethane® cardiovascular patches: Effect of silk fibroin concentraton on vascular remodeling in rat model, Journal of Materials Science: Materials in Medicine. 2017; 28(191).
Thai T, et al., In vivo evaluation of modified silk fibroin scaffolds with a mimicked microenvironment of fibronectin/decellularized pulp tissue for maxillofacial surgery, Biomedical Materials. 2018; 13(015009).
Taddei P et al., Silk fibres graafted with 2-hydroxyethyl methacrylate (HEMA) and 4-hydroxybutyl acrylate (HBA) for biomedical applications, International Journal of Biological Macromolecules. Feb. 2017; 537-548, 107 (Pt A).
Tokareva O, et al., Recombinant DNA production of spider silk proteins, Microbial Biotechnology. 2013; 651-663, 6(6).
Susanin A, et al., Study of the Rheological Characteristics of Solutions of Silk Fibroin in 1-Butyl-3-Methylimidazolium Acetate and Films Based on Them, Fibre Chemistry Jul. 2017; 88-96, 49(2).
Shi P, et al., Yolk shell nanocomposite particles as bioactive bone fillers and growth factor carriers, Nanoscale. 2017; 14520-14532, 9.
Sun J, et al., Controlled release of BMP-2 from a collagen-mimetic peptide-modified silk fibroin-nanohydroxyapatite scaffold for bone regeneration, Journal of Materials Chemistry B. 2017; 8770-8779, 5.
Shcherbank I, et al., Global metaanalysis of the nonlinear response of soil nitrous oxide (N2O) emissions to fertilizer nitrogen, Proceedings of the National Academy of Sciences of the United States of America. Jun. 24, 2014; 9199-9204, 111(25).
Shi W et al., Structurally and Functionally Optimized Silk-Fibroin-Gelatin Scaffold Using 3D Printing to Repair Cartilage Injury In Vitro and In Vivo, Advanced Materials. 2017; 29(1701089).
Ruan S, et al., Composite scaffolds loaded with bone mesenchymal stem cells promote the repair of radial bone defects in rabbit model, Biomedicine & Pharmacotherapy. 2018; 600-606, 97.
Seo, Y, et al., In vitro and in vivo evaluation of the duck's feet collagen sponge for hemostatic applications, Journal of Biomaterials Applications. 2017; 484-491, 32(4).
Pritchard, E et al., Effect of Silk Protein Processing on Drug Delivery from Silk Films, Macromol Biosci. Mar. 2013; 311-320, 13(3).
Perteghella, S et al., Stromal Vascular Fraction Loaded Silk Fibroin Mats Effectively Support the Survival of Diabetic Mice after Pancreatic Islet Transplantation, Macromolecular Bioscience. 2017; 17(1700131).
Price, R et al., Controlled Release from Recombinant Polymers, J Control Release. Sep. 28, 2014; 304-313, 190.
Park, B et al., Effect of molecular weight on electro-spinning performance of regenerated silk, International Journal of Biological Macromolecules. 2017 (dx.doi.org/10.1016/j.ijbiomac.2017.08.115).
Panke-Buisee, K et al., Selection on soil microbiomes reveals reproducible impacts on plant function, The ISME (International Society for Microbial Ecology) Journal. 2015; 980-989, 9.
Gholipourmalekabadi, M et al., Silk fibroin/amniotic membrane 3D bi-layered artificial skin, Biomedical Materials. 2018; 13(3).

McGill, M et al., Molecular and macro-scale analysis of enzyme-crosslinked silk hydrogels for rational biomaterial design, Acta Biomaterialia. 2017; 76-84, 63.
Morin, G et al., The Effect of Lubricants on Powder Flowability for Pharmaceutical Application, (AAPS) American Association of Pharmaceutical Scientists PharmSciTech. Sep. 2013; 1158-1168, 14(3).
Min, L et al., Enzymatic synthesis of quaternary ammonium chitosan-silk fibroin peptide copolymer and its characterization, International Journal of Biological Macromolecules. Apr. 2017; 1125-1131, 109.
Marelli, B et al., Silk Fibroin as Edible Coating for Perishable Food Preservation, Scientific Reports. 2016; 6(25263).
Mane, P et al., Designing Ecofriendly Bionanocomposite Assembly with Improved Antimicrobial and Potent on-site Zika Virus Vector Larvicidal Activistes with its Mode of Action, Scientific Reports. Nov. 14, 2017; 15531, 7.
Mao, KL et al., Skin-penetrating polymeric nanoparticles incorporated in silk fibroin hydrogel for topical delivery of curcumin to improve its therapeutic effect on psoriasis mouse model, Colloids and Surfaces B: Biointerfaces. Dec. 2017, 704-714, 160.
Manchineella, S et al., Radical-Scavenging Antioxidant Cyclic Dipeptides and Silk Fibroin Biomaterials, European Journal of Organic Chemistry Aug. 2017; 4363-4369, 2017(30).
Lo, H-Y et al., Morphological Transformation of hBMSC from 2D Monolayer to 3D Microtissue on Low-crystallinity SF-PCL Patch with Promotion of Cardiomyogenesis, Journal of Tissue Engineering and Regenerative Medicine. Apr. 2018; e1852-e1864, 12(4).
Li, Y et al., Poly(ethylene glycol)-modified silk fibroin membrane as a carrier for limbal epithelial stem cell transplantation in a rabbit LSCD model, Stem Cell Research & Therapy. 2017; 256, 8.
Ling, S et al., Polymorphic regenerated silk fibers assembled through bioinspired spinning, Nature Communications. 2017; 1387, 8.
Li, AB et al., Enhanced Stabilization in Dried Silk Fibroin Matrices, Biomacromolecules. 2017; 2900-2905, 18(9).
Liu, J et al., An asymmetric wettable chitosan-silk fibroin composite dressing with fixed silver nanoparticles for infected wound repair: in vitro and in vivo evaluation, Royal Society of Chemistry Advances. 2017, 43909, 7.
Li, Y-J et al., Continuous Insulin Releasing and Blood Sugar Monitoring via Dental Implant Supported Semi-Implanted Device, International Journal of Diabetes and Clinical Research. 2016; 057, 3(2).
Chen, Y et al., Bombyx mori Silk Fibroin Scaffolds with Antheraea pernyi Silk Fibroin Micro/Nano Fibers for Promoting EA. Hy926 Cell Proliferation, Materials. 2017; 1153, 10.
Li, J and Wang, Q et al., Producion of Composite Scaffold Containing Silk Fibroin, Chitosan, and Gelatin for 3D Cell Culture and Bone Tissue Regeneration, Medical Science Monitor. 2017; 5311-5320, 23.
Li, C and Yang, M et al., Honeysuckle flowers extract loaded Bombyx mori silk fibroin films for inducing apoptosis of Hela cells, Microscopy Research & Technique. 2017; 8(256).
Han, C et al., Electrophoretic Deposition of Gentamicin-loaded Silk Fibroin Coatings on 3D-printed Porous Cobalt- Chromium-Molybdenum Bone Substitutes to Prevent Orthopedic Implant Infections, BioMacromolecules. Nov. 13, 2017; 3776-3787, 18(11).
Jiang, P et al., Rational design of a high-strength bone scaffold platform based on in situ hybridization of bacterial cellulose/nano-hydroxyapatite framework and silk fibroin reinforcing phase, Journal of Biomaterials Science, Polymer Edition. 2017; 107-124, 29(2).
Huang, W et al., From EST to novel spider silk gene identification for production of spidroin-based biomaterials, Scientific Reports. 2017; 7(13354).
Guo, J et al., Multiscale design and synthesis of biomimetic gradient protein/biosilica composites for interfacial tissue engineering, Biomaterials. 2017; 44-55, 145.
Dubey, P et al., pH dependent sophorolipid assemblies and their influence on gelation of silk fibroin protein, Materials Chemistry and Physics. Jan. 1, 2018; 9-16, 203.
Depluch, T et al., Silk Materials Functionalized via Genetic Engineering for Biomedical Applications, Materials. 2017; 10(1417) (DOI: 10.3390/ma10121417).

(56) References Cited

OTHER PUBLICATIONS

Genovese, ME et al., Light Responsive Silk Nanofibers: An Optochemical Platform for Environmental Applications, ACS Applied Materials & Interfaces. 2017; 40707-40715, 9(46).

Gennari, CGM et al., In vitro and in vivo evaluation of silk fibroin functionalized with GABA and allopregnanolone for Schwann cell and neuron survival, Regenerative Medicine. Mar. 2017; 141-157, 13(2).

Fang, G et al., Precise correlation of macroscopic mechanical properties and microscopic mechanical properties and microscopic structures of animals silks—using Antheraea pernyi silkwork silk as an example, Journal of Materials Chemistry B. 2017; 6042-48, 5.

Du, GY et al., Bone Morphogenic Protein-2 (rhBMO2)—Loaded Silk Fobroin Scaffolds to Enhance the Osteoinductivity in Bone Tissue Engineering, Nanoscale Research Letters. 2017; 573, 12.

Bissoyi, A et al., Understanding the molecular mechanism of improved proliferation and osteogenic potential of human mesenchymal stem cells grown on a polyelectrolyte complex derived from non-mulberry silk fibroin and chitosan. Dec. 7, 2017; 13(1).

Ciocci, M et al., Injectable silk fibroin hydrogels functionalized with microspheres as adult stem cells-carrier systems, International Journal of Biological Macromolecules. Mar. 2017; 960-971, 108.

Agrawal P, et al., Enhanced chondrogenesis of mesenchymal stem cells over silk fibroin/chitosan-chondroitin Sulfate three dimensional scaffold in dynamic culture condition, J Biomed Mater Res Part B, 2018:00B:000-000.

Agrawal P, et al., In vitro cartilage construct generation from silk fibroin-chitosan porous scaffold and umbilical cord blood derived human mesenchymal stem cells in dynamic culture condition, J Biomed Mater Res Part A., Oct. 27, 2017. 106 (2): 397-407.

Ahmad S, et al., Electrically Conductive Polyaniline/Silk Fibroin Composite for Ammonia and Acetaldehyde Sensing, Polymer and Polymer Composites Mar. 26, 2018 (2): 177-187.

Amirikia M, et al., Impact of pre-incubation time of silk fibroin scaffolds in culture medium on cell proliferation and attachment, Tissue Cell, Sep. 20, 2017. 49 (6): 657-663.

Benvidi A, et al., Impedimetric PSA aptasensor based on the use of a glassy carbon electrode modified with titanium oxide nanoparticles and silk fibroin nanofibers, Microchim acta 185:50.

Bhunia BK, et al., Silk-based multilayered angle-ply annulus fibrosus construct to recapitulate form and function of the Intervertebral disc, Proc Natl Acad Sci USA. Dec. 27, 2017.115(3):477-482.

Bhuvaneswari K., et al., Silk fibroin linked Zn/Cd-doped SnO2 nanoparticles to purify the organically polluted water, T. Mater Res Express, 5 (2): 024004.

Teng, B., et al., Preparation and characterization of oriented scaffolds derived from cartilage extracellular matrix and Silk fibroin, West China J Stomat, Feb. 1, 2018; 36(1):17-22.

Buitrago JO, et al., Silk fibroin / collagen protein hybrid cell-encapsulating hydrogels with tunable gelation and Improved physical and biological properties, Acta Biomater. Feb. 1, 2018. pii: S1742-7061(17)30792-4.

Chaw RC, et al., Egg case silk gene sequences from Argiope spiders: evidence for multiple loci and a loss of function between paralogs, G3 (Bethesda). Nov. 10, 2017. 8 (1): 231-238.

Chen C, et al., Combination of silk fibroin and fiber alignment cues in nanofibers for tendon tissue engineering to repair the achilles tendon defects, Tissue Eng. Part A Dec. 1, 2017;23: S127-S128.

Chen X, et al., Fibroin/dodecanol floating solidification microextraction for the preconcentration of trace levels of flavonoids in complex matrix samples, J Chromatogr B Analyt Technol Biomed Life Sci. Jan. 1, 2018;1072:17-24.

Chen ZL, et al., Non-invasive monitoring of in vivo hydrogel degradation and cartilage regeneration by multiparametric MR imaging, Theranostics 8 (4): 1146-1158.

Cheng B, et al., Cooperative Assembly of a Peptide Gelator and Silk Fibroin Afford an Injectable Hydrogel for Tissue Engineering, ACS Appl Mater Interfaces. Mar. 27, 2018. doi: 10.1021/acsami.8b01725.

Choi JH, et al., Biofunctionalized Lysophosphatidic Acid/Silk Fibroin Film for Cornea Endothelial Cell Regeneration, Nanomaterials (Basel) Apr. 30, 2018;8(5). pii: E290.

Chomachayi MD, et al., Electrospun nanofibers comprising of silk fibroin/gelatin for drug delivery applications: thyme essential oil and doxycycline monohydrate release study, J Biomed Mater Res A. Dec. 6, 2017. doi: 10.1002/jbm.a.36303.

Coburn JM, et al., Manipulation of variables in local controlled release vincristine treatment in neuroblastoma, J Pediatr Surg., Sep. 4, 2017 52 (12): 2061-2065.

Collin MA, et al., Genomic perspectives of spider silk genes through target capture sequencing: Conservation of Stabilization mechanisms and homology-based structural models of Spidroin terminal regions, Int J Biol Macromol. Feb. 14, 2018. pii: S0141-8130(17)34900-0.

Colusso E, et al., Engineering optical defects in biopolymer photonic lattices, J Mater Chem C., 6 (5): 966-971.

Cui Y, et al., New insight into the mechanism underlying the silk gland biological process by knocking out fibroin heavy Chain in the silkworm, BMC Genomics. Mar. 26, 2018; 19(1):215.

Dondajewska E., et al., Heterotypic breast cancer model based on a silk fibroin scaffold to study the tumor microenvironment, Oncotarget Dec. 22, 2017; 9 (4): 4935-4950.

Dong XX, et al., Ultrabroadband Plasmonic Absorber Based on Biomimetic Compound Eye Structures, IEEE Photonics J., Feb. 2018. 10(1): 5700207.

Du J, et al., Potential applications of three-dimensional structure of silk fibroin/poly(ester-urethane) urea nanofibrous Scaffold in heart valve tissue engineering, Appl Surf Sci., 447: 269-278.

Ebrahimi A, et al., Preparation and characterization of silk fibroin hydrogel as injectable implants for sustained release of Risperidone, Drug Dev Ind Pharm., 44 (2): 199-205.

Fan L, et al., Creating Biomimetic Anisotropic Architectures with Co-Aligned Nanofibers and Macrochannels by Manipulating Ice Crystallization, ACS Nano. Jun. 1, 2018. doi: 10.1021/acsnano.8b01648.

Fard M, et al., Bilayer amniotic membrane/nano-fibrous fibroin scaffold promotes differentiation capability of menstrual blood stem cells into keratinocyte-like cells, Mol Biotechnol. Dec. 15, 2017. 60(2):100-110.

Galateanu B, et al., Fabrication of Novel Silk Fibroin-LDHs Composite Architectures for Potential Bone Tissue Engineering, Dec. 2017, Mater Plast. 54 (4): 659-665.

Gao KZ, et al., Cellulose nanofibers/silk fibroin nanohybrid sponges with highly ordered and multi-scale hierarchical honeycomb structure, Cellulose Nov. 2, 2017. 25 (1): 429-437.

Gao XC, et al., A silk fibroin based green nano-filter for air filtration, RSC Advances 8 (15): 8181-8189.

Gao Y, et al., Biomineralized poly (l-lactic-co-glycolic acid)-tussah silk fibroin nanofiber fabric with hierarchical architecture as a scaffold for bone tissue engineering, Mater Sci Eng C Mater Biol Appl. Mar. 1, 2018;84:195-207.

Gholipourmalekabadi M, et al., 3D Protein-Based Bilayer Artificial Skin for Guided Scarless Healing of 3rd degree Burn Wounds In vivo, Biomacromolecules. Mar. 12, 2018. doi: 10.1021/acs.biomac.7b01807.

Gholipourmalekabadi M, et al., Silk fibroin/amniotic membrane 3D bi-layered artificial skin, Biomed Maler., Feb. 2018. 13 (3): 035003.

Gilotra S, et al., Potential of silk sericin based nanofibrous mats for wound dressing applications, Journal Article, Mater Sci Eng C Mater Biol Appl. Sep. 1, 2018;90:420-432.

Guo C, et al., Comparative Study of Strain-Dependent Structural Changes of Silkworm Silks: Insight into the Structural Origin of Strain-Stiffening, Small Oct. 27, 2017. 13(47): 1702266.

Guo J, et al., Coding Cell Micropatterns Through Peptide Inkjet Printing for Arbitrary Biomineralized Architectures, Adv Funct Mater., 28(19) doi: 10.1002/adfm.201800228.

Guo K, et al., Improved strength of silk fibers in Bombyx mori trimollers induced by an anti-juvenile hormone compound, Biochim Biophys Acta. Feb. 13, 2018. pii: S0304-4165(18)30049-7.

Guo WH, et al., Sericin nanomicelles with enhanced cellular uptake and pH-triggered release of doxorubicin reverse Cancer drug resistance, Drug Deliv., 25 (1): 1103-1116.

(56) References Cited

OTHER PUBLICATIONS

Guo Y, et al., Dissolution and regeneration of non-mulberry Eriogyna Pyretorum silk fibroin, Mater Res Express, 4(10):105404.
Han X, et al., Silk fibroin improves the release of nerve growth factor from hydroxyapatite particles maintaining its pioactivity, 2018, Curr Drug Deliv., 15(6): 879-886.
Han YC, et al., Application of far-infrared spectroscopy to the structural identification of protein materials, Phys. Chem. Chem. Phys., 2018,20, 11643-11648.
He JY, et al., Stabilization of RNA Encapsulated in Silk, ACS Biomater Sci Eng., 4(5): 1708-1715.
He ZP, et al., Low pressure-induced secondary structure transitions of regenerated silk fibroin in its wet film studied by time-resolved infrared spectroscopy, Proteins. 86 (6): 621-628.
Heiby JC, et al., Conservation of folding and association within a family of spidroin N-terminal domains, Sci Rep. Dec. 1, 2017;7(1):16789.
Heimbach B, et al., High performance resorbable composites for load-bearing bone fixation devices, J Mech Behav Biomed Mater. Feb. 19, 2018;81:1-9.
Hong JH, et al., Preparation of conductive silk fibroin yarns coated with polyaniline using an improved method based on in situ polymerization, Synthetic Met., 235: 89-96.
House MD, et al., Mechanical and biochemical effects of progesterone on engineered cervical tissue, Tissue Eng Part A. Jun. 1, 2018. doi: 10.1089/ten.TEA.2018.0036.
Hu JH, et al., Apoptosis of posterior silk gland of Bombyx mori during spinning period and the role of PI3K/Akt pathway, Arch Insect Biochem Physiol. Feb. 5, 2018., doi: 10.1002/arch.21450.
Jackman SL, et al., Silk Fibroin Films Facilitate Single-Step Targeted Expression of Optogenetic Proteins, Cell Rep. Mar. 20, 2018; 22(12):3351-3361.
James E, et al., Silk Biomaterials-Mediated miRNA Functionalized Orthopedic Devices, Tissue Eng Part A. doi: 10.1089/ten.TEA.2017.0455.
Jastrzebska K, et al., Delivery of chemotherapeutics using spheres made of bioengineered spider silks derived from MaSp1 and MaSp2 proteins, Nanomedicine (Lond) Jan. 17, 2018; 13(4):439-454.
Chouhan, D et al., Functionalized PVA-Silk blended nanofibrous mats promote diabetic wound healing via regulation of extracellular matrix and tissue remodeling, Journal of Tissue Engineering and Regenerative Medicine. Mar. 2018; e1559-e1570, 12(3). (Doi: 10.1002/term.2581).
Costa, JB et al., Fast Setting Silk Fibroin Bioink for Bioprinting of Patient-Specific Memory-Shape Implants, Advanced Healthcare Materials. Nov. 22, 2017; 171021, 6(22).
Cheng, Q et al., Silk Nanofibers as Robust and Versatile Emulsifiers, ACS Applied Matrials & Interfaces. Sep. 29, 2017; 35693-35700, 9(41).
Aykac, A et al., Protective effect of silk fibroin in burn injury in rat model, Gene. Jan. 30, 2018; 287-291, 641.
Chen, J and Zhang, W et al., Substance P and patterned silk biomaterial stimulate periodontal ligament stem cells to form corneal stroma in a bioengineered three-dimensional model, Stem Cell Research & Therapy. Nov. 13, 2017; 260, 8.
Abdel-Naby, W et al., Treatment with solubilized Silk-Derived Protein (SDP) enhances rabbit corneal epithelial wound healing, Plos One. Nov. 20, 2017; 0188154, 12(11).
Ai, C et al., Surface modification of vascular endothelial growth factor-loaded silk fibroin to improve biological performance of ultra-high-molecular-weight polyethylene via promoting angiogenesis, International Journal of Nanomedicine. Oct. 20, 2017; 7737-7750, 12.
Cao, Y et al., Drug release from core-shell PVA/ silk fibroin nanoparticles fabricated by one-step electrospraying, Scientific Reports. Sep. 20, 2017; 7(11913).
Babu, PJ et al., Silver oxide nanoparticles embedded silk fibroin spuns: Microwave mediated preparation, characterization and their synergistic wound healing and anti-bacterial activity, Journal of Colloid and Interface Science. Mar. 1, 2018; 62-71, 513.
Cao, Y and Wang, B et al., Biodegradation of Silk Biomaterials, International Journal of Molecular Sciences. 2009; 1514-1524, 10.
Daithankar, A., et al., Moisturizing efficiency of silk protein hydrolysate: Silk Fibroin, Indian J. of Biotechnology. Jan. 2005., 115-121.
Jin, Hyoung-Joon, et al. Water stable silk films with reduced ß-sheet content., Advanced Functional Materials., 2005, 15, 1241-1247.
Lawrence, Brian D., et al., Bioactive silk protein biomaterial Systems for Optical Devices. Biomacromolecules 2008, 9, 1214-1220.
Sah, Mahesh K., et al., The extraction of fibroin protein from Bombyx mori silk cocoon: Optimization of process parameters., Int. J. of Bioinformatics Research., 2010, vol. 2 Issue 2, pp. 33-41.
Sofia, S. et al., Functionalized silk-based biomaterials for bone formation., J. Biomedical Materials Research., vol. 54, 139-148, 2001.
Wu, Xilong, et al., Impact of sterilization methods on the stability of silk fibroin solution. Adv. Mats. Research. vols. 311-313 (2011) pp. 1755-1759.
Zhao, Y., et al., The effects of different sterilization methods on silk fibroin., J. Biomedical Sci and Engr., 2011, 4, 397-402.
Zhu, Liang Jun, et al., Gelation of silk sericin and physical properties of the gel. J. Seric. Sci. Jpn. 64 (5), 415-419 (1995).
International Search Report and Written Opinion dated Jan. 16, 2019 in Application No. PCT/US2018/059998, entitled: Ocular Applications of Silk-Based Products.
Qian Q, et al., High-efficiency production of human serum albumin in the posterior silk glands of transgenic silkworms, Bombyx mori, PLOS One. Jan. 19, 2018;13(1):e0191507.
Qian Y, et al., Surface modification of nanofibrous matrices via layer-by-layer functionalized silk assembly for mitigating the foreign body reaction, Biomaterials. Feb. 20, 2018; 164:22-37.
Qin S, et al., MicroRNA profile of silk gland reveals different silk yields of three silkworm strains, Gene Feb. 8, 2018, 653: 1-9.
Ragona L, et al., Rhodamine binds to silk fibroin and inhibits its self-aggregation, BBA-Proteins Proteom., 1866 (5-6): 661-667.
Rahimi M, et al., Comparative effectiveness of three-dimensional scaffold, differentiation media and co-culture with hative cardiomyocytes to trigger in vitro cardiogenic differentiation of menstrual blood and bone marrow stem cells, Biologicals. Jun. 5, 2018. pii: S1045-1056(18)30136-2.
Rameshbabu AP, et al., Silk Sponges Ornamented with a Placenta-Derived Extracellular Matrix Augment Full-Thickness Cutaneous Wound Healing by Stimulating Neovascularization and Cellular Migration, ACS Appl Mater Interfaces. May 2, 2018. doi: 10.1021/acsami.7b19007.
Ran JB, et al., Rational design of a stable, effective, and sustained dexamethasone delivery platform on a titanium implant: An innovative application of metal organic frameworks in bone implants, Chem Eng J., Sep. 2017. 333: 20-33.
Ribeiro VP, et al., Combinatory approach for developing silk fibroin scaffolds for cartilage regeneration, Acta Biomater., 72: 167-181.
Rider PM, et al., Reactive Inkjet Printing of Regenerated Silk Fibroin Films for Use as Dental Barrier Membranes, Micromachines 9(2): 46.
Rodriguez RJ, et al., 3D freeform printing of silk fibroin, Acta Biomater. Mar. 15, 2018. pii: S1742-7061(18)30118-1.
Saravanan A, et al., Bio-industrial waste silk fibroin protein and carbon nanotube induced carbonized growth of one dimensional ZnObased bio-nanosheets and their enhanced optoelectronic properties, Chemistry. Jun. 1, 2018. doi: 10.1002/chem.201800702.
Sato S, et al., Development and validation of scFv-conjugated affinity silk protein for specific detection of Carcinoembryonic antigen, Sci. Rep., Nov. 22, 2017; 7:16077.
Saviane A, et al., Intrinsic antimicrobial properties of silk spun by genetically modified silkworm strains, Transgenic Res., Feb. 2018. 27 (1): 87-101.
Shaban L, et al., A 3D intestinal tissue model supports Clostridioides difficile germination, colonization, toxin production and epithelial damage, Anaerobe. Feb. 17, 2018. pii: S1075-9964(18)30034-9.
Shen T, et al., Dissolution behavior of silk fibroin in a low concentration CaCl2-methanol solvent: From morphology to nanostructure, Int J Biol Macromol. Feb. 5, 2018. pii: S0141-8130(17)35010-9.

(56) References Cited

OTHER PUBLICATIONS

Sheng W, et al., Enhanced activity and stability of papain by covalent immobilization on porous magnetic nanoparticles, J Biol Macromol. Mar. 19, 2018; 114:143-148.
Shera SS, et al., Preparation of Drug Eluting Natural Composite Scaffold Using Response Surface Methodology and Artificial Neural Network Approach, Tissue Eng Regen Med, Apr. 15, 2018 (2): 131-143.
Shimada K, et al., The effect of a silk Fibroin/Polyurethane blend patch on rat Vessels, Organogenesis 13(4): 115-124.
Shimada R, et al., Development of a new surgical sheet containing both silk fibroin and thermoplastic polyurethane for cardiovascular surgery, Surg Today, 48(5): 486-494.
Shimanovich U, et al., Biophotonics of native silk fibrils, Macromol Biosci. Jan. 29, 2018; 1700295.
Silva J, et al., Engineered tubular structures based on chitosan for tissue engineering applications, J Biomater Appl., Nov. 29, 2017. 32(7):841-852.
Song F, et al., ZnO-Based Physically Transient and Bioresorbable Memory on Silk Protein, IEEE Electr Device L., Nov. 2017. 39(1):31-34.
Song J, et al., Repair of rabbit radial bone defects using bone morphogenetic protein-2 combined with 3D porous silk fibroin/B-tricalcium phosphate hybrid scaffolds, Biomater Sci Polym Ed. Feb. 6, 2018:29(6): 716-729.
Sparkes J, et al., The rheological properties of native sericin, Acta Biomater. Feb. 1, 2018. pii: S1742-7061(17) 30792-4.
Stanton J, et al., Impact of ionic liquid type on the structure, morphology and properties of silk-cellulose biocomposite materials, Int J Biol Macromol., Mar. 2018; 108: 333-341.
Steffi C, et al., Estradiol-Loaded Poly(ϵ-caprolactone)/Silk Fibroin Electrospun Microfibers Decrease Osteoclast Activity and Retain Osteoblast Function, CS Appl Mater Interfaces. Mar. 7, 2018.
Stocco E, et al., Partially oxidized polyvinyl alcohol conduit for peripheral nerve regeneration, Sci Rep. Jan. 12, 2018; 8(1):604.
Suktham K, et al., Efficiency of resveratrol-loaded sericin nanoparticles: Promising bionanocarriers for drug delivery, Int J Pharmaceut, 537 (1-2): 48-56.
Tanaka T, et al., Comparison of the knitted silk vascular grafts coated with fibroin sponges prepared using glycerin, poly(ethylene glycol diglycidyl ether) and poly(ethylene glycol) as porogens, J Biomater Appl. Jan. 1, 2018:885328218758276.
Tang-Schomer MD, et al., In Vitro 3D Regeneration-like Growth of Human Patient Brain Tissue, J Tissue Eng Regen Med. Mar. 6, 2018. doi: 10.1002/term.2657.
Tao C, et al., Hierarchical micro/submicrometer-scale structured scaffolds prepared via coaxial electrospinning for bone regeneration, J. of Mater Chemistry B., Dec. 14, 2017; 5 (46): 9219-9228.
Tellado SF, et al., Heparin functionalization increases retention of TGF-B2 and GDF5 on biphasic silk fibroin scaffolds for tendon/ligament-to-bone tissue engineering, Acta Biomater., 72: 15-166.
Teshima T, et al., Cell assembly in self-foldable multilayered soft micro-rolls, Sci Rep., Dec. 22, 2017; 7: 17376.
Thu-Hien L, et al., Evaluation of the Morphology and Biocompatibility of Natural Silk Fibers/Agar Blend Scaffolds for Tissue Regeneration, Int J of Polym Sci, Jan. 8, 2018, 2018:5049728.
Tseng P, et al., Functional, RF-Trilayer Sensors for Tooth-Mounted, Wireless Monitoring of the Oral Cavity and Food Consumption, Adv Mater. Mar. 23, 2018:e1703257.
Tu FF, et al., Vascular Cell Co-Culture on Silk Fibroin Matrix, Polymers 2018. 10(1), 39.
Türkkan S, et al., Fabrication of functionalized citrus pectin/silk fibroin scaffolds for skin tissue engineering, J Biomed Mater Res B Appl Biomater. 2018.
Valentini L, et al., Ice-regenerated flame retardant and robust film of Bombyx mori silk fibroin and POSS nano-cages, RSC Adv., 8 (17): 9063-9069.
Valentini L, et al., Silkworm silk fibers vs PEEK reinforced rubber luminescent strain gauge and stretchable Composites, Compos Sci Technol., Mar. 2018. 156: 254-261.
Vidal Sel, et al., 3D biomaterial matrix to support long term, full thickness, immuno-competent human skin equivalents with nervous system components, Biomaterials. Apr. 24, 2018. pii: S0142-9612(18)30308-9.
Wang C, et al., Bioinspired, biocompatible and peptide-decorated silk fibroin coatings for enhanced osteogenesis of pioinert implant, J Biomater Sci Polym Ed. May 15, 2018. 1-40.
Wang C, et al., Silk fibroin enhances peripheral nerve regeneration by improving vascularization within nerve conduits, J Biomed Mater Res A. Mar. 25, 2018. doi: 10.1002/jbm.a.36390.
Wang C, et al., Ultra-robust Biochips with Metal-Organic Framework Coating for Point-of-Care Diagnosis, ACS Sens. Jan. 16, 2018. 3(2): 342-351.
Wang H, et al., Facile Fabrication of Porous ZnS and ZnO Films by Coaxial Electrospinning for Highly Efficient Photodegradation of Organic Dyes, Cell Transplant. Nov. 3, 2017. 26 (11): 1717-1732.
Wang JH, et al., Graphene Oxide Incorporated Collagen/Nano-Hydroxyapatite Composites with Improved Mechanical Properties for Bone Repair Materials, J Biomater Tiss Eng., Oct. 7, 2017 (10): 1000-1007.
Wang JH, et al., In Vitro and In Vivo Studies of a Collagen-Based Scaffold Carrying PLGA Microspheres for Sustained Release of Epidermal Growth Factor in Skin Regeneration, J Biomater Tiss Eng., 7 (12): 1336-1343.
Wang JL, et al., Analyzing the structure and glass transition behavior of silks for archaeology and conservation, J Roy Soc Interface., Feb. 2018; 15 (139).
Wang P, et al., A silk-based coating containing GREDVY peptide and heparin on Mg-Zn-Y-Nd ally: improved corrosion resistance, hemocompatibility and endothelialization, J Mater Chem B., Feb. 14, 2018. 6 (6): 966-978.
Qiu-Xu W, et al., Effect of Bone Marrow Mesenchymal Stem Cells on Hydroxyapatite/Silk Fibroin/Chitosan Composite 3D Scaffold for Rat Skull Defects Repair, J Biomater Tiss Eng., Oct. 7, 2017 (10): 978-983.
Wang SD, et al., Strong and biocompatible three-dimensional porous silk fibroin/graphene oxide scaffold prepared by phase separation, Int J Biol Macromol. Jan. 7, 2018; 111:237-246.

* cited by examiner

OCULAR APPLICATIONS OF SILK-BASED PRODUCTS

CROSS REFERENCE TO RELATED APPLICATIONS

This application is a divisional of U.S. application Ser. No. 16/762,544 filed on May 8, 2020, which is a § 371 of PCT/US2018/059998, filed on Nov. 9, 2018, which claims priority to 62/584,153 filed on Nov. 10, 2017 entitled Manufacture and Uses of Silk Fibroin, 62/659,209 filed Apr. 18, 2018 entitled Ocular Silk-Based Products and Methods of Use, and 62/680,371 filed Jun. 4, 2018 entitled Ocular Silk-Based Products and Methods of Use, the contents of each of which are herein incorporated by reference in their entirety.

FIELD OF THE INVENTION

The present invention relates to formulations and methods of maintaining and delivering therapeutic agents for ocular indications. Specifically provided are silk-based product formulations.

BACKGROUND OF THE INVENTION

Silk is a naturally occurring polymer. Most silk fibers are derived from silkworm moth (*Bombyx mori*) cocoons and include silk fibroin and sericin proteins. Silk fibroin is a fibrous material that forms a polymeric matrix bonded together with sericin. In nature, silk is formed from a concentrated solution of these proteins that are extruded through silkworm spinnerets to produce a highly insoluble fiber. These fibers have been used for centuries to form threads used in garments and other textiles.

Many properties of silk make it an attractive candidate for products serving a variety of industries. Polymer strength and flexibility has supported classical uses of silk in textiles and materials, while silk biocompatibility has gained attention more recently for applications in medicine.

Although a variety of products and uses related to silk are being developed, there remains a need for silk-based products that can meet the demands of modern medicine. Additionally, there remains a need for silk-based products that can leverage silk polymer strength, flexibility, and biocompatibility to meet needs in the field of medicine. The present disclosure addresses these needs by providing silk-based products and related methods of preparation and use in medical applications.

SUMMARY OF THE INVENTION

In some embodiments, the present disclosure provides a silk-based product (SBP) that includes processed silk and an ocular therapeutic agent. The SBP may be in the shape of a rod. The SBP may include from about 0.1% to about 98%, weight per weight (w/w), of the ocular therapeutic agent. The SBP may include from about 15% to about 95% (w/w) of the ocular therapeutic agent. The SBP may include from about 5% to about 85% (w/w) of the ocular therapeutic agent. The SBP may include from about 45% to about 75% (w/w) of the ocular therapeutic agent. The SBP may include a ratio of ocular therapeutic agent concentration to processed silk concentration of from about 0.01 to about 4.2. The ratio of ocular therapeutic agent concentration to processed silk concentration may be from about 0.01 to about 1. The ratio of ocular therapeutic agent concentration to processed silk concentration may be from about 1 to about 4.2. The SBP may include one or more excipients. The one or more excipients may include one or more of lactose, sorbitol, sucrose, mannitol, lactose USP, Starch 1500, microcrystalline cellulose, Avicel®, phosphate salts, sodium chloride, hydrochloric acid, polysorbate 80, potassium phosphate monobasic, potassium phosphate dibasic, sodium phosphate dibasic, sodium phosphate monobasic, phosphate buffer, phosphate buffered saline, sodium hydroxide, dibasic calcium phosphate dehydrate, tartaric acid, citric acid, fumaric acid, succinic acid, malic acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. The SBP may include sucrose. The SBP may include at least one excipient, wherein the at least one excipient is present at a concentration of from about 0.01% (w/w) to about 20% (w/w). The SBP may include a density of from about 0.7 g/mL to about 1.4 g/mL. Rod-shaped SBPs may have a diameter of from about 0.1 mm to about 1.5 mm. Rod-shaped SBPs may have a length of from about 8 mm to about 12 mm. The SBP may be a hydrogel. The SBP may be freeze dried. The SBP may include at least one excipient selected from one or more members of the group consisting of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremaphor EL), cremaphor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polyvinyl pyrrolidone, propylene carbonate, propylene glycol, solutol HS15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. The SBP may include silk fibroin, wherein the silk fibroin is present in the SBP at a concentration of from about 0.1% (w/v) to about 30% (w/v). The SBP may include from about 0.1% (w/v) to about 30% (w/v) of the ocular therapeutic agent. The SBP may include from about 0.1% (w/v) to about 30% (w/v) of the excipient. The SBP may include an osmolarity of from about 275 mOsm to about 285 mOsm. The SBP may include a ratio of silk fibroin concentration (w/v) to excipient concentration (w/v) of from about 0.01 to about 0.5. The ratio of silk fibroin concentration (w/v) to excipient concentration (w/v) may be about 0.3. The SBP may include a ratio of ocular therapeutic agent concentration (w/v) to silk fibroin concentration (w/v) of from about 0.3 to about 4.2. The SBP may include a ratio of ocular therapeutic agent concentration (w/v) to excipient concentration (w/v) of from about 0.1 to about 1. The ocular therapeutic agent may be a small molecule or a protein. The ocular therapeutic agent may be a non-steroidal anti-inflammatory drug (NSAID). The NSAID may include one or more of aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. The NSAID may be celecoxib. The ocular therapeutic agent may be a protein. The protein may be selected from the group consisting of lysozyme, bovine serum albumin (BSA), bevacizumab, and VEGF-related agents. The SBP may be formulated for intraocular administration. The SBP may be formulated for one or more of intravitreal administration, intraretinal administration, intracorneal administration, intrascleral administration, punctal administration, administration to the anterior sub-Tenon's, suprachoroidal administration, administration to the posterior sub-Tenon's, subretinal administration, administration to the fornix, administration to the lens, and intra-aqueous humor administration. The SBP may be biocompatible. The SBP may include a solution. The SBP may include a lyophilized powder. The SBP may stabilize the ocular therapeutic agent. The SBP may be non-immunogenic. The SBP may include the composition of any of the samples listed in any of Tables 1-41.

In some embodiments, the present disclosure provides a method of treating a subject that includes contacting the subject with an SBP described herein. The subject may have an ocular indication. The ocular indication may include inflammation. The ocular indication may include one or more of an infection, refractive errors, age related macular degeneration, cystoid macular edema, cataracts, diabetic retinopathy (proliferative and non-proliferative), glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorder, conjunctivitis, cancer, corneal ulcer, corneal abrasion, snow blindness, scleritis, keratitis, Thygeson's superficial punctate keratopathy, corneal neovascularization, Fuch's dystrophy, keratoconjunctivitis sicca, iritis, chorioretinal inflammation (e.g. chorioretinitis, choroiditis, retinitis, retinochoroiditis, pars planitis, Harada's disease, aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, retinal vein occlusion, and separation of retinal layers. The SBP may be administered via one or more of oral administration, intravenous administration, topical administration, and ocular administration. The SBP may be administered via one or more of intravitreal administration, intraretinal administration, intracorneal administration, intrascleral administration, and intra-aqueous humor administration. The SBP may be administered via intravitreal administration. The intravitreal administration may include intravitreal injection. The intravitreal injection may be performed by pushing a wire through a syringe and needle or cannula loaded with the SBP. The wire may be pushed until the wire extends past the needle or cannula. The SBP may be used to deliver the ocular therapeutic agent at a dose of from about 1 µg to about 5,000 µg. The dose may be about 750 µg. Contacting the subject with the SBP may result in a concentration of the ocular therapeutic agent in an eye of the subject of from about 0.01 ng/mL to about 60,500 ng/mL. The concentration of ocular therapeutic agent in one or more components of the eye may be from about 0.01 ng/mL to about 60,500 ng/mL. The one or more components of the eye may be selected from the group consisting of aqueous humor, vitreous humor, retina, choroid, sclera, lens, fornix, conjunctiva, lacrimal punctum, capsule of Tenon, iris, pupal, cornea, ciliary muscle, fovea, optic nerve, macula, blood vessel, anterior chamber, posterior chamber, and sub-tenon space. The concentration of ocular therapeutic agent in the aqueous humor may be from about 0.01 ng/mL to about 2.0 ng/mL. The one or more components of the eye may include the vitreous humor. The concentration of the ocular therapeutic agent in the vitreous humor may be from about 10 ng/mL to about 30,000 ng/mL. The one or more components of the eye may include the retina and/or choroid. The concentration of the ocular therapeutic agent in the retina and/or choroid may be from about 10 ng/mL to about 60,500 ng/mL. The ocular therapeutic agent may be detectable in one or more components of the eye for at least 3 months. The ocular therapeutic agent detected may remain at a steady level for at least 3 months. The ocular therapeutic agent may be detectable in one or more components of the eye for at least 6 months. The ocular therapeutic agent detected may remain at a steady level for at least 6 months. Intraocular pressure may be reduced. The SBP may be well tolerated. The subject may be contacted with a dose of the ocular therapeutic agent sufficient to achieve a concentration of the ocular therapeutic agent in an eye of the subject or a component of an eye of the subject that is equal to or greater than the effective concentration for the ocular therapeutic agent. The concentration of the ocular therapeutic agent in the eye or eye component may be greater than the effective concentration of the ocular therapeutic agent. The concentration of the ocular therapeutic agent in the eye or eye component may be at least 1.5-fold greater than the effective concentration of the ocular therapeutic agent. The eye component may include the vitreous humor. The concentration of ocular therapeutic agent may be at least 1.5-fold greater than the effective concentration of the ocular therapeutic agent. The eye component may include the retina and/or choroid. The concentration of ocular therapeutic agent may be at least 4-fold greater than the effective concentration of the ocular therapeutic agent. The SBP may be a rod. The SBP may be a hydrogel.

In some embodiments, the present disclosure provides a method of delivering an ocular therapeutic agent to a subject by contacting an eye of the subject with an SBP according to any of those described herein, wherein preparation of the SBP includes combining processed silk with the ocular therapeutic agent. The SBP may be prepared as a rod. The density of the SBP may be modulated by the concentration of processed silk. The SBP may be prepared by extrusion through a tube. The tube may be a needle. Extrusion may be carried out using a syringe. The SBP may be incubated at approximately 37° C. The SBP may be incubated for up to approximately 24 hours. The SBP may form a gel in the tube. The ocular therapeutic agent may be delivered to the subject's eye by release from the SBP while in contact with the subject's eye. Release of the ocular therapeutic agent from the SBP may be modulated by one or more of silk fibroin concentration, silk fibroin molecular weight, SBP volume, method used to dry the SBP, ocular therapeutic agent molecular weight, and inclusion of at least one excipient. The technique used to dry the SBP may include one or more of oven drying, lyophilization, and air drying. The SBP may include ocular therapeutic agent and silk fibroin at a w/w ratio of from about 1 to about 4.2. Release of the ocular therapeutic agent from the SBP may occur at a rate that includes an initial burst. From about 0.1% to about 100% of the ocular therapeutic agent may be released from the SBP during an initial release period associated with the initial burst. The rate of release of the therapeutic agent may be inversely related to the concentration of processed silk. The SBP may be a rod, and the amount of therapeutic agent released during the initial period associated with the initial burst may be inversely related to the density of the rod. Release of the ocular therapeutic agent from the SBP may include a daily release percentage of from about 0.1% (w/w) to about 5% (w/w). The SBP may be a rod, and the daily release percentage may be inversely related to the density of the rod. From about 1% to about 100% of the ocular therapeutic agent may be released from the SBP during a release period of from about 1 day to about 10 months. The release period may begin upon contacting an eye of the subject with the SBP. The release period may be from about 1 day to about 5 months. The SBP may be a rod, and the release period may be proportional to the density of the rod. From about 3% to about 100% of the ocular therapeutic agent may be released from the SBP over the release period.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale; emphasis instead being placed upon illustrating the principles of various embodiments of the invention.

DETAILED DESCRIPTION

Figure 1A:
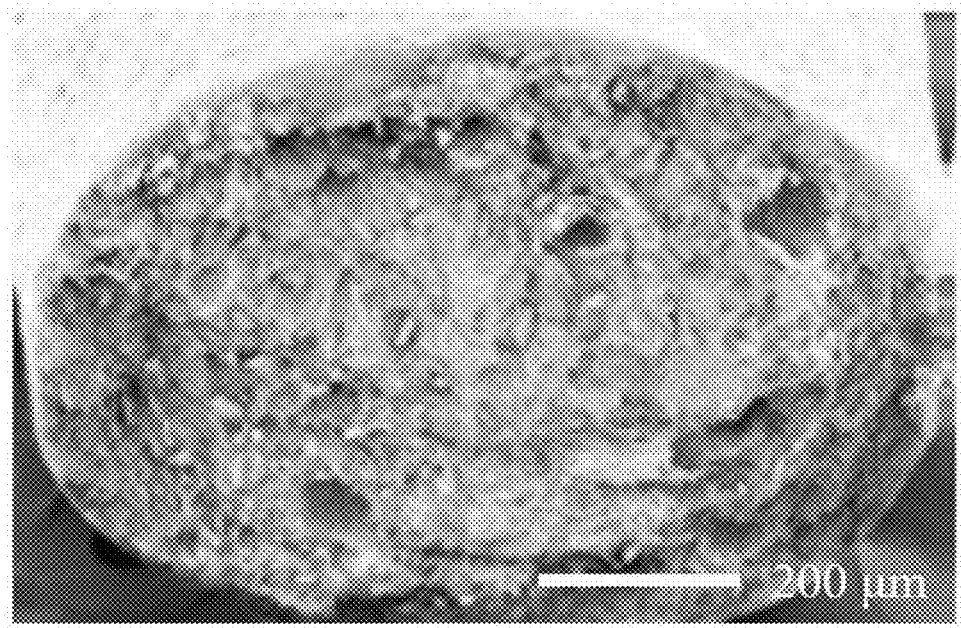
FIG. 1A is a scanning electron microscope (SEM) image showing a silk fibroin rod formulated with celecoxib.
Figure 1B:
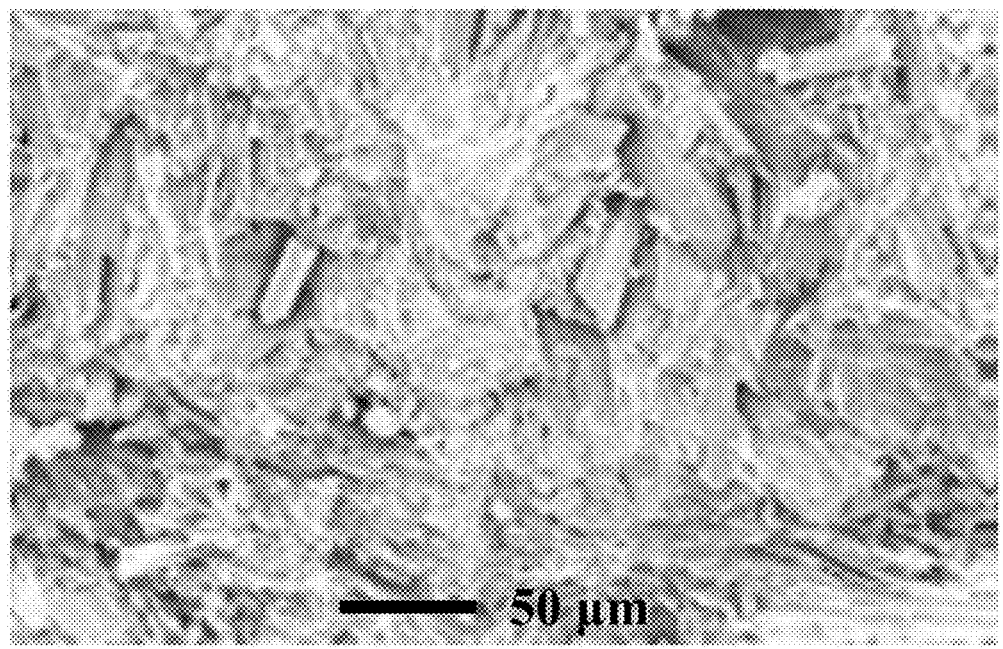
FIG. 1B is a scanning electron microscope (SEM) image showing a silk fibroin rod formulated with celecoxib.
Figure 1C:
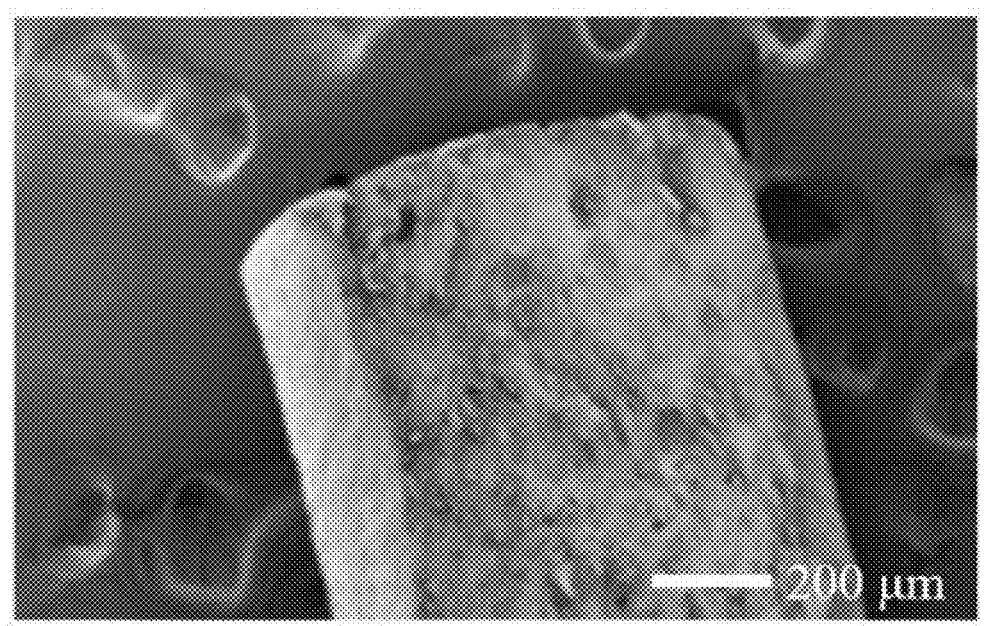
FIG. 1C is a scanning electron microscope (SEM) image showing a silk fibroin rod formulated with celecoxib.
Figure 1D:
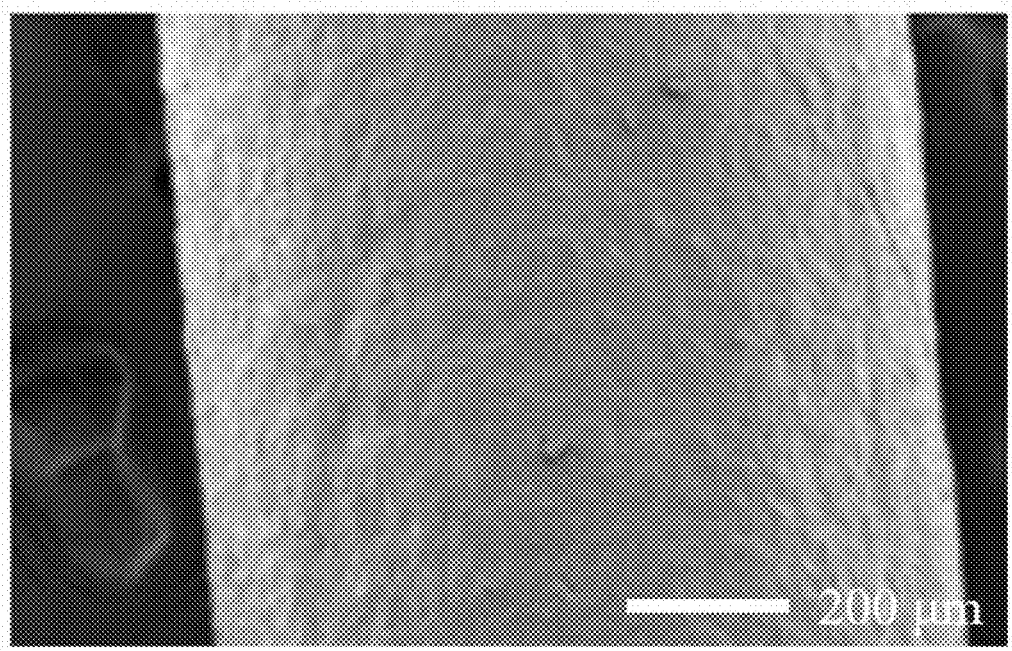
FIG. 1D is a scanning electron microscope (SEM) image showing a silk fibroin rod formulated with celecoxib.

Embodiments of the present disclosure relate to silk-based products (SBPs) and their methods of use. The term "silk" generally refers to a fibrous material formed by insects and some other species that includes tightly bonded protein filaments. Herein, the term "silk" is used in the broadest sense and may embrace any forms, variants, or derivatives of silk discussed.

Silk fibers from silkworm moth (*Bombyx mori*) cocoons include two main components, sericin (usually present in a range of 20-30%) and silk fibroin (usually present in a range of 70-80%). While not wishing to be bound by theory, structurally silk fibroin forms the center of the silk fibers and sericin acts as the gum coating the fibers. Sericin is a gelatinous protein that holds silk fibers together with many of the characteristic properties of silk (see Qi et al. (2017) Int J Mol Sci 18:237 and Deptuch et al. (2017) Materials 10:1417, the contents of each of which are herein incorporated by reference in their entireties). Silk fibroin is an insoluble fibrous protein consisting of layers of antiparallel beta sheets. Its primary structure mainly consists of recurrent serine, alanine, and glycine repeating units and the isoelectric point of silk fibroin has been determined to be around 4.2. Silk fibroin monomers include a complex of heavy chain (around 350 kDa) and light chain (around 25 kDa) protein components. Typically, the chains are joined by a disulfide bond. With some forms, heavy chain and light chain segments are non-covalently bound to a glycoprotein, p25. Polymers of silk fibroin monomers may form through hydrogen bonding between monomers, typically increasing mechanical strength (see Qi et al. (2017) Int J Mol Sci 18:237). During silk processing, fragments of silk fibroin monomers may be produced, including, but not limited to, fragments of heavy and/or light chains. These fragments may retain the ability to form hydrogen bonds with silk fibroin monomers and fragments thereof. Herein, the term "silk fibroin" is used in its broadest sense and embraces silk fibroin polymers, silk fibroin monomers, silk fibroin heavy and light chains, silk fibroin fragments, and variants, derivatives, or mixtures thereof from any of the wild type, genetically modified, or synthetic sources of silk described herein.

The present disclosure includes methods of preparing processed silk and SBPs, different forms of SBPs, and a variety of applications for utilizing processed silk and SBPs alone or in combination with various compounds, compositions, and devices.

I. Silk-Based Products

As used herein, the term "silk-based product" or "SBP" refers to any compound, mixture, or other entity that is made up of or that is combined with processed silk. "Processed silk," as used herein, refers to any forms of silk harvested, obtained, synthesized, formatted, manipulated, or altered through at least one human intervention. SBPs may include a variety of different formats suited for a variety of different applications. Examples of SBP formats include, but are not limited to, fibers, nanofibers, implants, rods, gels, hydrogels, and solutions. Additional formats are described herein. SBPs may find utility in variety of fields and for a variety of applications. Such utility may be due to the unique physical and chemical properties of silk. These physical and chemical properties include, but are not limited to, biocompatibility, biodegradability, bioresorbability, solubility, crystallinity, porosity, mechanical strength, thermal stability, and transparency. In some embodiments, SBPs may be used for one or more therapeutic applications. Such SBPs may include processed silk, wherein the processed silk is or is derived from one or more of raw silk, silk fibers, silk fibroin, and silk fibroin fragments. Processed silk present is some SBPs may include one or more silk fibroin polymers, silk fibroin monomers, and/or silk fibroin fragments. In some embodiments, silk fibroin fragments include silk fibroin heavy chain fragments and/or silk fibroin light chain fragments. Some silk fibroin present in SBPs include a plurality of silk fibroin fragments. Each of the plurality of silk fibroin fragments may have a molecular weight of from about 1 kDa to about 350 kDa. As a non-limiting example, the silk fibroin fragment may have a molecular weight of 1 kDa, 2 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 130 kDa, 135 kDa, 140 kDa, 145 kDa, 150 kDa, 155 kDa, 160 kDa, 165 kDa, 170 kDa, 175 kDa, 180 kDa, 185 kDa, 190 kDa, 195 kDa, 200 kDa, 205 kDa, 210 kDa, 215 kDa, 220 kDa, 225 kDa, 230 kDa, 235 kDa, 240 kDa, 245 kDa, 250 kDa, 255 kDa, 260 kDa, 265 kDa, 270 kDa, 275 kDa, 280 kDa, 285 kDa, 290 kDa, 295 kDa, 300 kDa, 305 kDa, 310 kDa, 315 kDa, 320 kDa, 325 kDa, 330 kDa, 335 kDa, 340 kDa, 345 kDa, or 350 kDa. As a non-limiting example, the silk fibroin fragment may have a molecular weight of 1-5 kDa, 1-10 kDa, 1-15 kDa, 1-25 kDa, 1-50 kDa, 1-75 kDa, 1-100 kDa, 1-150 kDa, 1-200 kDa, 1-250 kDa, 1-300 kDa, 1-350 kDa, 5-10 kDa, 5-15 kDa, 5-25 kDa, 5-50 kDa, 5-75 kDa, 5-100 kDa, 5-150 kDa, 5-200 kDa, 5-250 kDa, 5-300 kDa, 5-350 kDa, 10-15 kDa, 10-25 kDa, 10-50 kDa, 10-75 kDa, 10-100 kDa, 10-150 kDa, 10-200 kDa, 10-250 kDa, 10-300 kDa, 10-350 kDa, 15-25 kDa, 15-50 kDa, 15-75 kDa, 15-100 kDa, 15-150 kDa, 15-200 kDa, 15-250 kDa, 15-300 kDa, 15-350 kDa, 25-50 kDa, 25-75 kDa, 25-100 kDa, 25-150 kDa, 25-200 kDa, 25-250 kDa, 25-300 kDa, 25-350 kDa, 50-75 kDa, 50-100 kDa, 50-150 kDa, 50-200 kDa, 50-250 kDa, 50-300 kDa, 50-350 kDa, 75-100 kDa, 75-150 kDa, 75-200 kDa, 75-250 kDa, 75-300 kDa, 75-350 kDa, 100-150 kDa, 100-200 kDa, 100-250 kDa, 100-300 kDa, 100-350 kDa, 150-200 kDa, 150-250 kDa, 150-300 kDa, 150-350 kDa, 200-250 kDa, 200-300 kDa, 200-350 kDa, 250-300 kDa, 250-350 kDa, and 300-350 kDa.

Sources of Silk

SBPs may include processed silk obtained from any one of a variety of sources. Processed silk may include raw silk. "Raw silk," as used herein, refers to silk that has been harvested, purified, isolated, or otherwise collected from silk producers. The term "silk producer," as used herein, refers to any organism capable of producing silk. Raw silk has been processed in large quantities for thousands of years, primarily from silkworms (*Bombyx mori*), which use silk to form their cocoon. Raw silk from silkworm cocoons includes silk fibroin and sericin that is secreted onto silk fibroin during cocoon formation. Raw silk may be harvested as a silk fiber. As used herein, the term "silk fiber" refers to any silk that is in the form of a filament or thread. Silk fibers may vary in length and width and may include, but are not limited to, yarns, strings, threads, and nanofibers. In some embodiments, raw silk may be obtained in the form of a yarn.

Silk Producers

In some embodiments, processed silk includes silk obtained from a silk producer. There are many species of silk producers in nature capable of producing silk. Silk producers may be insect species, such as silkworms. Some silk producers include arachnid species. In some embodiments, silk producers include species of mollusk. Silk produced by different silk producing species may vary in physical and/or chemical properties. Such properties may include amino acid content, secondary structure (e.g. β-sheet content), mechanical properties (e.g. elasticity), and others.

In some embodiments, processed silk may be obtained from the silkworm species *Bombyx mori*. Other examples of silk producer species include, but are not limited to, *Bombyx mandarina, Bombyx sinesis, Anaphe moloneyi, Anaphe panda, Anaphe reticulate, Anaphe ambrizia, Anaphe carteri, Anaphe venata, Anapha infracta, Antheraea assamensis, Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Copaxa multifenestrata, Coscinocera hercules, Callosamia promethea, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia Cynthia*, and *Samia ricini*.

Silk Properties

In some embodiments, processed silk may be selected based on or prepared to include features affecting one or more properties of the processed silk. Such properties may include, but are not limited to, stability, complex stability, composition stability, payload retention or release, payload release rate, wettability, mechanical strength, tensile strength, elongation capabilities, elasticity, compressive strength, stiffness, shear strength, toughness, torsional stability, temperature stability, moisture stability, strength, flexibility, solubility, crystallinity, viscosity, density, thickness, and porosity. Features affecting one or more processed silk properties may include silk secondary structure. Secondary structure refers to three-dimensional arrangements of polypeptide chains based on local interactions between neighboring residues. Common secondary structures include β-pleated sheets and α-helices. Silk secondary structure may enhance or attenuate solubility. In some embodiments, β-sheet secondary structure content may enhance processed silk crystallinity. "Crystallinity" refers to the degree of structure and arrangement between atoms or molecules in a compound, with increased structure yielding greater crystallinity. β-sheet structures may be antiparallel β-sheets. In some embodiments, processed silk includes polypeptides with random coil secondary structure. Some processed silk includes polypeptides with coiled coil secondary structure. In some embodiments, processed silk includes a combination of two or more forms of secondary structure. In some embodiments, processed silk may include polypeptides with multiple repeats. As used herein when referring to polypeptides, the term "multiple repeat" refers to an amino acid sequence that is duplicated two or more times in succession within a polypeptide. Silk fibroin heavy chains include multiple repeats that enable static interactions between parallel silk fibroin heavy chains. Multiple repeats may include repeats of the sequences GAGAGS (SEQ ID NO: 1) and/or GA. In some embodiments, the A of GA dipeptides may be replaced with S or Y. In some embodiments, multiple repeats may include any of those presented in Qi et al. (2017) Int J Mol Sci 18:237, the contents of which are herein incorporated by reference in their entirety. Multiple repeats may enable formation of stable, crystalline regions of antiparallel β-sheets.

Processed silk may include silk fibroin forms described by Qi et al. (2017) Int J Mol Sci 18:237 and Cao et al. (2009) Int J Mol Sci 10:1514-1524, the contents of each of which are herein incorporated by reference in their entirety. These silk fibroin forms are referred to as silk I, silk II, and silk III. Silk I and silk II forms are commonly found in nature. Silk I predominantly includes random coil secondary structures. Silk II predominantly includes β-sheet secondary structure. Silk III predominantly includes an unstable structure.

Processed silk may be treated to modulate β-sheet content and/or crystallinity. In some embodiments these treatments are used to reduce the solubility of the silk fibroin or silk fibroin composition. Treatments may include, but are not limited to, alteration of the pH, sonication of the silk fibroin, incorporation of an excipient, increasing or decreasing the temperature, treatment with acid, treatment with formic acid, treatment with glycerol, treatment with an alcohol, treatment with methanol, treatment with ethanol, treatment with isopropanol, and/or treatment with a mixture of alcohol and water. In some embodiments, treatments result in transition between forms of silk I, II, or III. Such methods may include any of those described in Cao et al. (2009) Int J Mol Sci 10:1514-1524).

Porosity

In some embodiments, processed silk may include variations in porosity. As used herein, the term "porosity" refers to the frequency with which holes, pockets, channels, or other spaces occur in a material, in some cases influencing the movement of elements to and/or from the material. Processed silk porosity may influence one or more other silk properties or properties of an SBP that includes the processed silk. These properties may include, but are not limited to, stability, payload retention or release, payload release rate, wettability, mechanical strength, tensile strength, elongation capabilities, density, thickness, elasticity, compressive strength, stiffness, shear strength, toughness, torsional stability, temperature stability, and moisture stability. In some embodiments, processed silk porosity may control the diffusion or transport of agents from, within, or into the processed silk or SBP. Such agents may include, but are not limited to, therapeutics, biologics, chemicals, small molecules, oxidants, antioxidants, macromolecules, microspheres, nanospheres, cells, or any payloads described herein.

Processed silk porosity may be modulated during one or more processing steps or during fabrication of an SBP (e.g., see International Publication No. WO2014125505 and U.S. Pat. No. 8,361,617, the contents of each of which are herein incorporated by reference in their entirety). In some embodiments, processed silk porosity may be modulated by one or more of sonication, centrifugation, modulating silk fibroin concentration, modulating salt concentration, modulating pH, modulating secondary structural formats, applying shear stress, modulating excipient concentration, chemical modification, crosslinking, or combining with cells, bacteria, and/or viral particles.

Strength and Stability

Processed silk strength and stability are important factors for many applications. In some embodiments, processed silk may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk had a non-acidic microenvironment. In some embodiments, the non-acidic microenvironment enhances the stability of processed silk and or SBPs. In some embodiments, the non-acidic microenvironment enhances the stability of therapeutic agents formulated with the processed silk and/or SBP. In some embodiments, the tensile strength of processed silk is stronger than steel. In some embodiments, the tensile strength of an SBP is stronger than steel.

Biocompatibility

In some embodiments, processed silk may be selected based on or prepared to maximize biocompatibility. As used herein, the term "biocompatibility" refers to the degree with which a substance avoids provoking a negative biological response in an organism exposed to the substance. The negative biological response may include an inflammatory response, local sensitization, hemorrhage, and/or other complications known to those skilled in the art. In some embodiments, administration of processed silk or an SBP does not induce an inflammatory response, local sensitization, hemorrhage, and/or other complications known to those skilled in the art. In some embodiments, contact with processed silk or an SBP does not induce an inflammatory response, local sensitization, hemorrhage, and/or other complications known to those skilled in the art. In some embodiments, processed silk biocompatibility is enhanced through preparations that produce only non-toxic byproducts during degradation. In some embodiments, exposure to an SBP generates a tolerable biological response, within an acceptable threshold known to those skilled in the art. In some embodiments, processed silk is biocompatible in humans and human whole blood. In some embodiments, processed silk is biocompatible in animals. In some embodiments, processed silk produces no adverse reactions, no acute inflammation, and no immunogenicity in vivo. In some embodiments, the processed silk or SBP is safe to use in vivo. In some embodiments, processed silk or SBPs are biocompatible and/or tolerable in vitro. In some embodiments, processed silk or SBPs are biocompatible and/or tolerable in vivo. In some embodiments, no inflammatory response, local sensitization, hemorrhage, and/or other complications occur after up 1 day, up to 3 days, up to 1 week, up to 1 month, up to 3 months, up to 4 months, up to 6 months, up to 7 months, or up to 1 year of contact with processed silk or an SBP.

Biodegradability

In some embodiments, processed silk may be selected based on or prepared to maximize biodegradability. As used herein, the term "biodegradability" refers to the degree with which a substance avoids provoking a negative response to an environment exposed to the substance as it deteriorates. The negative environmental response may include a response to toxic byproducts generated as a substance deteriorates. In some embodiments, processed silk biodegradability is enhanced through preparations that produce only non-toxic byproducts during degradation. In some embodiments, processed silk biodegradability is enhanced through preparations that produce only inert amino acid byproducts. In some embodiments, the SBP and/or SBP by products are considered naturally derived and environmentally and/or eco-friendly.

Anti-Evaporative Properties

In some embodiments, processed silk may be selected based on or prepared to reduce the evaporation of a solution. In some embodiments, processed silk may reduce the evaporation of a solution. In some embodiments, an SBP may demonstrate anti-evaporative properties by creating a water barrier. In some embodiments, processed silk may extend the lifetime or residence time of an SBP product due to its ability to prevent evaporation. In some embodiments, processed silk may increase the amount of time required for a solution to evaporate. In some embodiments, processed silk may be selected based on or prepared to reduce the evaporation of a solution. In some embodiments, processed silk may reduce the evaporation of a solution. In some embodiments, processed silk may extend the lifetime or residence time of an SBP product due to its ability to prevent evaporation. In some embodiments, processed silk may increase the amount of time required for a solution to evaporate.

Anti-Inflammatory Properties

In some embodiments, processed silk or SBPs may have or be prepared to maximize anti-inflammatory properties. It has been reported that silk fibroin peptide derived from silkworm *Bombyx mori* exhibited anti-inflammatory activity in a mice model of inflammation (Kim et al., (2011) BMB Rep 44(12):787-92; the contents of which are incorporated by reference in their entirety). In some embodiments, processed silk or SBPs may be administered to a subject alone or in combination with other therapeutic agents to elicit anti-inflammatory effects. It is contemplated that processed silk or SBPs alone or combination with other therapeutic agents may be used to treat various inflammatory diseases. For example, processed silk or SBPs may reduce signs and symptoms of inflammation, such as but not limited to, swelling, redness, tenderness, rashes, fever, and pain.

Processed Silk and Related Methods

Various processing methods may be used to obtain specific forms or formats of processed silk. Such processing methods may include, but are not limited to, acidifying, air drying, alkalinizing, annealing, autoclaving, chemical cross-linking, chemical modification, concentration, cross-linking, degumming, dissolving, dry spinning, drying, electrifying, electrospinning, electrospraying, emulsifying, encapsulating, extraction, extrusion, gelation, harvesting, heating, lyophilization, molding, oven drying, pH alteration, precipitation, purification, shearing, sonication, spinning, spray drying, spray freezing, spraying, vapor annealing, vortexing, and water annealing. The processing steps may be used to prepare final SBPs or they may be used to generate processed silk preparations. As used herein, the term "processed silk preparation" is generally used to refer to processed silk or compositions that include processed silk that are prepared for or obtained during or after one or more processing steps. Processed silk preparations may be SBPs, may be components of SBPs, or may be used as a starting or intermediate composition in the preparation of SBPs. Processed silk preparations may include other components related to processing (e.g., solvents, solutes, impurities, catalysts, enzymes, intermediates, etc.). Processed silk preparations that include silk fibroin may be referred to as silk fibroin preparations. In some embodiments, processed silk manufacturing is simple, scalable, and/or cost effective.

In some embodiments, processed silk may be prepared as, provided as, or included in a yarn, thread, string, a nanofiber, a particle, a nanoparticle, a microsphere, a nanosphere, a powder, a solution, a gel, a hydrogel, an organogel, a mat, a film, a foam, a membrane, a rod, a tube, a patch, a sponge, a scaffold, a capsule, an excipient, an implant, a solid, a coating, and/or a graft.

In some embodiments, the formulations are prepared to be sterile. As used herein, the term "sterile" refers to something that is aseptic. In some embodiments, SBPs are prepared from sterile materials. In some embodiments, SBPs are prepared and then sterilized. In some embodiments, processed silk is degummed and then sterilized. In some embodiments, processed silk is sterilized and then degummed. Processed silk and/or SBPs may be sterilized via gamma radiation, autoclave (e.g., autoclave sterilization), filtration, electron beam, and any other method known to those skilled in the art.

In some embodiments, processed silk may be stored frozen or dried to a stable soluble form. Processed silk may be frozen with cryoprotectants. Cryoprotectants may include, but are not limited to, phosphate buffer, sucrose, trehalose, histidine, and any other cryoprotectant known to one of skill in the art. In some embodiments, SBPs may be stored frozen or dried to a stable soluble form. In some embodiments, the SBPs may be solutions.

Harvesting Silk

In some embodiments, processed silk is harvested from silk producer cocoons. Cocoons may be prepared by cultivating silkworm moths and allowing them to pupate. Once fully formed, cocoons may be treated to soften sericin and allow for unwinding of the cocoon to form raw silk fiber. The treatment may include treatment with hot air, steam, and/or boiling water. Raw silk fibers may be produced by unwinding multiple cocoons simultaneously. The resulting raw silk fibers include both silk fibroin and sericin. Subsequent processing may be carried out to remove sericin from the raw silk fibers or from later forms of processed silk or SBPs. In some embodiments, raw silk may be harvested directly from the silk glands of silk producers. Raw silk may be harvested from wild type or GMO silk producers.

Extraction of Sericin/Degumming

In some embodiments, sericin may be removed from processed silk, a process referred to herein as "degumming." The processed silk may include raw silk, which includes sericin secreted during cocoon formation. Methods of degumming may include heating (e.g., boiling) in a degumming solution. As used herein, the term "degumming solution" refers to a composition used for sericin removal that includes at least one degumming agent. As used herein, a "degumming agent" refers to any substance that may be used for sericin removal. Heating in degumming solution may reduce or eliminate sericin from processed silk. In some embodiments, heating in degumming solution includes boiling. Heating in degumming solution may be followed by rinsing to enhance removal of sericin that remains after heating. In some embodiments, raw silk is degummed before further processing or utilization in SBPs. In other embodiments, raw silk is further processed or otherwise incorporated into an SBP prior to degumming. Such methods may include any of those presented in European Patent No. EP2904134 or United States Publication No. US2017031287, the contents of each of which are herein incorporated by reference in their entirety.

Degumming agents and/or degumming solution may include, but are not limited to water, alcohols, soaps, acids, alkaline solutions, and enzyme solutions. In some embodiments, degumming solutions may include salt-containing alkaline solutions. Such solutions may include sodium carbonate. Sodium carbonate concentration may be from about 0.01 M to about 0.3 M. In some embodiments, sodium carbonate concentration may be from about 0.01 M to about 0.05 M, about 0.05 M to about 0.1 M, from about 0.1 M to about 0.2 M, or from about 0.2 M to about 0.3 M. In some embodiments, sodium carbonate concentration may be 0.02 M. In some embodiments, degumming solutions may include from about 0.01% to about 1% (w/v) sodium carbonate. In some embodiments, degumming solutions may include from about 0.01% to about 10% (w/v) sodium carbonate. In some embodiments, degumming solutions may include from about 0.01% (w/v) to about 1% (w/v), from about 1% (w/v) to about 2% (w/v), from about 2% (w/v) to about 3% (w/v), from about 3% (w/v) to about 4% (w/v), from about 4% (w/v) to about 5% (w/v), or from about 5% (w/v) to about 10% (w/v) sodium carbonate. In some embodiments, degumming solutions may include sodium dodecyl sulfate (SDS). Such degumming solutions may include any those described in Zhang et al. (2012) J Translational Med 10:117, the contents of which are herein incorporated by reference in their entirety. In some embodiments, degumming solutions include boric acid. Such solutions may include any of those taught in European Patent No. EP2904134, the contents of which are herein incorporated by reference in their entirety. In some embodiments, the degumming solution may have a pH of from about 0 to about 5, from about 2 to about 7, from about 4 to about 9, from about 5 to about 11, from about 6 to about 12, from about 6.5 to about 8.5, from about 7 to about 10, from about 8 to about 12, and from about 10 to about 14. In some embodiments, processed silk may be present in degumming solutions at concentrations of from about 0.1% to about 2%, from about 0.5% to about 3%, from about 1% to about 4%, or from about 2% to about 5% (w/v). In some embodiments, processed silk is present in degumming solutions at concentrations of greater than 5% (w/v).

Degumming may be carried out by boiling in degumming solutions at or near (e.g., within about 5% of) atmospheric boiling temperatures. Some boiling temperatures may be from about 60° C. to about 115° C. In some embodiments, boiling is carried out at 100° C. In some embodiments, boiling is carried out at about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., or about 110° C.

In some embodiments, degumming includes heating in degumming solution for a period of from about 10 seconds to about 45 seconds, from about 30 seconds to about 90 seconds, from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 500 min, from about 330 min to about 550 min, from about 360 min to about 600 min, from about 390 min to about 700 min, from about 420 min to about 800 min, from about 450 min to about 900 min, from about 480 min to about 1000 min, from about 510 min to about 1100 min, from about 540 min to about 1200 min, from about 570 min to about 1300 min, from about 600 min to about 1400 min, from about 630 min to about 1500 min, from about 660 min to about 1600 min, from about 690 min to about 1700 min, from about 720 min to about 1800 min, from about 1440 min to about 1900 min, from about 1480 min to about 2000 min, or longer than 2000 min.

In some embodiments, processed silk preparations may be characterized by the number of minutes boiling was carried out for preparation, a value referred to herein as "minute boil" or "mb." The minute boil value of a preparation may be associated with known or presumed characteristics of similar preparations with the same minute boil value. Such characteristics may include concentration and/or molecular weight of preparation compounds, proteins, or protein fragments altered during boiling. In some embodiments, processed silk preparations (e.g., silk fibroin preparations) have an mb value of from about 1 mb to about 5 mb, from about 2 mb to about 10 mb, from about 5 mb to about 15 mb, from about 10 mb to about 25 mb, from about 20 mb to about 35 mb, from about 30 mb to about 50 mb, from about 45 mb to about 75 mb, from about 60 mb to about 95 mb, from about 90 mb to about 125 mb, from about 120 mb to about 175 mb, from about 150 mb to about 200 mb, from about 180 mb to about 250 mb, from about 210 mb to about 350 mb, from about 240 mb to about 400 mb, from about 270 mb to about 450 mb, from about 300 mb to about 480 mb, or greater than 480 mb.

In some embodiments, degumming is carried out by treatment with high temperatures and/or pressures. Such methods may include any of those presented in International Publication No. WO2017200659, the contents of which are herein incorporated by reference in their entirety.

Processed Silk Preparation Characterization

Preparations of processed silk may include mixtures of silk fibroin polymers, silk fibroin monomers, silk fibroin heavy chains, silk fibroin light chains, sericin, and/or fragments of any of the foregoing. Where the exact contents and ratios of components in such processed silk preparations are unknown, the preparations may be characterized by one or more properties of the preparation or by conditions or methods used to obtain the preparations.

Solubility and Concentration

Processed silk preparations may include solutions that include processed silk (also referred to herein as "processed silk solutions"). Processed silk solutions may be characterized by processed silk concentration. For example, processed silk may be dissolved in a solvent after degumming to generate a processed silk solution of silk fibroin for subsequent use. Solvent used to dissolve processed silk may be a buffer. In some embodiments, solvent used is an organic solvent. Organic solvents may include, but are not limited to hexafluoroisopropanol (HFIP), methanol, isopropanol, ethanol, or combinations thereof. In some embodiments, solvents include a mixture of an organic solvent and water or an aqueous solution. Solvents may include water or aqueous solutions. Aqueous solutions may include aqueous salt solutions that include one or more salts. Such salts may include but are not limited to lithium bromide (LiBr), lithium thiocyanate, Ajisawa's reagent, a chaotropic agent, calcium nitrate, or other salts capable of solubilizing silk, including any of those disclosed in U.S. Pat. No. 9,623,147 (the content of which is herein incorporated by reference in its entirety). In some embodiments, solvents used in processed silk solutions may include Ajisawa's reagent, as described in Zheng et al. (2016) Journal of Biomaterials Applications 31:450-463, the content of which is herein incorporated by reference in its entirety. Ajisawa's reagent comprises a mixture of calcium chloride, ethanol, and water in a molar ratio of 1:2:8 respectively. In some embodiments, solvents used in processed silk solutions include high salt solutions. In some embodiments, the solution comprises 5 to 13 M LiBr. The concentration of LiBr may be 9.3 M.

In some embodiments, processed silk is present in processed silk solutions at a concentration of from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v). In some embodiments, the processed silk is silk fibroin.

Processed silk solutions may be characterized by the length of time and/or temperature needed for processed silk to dissolve. The length of time used to dissolve processed silk in solvent is referred to herein as "dissolution time." Dissolution times for dissolution of processed silk in various solvents may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 360 min, from about 270 min to about 420 min, from about 300 min to about 480 min, or longer than 480 minutes.

The temperature used to dissolve processed silk in solvent is referred to herein as "dissolution temperature." Dissolution temperatures used for dissolution of processed silk in solvent may include room temperature. In some embodiments, dissolution temperature may be from about 0° C. to about 10° C., from about 4° C. to about 25° C., from about 20° C. to about 35° C., from about 30° C. to about 45° C., from about 40° C. to about 55° C., from about 50° C. to about 65° C., from about 60° C. to about 75° C., from about 70° C. to about 85° C., from about 80° C. to about 95° C., from about 90° C. to about 105° C., from about 100° C. to about 115° C., from about 110° C. to about 125° C., from about 120° C. to about 135° C., from about 130° C. to about 145° C., from about 140° C. to about 155° C., from about 150° C. to about 165° C., from about 160° C. to about 175° C., from about 170° C. to about 185° C., from about 180° C. to about 200° C., or greater than 200° C. In some embodiments, the processed silk is silk fibroin. Dissolution of some processed silk solutions may use a dissolution temperature of 60° C. Dissolution of some processed silk solutions may use a dissolution temperature of 80° C., as described in Zheng et al. (2016) Journal of Biomaterials Applications 31:450-463. In some embodiments, dissolution includes boiling. In some embodiments, dissolution may be carried out by autoclaving. In some embodiments, silk fibroin solutions may be prepared according to any of the methods described in International Publication No. WO2017200659 or Abdel-Naby (2017) PLoS One 12(11):e0188154), the contents of each of which are herein incorporated by reference in their entirety.

In some embodiments, one or more of sucrose, phosphate buffer, tris buffer, trehalose, mannitol, citrate buffer, ascorbate, histidine, and/or a cryoprotective agent is added to processed silk solutions.

Chaotropic Agents

In some embodiments, processed silk may be dissolved with the aid of a chaotropic agent. As used herein, a "chaotropic agent" refers to a substance that disrupts hydrogen bonding networks in aqueous solutions to facilitate dissolution of a solute. Chaotropic agents typically modify the impact of hydrophobicity on dissolution. Chaotropic agents may be organic compounds. Such compounds may include, but are not limited to, sodium dodecyl sulfate, ethanol, methanol, phenol, 2-propanol, thiourea, urea, n-butanol, and any other chemicals capable of solubilizing silk. In some embodiments, the chaotropic agent is a salt, including, but not limited to, zinc chloride, calcium nitrate, lithium perchlorate, lithium acetate, sodium thiocyanate, calcium thiocyanate, magnesium thiocyanate, calcium chloride, magnesium chloride, guanidinium chloride, lithium bromide, lithium thiocyanate, copper salts, and other salts capable of solubilizing silk. Such salts typically create high ionic strength in the aqueous solutions which destabilizes the beta-sheet interactions in silk fibroin. In some embodiments, a combination of chaotropic agents is used to facilitate the dissolution of silk fibroin. In some embodiments, a chaotropic agent is used to dissolve raw silk during processing.

Molecular Weight

In some embodiments, processed silk preparations are characterized by the molecular weight of proteins present in the preparations. Different molecular weights may be present as a result of different levels of silk fibroin dissociation and/or fragmentation during degumming or other processing. When referring to silk fibroin molecular weight herein, it should be understood that the molecular weight may be associated with silk fibroin polymers, silk fibroin monomers, silk fibroin heavy and/or light chains, silk fibroin fragments, or variants, derivates, or mixtures thereof. Accordingly, silk fibroin molecular weight values may vary depending on the nature of the silk fibroin or silk fibroin preparation. In some embodiments, processed silk preparations are characterized by average molecular weight of silk fibroin fragments present in the preparation; by a range of silk fibroin fragment molecular weights; by a threshold of silk fibroin fragment molecular weights; or by combinations of averages, ranges, and thresholds.

In some embodiments, processed silk preparation may include silk fibroin with a molecular weight of, average molecular weight of, upper molecular weight threshold of, lower molecular weight threshold of, or range of molecular weights with an upper or lower range value of from about 1 kDa to about 4 kDa, from about 2 kDa to about 5 kDa, from about 3.5 kDa to about 10 kDa, from about 5 kDa to about 20 kDa, from about 7.5 kDa to about 32.5 kDa, from about 7.5 kDa to about 50 kDa, from about 7.5 kDa to about 100 kDa, from about 7.5 kDa to about 150 kDa, from about 7.5 kDa to about 200 kDa, from about 7.5 kDa to about 250 kDa, from about 10 kDa to about 35 kDa, from about 15 kDa to about 40 kDa, from about 20 kDa to about 45 kDa, from about 25 kDa to about 50 kDa, from about 30 kDa to about 55 kDa, from about 35 kDa to about 60 kDa, from about 40 kDa to about 65 kDa, from about 45 kDa to about 70 kDa, from about 50 kDa to about 75 kDa, from about 55 kDa to about 80 kDa, from about 60 kDa to about 85 kDa, from about 65 kDa to about 90 kDa, from about 70 kDa to about 95 kDa, from about 75 kDa to about 100 kDa, from about 80 kDa to about 105 kDa, from about 85 kDa to about 110 kDa, from about 90 kDa to about 115 kDa, from about 95 kDa to about 120 kDa, from about 100 kDa to about 125 kDa, from about 105 kDa to about 130 kDa, from about 110 kDa to about 135 kDa, from about 115 kDa to about 140 kDa, from about 120 kDa to about 145 kDa, from about 125 kDa to about 150 kDa, from about 130 kDa to about 155 kDa, from about 135 kDa to about 160 kDa, from about 140 kDa to about 165 kDa, from about 145 kDa to about 170 kDa, from about 150 kDa to about 175 kDa, from about 160 kDa to about 200 kDa, from about 170 kDa to about 210 kDa, from about 180 kDa to about 220 kDa, from about 190 kDa to about 230 kDa, from about 200 kDa to about 240 kDa, from about 210 kDa to about 250 kDa, from about 220 kDa to about 260 kDa, from about 230 kDa to about 270 kDa, from about 240 kDa to about 280 kDa, from about 250 kDa to about 290 kDa, from about 260 kDa to about 300 kDa, from about 270 kDa to about 310 kDa, from about 280 kDa to about 320 kDa, from about 290 kDa to about 330 kDa, from about 300 kDa to about 340 kDa, from about 310 kDa to about 350 kDa, from about 320 kDa to about 360 kDa, from about 330 kDa to about 370 kDa, from about 340 kDa to about 380 kDa, from about 350 kDa to about 390 kDa, from about 360 kDa to about 400 kDa, from about 370 kDa to about 410 kDa, from about 380 kDa to about 420 kDa, from about 390 kDa to about 430 kDa, from about 400 kDa to about 440 kDa, from about 410 kDa to about 450 kDa, from about 420 kDa to about 460 kDa, from about 430 kDa to about 470 kDa, from about 440 kDa to about 480 kDa, from about 450 kDa to about 490 kDa, from about 460 kDa to about 500 kDa, or greater than 500 kDa.

In one embodiment, the silk preparation may include silk fibroin with a molecular weight of or an average molecular weight of 5-60 kDa.

In one embodiment, the silk preparation may include silk fibroin with a molecular weight of or an average molecular weight of 30-60 kDa. In one aspect, silk fibroin in this range may be referred to as low molecular weight.

In one embodiment, the silk preparation may include silk fibroin with a molecular weight of or an average molecular weight of 100-300 kDa. In one aspect, silk fibroin in this range may be referred to as high molecular weight.

In one embodiment, the silk preparation may include silk fibroin with a molecular weight of or an average molecular weight of 361 kDa.

Processed silk preparations may be analyzed, for example, by polyacrylamide gel electrophoresis (PAGE) alongside molecular weight standards to determine predominate molecular weights of proteins and/or polymers present. Additional methods for determining the molecular weight range or average molecular weight for a processed silk preparation may include, but are not limited to, sodium dodecyl sulfate (SDS)-PAGE, size-exclusion chromatography (SEC), high pressure liquid chromatography (HPLC), non-denaturing PAGE, and mass spectrometry (MS).

Processed silk preparations may include low molecular weight silk fibroin. As used herein, the term "low molecular weight silk fibroin" refers to silk fibroin with a molecular weight below 200 kDa. Some processed silk preparations may include high molecular weight silk fibroin. As used herein, the term "high molecular weight silk fibroin" refers to silk fibroin with a molecular weight equal to or greater than 200 kDa. In some embodiments, the silk fibroin molecular weight is defined by the degumming boiling time. In some embodiments, silk fibroin with a 480-minute boil, or "mb" is considered to be low molecular weight silk fibroin. In some embodiments, silk fibroin with a 120-minute boil, or "mb" is considered to be high molecular weight silk fibroin.

In some embodiments, silk fibroin molecular weight is modulated by the method of degumming used during processing. In some embodiments, longer heating times during degumming are used (e.g., see International Publication No. WO2014145002, the contents of which are herein incorporated by reference in their entirety). Longer heating (e.g., boiling) time may be used during the degumming process to prepare silk fibroin with lower average molecular weights. In some embodiments, heating times may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 480 min, or more than 480 min. Additionally, the sodium carbonate concentration used in the degumming process, as well as the heating temperature, may also be altered to modulate the molecular weight of silk fibroin. In one embodiment, the alteration may cause an increase in the molecular weight of silk fibroin. As compared to silk fibroin where the sodium carbonate concentration and/or the heating temperature was not altered, the increase of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% higher. In one embodiment, the alteration may cause a decrease in the molecular weight of silk fibroin. As compared to silk fibroin where the sodium carbonate concentration and/or the heating temperature was not altered, the decrease of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% lower.

In some embodiments, silk fibroin molecular weight may be presumed, without actual analysis, based on methods used to prepare the silk fibroin. For example, silk fibroin may be presumed to be low molecular weight silk fibroin or high molecular weight silk fibroin based on the length of time that heating is carried out (e.g., by minute boil value).

In some embodiments, SBPs include a plurality of silk fibroin fragments generated using a dissociation procedure. The dissociation procedure may include one or more of heating, acid treatment, chaotropic agent treatment, sonication, and electrolysis. Some SBPs include a plurality of silk fibroin fragments dissociated from raw silk, silk fiber, and/or silk fibroin by heating. The heating may be carried out at a temperature of from about 30° C. to about 1,000° C. In some embodiments, heating is carried out by boiling. The raw silk, silk fiber, and/or silk fibroin may be boiled for from about 1 second to about 24 hours.

Silk Fibroin Boiling Time

SBP formulations with processed silk with varying molecular weights. In some embodiments, the silk fibroin molecular weight is defined by the degumming boiling time. In some embodiments, silk fibroin with a 480-minute boil, or "mb" may produce be a low molecular weight silk fibroin when compared to a silk fibroin produced with a 120-minute boil, or "mb". In some aspects, the 120 mb silk fibroin is considered to be high molecular weight silk fibroin in comparison to the 480 mb silk fibroin. In some embodiments, a longer boiling time is considered to be lower molecular weight silk fibroin. In some embodiments, a shorter boiling time is considered to be a higher molecular weight silk fibroin. In some embodiments, the boiling time is about 15 minutes, about 30 minutes, about 60 minutes, about 90 minutes, about 120 minutes, or about 480 minutes. In some embodiments, an SBP is prepared with processed silk with a single boiling time. In some embodiments, an SBP contains a blend of processed silk with different boiling times.

In one embodiment, the SBP formulation includes 30 mb silk fibroin.

In one embodiment, the SBP formulation includes 60 mb silk fibroin.

In one embodiment, the SBP formulation includes 90 mb silk fibroin.

In one embodiment, the SBP formulation includes 120 mb silk fibroin.

In one embodiment, the SBP formulation includes 480 mb silk fibroin.

Purification and Concentration

In some embodiments, processed silk preparations may be purified. Purification, as used herein, refers to any process used to segregate or extract one entity from another. In some embodiments, purification is manual or automated. Purification may include the removal of salts, impurities, or contaminants from processed silk preparations.

In some embodiments, processed silk may be purified by concentration from a processed silk solution. Methods of concentrating silk fibroin from processed silk solutions may include any of those described in the International Publication No. WO2017139684, the contents of which are incorporated herein by reference in their entirety. In some embodiments, purification and/or concentration may be carried out by one or more of dialysis, centrifugation, air drying, vacuum drying, filtration, and/or Tangential Flow Filtration (TFF).

In some embodiments, processed silk solutions may be purified by dialysis. Dialysis may be carried out to remove undesired salts and/or contaminants. In some embodiments, processed silk solutions are concentrated via dialysis. Purification and/or concentration of processed silk by dialysis may be carried out as described in International Publication No. WO2005012606, the contents of which are herein incorporated by reference in their entirety. In some embodiments, the dialysis is performed against a hygroscopic polymer to concentrate the silk fibroin solution. In some embodiments the dialysis is manual, with the use of a membrane and manual solvent changes. In some embodiments, the solvent is changed between 1 and 10 times over the course of the procedure. In some embodiments, the membrane is a dialysis cassette. The dialysis cassette may be a slide-a-lyzer dialysis cassette. In some embodiments, the membrane is dialysis tubing. The dialysis tubing may be regenerated cellulose dialysis tubing and/or snake skin. The dialysis tubing or cassette may be rinsed in distilled water for 30 minutes to prepare the membrane for use. In some embodiments, the dialysis tubing has a molecular weight cutoff of 3.5 kDa. In some embodiments, the dialysis is performed at a temperature of from about 1° C. to about 30° C. In some embodiments, dialysis is performed at room temperature. In other embodiments, the dialysis is performed at 4° C. Dialysis may be performed until desired concentrations of silk fibroin and salt are obtained from processed silk solutions. Dialysis may be performed for periods of time from about 30 minutes to about 24 hours or beyond. For example, dialysis may be carried out for from about 30 minutes to about 2 hours, from about 1 hour to about 6 hours, from about 3 hours to about 10 hours, from about 5 hours, to about 12 hours, from about 7 hours to about 15 hours, from about 11 hours to about 20 hours, or from about 16 hours to about 24 hours.

In some embodiments, dialysis may be automated. The dialysis may use an automated water change system. Such systems may include tanks of up to 10 L and may be able to hold multiple dialysis cassettes (e.g., see International Publication No. WO2017106631, the contents of which are herein incorporated by reference in their entirety). Automated equipment may enable purification of larger volumes of solution with greater efficiency. Automated controllers, programmed with the proper times and volumes, may be used to facilitate changes of solvent or buffer over the course of dialysis. The solvent may be replaced from about 1 to about 20 times or more during dialysis. In some embodiments, automated dialysis may be completed in about 48 hours.

Dialysis may be performed with various solvents depending on the nature of the preparation being processed. In some embodiments the solvent may be water. In some embodiments, the solvent may be an aqueous solution. In some embodiments the solvent includes a hygroscopic polymer. Hygroscopic polymers may include, but are not limited to polyethylene glycol (PEG), polyethylene oxide (PEO), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, and polyanhydrides. Additional examples of hygroscopic polymers and related dialysis methods that may be employed include any of those found in International Publication Numbers WO2005012606, WO2005012606 and WO2017106631, and U.S. Pat. Nos. 6,302,848, 6,395,734, 6,127,143, 5,263,992, 6,379,690, 5,015,476, 4,806,355, 6,372,244, 6,310,188, 5,093,489, 6,325,810, 6,337,198, 6,267,776, 5,576,881, 6,245,537, 5,902,800, and 5,270,419, the contents of each of which are herein incorporated by reference in their entirety. Hygroscopic polymer concentrations may be from about 20% (w/v) to about 50% (w/v). In some embodiments, dialysis may be performed in a stepwise manner in a urea solution, and the urea solution may be subsequently be replaced with urea solutions of a lower concentration during buffer changes, until it is ultimately replaced with water, as described in Zheng et al. (2016) Journal of Biomaterials Applications 31:450-463.

In some embodiments, processed silk preparations may be purified by filtration. Such filtration may include trans flow filtration (TFF), also known as tangential flow filtration. During TFF, solutions may be passed across a filter membrane. Anything larger than the membrane pores would is retained, and anything smaller passes through the membrane (e.g., see International Publication No. WO2017106631, the contents of which are herein incorporated by reference in their entirety). With the positive pressure and flow along the membrane, instead of through it, particles trapped in the membrane may be washed away. TFF may be carried out using an instrument. The instrument may be automated. The membranes may be housed in TFF tubes with vertical inlets and outlets. The flow of solvent may be controlled by peristaltic pumps. Some TFF tubes may include a dual chamber element. The dual chamber element may enable TFF filtration of processed silk solutions at higher concentrations, while reducing aggregation via the reduction of shear forces.

In some embodiments, processed silk solutions are purified and/or concentrated by centrifugation. Centrifugation may be performed before or after other forms of purification, which include, but are not limited to dialysis and tangential flow filtration. Centrifugation times and speeds may be varied to optimize purification and/or concentration according to optimal time frames. Purification and/or concentration by centrifugation may include pelleting of the processed silk and removal of supernatant. In some cases, centrifugation is used to push solvent through a filter, while retaining processed silk. Centrifugation may be repeated as many times as needed. In some embodiments, silk fibroin solutions are centrifuged two or more times during concentration and/or purification.

Drying Methods

In some embodiments, processed silk preparations may be dried to remove solvent. In some embodiments, SBP formulations may be rinsed prior to drying. Methods of drying may include, but are not limited to, air drying, oven drying, lyophilization, spray drying, spray freezing, and vacuum drying. Drying may be carried out to alter the consistency and/or other properties of processed silk preparations. One or more compounds or excipients may be combined with processed silk preparations to improve processed silk recovery and/or reconstitution after the drying process. For example, sucrose may be added to improve silk fibroin recovery and reconstitution from dried solutions. In some embodiments, drying may be carried out in the fabrication of a processed silk format or a SBP. Examples include, but are not limited to fabrication of fibers, nanofibers, mats, films, foams, membranes, rods, tubes, gels, hydrogels, microspheres, nanospheres, solutions, patches, grafts and powders. In some embodiments, drying processed silk may be carried out by oven drying, lyophilizing, and/or air drying.

Oven drying refers to any drying method that uses an oven. According to some methods, ovens are maintained at temperatures of from about 30° C. to about 90° C. or more. In some embodiment, oven drying is carried out at a temperature of 60° C. Processed silk preparations may be placed in ovens for a period of from about 1 hour to about 24 hours or more. In one embodiment, SBP formulations are oven dried at 60° C. for 2 hours. Oven drying may be used to dry silk fibroin preparations. In some embodiments, silk fibroin preparations are oven dried for 16 hours at 60° C. to obtain a desired format. In some cases, silk fibroin solutions are oven dried overnight. Examples of formats obtained by oven drying may include, but are not limited to, fibers, nanofibers, mats, films, foams, membranes, rods, tubes, gels, hydrogels, microspheres, nanospheres, solutions, patches, grafts, and powders.

In some embodiments, processed silk preparations are freeze dried. Freeze drying may be carried out by lyophilization. Freeze drying may require processed silk preparations to be frozen prior to freeze drying. Freezing may be carried out at temperatures of from about 5° C. and about −85° C. In some embodiments, freeze drying is carried out by lyophilization for up to 75 hours. In some embodiments, lyophilization is used to prepare processed silk formats or SBPs. Such formats may include, but are not limited to, fibers, nanofibers, mats, films, foams, membranes, rods, tubes, gels, hydrogels, microspheres, nanospheres, solutions, patches, grafts and powders. The use of lyophilization to fabricate SBPs may be carried out according to any of the methods described in Zhou et al. (2017) Acta Biomater S1742-7061(17)30569; Yang et al. (2017) Int J Nanomedicine 12:6721-6733; Seo et al. (2017) J Biomater Appl 32(4):484-491; Ruan et al. (2017) Biomed Pharmacother 97:600-606; Wu et al. (2017) J Mech Behav Biomed Mater 77:671-682; Zhao et al. (2017) Materials Letters 211:110-113; Chen et al. (2017) PLoS One 12(11):e0187880; Min et al. (2017) Int J Biol Macromol 17: 32855-8; Sun et at Journal of Materials Chemistry B 5:8770; and Thai et al. J Biomed Mater (2017) 13(1):015009, the contents of each of which are herein incorporated by reference in their entirety.

In some embodiments, processed silk preparations may be dried by air drying. "Air drying," as used herein refers to the removal of moisture by exposure to ambient or circulated gasses. Air drying may include exposing a preparation to air at room temperature (from about 18° C. to about 29° C.). Air drying may be carried out for from about 30 minutes to about 24 hours or more. In some embodiments, silk fibroin preparations are air dried to prepare SBPs. SBP formats that may be prepared may include, but are not limited to, fibers, nanofibers, mats, films, foams, membranes, rods, tubes, gels, hydrogels, microspheres, nanospheres, solutions, patches, grafts and powders. Some examples of the use of air drying for fabrication of SBPs are presented in Susanin et al. (2017) Fibre Chemistry 49(2):88-96; Lo et al. J Tissue Eng Regen Med (2017) doi.10.1002/term.2616; and Mane et al. Scientific Reports 7:15531, the contents of each of which are herein incorporated by reference in their entirety.

Spinning

In some embodiments, processed silk may be prepared by spinning. As used herein, the term "spinning" refers to a process of twisting materials together. Spinning may include the process of preparing a silk fiber by twisting silk proteins as they are secreted from silk producers. Other forms of spinning include spinning one or more forms of processed silk together to form a thread, filament, fiber, or yarn. The processed silk may already consist of a filamentous format prior to spinning. In some embodiments, processed silk is processed by spinning from a non-filamentous format (e.g., from a film, mat, or solution).

In some embodiments, spinning includes the technique of electrospinning. Electrospinning may be used to prepare silk fibers from silk fibroin. The silk fibroin may be dissolved in water or an aqueous solution before electrospinning. In other embodiments, silk fibroin is dissolved in an organic solvent before electrospinning. The organic solvent may be hexafluoroisopropanol (HFIP). In some embodiments, electrospinning may be carried out as described in Yu et al. (2017) Biomed Mater Res A doi. 10.1002/jbm.a.36297 or Chantawong et al. (2017) Mater Sci Mater Med 28(12):191, the contents of each of which are herein incorporated by reference in their entirety.

Electrospinning typically includes the use of an electrospinning apparatus. Processed silk may be added to the apparatus to produce silk fiber. The processed silk may be silk fibroin in solution. Electrospinning apparatus components may include one or more of a spinneret (also referred to as a spinnerette), needle, mandrel, power source, pump, and grounded collector. The apparatus may apply voltage to the dissolved silk fibroin, causing electrostatic repulsion that generates a charged liquid that is extruded from the end. Electrostatic repulsion also enables fiber elongation as it forms, and charged liquid cohesion prevents it from breaking apart. Resulting fiber may be deposited on the collector. In some embodiments, electrospinning methods may be carried out according to those described in European Patent No. EP3206725; Manchineella et al. (2017) European Journal of Organic Chemistry 30:4363-4369; Park et al. (2017) Int J Biomacromol S0141-8130(17):32645-4; Wang et al. (2017) J Biomed Mater Res A doi.10.1002/jbm.a.36225; Chendang et al. (2017) J Biomaterials and Tissue Engineering 7:858-862; Kambe et al. (2017) Materials (Basel) 10(10):E1153; Chouhan et al. (2017) J Tissue Eng Reneg Med doi.10.1002/term.2581; Genovese et al. (2017) ACS Appl Mater Interfaces doi.10.1021acsami.7b13372; Yu et al. (2017) Biomed Mater Res A doi. 10.1002/jbm.a.36297; Chantawong et al. (2017) Mater Sci Mater Med 28(12):191, the contents of each of which are herein incorporated by reference in their entirety.

In some embodiments, spinning may be carried out as dry spinning. Dry spinning may be carried out using a dry spinning apparatus. Dry spinning may be used to prepare silk fibers from processed silk preparations. The preparations may include silk fibroin solutions. The preparations may be aqueous solutions. Dry spinning apparatuses typically use hot air to dry processed silk as it is extruded. In some embodiments, dry spinning may be carried out according to any of the methods presented in Zhang et al. (2017) Int J Biol Macromol pii:S0141-8130(17):32857, the contents of which are herein incorporated by reference in their entirety.

Spraying

In some embodiments, processing methods include spraying. As used herein, the term "spraying" refers to the sprinkling or showering of a compound or composition in the form of small drops or particles. Spraying may be used to prepare SBPs by spraying processed silk. Spraying may be carried out using electrospraying. Processed silk used for spraying may include processed silk in solution. The solution may be a silk fibroin solution. Solutions may be aqueous solutions. Some solutions may include organic solvents. Electrospraying may be carried out in a manner similar to that of electrospinning, except that the charged liquid lacks cohesive force necessary to prevent extruding material from breaking apart. In some embodiments, spraying methods may include any of those presented in United States Publication No. US2017/333351 or Cao et al. (2017) Scientific Reports 7:11913, the contents of each of which are herein incorporated by reference in their entirety. In some embodiments, electrospray methods include a coaxial system for coaxial spraying.

Precipitation

In some embodiments, processing methods include precipitation. As used herein, the term "precipitation" refers to the deposition of a substance in solid form from a solution. Precipitation may be used to obtain solid processed silk from processed silk solutions. The processed silk may be silk fibroin. Processed silk may be precipitate from a solution. The solvent may be aqueous. In some embodiments, the solvent is organic. Examples of organic solvents include, but are not limited to, HFIP, methanol, ethanol, and other alcohols. In some embodiments, the solvent is water. In some embodiments the solvent is a mixture of an organic solvent and water. Aqueous solvents may contain one or more salts. Processed silk may be precipitated from processed silk solutions by modulating one or more components of the solution to alter the solubility of the processed silk and promote precipitation. Additional processing steps may be employed to initiate or speed precipitation. Such methods may include, but are not limited to sonication, centrifugation, increasing the concentration of processed silk, altering the concentration of salt, adding additional salt or salts, altering the pH, applying shear stress, adding excipients, or applying chemical modifications.

Altering Mechanical Properties

In some embodiments, the mechanical properties of processed silk may be altered by modulating physical and/or chemical properties of the processed silk. The mechanical properties include, but are not limited to, mechanical strength, tensile strength, elongation capabilities, elasticity, compressive strength, stiffness, shear strength, toughness, torsional stability, temperature stability, moisture stability, viscosity, and reeling rate. Examples of the physical and chemical properties used to tune the mechanical properties of processed silk include, but are not limited to, the temperature, formulations, silk concentration, β-sheet content, crosslinking, the molecular weight of the silk, the storage of the silk, storage, methods of preparation, dryness, methods of drying, purity, and degumming. Methods of tuning the mechanical strength of processed silk are taught in International Patent Application Publication No. WO2017123383, European Patent No. EP2904134, European Patent No. EP3212246, Fang et al., Wu et al., Susanin et al., Zhang et al., Jiang et al., Yu et al., Chantawong et al., and Zhang et al. (Fang et al. (2017) Journal of Materials Chemistry B 5(30):6042-6048; Wu et al. (2017) J Mech Behav Biomed Mater 77:671-682; Susanin et al. (2017) Fibre Chemistry 49(2):88-96; Zhang et al. (2017) Fibers and Polymers 203: 9-16; Jiang et al. (2017) J Biomater Sci Polym Ed 15:1-36; Yu et al. (2017) Biomed Mater Res A doi. 10.1002/jbm.a.36297; Chantawong et al. (2017) Mater Sci Mater Med 28(12):191; Zhang et al. (2017) Int J Biomacromol S0141-8310(17):32857), the contents of each of which are herein incorporated by reference in their entirety.

In some embodiments, the excipients which may be incorporated in a formulation may be used to control the modulus of processed silk preparations. In some embodiments, these processed silk preparations are hydrogels. In some embodiments, processed silk hydrogels are prepared with different excipients and tested for their mechanical properties, including the modulus. Processed silk preparations may be assessed for modulus, shear storage modulus, shear loss modulus, phase angle, and viscosity using a rheometer, and/or any other method known to one skilled in the art. Processed silk preparations may be tested both before and after gelation. In some embodiments, processed silk preparations are prepared, optionally with different excipients, and tested for their mechanical properties, including the modulus, shear storage modulus, the shear loss modulus, phase angle, and viscosity. As used herein, the term "shear storage modulus" refers to the measure of a material's elasticity or reversible deformation as determined by the material's stored energy. As used herein, the term "shear loss modulus" refer to the measure of a material's ability to dissipate energy, usually in the form of heat. As used herein, the term "phase angle" refers to the difference in the stress and strain applied to a material during the application of oscillating shear stress. As used herein, the term "viscosity" refers to a material's ability to resist deformation due to shear forces, and the ability of a fluid to resist flow. In some embodiments, processed silk hydrogels may possess similar viscosities but vary in the modulus.

In some embodiments, the processed silk preparations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain. In some embodiments, the concentration of processed silk may enable silk preparations to shear thin. In some embodiments the silk preparation is an SBP. In some embodiments, the SBP is a hydrogel. In some embodiments, the molecular weight of processed silk hydrogels may enable hydrogels to shear thin. In some embodiments, hydrogels prepared with low molecular weight silk fibroin may be injected with much less force than hydrogels of similar viscosity that are prepared with higher molecular weight silk fibroin. In some embodiments, hydrogels with low molecular weight silk fibroin display higher viscosity than hydrogels with high molecular weight silk fibroin.

Modulating Degradation/Resorption

In some embodiments, processed silks are or are processed to be biocompatible. As used herein, a "biocompatible" substance is any substance that is not harmful to most living organisms or tissues. With some processed silk, degradation may result in products that are biocompatible, making such processed silk attractive for a variety of applications. Some processed silk may degrade into smaller proteins or amino acids. Some processed silk may be resorbable under physiological conditions. In some embodiments, products of silk degradation may be resorbable in vivo. In some embodiments, the rate of degradation of processed silk may be tuned by altering processed silk properties. Examples of these properties include, but are not limited to, type and concentration of certain proteins, β-sheet content, crosslinking, silk fibroin molecular weight, and purity. In some embodiments, rate of processed silk degradation may be modulated by method of storage, methods of preparation, dryness, methods of drying, reeling rate, and degumming process.

In some embodiments, the bioresorbability and degradation of processed silk is modulated by the addition of sucrose, as taught in Li et al. (Li et al. (2017) Biomacromolecules 18(9):2900-2905), the contents of which are herein incorporated by reference in their entirety. Processed silk may be formulated with sucrose to enhance thermal stability. Furthermore, processed silk with sucrose may also be formulated with antiplasticizing agents to further enhance thermal stability of processed silk, SBPs, and/or therapeutic agents included in SBPs. Methods of increasing thermal stability using antiplasticizing agents may include any of those described in Li et al. (Li et al. (2017) Biomacromolecules 18(9):2900-2905), the contents of which are herein incorporated by reference in their entirety. In some embodiments, the addition of sucrose to processed silk preparations prior to lyophilization leads to an increased reconstitution efficiency. In some embodiments, the addition of sucrose may be used to create higher molecular weight processed silk preparations as well as to maintain long term storage stability. In some embodiments, the incorporation of sucrose into processed silk preparations described herein enables slower freezing during lyophilization cycle.

In some embodiments, the bioresorbability and degradation of processed silk may be tuned through formulation with additional bioresorbable polymer matrices, as taught in International Publication Numbers WO2017177281 and WO2017179069, the contents of each of which are herein incorporated by reference in their entirety. In some embodiments, the polymer matrix is polyurethane. In some embodiments, these polymer matrices may be polycaprolactone and a ceramic filler. The ceramic filler may include MgO.

In some embodiments, the bioresorbability and degradation of processed silk is tuned through the fabrication of a composite scaffold. Composite scaffolds, combinations of scaffolds or scaffolds formed from more than one material, may be formed from two or more processed silk preparations. In some embodiments, processed silk scaffolds comprising a combination of silk fibroin microspheres within a larger processed silk preparation may demonstrate slower degradation in comparison with other scaffolds, as taught in European Patent No. EP3242967, the contents of which are herein incorporated by reference in their entirety.

Excipients

In some embodiments, SBPs include one or more excipients. As used herein, the term "excipient" refers to any substance included in a composition with an active agent or primary component, often serving as a carrier, diluent, or vehicle for the active agent or primary component. In some embodiments, excipients may be compounds or compositions approved for use by the US Food and Drug Administration (FDA). In some embodiments, SBPs may include excipients that increase SBP stability or stability of one or more other SBP components. Some SBPs may include an excipient that modulates payload release. Excipients may include, but are not limited to, solvents, diluents, liquid vehicles, dispersion or suspension media or aids, surfactants, thickening agents, emulsifying agents, lipids, liposomes, isotonic agents, buffers, and preservatives. In some embodiments, excipients include lipidoids, lipid nanoparticles, polymers, lipoplexes, particles, core-shell nanoparticles, peptides, proteins, cells, hyaluronidase, and/or nanoparticle mimics. In some embodiments, processed silk and/or SBPs may be used as an excipient.

In some embodiments, excipients included in SBPs may be selected from one or more of lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, sucrose, mannitol, lactose USP, Starch 1500, microcrystalline cellulose, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. Excipients may include sucrose. Excipients may be present in SBPs at any concentration. In some embodiments, excipients are present at a concentration of from about 0.0001% weight per weight (w/w) of excipient to total SBP weight to about 20% (w/w). In some embodiments, excipients are present at a concentration of from about 1% (w/w) to about 20% (w/w).

In some embodiments, excipients included in SBPs may be selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremaphor EL), cremaphor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. Such SBPs may include hydrogels. In some embodiments, SBP hydrogels include one or more of polysorbate 80, poloxamer-188, PEG 4 kDa, and glycerol.

In one embodiment, the excipient is sorbitol.

In one embodiment, the excipient is mannitol.

Gelling Agents

In some embodiments, excipients may include gelling agents. As used herein, the term "gelling agent" refers to any substance that promotes viscosity and/or polymer cross-linking in compositions. Non-limiting examples of gelling agents include glycerol, glycerophosphate, sorbitol, hydroxyethyl cellulose, carboxymethyl cellulose, triethylamine, triethanolamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol formal, hydroxypropyl beta-cyclodextrin, kolliphor 124, kolliphor 181, kolliphor 188, kolliphor 407, kolliphor EL (cremaphor EL), cremaphor RH 40, cremaphor RH 60, d-alpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, PEG 4 kDa, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, beeswax, d-alpha-tocopherol, oleic acid, medium-chain mono- and diglycerides, alpha-cyclodextrin, beta-cyclodextrin, hydroxypropyl-beta-cyclodextrin, sulfobutylether-beta-cyclodextrin, hydrogenated soy phosphatidylcholine, distearoylphosphatidylglycerol, L-alphadimyristoylphosphatidylcholine, L-alphadimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate-SO, polyvinyl pyrrolidone, polyvinyl pyrrolidone-12, polyvinyl pyrrolidone-17, propylene carbonate, propylene glycol, solutol HS 15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, and glycerin. Additional examples of gelling agents include acacia, alginic acid, bentonite, CARBOPOLS® (also known as carbomers), carboxymethyl cellulose, ethylcellulose, gelatin, hydroxy ethyl cellulose, hydroxypropyl cellulose, magnesium aluminum silicate, methylcellulose, poloxamers, polyvinyl alcohol, sodium alginate, tragacanth, and xanthan gum.

PEGs which may be used as gelling agents and/or excipients may be selected from a variety of chain lengths and molecular weights. These compounds are typically prepared through ethylene oxide polymerization. In some embodiments, PEGs may have a molecular weight of from about 300 g/mol to about 100,000 g/mol. In some embodiments, PEGs may have a molecular weight of from about 3600 g/mol to about 4400 g/mol. In some embodiments, PEGS with a molecular weight of from about 300 g/mol to about 3000 g/mol, from about 350 g/mol to about 3500 g/mol, from about 400 g/mol to about 4000 g/mol, from about 450 g/mol to about 4500 g/mol, from about 500 g/mol to about 5000 g/mol, from about 550 g/mol to about 5500 g/mol, from about 600 g/mol to about 6000 g/mol, from about 650 g/mol to about 6500 g/mol, from about 700 g/mol to about 7000 g/mol, from about 750 g/mol to about 7500 g/mol, from about 800 g/mol to about 8000 g/mol, from about 850 g/mol to about 8500 g/mol, from about 900 g/mol to about 9000 g/mol, from about 950 g/mol to about 9500 g/mol, from about 1000 g/mol to about 10000 g/mol, from about 1100 g/mol to about 12000 g/mol, from about 1200 g/mol to about 14000 g/mol, from about 1300 g/mol to about 16000 g/mol, from about 1400 g/mol to about 18000 g/mol, from about 1500 g/mol to about 20000 g/mol, from about 1600 g/mol to about 22000 g/mol, from about 1700 g/mol to about 24000 g/mol, from about 1800 g/mol to about 26000 g/mol, from about 1900 g/mol to about 28000 g/mol, from about 2000 g/mol to about 30000 g/mol, from about 2200 g/mol to about 35000 g/mol, from about 2400 g/mol to about 40000 g/mol, from about 2600 g/mol to about 45000 g/mol, from about 2800 g/mol to about 50000 g/mol, from about 3000 g/mol to about 55000 g/mol, from about 10000 g/mol to about 60000 g/mol, from about 13000 g/mol to about 65000 g/mol, from about 16000 g/mol to about 70000 g/mol, from about 19000 g/mol to about 75000 g/mol, from about 22000 g/mol to about 80000 g/mol, from about 25000 g/mol to about 85000 g/mol, from about 28000 g/mol to about 90000 g/mol, from about 31000 g/mol to about 95000 g/mol, or from about 34000 g/mol to about 100000 g/mol are utilized.

Formats

SBPs may include or be prepared to conform to a variety of formats. In some embodiments, such formats include formulations of processed silk with various excipients and/or cargo. In some embodiments, SBP formats include, but are not limited to, gels, hydrogels, implants, and rods. In some embodiments, the formats are formulated with a therapeutic agent.

Formulations

In some embodiments, SBPs may be formulations. As used herein, the term "formulation" refers to a mixture of two or more components or the process of preparing such mixtures. In some embodiments, the formulations are low cost and eco-friendly. In some embodiments, the preparation or manufacturing of formulations is low cost and eco-friendly. In some embodiments, the preparation or manufacturing of formulations is scalable. In some embodiments, SBPs are prepared by extracting silk fibroin via degumming silk yarn. In some embodiments, the yarn is medical grade. In some embodiments the yarn may be silk sutures. The extracted silk fibroin may then be dissolved in a solvent (e.g. water, aqueous solution, organic solvent). The dissolved silk fibroin may then be dried (e.g., oven dried, air dried, or freeze-dried). In some embodiments, dried silk fibroin is formed into formats described herein. In some embodiments, that format is a solution. In some embodiments, that format is a powder. In some embodiments, formulations include one or more excipients, carriers, additional components, and/or therapeutic agents to generate SBPs. In some embodiments, formulations of processed silks are prepared during the manufacture of SBPs.

Formulation components and/or component ratios may be modulated to affect one or more SBP properties, effects, and/or applications. Variations in the concentration of silk fibroin, choice of excipient, the concentration of excipient, the osmolarity of the formulation, and the method of formulation represent non-limiting examples of differences in formulation that may alter properties, effects, and applications of SBPs. In some embodiments, the formulation of SBPs may modulate their physical properties. Examples of physical properties include solubility, density, and thickness. In some embodiments, the formulation of SBPs may modulate their mechanical properties. Examples of mechanical properties that may be modulated include, but are not limited to, mechanical strength, tensile strength, elongation capabilities, elasticity, compressive strength, stiffness, shear strength, toughness, torsional stability, temperature stability, moisture stability, viscosity, and reeling rate.

Cargo

In some embodiments, SBPs are or include cargo. As used herein, the term "cargo" refers to any substance that is embedded in, enclosed within, attached to, or otherwise associated with a carrier. SBPs may be carriers for a large variety of cargo. Such cargo may include therapeutic agents (e.g., biological agents, particles, lipids, liposomes, carbohydrates, small molecules, ions, metals, and minerals). In some embodiments, the cargo is or includes a payload. As used herein, the term "payload" refers to cargo that is delivered from a source or carrier to a target. Payloads may be released from SBPs, where SBPs serve as a carrier. Where SBPs are the payload, the SBPs may be released from a source or carrier. In some embodiments, payloads remain associated with carriers upon delivery. Payloads may be released in bulk or may be released over a period of time, also referred to herein as the "delivery period." In some embodiments, payload release is by way of controlled release. As used herein, the term "controlled release" refers to distribution of a substance from a source or carrier to a surrounding area, wherein the distribution occurs in a manner that includes or is affected by some manipulation, some property of the carrier, or some carrier activity.

In some embodiments, controlled release may include a steady rate of release of payload from carrier. In some embodiments, payload release may include an initial burst, wherein a substantial amount of payload is released during an initial release period followed by a period where less payload is released. In some embodiments, release rate slows over time. Payload release may be measured by assessing payload concentration in a surrounding area and comparing to initial payload concentration or remaining payload concentration in a carrier or source area. Payload release rate may be expressed as a quantity or mass of payload released over time (e.g., mg/min). Payload release rate may be expressed as a percentage of payload released from a source or carrier over a period of time (e.g., 5%/hour). Controlled release of a payload that extends the delivery period is referred to herein as "sustained release." Sustained release may include delivery periods that are extended over a period of hours, days, months, or years.

Some controlled release may be mediated by interactions between payload and carrier. Some controlled release is mediated by interactions between payload or carrier with surrounding areas where payload is released. With sustained payload release, payload release may be slowed or prolonged due to interactions between payload and carrier or payload and surrounding areas where payload is released. Payload release from SBPs may be controlled by SBP viscosity. Where the SBP includes processed silk gel, gel viscosity may be adjusted to modulate payload release.

In some embodiments, payload delivery periods may be from about 1 second to about 20 seconds, from about 10 seconds to about 1 minute, from about 30 seconds to about 10 minutes, from about 2 minutes to about 20 minutes, from about 5 minutes to about 30 minutes, from about 15 minutes to about 1 hour, from about 45 minutes to about 2 hours, from about 90 minutes to about 5 hours, from about 3 hours to about 20 hours, from about 10 hours to about 50 hours, from about 24 hours to about 100 hours, from about 48 hours to about 2 weeks, from about 72 hours to about 4 weeks, from about 1 week to about 3 months, from about 1 month to about 6 months, from about 3 months to about 1 year, from about 9 months to about 2 years, or more than 2 years.

In some embodiments, payload release may be consistent with near zero-order kinetics. In some embodiments, payload release may be consistent with first-order kinetics. In some embodiments, payload release may be modulated based on the density, loading, molecular weight, and/or concentration of the payload. Where the carrier is an SBP, payload release may be modulated by one or more of SBP drying method, silk fibroin molecular weight, and silk fibroin concentration.

In some embodiments, SBPs maintain and/or improve cargo stability, purity, and/or integrity. For example, SBPs may be used to protect therapeutic agents or macromolecules during lyophilization. The maintenance and/or improvement of stability during lyophilization may be determined by comparing SBP cargo stability to formulations lacking processed silk or to standard formulations in the art.

Viscosity

In some embodiments, SBPs may be formulated to modulate SBP viscosity. As used herein, the term "viscosity" refers to a measure of a material's resistance to flow. The viscosity of a composition (e.g., a gel or hydrogel) provided herein can be determined using a rotational viscometer or rheometer. Additional methods for determining the viscosity of a composition and other gel or rheological properties may include any of those known in the art. In some embodiments, the SBP viscosity may be controlled via the concentration of processed silk. In some embodiments, the SBP viscosity may be controlled via the molecular weight of processed silk. In some embodiments, the SBP viscosity may be controlled via the boiling time of the processed silk. In some embodiments, SBP viscosity is altered by the incorporation of an excipient. In some embodiments, SBP viscosity may be altered by the incorporation of an excipient that is a gelling agent. In some embodiments, the identity of the excipient (e.g., PEG or poloxamer) may be altered to modulate SBP viscosity. In some embodiments, the viscosity of SBPs may be tuned for the desired application (e.g., drug delivery system, surgical implant, etc.). In some embodiments, the viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, or from about 700 cP to about 1000 cP. In some embodiments, the viscosity of an SBP is from about 0.0001 Pa*s to about 0.001 Pa*s, from about 0.001 Pa*s to about 0.01 Pa*s, from about 0.01 Pa*s to about 0.1 Pa*s, from about 0.1 Pa*s to about 1 Pa*s, from about 1 Pa*s to about 10 Pa*s, from about 2 Pa*s to about 20 Pa*s, from about 3 Pa*s to about 30 Pa*s, from about 4

Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pa*s, from about 600 Pa*s to about 800 Pa*s, from about 650 Pa*s to about 900 Pa*s, from about 700 Pa*s to about 1000 Pa*s or from about 10 Pa*s to about 2500 Pa*s. In some embodiments, the processed silk preparations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain.

Stress Resistance

In some embodiments, SBPs may be formulated to modulate SBP resistance to stress. Resistance to stress may be measured using one or more rheological measurements. Such measurements may include, but are not limited to tensile elasticity, shear or rigidity, volumetric elasticity, and compression. Additional rheological measurements and properties may include any of those taught in Zhang et al. (2017) Fiber and Polymers 18(10):1831-1840; McGill et al. (2017) Acta Biomaterialia 63:76-84; and Choi et al. (2015) In-Situ Gelling Polymers, Series in BioEngineering doi. 10.1007/978-981-287-152-7_2, the contents of each of which are herein incorporated by reference in their entirety. In some embodiments, stress resistance may be modulated through incorporation of excipients (e.g., PEG or poloxamer). In some embodiments, SBP stress-resistance properties may be modulated to suit a specific application (e.g., tissue engineering scaffold, drug delivery system, surgical implant, etc.).

Concentrations and Ratios of SBP Components

SBPs may include formulations of processed silk with other components (e.g., excipients and cargo), wherein each SBP component is present at a specific concentration, ratio, or range of concentrations or ratios, depending on SBP format and/or application. In some embodiments, the concentration of processed silk or other SBP component (e.g., excipient or cargo) is present in SBPs at a concentration of from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v).

In some embodiments, the concentration of processed silk or other SBP component (e.g., excipient or cargo) is present in SBPs at a concentration of from about 0.01% (v/v) to about 1% (v/v), from about 0.05% (v/v) to about 2% (v/v), from about 1% (v/v) to about 5% (v/v), from about 2% (v/v) to about 10% (v/v), from about 4% (v/v) to about 16% (v/v), from about 5% (v/v) to about 20% (v/v), from about 8% (v/v) to about 24% (v/v), from about 10% (v/v) to about 30% (v/v), from about 12% (v/v) to about 32% (v/v), from about 14% (v/v) to about 34% (v/v), from about 16% (v/v) to about 36% (v/v), from about 18% (v/v) to about 38% (v/v), from about 20% (v/v) to about 40% (v/v), from about 22% (v/v) to about 42% (v/v), from about 24% (v/v) to about 44% (v/v), from about 26% (v/v) to about 46% (v/v), from about 28% (v/v) to about 48% (v/v), from about 30% (v/v) to about 50% (v/v), from about 35% (v/v) to about 55% (v/v), from about 40% (v/v) to about 60% (v/v), from about 45% (v/v) to about 65% (v/v), from about 50% (v/v) to about 70% (v/v), from about 55% (v/v) to about 75% (v/v), from about 60% (v/v) to about 80% (v/v), from about 65% (v/v) to about 85% (v/v), from about 70% (v/v) to about 90% (v/v), from about 75% (v/v) to about 95% (v/v), from about 80% (v/v) to about 96% (v/v), from about 85% (v/v) to about 97% (v/v), from about 90% (v/v) to about 98% (v/v), from about 95% (v/v) to about 99% (v/v), from about 96% (v/v) to about 99.2% (v/v), from about 97% (v/v) to about 99.5% (v/v), from about 98% (v/v) to about 99.8% (v/v), from about 99% (v/v) to about 99.9% (v/v), or greater than 99.9% (v/v).

In one embodiment, the concentration of processed silk or other SBP component (e.g., excipient or cargo) is present in SBPs at a concentration of 1% (w/v).

In one embodiment, the concentration of processed silk or other SBP component (e.g., excipient or cargo) is present in SBPs at a concentration of 2% (w/v).

In one embodiment, the concentration of processed silk or other SBP component (e.g., excipient or cargo) is present in SBPs at a concentration of 3% (w/v).

In one embodiment, the concentration of processed silk or other SBP component (e.g., excipient or cargo) is present in SBPs at a concentration of 4% (w/v).

In one embodiment, the concentration of processed silk or other SBP component (e.g., excipient or cargo) is present in SBPs at a concentration of 5% (w/v).

In one embodiment, the concentration of processed silk or other SBP component (e.g., excipient or cargo) is present in SBPs at a concentration of 6% (w/v).

In one embodiment, the concentration of processed silk or other SBP component (e.g., excipient or cargo) is present in SBPs at a concentration of 10% (w/v).

In one embodiment, the concentration of processed silk or other SBP component (e.g., excipient or cargo) is present in SBPs at a concentration of 20% (w/v).

In one embodiment, the concentration of processed silk or other SBP component (e.g., excipient or cargo) is present in SBPs at a concentration of 30% (w/v).

In one embodiment, the concentration of processed silk or other SBP component (e.g., excipient or cargo) is present in SBPs at a concentration of 16.7% (w/w).

In one embodiment, the concentration of processed silk or other SBP component (e.g., excipient or cargo) is present in SBPs at a concentration of 20% (w/w).

In one embodiment, the concentration of processed silk or other SBP component (e.g., excipient or cargo) is present in SBPs at a concentration of 23% (w/w).

In one embodiment, the concentration of processed silk or other SBP component (e.g., excipient or cargo) is present in SBPs at a concentration of 25% (w/w).

In one embodiment, the concentration of processed silk or other SBP component (e.g., excipient or cargo) is present in SBPs at a concentration of 27.3% (w/w).

In one embodiment, the concentration of processed silk or other SBP component (e.g., excipient or cargo) is present in SBPs at a concentration of 28.6% (w/w).

In one embodiment, the concentration of processed silk or other SBP component (e.g., excipient or cargo) is present in SBPs at a concentration of 33.3% (w/w).

In one embodiment, the concentration of processed silk or other SBP component (e.g., excipient or cargo) is present in SBPs at a concentration of 40% (w/w).

In one embodiment, the concentration of processed silk or other SBP component (e.g., excipient or cargo) is present in SBPs at a concentration of 50% (w/w).

In some embodiments, the concentration of processed silk or other SBP component (e.g., excipient or cargo) is present in SBPs at a concentration of from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 8% (w/w) to about 24% (w/w), from about 10% (w/w) to about 30% (w/w), from about 12% (w/w) to about 32% (w/w), from about 14% (w/w) to about 34% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35% (w/w) to about 55% (w/w), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/w), from about 90% (w/w) to about 98% (w/w), from about 95% (w/w) to about 99% (w/w), from about 96% (w/w) to about 99.2% (w/w), from about 97% (w/w) to about 99.5% (w/w), from about 98% (w/w) to about 99.8% (w/w), from about 99% (w/w) to about 99.9% (w/w), or greater than 99.9% (w/w).

In some embodiments, the concentration of processed silk (e.g., silk fibroin) or other SBP component (e.g., excipient or cargo) is present in SBPs at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

In one embodiment, the concentration of processed silk (e.g., silk fibroin) or other SBP component (e.g., excipient or cargo) is present in SBPs at a concentration of 5 mg/mL.

In one embodiment, the concentration of processed silk (e.g., silk fibroin) or other SBP component (e.g., excipient or cargo) is present in SBPs at a concentration of 2.5 mg/mL.

In one embodiment, the concentration of processed silk (e.g., silk fibroin) or other SBP component (e.g., excipient or cargo) is present in SBPs at a concentration of 1.25 mg/mL.

In one embodiment, the concentration of processed silk (e.g., silk fibroin) or other SBP component (e.g., excipient or cargo) is present in SBPs at a concentration of 0.625 mg/mL.

In one embodiment, the concentration of processed silk (e.g., silk fibroin) or other SBP component (e.g., excipient or cargo) is present in SBPs at a concentration of 0.3125 mg/mL.

In some embodiments, the concentration of processed silk (e.g., silk fibroin) or other SBP component (e.g., excipient or cargo) is present in SBPs at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

In some embodiments, SBPs may be formatted as a gel. Such gels may include hydrogels. In some embodiments, such hydrogels are formulated with therapeutic agents. Therapeutic agents may include a nonsteroidal anti-inflammatory drug (NSAID), for example, celecoxib.

Appearance: Transparent, Opaque, Translucent

In some embodiments, the appearance of SBPs described in the present disclosure may be tuned for the application for which they were designed. In some embodiments, SBPs may be transparent. In some embodiments, SBPs may be translucent. In some embodiments, SBPs may be opaque. In some embodiments, SBP preparation methods may be used to modulate clarity, as taught in International Patent Application Publication No. WO2012170655, the contents of which are herein incorporated by reference in their entirety. In some embodiments, the incorporation of excipients may be used to tune the clarity of processed silk preparations. In some embodiments, the excipient is sucrose. In some embodiments, the sucrose may also increase protein reconstitution during lyophilization. In some embodiments, sucrose may improve processed silk hydrogel clarity (optical transparency). In some embodiments, optically transparent SBPs may be used for ocular applications, e.g., treatment of ocular conditions, diseases, and/or indications. In some embodiments, SBPs herein may be used to label products, as taught in International Patent Application Publication No. WO2009155397, the contents of which are herein incorporated by reference in their entirety. The transparency of SBPs, as well as other properties, may render resulting labels edible, biodegradable, and/or holographic.

Residence Time

In some embodiments, SBP formulations may be prepared to have desired residence time according to the application for which they are designed. As used herein, the term "residence time" refers to the average length of time during which a substance (e.g., SBP formulations) is in a given location or condition. In some embodiments, residence time of SBP formulations described herein may vary from a few hours to several months. For example, residence time of SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or longer than 1 year.

pH

SBPs may have a pH from about 3 to about 10. In some embodiments, the pH is from about 3 to about 6, from about 6 to about 8, or from about 8 to about 10. In some embodiments, the pH of the SBP is about 7.4. In some embodiments, the pH of the SBP is 7.06. In some embodiments, the pH of the SBP is 7.15.

Exemplary Formulations

In one embodiment, the SBP formulation may include 480 mb silk fibroin at a concentration of 3%, an excipient at a concentration of 10% and cargo at a concentration of 10%. The excipient cargo may be, but is not limited to, poloxamer-188 (P188) and PEG4k, and the cargo may be, celecoxib (CXB), bovine serum albumin (BSA), lysozyme or bevacizumab. The osmolarity of the SBP formulation may be the range of 290-320 mOsm/L.

In one embodiment, the SBP formulation may include 480 mb silk fibroin at a concentration of 3%, an excipient at a concentration of 20% and cargo at a concentration of 1%. The excipient cargo may be, but is not limited to, poloxamer-188 (P188) and PEG4k, and the cargo may be, celecoxib (CXB), bovine serum albumin (BSA), lysozyme or bevacizumab. The osmolarity of the SBP formulation may be the range of 290-320 mOsm/L.

In one embodiment, the SBP formulation may include 480 mb silk fibroin at a concentration of 3%, an excipient at a concentration of 50% and cargo at a concentration of 1%. The excipient cargo may be, but is not limited to, poloxamer-188 (P188) and PEG4k, and the cargo may be, celecoxib (CXB), bovine serum albumin (BSA), lysozyme or bevacizumab. The osmolarity of the SBP formulation may be the range of 290-320 mOsm/L.

In one embodiment, the SBP formulation may include 120 mb silk fibroin at a concentration of 2%, 3%, 4%, 5%, or 6%. The SBP formulation may include an excipient at a concentration of 40% and may be PEG300 or glycerol and/or cargo a concentration of 10%. The cargo may be, celecoxib (CXB), bovine serum albumin (BSA), lysozyme or bevacizumab. Additionally 0.2% polysorbate-80 and 22 mM phosphate buffer may be included in the formulation.

Combinations

In some embodiments, SBPs are presented in a combinatorial format. A combinatorial format may consist of two or more different materials that have been combined to form a single composition. In some embodiments, two or more SBPs of different formats (e.g. rod, hydrogel etc.) are combined to form a single composition (e.g., see European Publication Number EP3212246, the contents of which are herein incorporated by reference in their entirety). In some embodiments, one or more SBP is combined with a different material (e.g. a polymer, a mat, a particle, a microsphere, a nanosphere, a metal, a scaffold, etc.) to form a single composition (e.g., see International Publication Number WO2017179069, the contents of which are herein incorporated by reference in their entirety). In some embodiments, combinatorial formats are prepared by formulating two or more SBPs of different formats as a single composition (e.g., see Kambe et al. (2017) Materials (Basel) 10(10):1153, the contents of which are herein incorporated by reference in their entirety). In some embodiments, combinatorial formats are prepared by formulating two or more SBPs of different formats, along with another material, as a single composition (e.g., see International Publication Number WO2017177281, the contents of which are herein incorporated by reference in their entirety). In some embodiments, combinatorial formats include adding one or more SBPs to a first SBP of a different format (e.g., see European Patent Number EP3212246, the contents of which are herein incorporated by reference in their entirety). In some embodiments, combinatorial formats include adding one or more SBPs to a first composition comprising a different material (e.g., see Jiang et al. (2017) J Biomater Sci Polym Ed 15:1-36, the contents of which are herein incorporated by reference in their entirety). In some embodiments, the combinatorial formats are prepared by adding one or more materials to one or more first formed SBPs (e.g., see Babu et al. (2017) J Colloid Interface Sci 513:62-72, the contents of which are herein incorporated by reference in their entirety).

Distribution

SBP components may be distributed equally or unequally, depending on format and application. Non-limiting examples of unequal distribution include component localization in SBP regions or compartments, on SBP surfaces, etc. In some embodiments, components include cargo. Such cargo may include payloads, for example, therapeutic agents. In some embodiments, therapeutic agents are present on the surface of an SBP (e.g., see Han et al. (2017) Biomacromolecules 18(11):3776-3787; Ran et al. (2017) Biomacromolecules 18(11):3788-3801, the contents of each of which are herein incorporated by reference in their entirety). In some embodiments, components (e.g., therapeutic agents) are homogenously mixed with processed silk to generate a desired distribution (e.g., see United States Publication No. US20170333351; Sun et al. (2017) Journal of Materials Chemistry B 5:8770-8779; and Du et al. (2017) Nanoscale Res Lett 12(1):573, the contents of each of which are herein incorporated by reference in their entirety). In some embodiments, components (e.g., therapeutic agents) are encapsulated in SBPs (e.g., see Shi et al. (2017) Nanoscale 9:14520, the contents of which are herein incorporated by reference in their entirety).

Solubility

In some embodiments, SBPs or components thereof are water soluble. The water solubility, along with the rate of degradation, of SBPs may modulate payload (e.g., therapeutic agent) release rate and/or release period. An increasing amount of payload may be released into surrounding medium as surrounding matrix dissolves (e.g., see International Publication Numbers WO2013126799 and WO2017165922; and U.S. Pat. No. 8,530,625, the contents of each of which are herein incorporated by reference in their entirety). Longer time periods required to dissolve SBPs or components thereof may result in longer release periods. In some embodiments, SBP solubility may be modulated in order to control the rate of payload release in the surrounding medium. The solubility of SBPs may be modulated via any method known to those skilled in the art. In some embodiments, SBP solubility may be modulated by altering included silk fibroin secondary structure (e.g., increasing β-sheet content and/or crystallinity). In some embodiments, SBP solubility may be modulated by altering SBP format. In some embodiments, SBP solubility and/or rate of degradation may be modulated to facilitate extended release of therapeutic agent payloads in vitro and/or in vivo.

Coating Agents

In some embodiments, SBPs may be used as coating agents. As used herein, the term "coating agent" refers to a substance covering or used to cover an article, wherein the substance adheres to the article (also referred to herein as "coatings"). SBP coating agents may be used, for example, to coat cargo, payloads, devices, or device components. SBP coatings may include therapeutic agent payloads (e.g., ocular therapeutic agents) and may be used to coat articles (e.g., implants) used to deliver such therapeutic agent payloads.

Rods

In some embodiments, SBPs are prepared as rods. As used herein when referring to processed silk preparations or SBPs, the term "rod" refers to an elongated format, typically cylindrical, that may have blunted or tapered ends. Rods may be suitable for implantation or similar administration methods as it may be possible to deliver rods by injection. Rods may also be obtained simply by passing suitably viscous processed silk preparations through a needle, cannula, tube, or opening. In some embodiments, rods are prepared by one or more of injection molding, heated or cooled extrusion, extrusion through a coating agent, milling with a therapeutic agent, and combining with a polymer followed by extrusion.

In some embodiments, SBP rods include processed silk (e.g., silk fibroin) rods. Some rods may include coterminous luminal cavities in whole or in part running through the rod. Rods may be of any cross-sectional shape, including, but not limited to, circular, square, oval, triangular, irregular, or combinations thereof.

In some embodiments, rods are prepared from silk fibroin preparations. The silk fibroin preparations may include lyophilized silk fibroin. The lyophilized silk fibroin may be dissolved in water to form silk fibroin solutions used in rod preparation. Silk fibroin solutions may be prepared as stock solutions to be combined with additional components prior to rod preparation. In some embodiments silk fibroin stock solutions have a silk fibroin concentration of between 10% (w/v) and 40% (w/v). In some embodiments, the silk fibroin stock solution for the preparation of silk fibroin rods has a concentration of at least 10% (w/v), at least 20% (w/v), at least 30% (w/v), at least 40% (w/v), or at least 50% (w/v).

In one embodiment, the silk fibroin stock solution has a concentration of 10% (w/v).

In one embodiment, the silk fibroin stock solution has a concentration of 20% (w/v).

In one embodiment, the silk fibroin stock solution has a concentration of 30% (w/v).

In one embodiment, the silk fibroin stock solution has a concentration of 40% (w/v).

In one embodiment, the silk fibroin stock solution has a concentration of 50% (w/v).

In some embodiments, silk fibroin stock solution prepared for rod formation are mixed with one or more other components intended to be include in the final processed silk rods. Examples of such other components include, but are not limited to, excipients, salts, therapeutic agents, biological agents, proteins, small molecules, and polymers. In some embodiments, processed silk rods may include between 20 to 55% (w/w) silk fibroin. In some embodiments, processed silk rods may include between 40 to 80% (w/w) therapeutic agent. In some embodiments, processed silk rods may include 35% (w/w) silk fibroin and 65% (w/w) therapeutic agent. In some embodiments, processed silk rods may include 30% (w/w) silk fibroin and 70% (w/w) therapeutic agent. In some embodiments, processed silk rods may include 40% (w/w) silk fibroin and 60% (w/w) therapeutic agent. In some embodiments, processed silk rods may include 26% (w/w) silk fibroin and 74% (w/w) therapeutic agent. In some embodiments, processed silk rods may include 37% (w/w) silk fibroin and 63% (w/w) therapeutic agent. In some embodiments, processed silk rods may include 33% (w/w) silk fibroin and 66% (w/w) therapeutic agent. In some embodiments, processed silk rods may include 51% (w/w) silk fibroin and 49% (w/w) therapeutic agent. In some embodiments, the silk fibroin may be included at a concentration (w/w) of 0.01% to about 1%, from about 0.05% to about 2%, from about 0.1% to about 30%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

In some embodiments, processed silk rods are prepared by extrusion. As used herein, the term "extrusion" refers to a process by which a substance is forced through an opening, tube, or passage. In some embodiments, processed silk rods are formed by extruding processed silk preparations through a needle or cannula. Processed silk preparations used for rod formation may have varying levels of viscosity. Preparation viscosity may depend on the presence and/or identity of excipients present. In some embodiments, processed silk preparations may include compounds or compositions intended to be embedded in rods prepared by extrusion. Excipients, compounds, or compositions included in processed silk preparations used for extrusion may include, but are not limited to, salts, therapeutic agents, biological agents, proteins, small molecules, and polymers. Extrusion may be carried out manually or by an automated process.

In some embodiments, extrusion may be carried out using a syringe. The syringe may be fitted with a needle, tube, or cannula. The needle, tube, or cannula may have a sharpened end or a blunt end. The needle may have a diameter of from about 0.1 mm to about 0.3 mm, from about 0.2 mm to about 0.7 mm, from about 0.4 mm to about 1.1 mm, from about 0.6 mm to about 1.5 mm, from about 0.8 mm to about 1.9 mm, from about 1 mm to about 2.3 mm, from about 1.2 mm to about 2.7 mm, from about 1.6 mm to about 3.1 mm, or from about 2 mm to about 3.5 mm, to provide extruded rods with a uniform diameter. Processed silk preparations may be used to fill tubes, wherein the processed silk preparations are incubated in the tubes for various periods of time under various conditions (e.g., various temperatures). In some embodiments, tubing filled with processed silk preparation may be incubated at 37° C. for from about 2 hours to about 36 hours or more. In some embodiments, processed silk filled tubing is incubated for 24 hours. In some embodiments, processed silk preparations remain in tubing after the 37° C. incubation. In some embodiments, processed silk preparations are removed from the tubing after the incubation at 37° C. Processed silk preparations removed from tubing may maintain a rod-shaped format. Such preparations may be dried after removal from tubing. In some embodiments, processed silk preparations may be encased in tubing while drying. Rods may be dried by one or more of freeze-drying, oven drying, and air drying. Some processed silk preparations may be removed tubing after drying.

Tubing used for extrusion may be composed of various materials. In some embodiments, tubing is made from one or more of silicone, polyetheretherketone (PEEK), polytetrafluoroethylene (PTFE), amorphous fluoroplastics, fluorinated ethylene propylene, perfluoroalkoxy copolymers, ethylene-tetrafluoroethylene, polyolefins, and nylon.

In some embodiments, rods may have a diameter of from about 0.05 μm to about 10 μm, from about 1 μm to about 20 μm, from about 2 μm to about 30 μm, from about 5 μm to about 40 μm, from about 10 μm to about 50 μm, from about 20 μm to about 60 μm, from about 30 μm to about 70 μm, from about 40 μm to about 80 μm, from about 50 μm to about 90 μm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 8 mm to about 16 mm, from about 10 mm to about 50 mm, from about 20 mm to about 100 mm, from about 40 mm to about 200 mm, from about 60 mm to about 300 mm, from about 80 mm to about 400 mm, from about 250 mm to about 750 mm, or from about 500 mm to about 1000 mm. In some embodiments, rods include a diameter of at least 0.5 μm, at least 1 μm, at least 10 μm, at least 100 μm, at least 500 μm, at least 1 mm, at least 10 mm, or at least 100 mm. In one embodiment, the rods have a diameter of 1 mm. In another embodiment, the rods have a diameter of 0.5 mm. In another embodiment, the rods have a diameter of 400 μm. In another embodiment, the rods have a diameter of 430 μm.

In some embodiments, the rods described herein may have a density of from about 0.01 μg/mL to about 1 μg/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

Gels and Hydrogels

In some embodiments, SBPs are or are combined with gels or hydrogels. As used herein, the term "gel" refers to a dispersion of liquid molecules in a solid medium. Gels in which the dispersed liquid molecules include water are referred to herein as "hydrogels." Gels in which the dispersed liquid molecules include an organic phase are referred to herein as "organogels." The solid medium may include polymer networks.

In some embodiments, SBP gels or hydrogels are prepared with processed silk. In processed silk gels, polymer networks may include silk fibroin. In some embodiments, gels are prepared with one or more therapeutic agents. In some embodiments, gels include one or more excipients. The excipients may be selected from any of those described herein. In some embodiments, excipients may include salts. In some embodiments, the excipients may include gelling agents. In some embodiments, gels are prepared with one or more therapeutic agents, biological agents, proteins, small molecules, and/or polymers.

Gel preparation may require varying temperatures and incubation times for gel polymer networks to form. In some embodiments, processed silk preparations are heated to 37° C. to prepare gels. In some embodiments, processed silk preparations are incubated for from about 2 hours to about 36 hours or more to promote gel formation. In some embodiments, gel formation requires mixing with one or more gelling agents or excipients. Mixing may be carried out under various temperatures and lengths of time to allow gel polymer networks to form. Gel formation may require homogenous dispersion of gelling agents or excipients. In some embodiments, processed silk preparations used to prepare gels include silk fibroin. Gel formation for processed silk gels may require incubation at 37° C. for up to 24 hours. Some gels may be stored for later use or processing. In some embodiments, gels are stored at 4° C.

In some embodiments, processed silk gels include excipient or gelling agent at a concentration of from about 0.01% to about 0.1%, from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk gels (e.g., hydrogels or organogels) include silk fibroin at a concentration of from about 0.01% to about 0.1%, from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v). Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa, from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

Gelling agents may be used to facilitate sol-gel transition. As used herein, the term "sol-gel transition" refers to the shift of a formulation from a solution to a gel. In some embodiments, the use of gelling agents may be carried out according to any of such methods described in International Publication No. WO2017139684, the contents of which are herein incorporated by reference in their entirety. Gelling agents may be water-soluble, waxy solids. In some embodiments, gelling agents may be water-soluble and hygroscopic in nature. In some embodiments, gelling agents may include polar molecules. Gelling agents may have net positive, net negative, or net neutral charges at a physiological pH (e.g., pH of about 7.4). Some gelling agents may be amphipathic. Additional examples of gelling agents include oils (e.g., castor, corn oil, cottonseed oil, olive oil, peanut oil, peppermint oil, safflower oil, sesame oil, soybean oil, hydrogenated vegetable oil, hydrogenated soybean oil, and medium-chain triglycerides of coconut oil and/or palm seed oil), emulsifiers [e.g., polyoxyl 40 stearate (PEG 1750 monosterate), polyoxyl 8 stearate (PEG 400 monosterate), polysorbate 20, polysorbate-SO, or poloxamer], surfactants (e.g., polysorbate, poloxamer, sodium dodecyl sulfate, Triton X100, or tyloxapol), and suspending agents (e.g., polyvinyl pyrrolidone, polyvinyl pyrrolidone-12, polyvinyl pyrrolidone-17, hydroxyethyl cellulose, or carboxymethyl cellulose).

In some embodiments, gel formation is induced by applying one or more of the following to processed silk preparations: ultrasound, sonication, shear forces, temperature change (e.g., heating), addition of precipitants, modulation of pH, changes in salt concentration, chemical cross-linking, chemical modification, seeding with preformed hydrogels, increasing silk fibroin concentration, modulating osmolarity, use of electric fields, or exposure to electric currents. In some embodiments, methods of inducing gel formation may include, but are not limited to any of those described in International Publication No. WO2005012606 or United States Publication No. US2011/0171239, the contents of each of which are herein incorporated by reference in their entirety.

In some embodiments, processed silk gel preparation may be carried with the aid of sonication. As used herein, the term "sonication" refers to a process of agitation using sound energy. Sonication conducted at frequencies greater than 20 kHz is referred to as ultrasonication. Sonication may aid in gel formation by dispersing and/or agitating polymer components within a solution to foster an arrangement that favors polymer network formation. The polymer network may include silk fibroin. In some embodiments, the use of sonication for gel preparation may be carried out according to any of the methods described in Zhao et al. (2017) Materials Letters 211:110-113 or Mao et al. (2017) Colloids Surf B Biointerfaces 160:704-714), the contents of each of which are herein incorporated by reference in their entirety.

In some embodiments, processed silk gel formation may be carried out using shear forces. As used herein, the term "shear forces" refers to unaligned forces that apply pressure to two or more different parts of an object or medium from different or opposing directions. Shear forces are distinct from compression forces, which are directed toward each other. Shear forces may be applied during processed silk gel preparation using a syringe, tubing, needle, or other apparatus capable of increasing shear forces. Processed silk preparation may be pushed through a syringe, tubing, needle, or other apparatus to generate shear forces. The use of shear forces in gel formation may include any of those described in United States Publication No. US2011/0171239, the contents of which are herein incorporated by reference in their entirety.

In some embodiments, changes in temperature may be used to aid in processed silk gel formation. Changes in temperature may be used to disperse or align polymer components in an arrangement that promotes gel polymer network formation. The polymer components may include silk fibroin. In some embodiments, gel formation may be carried out by raising or lowering the temperature of a processed silk preparation to from about 0° C. to about 5° C., from about 2° C. to about 6° C., from about 4° C. to about 12° C., from about 8° C. to about 16° C., from about 10° C. to about 26° C., from about 15° C. to about 28° C., from about 20° C. to about 32° C., from about 25° C. to about 34° C., from about 30° C. to about 45° C., from about 35° C. to about 55° C., from about 37° C. to about 65° C., from about 40° C. to about 75° C., from about 50° C. to about 100° C., from about 60° C. to about 120° C., from about 70° C. to about 140° C., from about 80° C. to about 160° C., or from about 100° C. to about 300° C. In some embodiments, one or more excipients or gelling agents may be included to lower the temperature necessary for gel formation to occur. Such embodiments may be employed to protect temperature-sensitive components embedded within gels. In some embodiments, gel formation is carried out at 4° C. Glycerol, polyethylene glycol (PEG), and/or polymers of PEG (e.g., PEG400) may be included in processed silk preparations as excipients to lower the temperature necessary to form a gel. The gel may be a silk fibroin gel. Excipient concentration may be about 30% (w/v). Silk fibroin concentration may be from about 2% to about 30%.

In some embodiments, gel formation is carried out by applying an electric current, also referred to as "electrogelation." Electrogelation may be carried out according to any of the methods presented in International Publication No. WO2010036992, the contents of which are herein incorporated by reference in their entirety. In some embodiments, a reverse voltage may be applied to reverse gel formation and regenerate a processed silk solution.

In some embodiments, gel formation is carried out by modulating the pH of processed silk preparations. Gel formation through pH modulation may be carried out according to the methods described in International Publication No. WO2005012606, United States Publication No. US2011/0171239, and Dubey et al. (2017) Materials Chemistry and Physics 203:9-16, the contents of each of which are herein incorporated by reference in their entirety.

In some embodiments, gel formation may be carried out in association with modulating the osmolarity of a processed silk preparation. As used herein, the term "osmolarity" or "osmotic concentration" refers to the number of osmoles of solute in solution on a per liter basis (Osm/L). Unlike molarity, which is a measure of the number of moles solute per liter of solvent (M), osmolarity factors in the effect of ions on osmotic pressure. For example, a 1 M solution of NaCl would have an osmolarity of 2 Osm/L while a 1 M solution of MgCl2 would have an osmolarity of 3 Osm/L. Hypo- or hyper-osmotic formulations can lead to local tissue damage and reduced biocompatibility. In some embodiments, the osmolarity of processed silk gels is modulated by controlling the type, molecular weight, and/or concentration of excipients included. Osmolarity may be modulated by varying the concentration and/or molecular weight of salts used in processed silk preparations. In some embodiments, osmolarity is reduced by using lower molecular weight gelling agents. For example, 4 kDa PEG may be used in place of PEG400. The use of Poloxamer 188 at 10% (w/v) may reduce osmolarity in comparison to lower molecular weight species such as glycerol. In some embodiments, sodium chloride may be added to increase osmolarity. In some embodiments, osmolarity is adjusted to fall between 280 and 320 mOsm/L.

In some embodiments, gel formation may be carried out through seeding. As used herein when referring to gel formation, "seeding" refers to a process of inducing gel formation using a small amount of pre-formed gel. Seeding may promote gel formation by encouraging polymer network formation to build off of the pre-formed gel introduced. In some embodiments the gel includes silk fibroin. Seeding with a pre-formed silk fibroin hydrogel may be used to promote transition of a silk fibroin solution into a silk fibroin gel. In some embodiments, seeding reduces the need for gelling agents and/or excipients to form gels.

In some embodiments, gel formation may be carried out using chemical cross-linking. As used herein, the term "chemical cross-linking" refers to a process of forming covalent bonds between chemical groups from different molecules or between chemical groups present on different parts of the same molecule. In some embodiments, chemical cross-linking may be carried out by contacting processed silk preparations with ethanol. Such methods may be carried out according to those described in Shi et al. (2017) Advanced Material 29(29):1701089, the contents of which are herein incorporated by reference in their entirety. In some embodiments, cross-linking may be carried out using enzymes. Methods of enzyme cross-linking using horse radish peroxidase may include any of those described in McGill et al. (2017) Acta Biomaterialia 63:76-84 or Guo et al. (2017) Biomaterials 145:44-55, the contents of each of which are herein incorporated by reference in their entirety. In some embodiments, chemical cross-linking may be photo-initiated, as disclosed in International Publication No. WO2017123383 and in Zhang et al. (2017) Fibers and Polymers 18(10):1831-1840, the contents of each of which are herein incorporated by reference in their entirety.

In some embodiments, other chemical modifications may be used during processed silk gel preparation. Some chemical modifications may be used to induce silk fibroin β-sheet conformations. In some embodiments, this process involves contact with a chemical. Chemicals may include, but are not limited to, ethanol. In some embodiments, silk fibroin may be chemically crosslinked with other materials during gel preparation. Such materials may include other peptides (e.g., see Guo et al. (2017) Biomaterials 145:44-55, the contents of which are herein incorporated by reference in their entirety). In some embodiments, processed silk gels are prepared by formation of internal chemical cross-links. These crosslinks may be dityrosine crosslinks (e.g., see International Publication No. WO2017123383, the contents of which are herein incorporated by reference in their entirety). In some embodiments, photosensitive materials may be used to promote chemical modifications. Such materials may include riboflavin (e.g., see International Publication No. WO2017123383). In some embodiments, processed silk gels may be functionalized with particles. These particles may be microspheres and/or nanospheres (e.g., see Ciocci et al. (2017) Int J Biol Macromol 50141-8130(17):32839-8, the contents of which are herein incorporated by reference in their entirety).

Particles

In some embodiments, SBPs may be particles. As used herein, the term "particle" refers to a minute portion of a substance. SBP particles may include particles of processed silk. Processed silk particles may include silk fibroin particles. Silk fibroin particles may be tiny clusters of silk fibroin or they may be arranged as more ordered structures. Particles may vary in size. Processed silk particles may be visible or may be too tiny to view easily with the naked eye. Particles with a width of from about 0.1 µm to about 100 µm are referred to herein as "microparticles." Particles with a width of about 100 nm or less are referred to herein as "nanoparticles." Microparticles and nanoparticles that are spherical in shape are termed microspheres and nanospheres, respectively. Processed silk particle preparations may include particles with uniform width or with ranges of widths. In some embodiments, processed silk particle preparations include average particle widths of or ranges of particle widths of from about 10 nm to about 25 nm, from about 20 nm to about 50 nm, from about 30 nm to about 75 nm, from about 40 nm to about 80 nm, from about 50 nm to about 100 nm, from about 0.05 µm to about 10 µm, from about 1 µm to about 20 µm, from about 2 µm to about 30 µm, from about 5 µm to about 40 µm, from about 10 µm to about 50 µm, from about 20 µm to about 60 µm, from about 30 µm to about 70 µm, from about 40 µm to about 80 µm, from about 50 µm to about 90 µm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 10 nm to about 100 µm, from about 10 µm to about 10 mm, from about 50 nm to about 500 µm, from about 50 µm to about 5 mm, from about 100 nm to about 10 mm, or from about 1 µm to about 10 mm. In some embodiments, processed silk particle preparations include average particle widths of at least 10 nm, at least 100 nm, at least 0.5 µm, at least 1 µm, at least 10 µm, at least 100 µm, at least 500 µm, at least 1 mm, or at least 10 mm.

Processed silk particles may be formed through spraying of a processed silk preparation. In some embodiments, electrospraying is used. Electrospraying may be carried out using a coaxial electrospray apparatus (e.g., see Cao et al. (2017) Scientific Reports 7:11913, the contents of which are herein incorporated by reference in their entirety). In some embodiments, silk fibroin microspheres or nanospheres may be obtained by electrospraying a silk fibroin preparation into a collector and flash freezing the sprayed particles (e.g., see United States Publication No. US2017/0333351, the contents of which are herein incorporated by reference in their entirety). The flash frozen silk fibroin particles may then be lyophilized. In some embodiments, processed silk particles may be prepared using centrifugal washing, followed by lyophilization, as taught in United States Publication No. US2017/0340575, the contents of which are herein incorporated by reference in their entirety. In some embodiments, processed silk microspheres may be formed through the use of a microfluidic device (e.g., see Sun et al. (2017) Journal of Materials Chemistry B 5:8770-8779, the contents of which are herein incorporated by reference in their entirety). In some embodiments, microspheres are formed via coagulation in a methanol bath, as taught in European Patent No. EP3242967, the contents of which are herein incorporated by reference in their entirety.

Scaffolds

In some embodiments, SBPs include scaffolds. As used herein, a "scaffold" refers to a framework used for support. SBP scaffolds may include scaffolds formed using processed silk frameworks. Processed silk may include a polymeric network that provides a framework to support a variety of materials related to a variety of applications. Such application may include, but are not limited to, therapeutic applications. In some embodiments, processed silk scaffolds include polymeric networks that include silk fibroin. In some embodiments, processed silk scaffolds include one or more of silk fibers, nanofibers, mats, films, foams, membranes, rods, tubes, gels, hydrogels, microspheres, nanospheres, solutions, patches, grafts, and powders. In some embodiments, processed silk scaffolds include other agents. Such agents may include, but are not limited to, therapeutic agents (e.g., ocular therapeutic agents, for example, NSAIDS).

In some embodiments, processed silk scaffolds are prepared by casting a processed silk preparation into a mold, and allowing the preparation to solidify to obtain the desired shape. Any mold shape may be used. In some embodiments, injection molding machines are used. Molding may be performed at various temperatures needed to facilitate filling of molds and solidification into final molded form. In some embodiments, molding is performed at room temperature. In other embodiments, the molding is performed at 160° C. In some embodiments, molding is carried out according to the methods described in International Publication No. WO2017179069, Thai et al. J Biomed Mater (2017) 13(1): 015009, or Chen et al. (2017) PLoS One 12(11):e0187880, the contents of each of which are herein incorporated by reference in their entirety.

In some embodiments, processed silk scaffolds are prepared by coating a scaffold formed from non-silk materials with a processed silk preparation. The processed silk may include silk fibroin. The non-silk materials may include, but are not limited to, natural or synthetic polymers, fibers, nanofibers, mats, films, foams, membranes, rods, tubes, gels, hydrogels, microspheres, nanospheres, nanoparticles, particles, solutions, patches, and/or grafts. Methods of coating a scaffold with a processed silk preparation are taught in Ai et al. (2017) International Journal of Nanomedicine 12:7737-7750 and Jiang et al. (2017) J Biomater Sci Polym Ed 15:1-36, the contents of each of which are herein incorporated by reference in their entirety.

Devices

In some embodiments, SBPs may be devices or may be included as device components. As used herein, the term "device" refers to any article constructed or modified to suit a particular purpose. Devices may be designed for a variety of purposes, including, but not limited to, therapeutic applications. In some embodiments, SBPs are embedded or incorporated into devices. Some devices include SBPs as coatings or lubricants. In some embodiments, devices include implants, medical devices, or surgical devices. Additional devices are described herein.

Ocular SBPs

SBPs described herein may include ocular SBPs. As used herein, the term "ocular SBP" refers to an SBP used in any application related to the eye. Ocular SBPs may be used in therapeutic applications. Such therapeutic applications may include treating or otherwise addressing one or more ocular indications.

Ocular SBPs may be prepared in a variety of formats. Some ocular SBPs are prepared in the shape of a rod. Some ocular SBPs may be in the form of a lyophilized powder. Some ocular SBPs are in the form of a hydrogel. Other ocular SBPs may be in the form of a solution. Ocular SBPs may include ocular therapeutic agents. The ocular therapeutic agents may include any of those described herein. In some embodiments, ocular therapeutic agents include one or more of processed silk, biological agents, small molecules, proteins, NSAIDs, and VEGF-related agents. Ocular therapeutic agent proteins may include, but are not limited to, lysozyme, bovine serum albumin (BSA), bevacizumab, or VEGF-related agents. NSAIDs may include, but are not limited to, aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, the SBPs stabilize ocular therapeutic agents included. Ocular SBPs may include ocular therapeutic agent concentrations [expressed as percentage of ocular therapeutic agent weight contributing to total SBP weight] of from about 0.1% to about 98% (w/w). For example, SBPs may include ocular therapeutic agents at a concentration of from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 5% (w/w) to about 85% (w/w), from about 8% (w/w) to about 24% (w/w), from about 10% (w/w) to about 30% (w/w), from about 12% (w/w) to about 32% (w/w), from about 14% (w/w) to about 34% (w/w), from about 15% (w/w) to about 95% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35% (w/w) to about 55% (w/w), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/w), from about 90% (w/w) to about 98% (w/w), from about 95% (w/w) to about 99% (w/w), from about 96% (w/w) to about 99.2% (w/w), or from about 97% (w/w) to about 98% (w/w). The SBPs may include a ratio of ocular therapeutic agent (by weight, volume, or concentration) to processed silk (by weight, volume, or concentration) of from about 0.001:1 to about 1:1, from about 0.005:1 to about 5:1, from about 0.01:1 to about 1:1, from about 0.01:1 to about 4.2:1, from about 0.01:1 to about 10:1, from about 0.02:1 to about 20:1, from about 0.03:1 to about 30:1, from about 0.04:1 to about 40:1, from about 0.05:1 to about 50:1, from about 0.06:1 to about 60:1, from about 0.07:1 to about 70:1, from about 0.08:1 to about 80:1, from about 0.09:1 to about 90:1, from about 0.1:1 to about 100:1, from about 0.2:1 to about 150:1, from about 0.3:1 to about 200:1, from about 0.3:1 to about 4.2:1, from about 0.4:1 to about 250:1, from about 0.5:1 to about 300:1, from about 0.6:1 to about 350:1, from about 0.7:1 to about 400:1, from about 0.8:1 to about 450:1, from about 0.9:1 to about 500:1, from about 1:1 to about 4.2:1, from about 1:1 to about 550:1, from about 2:1 to about 600:1, from about 3:1 to about 650:1, from about 4:1 to about 700:1, from about 5:1 to about 750:1, from about 6:1 to about 800:1, from about 7:1 to about 850:1, from about 8:1 to about 900:1, from about 9:1 to about 950:1, from about 10:1 to about 960:1, from about 50:1 to about 970:1, from about 100:1 to about 980:1, from about 200:1 to about 990:1, or from about 500:1 to about 1000:1. The processed silk may be or include silk fibroin.

Ocular SBPs may include one or more excipients. The excipients may include any of those described herein. In some embodiments, the excipients include one or more of lactose, sorbitol, sucrose, mannitol, lactose USP, Starch 1500, microcrystalline cellulose, Avicel, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, hydrochloric acid, dibasic calcium phosphate dehydrate, tartaric acid, citric acid, fumaric acid, succinic acid, malic acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. SBPs may include at least one excipient at a concentration of from about 1% to about 20% (w/w). In some embodiments, SBPs include at least one excipient at a concentration of from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%. SBPs may include a ratio of ocular therapeutic agent (by weight, volume, or concentration) to at least one excipient (by weight, volume, or concentration) of from about 0.001:1 to about 1:1, from about 0.005:1 to about 5:1, from about 0.01:1 to about 0.5:1, from about 0.01:1 to about 10:1, from about 0.02:1 to about 20:1, from about 0.03:1 to about 30:1, from about 0.04:1 to about 40:1, from about 0.05:1 to about 50:1, from about 0.06:1 to about 60:1, from about 0.07:1 to about 70:1, from about 0.08:1 to about 80:1, from about 0.09:1 to about 90:1, from about 0.1:1 to about 100:1, from about 0.2:1 to about 150:1, from about 0.3:1 to about 200:1, from about 0.4:1 to about 250:1, from about 0.5:1 to about 300:1, from about 0.6:1 to about 350:1, from about 0.7:1 to about 400:1, from about 0.8:1 to about 450:1, from about 0.9:1 to about 500:1, from about 1:1 to about 550:1, from about 2:1 to about 600:1, from about 3:1 to about 650:1, from about 4:1 to about 700:1, from about 5:1 to about 750:1, from about 6:1 to about 800:1, from about 7:1 to about 850:1, from about 8:1 to about 900:1, from about 9:1 to about 950:1, from about 10:1 to about 960:1, from about 50:1 to about 970:1, from about 100:1 to about 980:1, from about 200:1 to about 990:1, or from about 500:1 to about 1000:1. In some embodiments, ocular SBPs contain trace amounts of excipient. In some embodiments, the excipient is phosphate buffer or phosphate buffered saline.

Ocular SBPs may have a density of from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 0.7 g/mL to about 1.4 g/mL, from about 1 g/mL to about 5 g/mL, from about 2 g/mL to about 10 g/mL, from about 4 g/mL to about 16 g/mL, from about 5 g/mL to about 20 g/mL, from about 8 g/mL to about 24 g/mL, from about 10 g/mL to about 30 g/mL, from about 12 g/mL to about 32 g/mL, from about 14 g/mL to about 34 g/mL, from about 16 g/mL to about 36 g/mL, from about 18 g/mL to about 38 g/mL, from about 20 g/mL to about 40 g/mL, from about 22 g/mL to about 42 g/mL, from about 24 g/mL to about 44 g/mL, from about 26 g/mL to about 46 g/mL, from about 28 g/mL to about 48 g/mL, from about 30 g/mL to about 50 g/mL, from about 35 g/mL to about 55 g/mL, from about 40 g/mL to about 60 g/mL, from about 45 g/mL to about 65 g/mL, from about 50 g/mL to about 75 g/mL, from about 60 g/mL to about 240 g/mL, from about 70 g/mL to about 350 g/mL, from about 80 g/mL to about 400 g/mL, from about 90 g/mL to about 450 g/mL, or from about 100 g/mL to about 500 g/mL.

Ocular SBPs may be in the shape of a rod. Such SBPs may include a diameter of from about 0.05 μm to about 10 μm, from about 1 μm to about 20 μm, from about 2 μm to about 30 μm, from about 5 μm to about 40 μm, from about 10 μm to about 50 μm, from about 20 μm to about 60 μm, from about 30 μm to about 70 μm, from about 40 μm to about 80 μm, from about 50 μm to about 90 μm, from about 45 μm to about 100 μm, from about 50 μm to about 110 μm, from about 55 μm to about 120 μm, from about 60 μm to about 130 μm, from about 65 μm to about 140 μm, from about 70 μm to about 150 μm, from about 75 μm to about 160 μm, from about 80 μm to about 170 μm, from about 85 μm to about 180 μm, from about 90 μm to about 190 μm, from about 95 μm to about 200 μm, from about 100 μm to about 210 μm, from about 115 μm to about 220 μm, from about 125 μm to about 240 μm, from about 135 μm to about 260 μm, from about 145 μm to about 280 μm, from about 155 μm to about 300 μm, from about 165 μm to about 320 μm, from about 175 μm to about 340 μm, from about 185 μm to about 360 μm, from about 195 μm to about 380 μm, from about 205 μm to about 400 μm, from about 215 μm to about 420 μm, from about 225 μm to about 440 μm, from about 235 μm to about 460 μm, from about 245 μm to about 500 μm, from about 0.05 mm to about 2 mm, from about 0.1 mm to about 1.5 mm, from about 0.1 mm to about 3 mm, from about 0.2 mm to about 4 mm, from about 0.3 mm to about 1.2 mm, from about 0.5 mm to about 5 mm, from about 1 mm to about 6 mm, from about 2 mm to about 7 mm, or from about 5 mm to about 10 mm. SBP rods may have a length of from about 0.05 mm to about 2 mm, from about 0.1 mm to about 3 mm, from about 0.2 mm to about 4 mm, from about 0.3 mm to about 1.2 mm, from about 0.5 mm to about 5 mm, from about 1 mm to about 6 mm, from about 2 mm to about 7 mm, from about 5 mm to about 10 mm, from about 8 mm to about 12 mm, from about 10 mm to about 15 mm, from about 12 mm to about 18 mm, from about 15 mm to about 25 mm, or from about 20 mm to about 30 mm.

Ocular SBPs may be hydrogels. Such SBPs may include at least one excipient selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremaphor EL), cremaphor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa.

The SBPs may have an osmotic concentration of from about 1 mOsm to about 10 mOsm, from about 2 mOsm to about 20 mOsm, from about 3 mOsm to about 30 mOsm, from about 4 mOsm to about 40 mOsm, from about 5 mOsm to about 50 mOsm, from about 6 mOsm to about 60 mOsm, from about 7 mOsm to about 70 mOsm, from about 8 mOsm to about 80 mOsm, from about 9 mOsm to about 90 mOsm, from about 10 mOsm to about 100 mOsm, from about 15 mOsm to about 150 mOsm, from about 25 mOsm to about 200 mOsm, from about 35 mOsm to about 250 mOsm, from about 45 mOsm to about 300 mOsm, from about 55 mOsm to about 350 mOsm, from about 65 mOsm to about 400 mOsm, from about 75 mOsm to about 450 mOsm, from about 85 mOsm to about 500 mOsm, from about 125 mOsm to about 600 mOsm, from about 175 mOsm to about 700 mOsm, from about 225 mOsm to about 800 mOsm, from about 275 mOsm to about 285 mOsm, from about 280 mOsm to about 900 mOsm, or from about 325 mOsm to about 1000 mOsm.

The SBPs may have an osmolarity of from about 1 mOsm/L to about 10 mOsm/L, from about 2 mOsm/L to about 20 mOsm/L, from about 3 mOsm/L to about 30 mOsm/L, from about 4 mOsm/L to about 40 mOsm/L, from about 5 mOsm/L to about 50 mOsm/L, from about 6 mOsm/L to about 60 mOsm/L, from about 7 mOsm/L to about 70 mOsm/L, from about 8 mOsm/L to about 80 mOsm/L, from about 9 mOsm/L to about 90 mOsm/L, from about 10 mOsm/L to about 100 mOsm/L, from about 15 mOsm/L to about 150 mOsm/L, from about 25 mOsm/L to about 200 mOsm/L, from about 35 mOsm/L to about 250 mOsm/L, from about 45 mOsm/L to about 300 mOsm/L, from about 55 mOsm/L to about 350 mOsm/L, from about 65 mOsm/L to about 400 mOsm/L, from about 75 mOsm/L to about 450 mOsm/L, from about 85 mOsm/L to about 500 mOsm/L, from about 125 mOsm/L to about 600 mOsm/L, from about 175 mOsm/L to about 700 mOsm/L, from about 225 mOsm/L to about 800 mOsm/L, from about 275 mOsm/L to about 285 mOsm/L, from about 280 mOsm/L to about 900 mOsm/L, or from about 325 mOsm/L to about 1000 mOsm/L.

In some embodiment, the SBP formulation has an osmolarity from about 280-320 mOsm/L.

In some embodiment, the SBP formulation has an osmolarity from about 290-320 mOsm/L.

In some embodiment, the SBP formulation has an osmolarity of 280 mOsm/L.

In some embodiment, the SBP formulation has an osmolarity of 290 mOsm/L. Ocular SBPs may have a pH from about 3 to about 10. In some embodiments, the pH is from about 3 to about 6, from about 6 to about 8, or from about 8 to about 10. In some embodiments, the pH of the SBP is about 7.4.

Ocular SBPs may include silk fibroin. The silk fibroin may be included at a concentration (w/w or w/v) of 0.01% to about 1%, from about 0.05% to about 2%, from about 0.1% to about 30%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%. SBPs may include a ratio of silk fibroin (by weight, volume, or concentration) to at least one excipient and/or ocular therapeutic agent (by weight, volume, or concentration) of from about 0.001:1 to about 1:1, from about 0.005:1 to about 5:1, from about 0.01:1 to about 0.5:1, from about 0.01:1 to about 10:1, from about 0.02:1 to about 20:1, from about 0.03:1 to about 30:1, from about 0.04:1 to about 40:1, from about 0.05:1 to about 50:1, from about 0.06:1 to about 60:1, from about 0.07:1 to about 70:1, from about 0.08:1 to about 80:1, from about 0.09:1 to about 90:1, from about 0.1:1 to about 100:1, from about 0.2:1 to about 150:1, from about 0.3:1 to about 200:1, from about 0.4:1 to about 250:1, from about 0.5:1 to about 300:1, from about 0.6:1 to about 350:1, from about 0.7:1 to about 400:1, from about 0.8:1 to about 450:1, from about 0.9:1 to about 500:1, from about 1:1 to about 550:1, from about 2:1 to about 600:1, from about 3:1 to about 650:1, from about 4:1 to about 700:1, from about 5:1 to about 750:1, from about 6:1 to about 800:1, from about 7:1 to about 850:1, from about 8:1 to about 900:1, from about 9:1 to about 950:1, from about 10:1 to about 960:1, from about 50:1 to about 970:1, from about 100:1 to about 980:1, from about 200:1 to about 990:1, or from about 500:1 to about 1000:1. In some embodiments, ocular SBPs contain trace amounts of excipient. In some embodiments, the excipient is phosphate buffer or phosphate buffered saline.

SBP viscosity may be modulated by modulating silk fibroin molecular weight and/or concentration. In some embodiments, SBP viscosity increases with increasing levels of silk fibroin. In some embodiments, SBP viscosity may be tuned by the molecular weight of processed silk, as defined by the minute boil. In some embodiments, the viscosity of an SBP is proportional to the molecular weight of the processed silk. In some embodiments, the viscosity of an SBP is from about 7 Pa s-1 to about 170 Pa s-1. In some embodiments, the viscosity of an SBP is from about 5 Pa s-1 to about 200 Pa s-1. In some embodiments, the viscosity of an SBP is from about 5 Pa s-1 to about 25 Pa s-1, from about 25 Pa s-1 to about 50 Pa s-1, from about 50 Pa s-1 to about 75 Pa s-1, from about 75 Pa s-1 to about 100 Pa s-1, from about 100 Pa s-1 to about 125 Pa s-1, from about 125 Pa s-1 to about 150 Pa s-1, from about 150 Pa s-1 to about 175 Pa s-1, or from about 175 Pa s-1 to about 200 Pa s-1. In some embodiments, the stiffness of the SBP may be tuned with the molecular weight of the processed silk. In some embodiments, a preparation of an SBP from processed silk with a longer boiling time may enhance the stiffness of the SBP. In some embodiments, the viscosity and/or the stiffness of the SBP may be modulated without altering the release kinetics of a therapeutic agent from the SBP.

In some embodiments, ocular SBPs are formulated for intraocular administration. In some embodiments, ocular SBPs are formulated for one or more of intravitreal administration, intraretinal administration, intracorneal administration, intrascleral administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Ocular SBPs may be biocompatible, well tolerated, and/or non-immunogenic.

In some embodiments, the present disclosure provides methods of treating subjects by contacting them with ocular SBPs. The subjects may have, may be suspected of having, and/or may be at risk for developing one or more ocular indications. Such ocular indications may include any of those described herein. In some embodiments, ocular indications include inflammation. In some embodiments, ocular indications include one or more of an infection, refractive errors, macular edema, age related macular degeneration, cystoid macular edema, cataracts, diabetic retinopathy (proliferative and non-proliferative), glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorder, conjunctivitis, cancer, corneal ulcer, corneal abrasion, snow blindness, scleritis, keratitis, Thygeson's superficial punctate keratopathy, corneal neovascularization, Fuch's dystrophy, keratoconjunctivitis sicca, iritis, chorioretinal inflammation (e.g. chorioretinitis, choroiditis, retinitis, retinochoroiditis, pars planitis, Harada's disease, aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, retinal vein occlusion, and separation of retinal layers.

In some embodiments, the ocular indication is DME. In some embodiments, the ocular indication is diabetic retinopathy. In some embodiments, the ocular indication is non-proliferative diabetic retinopathy.

In some embodiments, the SBPs of the present disclosure may be administered to treat subjects with diabetic macular edema. In some embodiments, the SBPs of the present disclosure may be used to treat diabetic retinopathy in subjects with DME. In some embodiments, DME is non-proliferative. In some embodiments, diabetic retinopathy is non-proliferative (NPDR). In some embodiments SBPs of the present disclosure may be used to achieve the sustained release of one or more known NSAID with intravitreal triamcinolone (IVT). In some embodiments, SBPs of the present disclosure may be used to achieve the sustained release of one or more known NSAID with intravitreal triamcinolone acetonide. In some embodiments, the SBP comprises one or more NSAID and is administered alongside intravitreal triamcinolone or triamcinolone acetonide. In some embodiments, the SBP comprises one or more NSAID and triamcinolone or triamcinolone acetonide. In some embodiments, the mechanism of action of the treatment is novel compared to that of existing treatments of NPDR (e.g. VEGF or steroids). In some embodiments, the mechanism of action of the treatment is additive to that of VEGF antagonist with respect to the mean improvement in BCVA ETDRS. In some embodiments, the mechanism of action of the treatment is additive to that of VEGF alone with respect to the mean improvement in BCVA ETDRS. In some embodiments, the efficacy of the treatment is similar to that of intravitreal triamcinolone or triamcinolone acetonide. In some embodiments, the efficacy of the treatment is improved over that of intravitreal triamcinolone or triamcinolone acetonide. In some embodiments, the safety of the treatment is improved over that of intravitreal triamcinolone or triamcinolone acetonide. In some embodiments, the adverse event burden is better or similar to that of a VEGF antagonist. In some embodiments, the adverse event burden is better than that of an IVT steroid. In some embodiments, the SBP is administered via injection. In some embodiments, the SBP is administered every 6 months. In some embodiments, the SBP is administered every 3 months.

In some embodiments, subjects with NPDR may be evaluated as a part of a population of subjects with DME. In some embodiments, SBPs of the present disclosure may be administered adjunctive with a VEGF antagonist. In some embodiments, SPBs of the present disclosure may be administered adjunctive with VEGF and/or VEGF sub-optimal responders. In some embodiments, treatment of DME and DME in subjects with NPDR may be measured by refraction and Best Corrected Visual Acuity using Early Treatment in Diabetic Retinopathy Study Methodology (BCVA ETDRS). In some embodiments, treatment is measured by the mean change in BCVA ETDRS score at 9 months. In some embodiments, the treatment with SBPs results in an improvement in NPDR score. In some embodiments, the improvement is at least two steps.

Methods of treating subjects with ocular SBPs may include one or more of oral administration, intravenous administration, topical administration, and ocular administration. Ocular administration may include one or more of intravitreal administration, intraretinal administration, intracorneal administration, intrascleral administration, administration to the anterior segment, administration to the posterior segment, and intra-aqueous humor administration. In some embodiments, the SBP adheres to the ocular surface. In some embodiments, the SBP adheres to the ocular surface in a manner similar to a mucin layer. Intravitreal administration may include intravitreal injection. Intravitreal administration may be performed at any injection site that would enable the administration of the SBP to the intravitreal space. Intravitreal injection may be performed by pushing a wire through a syringe and needle or cannula loaded with ocular SBP. The wire may be pushed until it extends past the needle or cannula.

In some embodiments, the residence time of an SBP will be analyzed after SBP administration, using any method known to one skilled in the art. In some embodiments, the efficacy of an SBP will be analyzed after SBP administration, using any method known to one skilled in the art. In some embodiments, the pharmacokinetics of an SBP will be analyzed after SBP administration, using any method known to one skilled in the art. In some embodiments, the irritability of an SBP will be analyzed after SBP administration, using any method known to one skilled in the art. In some embodiments, the use of an SBP to treat irritation will be analyzed after SBP administration, using any method known to one skilled in the art. In some embodiments, the toxicity of an SBP will be analyzed after SBP administration, using any method known to one skilled in the art.

Ocular SBPs may be used to treat subjects by delivering ocular therapeutic agents at a dose of from about 0.01 μg to about 1 μg, from about 0.05 μg to about 2 μg, from about 1 μg to about 5 μg, from about 2 μg to about 10 μg, from about 4 μg to about 16 μg, from about 5 μg to about 20 μg, from about 8 μg to about 24 μg, from about 10 μg to about 30 μg, from about 12 μg to about 32 μg, from about 14 μg to about 34 μg, from about 16 μg to about 36 μg, from about 18 μg to about 38 μg, from about 20 μg to about 40 μg, from about 22 μg to about 42 μg, from about 24 μg to about 44 μg, from about 26 μg to about 46 μg, from about 28 μg to about 48 μg, from about 30 μg to about 50 μg, from about 35 μg to about 55 μg, from about 40 μg to about 60 μg, from about 45 μg to about 65 μg, from about 50 μg to about 75 μg, from about 60 μg to about 240 μg, from about 70 μg to about 350 μg, from about 80 μg to about 400 μg, from about 90 μg to about 450 μg, from about 100 μg to about 500 μg, from about 200 μg to about 750 μg, from about 300 μg to about 1000 μg, from about 1 μg to about 5000 μg, or from about 500 μg to about 5000 μg. In some embodiments, subjects are contacted with a dose of ocular therapeutic agents sufficient to achieve concentrations in subject eyes (or components of subject eyes) greater than or equal to the effective concentration for such ocular therapeutic agents. The concentrations may be 1.5-fold, 2-fold, 4-fold, 5-fold, 10-fold, or more than 10-fold greater than the effective concentration.

In some embodiments, contacting subjects with ocular SBPs results in ocular therapeutic agent concentrations in subject eyes of from about 0.01 ng/mL to about 70,000 ng/ml. In some embodiments, the resulting concentration in subject eyes is from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 μg/mL to about 1 μg/mL, from about 0.05 μg/mL to about 2 μg/mL, from about 1 μg/mL to about 5 μg/mL, from about 2 μg/mL to about 10 μg/mL, from about 4 μg/mL to about 16 μg/mL, from about 5 μg/mL to about 20 μg/mL, from about 8 μg/mL to about 24 μg/mL, from about 10 μg/mL to about 30 μg/mL, from about 12 μg/mL to about 32 μg/mL, from about 14 μg/mL to about 34 μg/mL, from about 16 μg/mL to about 36 μg/mL, from about 18 μg/mL to about 38 μg/mL, from about 20 μg/mL to about 40 μg/mL, from about 22 μg/mL to about 42 μg/mL, from about 24 μg/mL to about 44 μg/mL, from about 26 μg/mL to about 46 μg/mL, from about 28 μg/mL to about 48 μg/mL, from about 30 μg/mL to about 50 μg/mL, from about 35 μg/mL to about 55 μg/mL, from about 40 μg/mL to about 60 μg/mL, from about 45 μg/mL to about 65 μg/mL, from about 50 μg/mL to about 75 μg/mL, from about 60 μg/mL to about 240 μg/mL, from about 70 μg/mL to about 350 μg/mL, from about 80 μg/mL to about 400 μg/mL, from about 90 μg/mL to about 450 μg/mL, from about 100 μg/mL to about 500 μg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 35 mg/mL, or from about 35 mg/mL to about 70 mg/mL. The ocular therapeutic agent concentration in subject eyes may include concentration in one or more eye components. The components may include, but are not limited to, the aqueous humor, vitreous humor, retina, choroid, sclera, lens, fornix, conjunctiva, lacrimal punctum, capsule of Tenon, iris, pupal, cornea, ciliary muscle, fovea, optic nerve, macula, blood vessel, anterior chamber, posterior chamber, and sub-tenon space. In some embodiments, contacting subjects with ocular SBPs may result in ocular therapeutic agent concentration in subject aqueous humor of from about 0.01 ng/mL to about 2.0 ng/mL. In some embodiments, vitreous humor concentration may be from about 10 ng/mL to about 20,000 ng/ml. In some embodiments, retina and/or choroid concentrations may be from about 10 ng/mL to about 70,000 ng/mL. Ocular therapeutic agent levels may be detectable in subject eyes for at least 1 day, for at least 2 days, for at least 3 days, for at least 1 week, for at least 2 weeks, for at least 1 month, for at least 3 months, for at least 6 months, or for at least 1 year. In some embodiments, ocular therapeutic agent levels remain at a steady level for at least 1 day, for at least 2 days, for at least 3 days, for at least 1 week, for at least 2 weeks, for at least 1 month, for at least 3 months, for at least 6 months, or for at least 1 year. In some embodiments, the concentration of the ocular therapeutic agent in the subject eye or component of the eye is at a level at or near the effective concentration. In some embodiments, the concentration of the ocular therapeutic agent in the subject eye or component of the eye is sustained at a level at or near the effective concentration. In some embodiments, the concentration of the ocular therapeutic agent in the subject eye or component of the eye is sustained at a level greater than the effective concentration. In some embodiments the effective concentration is the IC50, the EC50, or the EC80.

In some embodiments, the ocular SBPs may be hydrogels. In some embodiments, the ocular SBPs are rods. In some embodiments, the ocular SBPs are administered via intravitreal administration. In some embodiments, the ocular SBPs are formulated with celecoxib. In some embodiments, the intravitreal administration of the ocular SBPs enables at least 3 months of sustained release at or above the effective concentration of celecoxib. In some embodiments, the intravitreal administration of the ocular SBPs enables at least 6 months of sustained release at or above the effective concentration of celecoxib. In some embodiments the effective concentration is the IC50. In some embodiments, the effective concentration is the EC80. In some embodiments, the IC50 is 40 nM. In some embodiments, the EC80 is 1-3 μM.

In some embodiments, ocular SBPs may be used to reduce ocular pressure. In some embodiments, the intravitreal administration of the ocular SBPs results in a sustained intraocular pressure. In some embodiments, the reduced or sustained intraocular pressure may be observed for at least 1 day, at least 3 days, at least 1 week, at least 2 weeks, at least 1 month, at least 3 months, at least 4 months, at least 6 months, or at least 1 year after SBP administration.

In some embodiments, the ocular SBPs of the present disclosure are biocompatible in the ocular space. In some embodiments, administration of the ocular SBP does not cause local inflammation in the ocular space. In some embodiments, the SBP is tolerable in the ocular space. In some embodiments, the retinal tissue remains normal after the administration of the ocular SBP. In some embodiments, the SBPs are biocompatible and tolerable in the ocular space for at least 1 day, at least 3 days, at least 1 week, at least 2 weeks, at least 1 month, at least 3 months, at least 4 months, at least 6 months, or at least 1 year.

In some embodiments, the present disclosure provides methods of delivering ocular therapeutic agents to subjects by contacting subject eyes with ocular SBPs. Such ocular SBPs may be prepared by combining processed silk with ocular therapeutic agents. The SBPs may be prepared with a low temperature, aqueous processing procedure. The SBPs may be prepared as rods. The rods may be prepared by extrusion through a tube. The tube may be a needle. Extrusion may be carried out using a syringe. Ocular therapeutic agents may be delivered to subject eyes by release from SBPs while SBPs are in contact with the eyes. Release of ocular therapeutic agents from SBPs may be modulated by one or more of silk fibroin concentration, silk fibroin molecular weight, SBP volume, method used to dry SBPs, ocular therapeutic agent molecular weight, and inclusion of at least one excipient. Methods used to dry SBPs may include one or more of oven drying, lyophilizing, and air drying. In some embodiments, an ocular SBP is prepared as a gel, before drying to obtain the SBP in a rod format. Ocular SBP rods may include ocular therapeutic agents and silk fibroin at a w/w ratio of from about 1 to about 5.

Release of ocular therapeutic agents from ocular SBPs may occur at a rate that includes an initial burst. From about 0.01% to about 100% of ocular therapeutic agents may be released from SBPs during an initial release period associated with the initial burst. In some embodiments, from about 5% to about 20% of ocular therapeutic agents may be released from SBPs during an initial release period associated with the initial burst. Release of ocular therapeutic agent from SBPs may include a daily release percentage of from about 0.1% (w/w) to about 5% (w/w). In some embodiments the release rates of the therapeutic agents are tunable. In some embodiments, the release rates are tunable on the order of days to weeks. In some embodiments the release rates are tunable on the order of weeks to months.

In some embodiments, the release rates are tuned by varying the API loading, the silk fibroin molecular weight, the silk fibroin concentration, the drying method, and the density of the ocular SBP during formulation. In some embodiments, the release kinetics of an API from an SBP may be tuned by the density of the SBP. In some embodiments, the daily release percentage and the initial burst may be decreased by preparation of a denser SBP. In some embodiments, the release kinetics of an API from an SBP may be tuned by the concentration of processed silk in the SBP. In some embodiments, the daily release percentage and the initial burst may be decreased by preparation with a higher concentration of processed silk. In some embodiments, the release of an API from an ocular SBP is biphasic, in that the release rate changes between two portions of the study.

In some embodiments, from about 1% to about 100% of ocular therapeutic agents are released from ocular SBPs during a release period. The release period may be from about 1 day to about 10 months. The release period may begin upon contacting an eye of a subject with an SBP. The release period may be from about 1 day to about 5 months. The release period may be from about 1 day to about 6 months. In some embodiments, the API is released over a period of at least 1 day, for at least 2 days, for at least 3 days, for at least 1 week, for at least 2 weeks, for at least 1 month, for at least 3 months, for at least 6 months, or for at least 1 year. In some embodiments, 0.1%-100% of ocular therapeutic agents may be released from SBPs over release periods. In some embodiments, from about 40% to about 60% of ocular therapeutic agents may be released from SBPs over release periods. The ocular therapeutic agents may be released from the ocular SBPs via diffusion, degradation, and/or solvent penetration. In some embodiments, the release of the therapeutic agents from ocular SBPs follows first order kinetics. In some embodiments, the release of therapeutic agents from ocular SBPs follows zero order kinetics. In some embodiments the release periods of the therapeutic agents are tunable. In some embodiments, the release rates are tunable on the order of days to weeks. In some embodiments the release periods are tunable on the order of weeks to months. In some embodiments, the release periods are tuned by varying the API loading, API hydrophobicity, API molecular weight, the silk fibroin molecular weight, the silk fibroin concentration, the hydrophobicity of the SBP formulation, depot surface area, matrix porosity/density, and/or the density of the ocular SBP during formulation. In some embodiments, the therapeutic agent is an NSAID. In some embodiments, the SBP formulated with NSAID has a release period of at least 1 day, at least 3 days, at least 1 week, at least 1 month, at least 3 months, at least 6 months, or at least 1 year in vitro. In some embodiments, the SBP formulated with NSAID has a release period of at least 1 day, at least 3 days, at least 1 week, at least 1 month, at least 3 months, at least 6 months, or at least 1 year in vivo.

In some embodiments, the ocular SBP is a rod, and the release duration of CXB is related to the rod density. In some embodiments, increased density of a rod results in increased release times. In some embodiments, the density of the rod is tuned by varying the starting concentration of the silk-fibroin used during formulation. In some embodiments, the rods with a density below 1.0 g/mL reach complete release about 64 days or less. In some embodiments, the rods with a density between 1.0 g/mL and 1.1 g/mL reach complete release in about 98 days. In some embodiments, the rods with a density above 1.1 g/mL reach complete release in greater than 98 days.

In some embodiments, the ocular SBP may comprise one of more of the following components: silk fibroin, one or more excipients, a nonsteroidal anti-inflammatory drug, and Tween-80. Such ocular SBP may be formatted as hydrogels or rods.

In some embodiments, the ocular SBP comprises one of more of the following components: silk fibroin, poloxamer 188 (P188), celecoxib (CXB), phosphate buffer, and Tween-80. The silk fibroin may be present in a concentration between 1 to 5% (w/v). The silk fibroin may have a minute boil in the range of 120 to 480. Poloxamer 188 (P188) may be present in a concentration between 1 to 30% (w/v). Celecoxib (CXB) may be present in a concentration between 0.1 to 20% (w/v). The phosphate buffer may be present in the concentration between 10 to 30 mM. The phosphate buffer may have a pH between 7.2 to 7.6. Tween-80 may be present in a concentration between 0.1 to 0.5%. The ocular SBP may have an osmolarity between 280 to 300 mOsm/L. Such ocular SBP may be formatted as hydrogels.

As a non-limiting example, the ocular SBP comprises about 3% (w/v) silk fibroin with a 480-minute boil, about 10% poloxamer 188 (P188), about 10% celecoxib (CXB), about 22 mM phosphate buffer with a pH of 7.4, and about 0.2% Tween-80, and the ocular SBP has an osmolarity of about 290 mOsm/L and is formatted as hydrogels.

II. Therapeutic Applications

In some embodiments, SBPs may be used in a variety of therapeutic applications. As used herein, the term "therapeutic application" refers to any method related to restoring or promoting the health, nutrition, and/or wellbeing of a subject; supporting or promoting reproduction in a subject; or treating, preventing, mitigating, alleviating, curing, or diagnosing a disease, disorder, or condition. As used herein, the term "condition" refers to a physical state of wellbeing. Therapeutic applications may include, but are not limited to, medical applications, surgical applications, and veterinary applications. As used herein, the term "medical application" refers to any method or use that involves treating, diagnosing, and/or preventing disease according to the science of medicine. "Surgical applications" refer to methods of treatment and/or diagnosis that involve operation on a subject, typically requiring incision and the use of instruments. "Veterinary applications" refer to therapeutic applications where the subject is a non-human animal. In some embodiments, therapeutic applications may include, but are not limited to, experimental, diagnostic, or prophylactic applications. In some embodiments, therapeutic applications include preparation and/or use of therapeutic devices. As used herein, the term "therapeutic device" refers to any article prepared or modified for therapeutic use.

SBPs used for therapeutic applications may include or may be combined with one or more pharmaceutical compositions, implants, therapeutic agents, coatings, excipients, or devices. In some embodiments, SBPs facilitate the delivery and/or controlled release of therapeutic agent payloads. In some embodiments, SBPs described herein may be used to stabilize therapeutic agents. Some SBPs may be used as tools, materials, or devices in therapeutic applications. Such SBPs may include, but are not limited to, delivery vehicles, and scaffolds.

Subjects

Therapeutic applications of the present disclosure may be applied to a variety of subjects. As used herein, the term "subject" refers to any entity to which a particular process or activity relates to or is applied. Subjects of therapeutic applications described herein may be human or non-human. Human subjects may include humans of different ages, genders, races, nationalities, or health status. Non-human subjects may include non-human animal subjects (also simply referred to herein as "animal subjects"). Animal subjects may be non-human vertebrates or invertebrates. Some animal subjects may be wild type or genetically modified organisms (e.g., transgenic). In some embodiments, subjects include patients. As used herein, the term "patient" refers to a subject seeking treatment, in need of treatment, requiring treatment, receiving treatment, expecting treatment, or who is under the care of a trained (e.g., licensed) professional for a particular disease, disorder, and/or condition.

Veterinary Applications

In some embodiments, SBPs may be used in veterinary applications to restore or promote the health and/or wellbeing of a non-human animal subject and/or to treat, prevent, alleviate, cure, or diagnose a disease, disorder, or condition of a non-human animal subject. As a non-limiting example, the SBPs may be used for companion animal health. As another non-limiting example, the SBPs may be used for farm animal health.

In one embodiment, the veterinary indication is dry eye disease.

Therapeutic Agents

In some embodiments, therapeutic applications involve the use of SBPs that are therapeutic agents or are combined with one or more therapeutic agents. As used herein, the term "therapeutic agent" refers to any substance used to restore or promote the health and/or wellbeing of a subject and/or to treat, prevent, alleviate, cure, or diagnose a disease, disorder, or condition. Examples of therapeutic agents include, but are not limited to, adjuvants, analgesic agents, antiallergic agents, antiangiogenic agents, antiarrhythmic agents, antibacterial agents, antibiotics, antibodies, anticancer agents, anticoagulants, antidementia agents, antidepressants, antidiabetic agents, antigens, antihypertensive agents, anti-infective agents, anti-inflammatory agents, antioxidants, antipyretic agents, anti-rejection agents, antiseptic agents, antitumor agents, antiulcer agents, antiviral agents, biological agents, birth control medication, carbohydrates, cardiotonics, cells, chemotherapeutic agents, cholesterol lowering agents, cytokines, endostatins, enzymes, fats, fatty acids, genetically engineered proteins, glycoproteins, growth factors, health supplements, hematopoietics, herbal preparations, hormones, hypotensive diuretics, immunological agents, inorganic synthetic pharmaceutical drugs, ions, lipoproteins, metals, minerals, nanoparticles, naturally derived proteins, NSAIDs, nucleic acids, nucleotides, organic synthetic pharmaceutical drugs, oxidants, peptides, pills, polysaccharides, proteins, protein-small molecule conjugates or complexes, psychotropic agents, small molecules, sodium channel blockers, statins, steroids, stimulants, therapeutic agents for osteoporosis, therapeutic combinations, thrombopoietics, tranquilizers, vaccines, vasodilators, VEGF-related agents, veterinary agents, viruses, virus particles, and vitamins. Other therapeutic agents may include, but are not limited to, anthocyanidin, anthoxanthin, apigenin, dihydrokaempferol, eriodictyol, fisetin, flavan, flavan-3,4-diol, flavan-3-ol, flavan-4-ol, flavanone, flavanonol, flavonoid, furanoflavonols, galangin, hesperetin, homoeriodictyol, isoflavonoid, isorhamnetin, kaempferol, luteolin, myricetin, naringenin, neoflavonoid, pachypodol, proanthocyanidins, pyranoflavonols, quercetin, rhamnazin, tangeritin, taxifolin, theaflavin, thearubigin, chondrocyte-derived extracellular matrix, macrolide, erythromycin, roxithromycin, azithromycin and clarithromycin. In some embodiments, SBP therapeutics and methods of delivery may include any of those taught in International Publication Numbers WO2017139684, WO2010123945, WO2017123383, or United States Publication Numbers US20170340575, US20170368236, and US20110171239 the contents of each of which are herein incorporated by reference in their entirety.

Processed Silk as a Therapeutic Agent

In some embodiments, SBPs that consist of or include processed silk are used as therapeutic agents, wherein processed silk is an active therapeutic component. The processed silk may include, but is not limited to one or more of silk fibroin, fragments of silk fibroin, chemically altered silk fibroin, and mutant silk fibroin. Therapeutic applications including such SBPs may include any of those taught in International Publication Number WO2017200659; Aykac et al. (2017) Gene s0378-1119(17)30865-8; and Abdel-Naby (2017) PLoS One 12(11):e0188154, the contents of each of which are herein incorporated by reference in their entirety. Processed silk may be administered as a therapeutic agent for treatment of a localized indication or for treatment of an indication further from the SBP application site. In some embodiments, therapeutic agents are combinations of processed silk and some other active component. In some embodiments, therapeutic agent activity requires cleavage or dissociation from silk. Therapeutic agents may include silk fibroin and/or chemically modified silk fibroin. In some embodiments, such therapeutic agents may be used to treat burn injury, inflammation, wound healing, or corneal injury. These and other treatments may be carried out according to any of the methods described in International Publication Number WO2017200659; United States Publication Number US20140235554; Aykac et al. (2017) Gene s0378-1119 (17)30868-30865; or Abdel-Naby (2017) PLoS One 12(11): e0188154, the contents of each of which are herein incorporated by reference in their entirety. In some embodiments, SBPs are silk fibroin solutions used to facilitate wound healing, as described in Park et al. (2017) Acta Biomater 67:183-195, the contents of which are herein incorporated by reference in their entirety. These SBPs may enhance wound healing via a nuclear factor kappa enhancer binding protein (NF-κB) signaling pathway. In some embodiments, SBPs are therapeutic agents used to facilitate delivery and/or release of therapeutic agent payloads. Such therapeutic agents and/or methods of use may include, but are not limited to, any of those described in International Publication Number WO2017139684, the contents of which are herein incorporated by reference in their entirety.

Lubricants

In some embodiments, processed silk and/or SBPs may be used as a lubricant. In some embodiments, processed silk may be selected base on or prepared to maximize its use as a lubricant. As used herein, the term "lubricant" refers to a substance that reduces the friction between two or more surfaces. In some embodiments, the surfaces in need of lubrication may be part of a subject. In some embodiments, surfaces in need of lubrication include, but are not limited to, the body, eyes, skin, scalp, mouth, vagina, nose, hands, feet, and lips. In some embodiments, SBPs are used for ocular lubrication. As used herein, the term "ocular lubrication" refers to a method of the reduction of friction and/or irritation in the eye. In some embodiments, processed silk and/or SBPs may be used to reduce friction caused by dryness, as taught in U.S. Pat. No. 9,907,836 (the content of which is herein incorporated by reference in its entirety). This dryness may be dryness in the eye.

In some embodiments, the coefficient of friction of an SBP is approximately that of naturally occurring, biological and/or protein lubricants (e.g. lubricin). In some embodiments, SBPs may be incorporated into a lubricant. Such methods may include any of those presented in International Publication No. WO2013163407, the contents of which are herein incorporated by reference in their entirety. In some embodiments, processed silk and/or SBPs may be used as an excipient. In some embodiments, processed silk and/or SBPs may be used as an excipient to prepare a lubricant.

Biological Agents

In some embodiments, therapeutic agents include biological agents (also referred to as "biologics" or "biologicals"). As used herein, a "biological agent" refers to a therapeutic substance that is or is derived from an organism or virus. Examples of biological agents include, but are not limited to, proteins, organic polymers and macromolecules, carbohydrates, complex carbohydrates, nucleic acids, cells, tissues, organs, organisms, DNA, RNA, oligonucleotides, genes, and lipids. Biological agents may include processed silk.

In some embodiments, SBPs may be used to deliver or administer biological agents. In some embodiments, delivery may include controlled release of one or more biological agents. Delivery may be carried out in vivo. In some embodiments, delivery is in vitro. Processed silk may be used to facilitate delivery and/or maintain stability of biological agents.

In some embodiments, SBPs are used to deliver proteins. Non-limiting examples of proteins that may be delivered with SBPs include monoclonal antibodies, immunoglobulins (e.g., IgG), anti-VEGF antibodies (e.g., AVASTIN®), lysozyme, and bovine serum albumin (BSA). SBPs may provide controlled release of a stable protein over a desired administration period, for example, for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 6 months, at least 9 months, or at least 1 year. In one embodiment, SBPs provide controlled release of a stable protein for at least 7 days.

SBP formulations used for protein delivery may be tailored based on variables such as the molecular weight of the protein to be delivered, the loading of the protein, the molecular weight of the silk fibroin, and the silk fibroin concentration used in the formulations.

Ocular Therapeutic Agents

In some embodiments, therapeutic agents include ocular therapeutic agents. As used herein, the term "ocular therapeutic agent" refers to any compound that has a healing, corrective, diagnostic, and/or prophylactic effect and/or elicits a desired biological and/or pharmacological effect on the eye. In some embodiments, ocular therapeutic agents include one or more of processed silk, biological agents, small molecules, proteins, nonsteroidal anti-inflammatory drugs, and vascular endothelial growth factor-related agents. Ocular therapeutic agent proteins may include, but are not limited to, lysozyme, bovine serum albumin (BSA), bevacizumab, or VEGF-related agents. In some embodiments, ocular therapeutic agents may be used to treat one or more of the ocular therapeutic indications described herein.

Nonsteroidal Anti-Inflammatory Drugs

Therapeutic agents may include nonsteroidal anti-inflammatory drugs. A nonsteroidal anti-inflammatory drug (NSAID) is a class of non-opioid analgesics used to reduce inflammation and associated pain. NSAIDs may include small molecules. NSAIDs may include, but are not limited to, aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, NSAIDs may be used to treat one or more of the ocular therapeutic indications described herein. In some embodiments, the NSAID is celecoxib. Some SBPs include gels or hydrogels that are combined with NSAIDs (e.g., celecoxib). Such SBPs may be used as carriers for NSAID payload delivery. NSAID delivery may include controlled release of the NSAID.

Vascular Endothelial Growth Factor-Related Agents

In some embodiments, therapeutic agents include modulators of angiogenesis. Such therapeutic agents may include vascular endothelial growth factor (VEGF)-related agents. As used herein, the term "VEGF-related agent" refers to any substance that affects VEGF expression, synthesis, stability, biological activity, degradation, receptor binding, cellular signaling, transport, secretion, internalization, concentration, or deposition (e.g., in extracellular matrix). In some embodiments, VEGF-related agents may be used to treat one or more of the ocular therapeutic indications described herein.

In some embodiments, VEGF-related agents are angiogenesis inhibitors. In some embodiments, the angiogenesis inhibitor includes any of those taught in International Publication Number WO2013126799, the contents of which are herein incorporated by reference in their entirety. In some embodiments, VEGF-related agents may include antibodies. VEGF-related agents may include VEGF agonists, including, but not limited to, toll-like receptor agonists. In some embodiments, the therapeutic agent is a VEGF antagonist. VEGF agonists or antagonists may be small molecules. In some embodiments, VEGF agonists or antagonists may be macromolecules or proteins. Angiogenesis inhibitors may include, but are not limited to, MACUGEN® or another VEGF nucleic acid ligand; LUCENTIS®, AVASTIN®, or another anti-VEGF antibody; combretastatin or a derivative or prodrug thereof such as Combretastatin A4 Prodrug (CA4P); VEGF-Trap (Regeneron); EVIZON™ (squalamine lactate); AG-013958 (Pfizer, Inc.); JSM6427 (Jerini AG); a short interfering RNA (siRNA) that inhibits expression of one or more VEGF isoforms (e.g., $VEGF_{165}$); an siRNA that inhibits expression of a VEGF receptor (e.g., VEGFR1), endogenous or synthetic peptides, angiostatin, combstatin, arresten, tumstatin, thalidomide, thalidomide derivatives, canstatin, endostatin, thrombospondin, and 132-glycoprotein 1.

Therapeutic Indications

In some embodiments, SBPs may be used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment).

SBP treatment of therapeutic indications may include contacting subjects with SBPs. SBPs may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

Ocular Indications

In some embodiments, therapeutic indications include ocular indications. As used herein, the term "ocular indication" refers to any therapeutic indication related to the eye. In some embodiments, the therapeutic indication is an ophthalmology or ophthalmology-related disease and/or disorder. Treatment of such indications in subjects may include contacting subjects with SBPs. SBPs may include therapeutic agents (e.g., any of those described herein) as cargo or payloads for treatment. In some embodiments, payload release may occur over a period of time (the payload release period). The payload release rate and/or length of the payload release period may be modulated by SBP components or methods of preparation. In some embodiments, SBPs may be provided in the form of a solution or may be incorporated into a solution for ocular administration. Such solutions may be administered topically (e.g., in the form of drops, creams, or sprays) or by injection. In some embodiments, SBPs may be provided in the format of a lens or may be incorporated into lenses that are placed on eye. In some embodiments, SBPs are provided in the form of implants or are incorporated into implants that may be placed around the eye, on a surface of the eye, in a periocular space or compartment, or intraocularly. Implants may be solid or gelatinous (e.g., a gel or slurry) and may be in the form of a bleb, rod, or plug. Some gelatinous implants may harden after application. In some embodiments, implants include punctal plugs. Such plugs may be inserted into tear ducts. In some embodiments, SBPs may be used to repair ocular damage. In some embodiments, the SBP adheres to the ocular surface. In some embodiments, the SBP adheres to the ocular surface in a manner similar to a mucin layer.

Non-limiting examples of ocular indications include infection, refractive errors, age related macular degeneration, cystoid macular edema, cataracts, diabetic retinopathy (proliferative and non-proliferative), glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorders (e.g. age related macular degeneration), conjunctivitis, cancer, corneal ulcer, corneal abrasion, snow blindness, scleritis, keratitis, Thygeson's superficial punctate keratopathy, corneal neovascularization, Fuch's dystrophy, keratoconjuctitivis sicca, iritis, chorioretinal inflammation (e.g. chorioretinitis, choroiditis, retinitis, retinochoroiditis, pars planitis, and Harada's disease), aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, separation of retinal layers, retinal vein occlusion, and other visual impairments. In some embodiments, ocular indications include inflammation of the eye.

Ocular indications may include dry eye. Dry eye is a condition involving a lack of hydration on the eye surface that may be caused by one or more of a variety of factors (e.g., cellular/tissue dysfunction or environmental irritants). In some embodiments, SBPs used to treat dry eye are provided as or included in solutions or devices. Solutions may be administered topically (e.g., by cream, spray, or drops) or by injection to periocular or intraocular areas. Solutions may include viscous solutions, such as gels or slurries. Devices may include, but are not limited to, implants, lenses, and plugs. Devices may be hardened structures or gelatinous. In some embodiments, devices are gelatinous, but harden after placement. Devices may include lacrimal or punctal plugs that treat dry eye via tear duct insertion. SBPs used to treat dry eye may include therapeutic agent payloads. The therapeutic agents may include any of those described herein. In some embodiments, therapeutic agents include one or more of cyclosporine, corticosteroids, tetracyclines, and essential fatty acids. Therapeutic agent release from SBPs may occur over an extended payload release period. The payload release period may be from about 1 hour to about 48 hours, from about 1 day to about 14 days, or from about 1 week to about 52 weeks, or more than 52 weeks. In some embodiments, ocular SBPs may be used as an anti-inflammatory treatment for dry eye disease, as described in Kim et al. (2017) Scientific Reports 7: 44364, the contents of which are herein incorporated by reference in their entirety. It has been demonstrated that the administration of 0.1 to 0.5% silk fibroin solutions in a mouse model of dry eye disease enhances corneal smoothness and tear production, while reducing the amount of inflammatory markers detected.

Ocular indications may include glaucoma. The term "glaucoma" refers to a group of ocular disorders that cause optic nerve damage, sometimes leading to loss of vision or blindness. Glaucoma is often associated with elevated intraocular pressure. The pressure may be caused by inefficient drainage of intraocular fluid. The optic nerve is sensitive to intraocular pressure and increased pressure can lead to damage. "Refractory glaucoma" refers to glaucoma that persists or is at risk to persist after attempts to reduce intraocular pressure (e.g., surgical intervention).

Ocular indications may include diabetic retinopathy. The term "diabetic retinopathy" refers to the damage to the blood vessels in the back of the eye caused by complications of diabetes. Both type I and type II diabetes can lead to diabetic retinopathy. The early stages of the indication, known as non-proliferative diabetic retinopathy, include weakened blood vessels and microaneurysms. The later stages of the indication, known as proliferative diabetic retinopathy, may lead to a lack of circulation in the retina and improper blood vessel growth.

Ocular indications may include diabetic macular edema. The term "diabetic macular edema" refers to an accumulation of the fluid in the macula, the area of the eye responsible for high-resolution central vision. Diabetic macular edema may be caused by diabetic retinopathy. Treatments for diabetic macular edema may include VEGF-related agents (e.g. antibodies or antagonists), and steroids (e.g. triamcinolone).

In some embodiments, ocular indications may include cystoid macular edema (CME). CME is caused by cyst-like (cystoid) areas of accumulated fluid inside the retina in the macular area. Cystoid macular edema can be diagnosed via dilated retinal exam, fluorescein angiography, or optical coherence tomography. Current treatment options for CME include laser therapy, topical nonsteroidal anti-inflammatory drugs (NSAIDs) (e.g., Ketorolac, OCUFEN®, Diclofenac Sodium, PROLENSA®, ILEVRO®, and NEVANAC®), corticosteroids (e.g., triamcinolone), and other therapeutic options such as carbonic anhydrase inhibitors, intravitreal anti-VEGF agents, and possibly surgery. SBPs described herein may be used alone or in combination with an existing treatment method for treating CME.

In some embodiments, ocular indications may include post-operative cystoid macular edema (CME). In some embodiments, ocular indications may include age-related macular degeneration (AMD), whether wet or dry. In some embodiments, ocular indications may include diabetic macular edema (DME).

Combinations

In some embodiments, SBPs may be administered in combination with other therapeutic agent and/or methods of treatment, e.g., with known pharmaceuticals and/or known therapeutic methods, such as, for example, those which are currently employed for treating these disorders. For example, SBPs used to treat ocular indications may be administered in combination with other therapeutic agents used to treat ocular indications.

Pharmaceutical Compositions

In some embodiments, SBPs are or are included in pharmaceutical compositions. As used herein, the term "pharmaceutical composition" refers to a composition designed and/or used for medicinal purposes (e.g., the treatment of a disease and/or disorder).

In some embodiments, pharmaceutical compositions include one or more excipients and/or one or more therapeutic agents. Excipients and/or therapeutic agents included in pharmaceutical compositions may include, but are not limited to, any of those described herein. Relative amounts of therapeutic agents, excipient, and/or any additional ingredients in pharmaceutical compositions may vary, depending upon the identity, size, and/or condition of subjects being treated and further depending upon routes by which compositions are administered. For example, the compositions may include from about 0.1% to about 99% (w/w) of a therapeutic agent.

Some excipients may include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of therapeutic agent or other compound. The amount of therapeutic agent may generally be equal to the dosage of therapeutic agent administered to a subject and/or a convenient fraction of such dosage including, but not limited to, one-half or one-third of such a dosage.

In some embodiments, pharmaceutical compositions may include between 20 to 55% (w/w) silk fibroin. In some embodiments, the formulations of silk fibroin rods described herein may include between 40 to 80% (w/w) therapeutic agent. In some embodiments, pharmaceutical compositions may include about 33% (w/w) silk fibroin and about 67% (w/w) therapeutic agent. In some embodiments, pharmaceutical compositions may include about 25% (w/w) silk fibroin and about 75% (w/w) therapeutic agent. In some embodiments, pharmaceutical compositions may include about 20% (w/w) silk fibroin and about 80% (w/w) therapeutic agent. In some embodiments, pharmaceutical compositions may include about 40% (w/w) silk fibroin and about 60% (w/w) therapeutic agent. In some embodiments, pharmaceutical compositions may include about 29% (w/w) silk fibroin and about 71% (w/w) therapeutic agent. In some embodiments, pharmaceutical compositions may include about 40% (w/w) silk fibroin and about 60% (w/w) therapeutic agent.

In some embodiments, pharmaceutical compositions may include 35% (w/w) silk fibroin and 65% (w/w) therapeutic agent. In some embodiments, pharmaceutical compositions may include 30% (w/w) silk fibroin and 70% (w/w) therapeutic agent. In some embodiments, pharmaceutical compositions may include 40% (w/w) silk fibroin and 60% (w/w) therapeutic agent. In some embodiments, pharmaceutical compositions may include 26% (w/w) silk fibroin and 74% (w/w) therapeutic agent. In some embodiments, pharmaceutical compositions may include 37% (w/w) silk fibroin and 63% (w/w) therapeutic agent. In some embodiments, pharmaceutical compositions may include 33% (w/w) silk fibroin and 66% (w/w) therapeutic agent. In some embodiments, pharmaceutical compositions may include 51% (w/w) silk fibroin and 49% (w/w) therapeutic agent.

Dosing

In some embodiments, the present disclosure provides methods of administering pharmaceutical compositions that are or include SBPs to subjects in need thereof. Such methods may include providing pharmaceutical compositions at one or more doses and/or according to a specific schedule. In some embodiments, doses may be determined based on desired amounts of therapeutic agent or SBP to be delivered. Doses may be adjusted to accommodate any route of administration effective for a particular therapeutic application. The exact amount required will vary from subject to subject, depending on the species, age, and general condition of the subject, the severity of the disease, the particular composition, its mode of administration, its mode of activity, and the like. The frequency of dosing required will also vary from subject to subject, depending on the species, age, and general condition of the subject, the severity of the disease, the particular composition, its mode of administration, its mode of activity, and the like.

SBPs may be formulated in dosage unit form. Such forms may allow for ease of administration and uniformity of dosage. Total daily SBP usage may be decided by an attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, pharmaceutical compositions that are or include SBPs may include a therapeutic agent or SBP at a concentration of from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 40 mg/mL to about 100 mg/mL, or more than 100 mg/mL.

In some embodiments, pharmaceutical compositions that are or include SBPs may be administered at a dose that provides subjects with a mass of therapeutic agent or SBP per unit mass of the subject (e.g., mg therapeutic agent or SBP per kg of subject [mg/kg]). In some embodiments, therapeutic agents or SBPs are administered at a dose of from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, or more than 5 g/kg.

In some embodiments, pharmaceutical compositions that are or include SBPs may be administered at a dose sufficient to yield desired therapeutic agent or SBP concentration levels in subject tissue or fluids (e.g., blood, plasma, urine, etc.). In some embodiments, doses are adjusted to achieve subject therapeutic agent or SBP concentration levels in subject tissues or fluids of from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL.

In some embodiments, pharmaceutical compositions that are or include SBPs are provided in one or more doses and are administered one or more times to subjects. Some pharmaceutical compositions are provided in only a single administration. Some pharmaceutical compositions are provided according to a dosing schedule that include two or more administrations. Each administration may be at the same dose or may be different from a previous and/or subsequent dose. In some embodiments, subjects are provided an initial dose that is higher than subsequent doses (referred to herein as a "loading dose"). In some embodiments, doses are decreased over the course of administration. In some embodiments, dosing schedules include pharmaceutical composition administration from about every 2 hours to about every 10 hours, from about every 4 hours to about every 20 hours, from about every 6 hours to about every 30 hours, from about every 8 hours to about every 40 hours, from about every 10 hours to about every 50 hours, from about every 12 hours to about every 60 hours, from about every 14 hours to about every 70 hours, from about every 16 hours to about every 80 hours, from about every 18 hours to about every 90 hours, from about every 20 hours to about every 100 hours, from about every 22 hours to about every 120 hours, from about every 24 hours to about every 132 hours, from about every 30 hours to about every 144 hours, from about every 36 hours to about every 156 hours, from about every 48 hours to about every 168 hours, from about every 2 days to about every 10 days, from about every 4 days to about every 15 days, from about every 6 days to about every 20 days, from about every 8 days to about every 25 days, from about every 10 days to about every 30 days, from about every 12 days to about every 35 days, from about every 14 days to about every 40 days, from about every 16 days to about every 45 days, from about every 18 days to about every 50 days, from about every 20 days to about every 55 days, from about every 22 days to about every 60 days, from about every 24 days to about every 65 days, from about every 30 days to about every 70 days, from about every 2 weeks to about every 8 weeks, from about every 3 weeks to about every 12 weeks, from about every 4 weeks to about every 16 weeks, from about every 5 weeks to about every 20 weeks, from about every 6 weeks to about every 24 weeks, from about every 7 weeks to about every 28 weeks, from about every 8 weeks to about every 32 weeks, from about every 9 weeks to about every 36 weeks, from about every 10 weeks to about every 40 weeks, from about every 11 weeks to about every 44 weeks, from about every 12 weeks to about every 48 weeks, from about every 14 weeks to about every 52 weeks, from about every 16 weeks to about every 56 weeks, from about every 20 weeks to about every 60 weeks, from about every 2 months to about every 6 months, from about every 3 months to about every 12 months, from about every 4 months to about every 18 months, from about every 5 months to about every 24 months, from about every 6 months to about every 30 months, from about every 7 months to about every 36 months, from about every 8 months to about every 42 months, from about every 9 months to about every 48 months, from about every 10 months to about every 54 months, from about every 11 months to about every 60 months, from about every 12 months to about every 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than every 50 years.

In some embodiments, pharmaceutical compositions that are or include SBPs may be administered at a dose sufficient to provide a therapeutically effective amount of therapeutic agents or SBPs. As used herein, the term "therapeutically effective amount" refers to an amount of an agent sufficient to achieve a therapeutically effective outcome. As used herein, the term "therapeutically effective outcome" refers to a result of treatment where at least one objective of treatment is met. In some embodiments, a therapeutically effective amount is provided in a single dose. In some embodiments, a therapeutically effective amount is administered according to a dosing schedule that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Administration

In some embodiments, pharmaceutical compositions that are or include SBPs may be administered according to one or more administration routes. In some embodiments, administration is transdermal, intravenous bolus, intralesional (within or introduced directly to a localized lesion), intraocular (within the eye), intracartilaginous (within a cartilage), insufflation (snorting), intravascular (within a vessel or vessels), buccal (directed toward the cheek), percutaneous, submucosal, cutaneous, epicutaneous (application onto the skin), intramedullary (within the marrow cavity of a bone), intramuscular (into a muscle), subcutaneous (under the skin), intragastric (within the stomach), nasal administration (through the nose), endosinusial, soft tissue, subconjunctival, oral (by way of the mouth), periodontal, periarticular, auricular (in or by way of the ear), intratubular (within the tubules of an organ), intradermal (into the skin itself), intravitreal (through the eye), irrigation (to bathe or flush open wounds or body cavities), in ear drops, endotracheal, intraosseous infusion (into the bone marrow), caudal block, intraarticular, intracorneal (within the cornea), extracorporeal, transmucosal (diffusion through a mucous membrane), topical, oropharyngeal (directly to the mouth and pharynx), occlusive dressing technique (topical route administration which is then covered by a dressing which occludes the area), intraarterial (into an artery), intrasinal (within the nasal or periorbital sinuses), intraductal (within a duct of a gland), transdermal (diffusion through the intact skin for systemic distribution), retrobulbar (behind the pons or behind the eyeball), intravenous (into a vein), intrasynovial (within the synovial cavity of a joint), intratumor (within a tumor), eye drops (onto the conjunctiva), respiratory (within the respiratory tract by inhaling orally or nasally for local or systemic effect), and/or ophthalmic (to the external eye).

In some embodiments, pharmaceutical compositions that are or include SBPs may be administered by intravitreal administration, intraretinal administration, intracorneal administration, intrascleral administration, punctal administration, administration to the anterior sub-Tenon's, suprachoroidal administration, administration to the posterior sub-Tenon's, subretinal administration, administration to the fornix, administration to the lens, intra-aqueous humor administration, transmucosal administration, transdermal administration, soft tissue administration, subcutaneous administration, topical administration, insufflation, enema, eye drops, ear drops, or intravesical infusion. In some embodiments, the SBPs described herein may be administered via injection. Injection site reactions may be monitored via any method known to one skilled in the art.

In some embodiments, SBPs may be administered for localized treatment (e.g., see United States Publication Numbers US20170368236 and US20110171239, the contents of each of which are herein incorporated by reference in their entirety). In some embodiments, SBPs may be administered for treatment of areas located further away from administration sites (e.g., see Aykac et al. (2017) Gene s0378-1119(17)30868-30865, the contents of which are herein incorporated by reference in their entirety).

In some embodiments, administration includes ocular administration. As used herein, the term "ocular administration" refers to delivery of an agent to an eye. Ocular administration may include, but is not limited to, topical administration (e.g., using eye drops, ointments, or creams), intraocular administration, intravitreal administration, intraretinal administration, intracorneal administration, intrascleral administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Administration may include intravitreal injection. In some embodiments, intraocular SBP administration reduces intraocular pressure.

In some embodiments, SBPs described herein may be administered using any form of injection device, for example a syringe/needle device of a gauge suitable for the application. As a non-limiting example, SBPs may be administered using a syringe/needle with a gauge of 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 27, 28, 29, 30, 31, 32, 33, or 34. In some embodiments the administration is intravitreal using a 22-gauge needle. In some embodiments, the administration is intravitreal using a 27-gauge needle.

In some embodiments, the SBP is formatted as hydrogels and administered using a needle with a gauge of at least 27. For example, SBP hydrogels may be administered using a needle with a gauge of 27, 28, 29, 30, 31, 32, 33, or 34. In one embodiment, SBP hydrogels may be administered using a 27-gauge needle.

In some embodiments, the SBP is formatted as rods and administered using a needle with a gauge of at least 20. For example, SBP rods may be administered using needles with a gauge of 20, 20.5, 21, 21.5, 22, 22.5, 23, 23.5, 24, 24.5, 25, 25.5, 26, 26.5, 27, 28, 29, 30, or more than 30. In one embodiment, SBP rods are administered using a 21-gauge needle. In one embodiment, SBP rods are administered using a 22-gauge needle.

In some embodiments, SBP administration does not result in an inflammatory response beyond transient local foreign body reaction. In some embodiments, SBPs are biocompatible. In some embodiments, SBPs are well tolerated after administration. In some embodiments, SBPs are well tolerated after intravitreal administration.

In some embodiments, intraocular SBP administration provides continuous delivery of therapeutic agents. In some embodiments, the intraocular SBP administration results in detectable levels of ocular therapeutic agent in vitreous humor. Ocular therapeutic agents may be detectable in vitreous humor for from about 1 day to about 60 days, from about 1 week to about 24 weeks, from about 1 month to about 6 months, from about 3 months to about 24 months, from about 1 year to about 5 years, or for more than 5 years. Ocular therapeutic agent levels may steady over any of such periods of time.

In some embodiments, SBP administration or SBP-based therapeutic agent administration occurs over a period of time, referred to herein as the "administration period." During administration periods, administration may be continuous or may be separated into two or more administrations. In some embodiments, administration periods may be from about 1 min to about 30 min, from about 10 min to about 45 min, from about 20 min to about 60 min, from about 40 min to about 90 min, from about 2 hours to about 10 hours, from about 4 hours to about 20 hours, from about 6 hours to about 30 hours, from about 8 hours to about 40 hours, from about 10 hours to about 50 hours, from about 12 hours to about 60 hours, from about 14 hours to about 70 hours, from about 16 hours to about 80 hours, from about 18 hours to about 90 hours, from about 20 hours to about 100 hours, from about 22 hours to about 120 hours, from about 24 hours to about 132 hours, from about 30 hours to about 144 hours, from about 36 hours to about 156 hours, from about 48 hours to about 168 hours, from about 2 days to about 10 days, from about 4 days to about 15 days, from about 6 days to about 20 days, from about 8 days to about 25 days, from about 10 days to about 30 days, from about 12 days to about 35 days, from about 14 days to about 40 days, from about 16 days to about 45 days, from about 18 days to about 50 days, from about 20 days to about 55 days, from about 22 days to about 60 days, from about 24 days to about 65 days, from about 30 days to about 70 days, from about 2 weeks to about 8 weeks, from about 3 weeks to about 12 weeks, from about 4 weeks to about 16 weeks, from about 5 weeks to about 20 weeks, from about 6 weeks to about 24 weeks, from about 7 weeks to about 28 weeks, from about 8 weeks to about 32 weeks, from about 9 weeks to about 36 weeks, from about 10 weeks to about 40 weeks, from about 11 weeks to about 44 weeks, from about 12 weeks to about 48 weeks, from about 14 weeks to about 52 weeks, from about 16 weeks to about 56 weeks, from about 20 weeks to about 60 weeks, from about 2 months to about 6 months, from about 3 months to about 12 months, from about 4 months to about 18 months, from about 5 months to about 24 months, from about 6 months to about 30 months, from about 7 months to about 36 months, from about 8 months to about 42 months, from about 9 months to about 48 months, from about 10 months to about 54 months, from about 11 months to about 60 months, from about 12 months to about 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than 50 years.

Depot Administration

In some embodiments, SBPs may be administered by or be used to administer therapeutic agents by depot administration. As used herein, the term "depot" refers to a concentration of one or more agents in a particular region or in association with a composition or device. With depot administration, the one or more agents exit or diffuse from the concentration into surrounding areas. Agents administered by depot administration may be SBPs. In some embodiments, SBPs are depots for therapeutic agents, wherein the therapeutic agents exit or diffuse from the SBPs. In some embodiments, the SBPs may be utilized for the local delivery of therapeutic agents. In some embodiments, depots are implants. In some embodiments, depots are gels or hydrogels. In some embodiments, depot administration of an SBP may reduce the number of times a therapeutic agent needs to be administered. In some embodiments, depot administration of an SBP may replace oral administration of a therapeutic agent.

Controlled Release

In some embodiments, SBPs and related methods described herein be may be used for controlled release of therapeutic agents. As used herein, the term "controlled release" refers to regulated movement of factors from specific locations to surrounding areas. In some embodiments, the specific location is a depot. Controlled release of factors from depots may be regulated by interactions between therapeutic agents and depot components. Such interactions may, for example, modulate therapeutic agent diffusion rate and/or affect therapeutic agent stability and/or degradation. In some embodiments, the depot is an SBP. In some embodiments, factors subject to controlled release from depots are SBPs. In some embodiments, therapeutic agents are subject to controlled release from SBP depots.

In some embodiments, SBPs may control payload release by extending payload half-life. As used herein, the term "half-life" refers to the length of time necessary for levels of a factor to be reduced (e.g., through clearance or degradation) by 50%. Some payloads may exhibit shortened half-life in water (e.g., due to hydrolysis). SBPs may protect payloads from exposure to water, thereby improving payload half-life. In some embodiments, methods of increasing payload half-life using SBPs may include any of those described in United States Publication US20100028451, the contents of which are herein incorporated by reference in their entirety. Methods of improving payload half-life may be carried out in vitro or in vivo. In some embodiments, SBP-based methods of improving payload half-life may enable therapeutic indication treatment with fewer doses and/or treatments. Such methods may include any of those described in International Publication Number WO2017139684, the contents of which are herein incorporated by reference in their entirety. In some embodiments, payload half-life may be extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115%, from about 38% to about 120%, from about 40% to about 125%, from about 42% to about 130%, from about 44% to about 135%, from about 46% to about 140%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 4000%, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, or more than 10000%.

In some embodiments, SBP depots may be used for controlled release of therapeutic agents, wherein release is facilitated by diffusion. Such methods may include any of those described in United States Publication Number US20170333351, the contents of which are herein incorporated by reference in their entirety. Therapeutic agent diffusion may be slowed (i.e., controlled) by SBP depots leading to extended release periods. Extended therapeutic agent release periods may enable longer administration periods. In some embodiments, administration periods are extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115%, from about 38% to about 120%, from about 40% to about 125%, from about 42% to about 130%, from about 44% to about 135%, from about 46% to about 140%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 4000%, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, In some embodiments, the controlled release of a therapeutic agent for the treatment of a condition, disease, or indication may be facilitated by the degradation and/or dissolution of SBPs. Such methods may be carried according to those described in International Publication Numbers WO2013126799, WO2017165922, and U.S. Pat. No. 8,530,625, the contents of each of which are herein incorporated by reference in their entirety. SBP degradation and/or dissolution may expose increasing amounts of therapeutic agents over time for treatment of therapeutic indications.

In some embodiments, therapeutic agent release from SBPs may be monitored via high performance liquid chromatography (HPLC), ultra-performance liquid chromatography (UPLC), and/or other methods known to those skilled in the art.

SBP hydrogels may be used to extend payload release periods (e.g., as shown for extended release of small molecule in International Publication Number WO2017139684, the contents of which are herein incorporated by reference in their entirety. In some embodiments, SBP hydrogels are used to provide extended release of therapeutic agents (e.g., biological agents). Hydrogel networks may stabilize such agents and support their release as the hydrogel degrades. This effect serves to extend agent release and may be modulated by varying factors including processed silk molecular weight, concentration, excipient type, pH, and temperature. In some embodiments, processed silk molecular weight, concentration, excipient type, pH, and processing temperature used to prepare SBPs may be modulated to achieve desired payload release periods for specific therapeutic agents.

In some embodiments, SBPs may be lyophilized together with therapeutic agents. In some embodiments, combined lyophilization may induce further interactions between therapeutic agents and SBPs. These interactions may be maintained through SBP preparation and support extended payload release. Payload release may be dependent on SBP degradation and/or dissolution. In some embodiments, SBP β-sheet content is increased (e.g., via water annealing), thereby increasing SBP insolubility in water. Such SBPs may exhibit increased payload release periods. In some embodiments, these SBPs may include therapeutic agent stabilizing properties to extend administration periods and/or therapeutic agent half-life.

In some embodiments, SBPs described herein maintain and/or improve the controlled delivery of a therapeutic agent. In some embodiments, SBPs lengthen payload release period and/or administration period by at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In some embodiments, SBPs lengthen payload release period and/or administration period by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 6 months, at least 9 months, or at least 1 year.

In some embodiments, SBPs may be used to modulate depot release of therapeutic agents. Some SBPs may release therapeutic agents according to near zero-order kinetics. In some embodiments, SBPs may release therapeutic agents according to first-order kinetics. In some embodiments, therapeutic agent release rate may be modulated by preparing SBP depots with modification of one or more of density, loading, drying method, silk fibroin molecular weight, and silk fibroin concentration.

In some embodiments, SBPs are prepared to release from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100% of the total amount of therapeutic or macromolecular therapeutic agent to be delivered.

In some embodiments, the SBPs (e.g. hydrogels) demonstrate a sustained release of a therapeutic agent, with near steady state concentrations. In some embodiments, the sustained release is at a level at or near the effective concentration. In some embodiments, the sustained release is at greater than or equal to the effective concentration. In some embodiments the effective concentration is the $IC_{50}$, the $EC_{50}$, or the $EC_{80}$.

Delivery

SBPs may be delivered to cells, tissues, organs and/or organisms in naked form. As used herein in, "naked" delivery refers to delivery of an active agent with minimal or with no additional formulation or modification. Naked SBPs may be delivered to cells, tissues, organs and/or organisms using routes of administration known in the art and described herein. In some embodiments, naked delivery may include formulation in a simple buffer such as saline, phosphate buffer, or PBS.

In some embodiments, SBPs may be prepared with one or more cell penetration agents, pharmaceutically acceptable carriers, delivery agents, bioerodible or biocompatible polymers, solvents, and/or sustained-release delivery depots. SBPs may be delivered to cells using routes of administration known in the art and described herein. In some embodiments, SBPs may be formulated for direct delivery to organs or tissues in any of several ways in the art including, but not limited to, direct soaking or bathing, via a catheter, by gels, powder, ointments, creams, gels, lotions, and/or drops, or by using substrates (e.g., fabric or biodegradable materials) coated or impregnated with SBPs.

Detectable Agents and Labels

In some embodiments, SBPs described herein may be formulated with detectable labels. As used herein, the term "detectable label" refers to any incorporated compound or entity that facilitates some form of identification. Detectable labels may include, but are not limited to various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, $^{3}H$, or $^{99m}Tc$ (e.g., as pertechnetate (technetate(VII), $TcO^{4-}$)), contrast agents (e.g., gold, gold nanoparticles, gadolinium, chelated Gd, iron oxides, superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2, 2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and -6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,ndiethylethanamine(1:1) (IR144); 5-chloro-2-[2-[3-[(5-chloro-3-ethyl-2(3H)-benzothiazolylidene) ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-Xrhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable labels may include non-detectable precursors that becomes detectable upon activation (e.g., fluorogenic tetrazine-fluorophore constructs, tetrazine-BODIPY FL, tetrazine-Oregon Green 488, or tetrazine-BODIPY TMR-X) or enzyme activatable fluorogenic agents (e.g., PROSENSE® (VisEn Medical)). In vitro assays in which enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Therapeutic Devices

In some embodiments, SBPs may be or may be included in therapeutic devices. In some embodiments, therapeutic devices may be coated with SBPs described herein. Some therapeutic devices may include therapeutic agents. In some embodiments, the use of SBPs within therapeutic devices may enable the delivery of therapeutic agents via such therapeutic devices. Some therapeutic devices may include synthetic materials. In some embodiments, therapeutic devices include, but are not limited to, artificial blood vessels, artificial liver, artificial organ, bandage, breast augmentation, cartilage replacement, ear drum repair, filler, hemostatic sponge, implant, silk contact lens, stem cell, surgical mesh, surgical suture, tissue replacement, vascular patch, wound dressing, antenna, applier, artificial heart, artificial heart valve, assembly, balloon, barrier, biosensor, biotransducer, breast implant, cable assembly, caliper, capacitor, carrier, clamp, cochlear implant, connector, corneal implant, coronary stent, cryotome, degradable device, delivery device, dental implant, dermatome, detector, diagnostic device, dilator, diode, discharge device, display technology, distractor, drill bit, electronic device, gastric stimulator, graft, grasper, harmonic scalpel, hemostatic device, imaging apparatus, implant, implant for continuous drug delivery, implantable cardioverter-defibrillator, integrated circuit, intraocular lens, intrauterine device, lancet, LIGASURE™, liner, magnetic or inductive device, magnetic resonance imaging apparatus, mechanical assembly, medical device, memristor, module, needle, nerve stimulator, network, neurostimulator, occluder, optoelectronic device, pacemaker, patch, pen, piezoelectric device, pin, pipe, plate, positioner, power source, probe, prosthesis, prosthetic, protection device, removable device, resistor, retractor, rod, rongeur, rope, ruler, scalpel, scope, screw, semiconductor, sensor, solution, specula, stent, stent, sterotactic device, suction tip, suction tube, surgical device, surgical mesh, surgical scissor, surgical staple, suture, switch, temperature sensor, terminal, tie, tip, transducer, transistor, tube, tympanostomy tube, ultrasound tissue disruptor, vacuum tube, vacuum valve, ventilation system, water balloon, wire, bleb, gel, gel that hardens after implantation, implant, lacrimal plug, lens, plug, punctal plug, rod, slurry, slurry that hardens after implantation, and solids.

In some embodiments, therapeutic devices include implants. As used herein, the term "implant" refers to a device that may be embedded in or within a carrier. Implants used in therapeutic applications are typically embedded in subjects to support, repair, replace, or enhance one or more tissues or features. In some embodiments, implants include one or more excipients and/or one or more therapeutic agents (e.g., any of the excipients or therapeutic agents presented herein. Implants may include depots for therapeutic agent release, as described herein. In some embodiments, implants may include one or more coatings, gels, hydrogels, scaffolds, particles, or therapeutic devices (e.g., any of those listed above).

Some implants may be prepared by mixing a therapeutic agent with a processed silk solution. The solution may be heated to form the hydrogel. Some hydrogels may be heated to dryness and some hydrogels may be frozen and lyophilized to form an implant. Further, implants may be compressed to slow hydration as well as to slow the release of therapeutic agent. Excipients may be incorporated into processed silk solutions prior to hydrogel formation to allow for scaffold formation during the freezing/lyophilization process. Excipients may include gelling agents such as, but are not limited to, poloxamers, PEG's, mannitol, sorbitol, etc. Rods or scaffolds may be formed from hydrogels by compression or extrusion. The rods may be formed taking into consideration the dimensions and/or properties that allow for injection through small gauge needles (e.g., with a gauge of more than 20). As non-limiting examples, SBP rods may be injectable through needles with a gauge of 20, 20.5, 21, 21.5, 22, 22.5, 23, 23.5, 24, 24.5, 25, 25.5, 26, 26.5, 27, 28, 29, 30, or more than 30. In one embodiment, SBP rods are injectable with a 21-gauge needle. In one embodiment, SBP rods are injectable with a 21-gauge needle. In one embodiment, SBP rods are injectable with a 22-gauge needle. Some rods may be formed for subcutaneous delivery. Some rods may be formed for other delivery formats, which may include, but are not limited to, intravitreal, intratympanic, and intraarticular delivery.

Definitions

Absolute value: As used herein, the term "absolute value" describes the magnitude of a numerical number or measurement. The magnitude is listed as a non-negative number, but it can represent both positive and negative values.

Active pharmaceutical agent (API): As used herein, the term "active pharmaceutical agent," or "API," describes the component of a pharmaceutical composition that exhibits biological activity.

Cumulative release percentage: As used herein, the term "cumulative release percentage" describes the total percentage of a factor released from a source or depot over the course of a release period. This percentage may be determined from the total mass of released factor divided by initial mass of the factor in the source or depot. The "daily release percentage" describes the cumulative release percentage of factor per day. This value may be calculated from the best fit line slope of a plot of cumulative release percentage over time.

Effective concentration: As used herein, the term "effective concentration" refers to the concentration of a compound or factor required to elicit a particular response. The concentration needed to elicit half of a complete response is referred to as the "half maximal effective concentration" or "EC50." The concentration of compound needed to elicit 80% of a complete response is referred to as the "EC80". Where the compound or factor is inhibitory, the concentration needed to reduce or inhibit the response by half is referred to herein as the half maximal inhibitory concentration, or "IC50."

Initial burst: As used herein, the term "initial burst" refers to a rate of factor release from a source or depot over an initial release period (e.g., after administration or other placement, for example in solution during experimental analysis) that is higher than rates during one or more subsequent release periods.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. The present invention is further illustrated by the following nonlimiting examples.

EXAMPLES

Example 1. Formulation of Blank Silk Fibroin Rods

Silk Fibroin Isolation

Silk yarn, purchased from Jiangsu SOHO International Group, was degummed to remove sericin. 30 grams of cut silk yarn were boiled at 100° C. in 3 L of deionized (DI) water with 0.02 M sodium carbonate for 240 minutes with stirring. The yarn was then transferred to a new boiling 0.02 M sodium carbonate aqueous solution and boiled at 100° C. for an additional 240 minutes with stirring. The total boiling time was discussed in terms of minute boil, or "mb." The fibroin was then placed in DI water at 60-70° C. for 20 minutes with stirring, and then rinsed with clean DI water. This process was repeated 3 times. The fibroin was placed in clean DI water, stirred for 20 minutes, then rinsed with clean DI water, and this process was repeated for a total of 3×20 min.-rinse cycles. The fibroin was dried overnight, weighed, and dissolved at 20% (w/v) in a 9.3 M aqueous solution of lithium bromide (from Sigma-Aldrich, St. Louis, Mo.) for 5 hours at 60° C. The resulting fibroin solution was dialyzed against water at 4° C. in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water. Samples for a standard curve were prepared for an A280 assay by diluting pre-measured fibroin solutions to 5, 2.5, 1.25, 0.625, 0.3125, and 0 mg/mL in water. The silk concentration of the 1:20 and 1:40 diluted silk fibroin samples was measured against the standard curve by the absorbance at 280 nm.

The fibroin solutions were diluted to a final concentration of 3% (w/v) in 10 mM phosphate buffer (from Sigma Aldrich Fine Chemicals, St. Louis, Mo.), pH 7.4, and they were filtered through a 0.2 µm filter using a vacuum filter unit. 10 mL of each solution was aliquoted into 50 mL conical tubes, snap frozen in liquid nitrogen for 10 minutes, transferred for 20 minutes in −80° C., and lyophilized for 72 hours.

Formulation of Silk Fibroin Rods

Lyophilized silk fibroin was dissolved in ultrapure water to obtain a concentration of 40% (w/v). The solution was extruded out of a syringe into tubing with a variety of diameters, dependent on the indication. For this example, the sample listed in Table 1 was extruded into approximately 12 cm lengths of 0.508 mm diameter polyetheretherketone (PEEK) (from Van Waters and Rogers (VWR), PA, USA, product 53500-690). The ends of the tubing were covered in parafilm, and the tubing was then incubated at 37° C. for 24 hours, after which it was cut to the necessary size, typically 2 cm lengths, frozen to −80° C. for at least four hours, and lyophilized. The final rods contained trace amounts of potassium phosphate buffer (with potassium phosphate dibasic and potassium phosphate monobasic). The final concentration of phosphate buffer was 133.3 mM.

TABLE 1

SAMPLES OF SILK-FIBROIN RODS

| Sample No. | Silk Prep Boil Time (min) | Silk-Fibroin Final % (w/w) |
|---|---|---|
| 1 | 480 | 100 |

The resulting rods were imaged via scanning electron microscopy (SEM). The rods were approximately 400 µm in diameter. The outer surfaces and cross-sectional surfaces of the silk-fibroin rods were smooth, with few to no ridges. The silk-fibroin rods were densely-packed, and the cross-sectional surfaces appeared smooth and contained few to no internal pores.

Example 2. In Vitro Release of Small Molecules from 1 mm Silk Fibroin Rods

The silk yarn was purchased from Jiangsu SOHO International Group (Jiangsu, China). Lithium bromide was purchased from Sigma Aldrich (St. Louis, Mo.). The potassium phosphate monobasic and potassium phosphate dibasic were purchased from Sigma Aldrich Fine Chemicals (SAFC) (St. Louis, Mo.). The sodium carbonate and the sodium azide were purchased from Fisher Chemical (Waltham, Mass.). The celecoxib (CXB) was purchased from Cipla (Miami, Fla.).

Silk Fibroin Isolation

Silk yarn, purchased from Jiangsu SOHO International Group, was degummed to remove sericin. 30 grams of cut silk yarn were boiled at 100° C. in 3 L of deionized (DI) water with 0.02 M sodium carbonate for 240 minutes with stirring. The yarn was then transferred to a boiling 0.02 M sodium carbonate aqueous solution and boiled at 100° C. for an additional 240 minutes with stirring. The fibroin was then placed in DI water at 60-70° C. for 20 minutes with stirring, and then rinsed with clean DI water. This process was repeated 3 times. The fibroin was placed in clean DI water, stirred for 20 minutes, then rinsed with clean DI water. This process was repeated for a total of three 20 minute rinse cycles. The fibroin was dried overnight, weighed, and dissolved at 20% (w/v) in a 9.3 M aqueous solution of lithium bromide (from Sigma Aldrich, St. Louis, Mo.) for 5 hours at 60° C. The resulting fibroin solution was dialyzed against water at 4° C. in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water. Samples for a standard curve were prepared for an A280 assay by diluting pre-measured fibroin solutions to 5, 2.5, 1.25, 0.625, 0.3125, and 0 mg/mL in water. The silk concentration of the 1:20 and 1:40 diluted silk fibroin samples was measured against the standard curve by the absorbance at 280 nm.

The silk fibroin solutions were diluted to a final concentration of 3% (w/v) in 10 mM phosphate buffer (from Sigma Aldrich Fine Chemicals, St. Louis Mo.), pH 7.4, and they were filtered through a 0.2 μm filter using a vacuum filter unit. 10 mL of each solution was aliquoted into 50 mL conical tubes, snap frozen in liquid nitrogen for 10 minutes, transferred for 20 minutes in −80° C., and lyophilized for 72 hours.

1 mm Silk Fibroin Rod Preparation

Lyophilized silk fibroin was dissolved with ultrapure water to obtain silk concentrations of 20, 30, and 40% (w/v). The relevant amount of celecoxib (CXB) (from Cipla, Miami Fla.) was weighed into a 4 mL glass vial. 250 μl of the relevant silk-fibroin solution (for example, Samples 8-58-1 through 8-58-3 use 250 μl of 20% (w/v) silk-fibroin to reach 50 mg) were then added to the dry CXB. The vial was briefly vortexed. A metal spatula was then used to manually mix the suspension until it became homogeneous. Using the spatula, the viscous suspension was loaded into the back of a 1 cc. syringe. The viscous mixture was then extruded out of the syringe into tubing with a variety of diameters, dependent on the indication. For this example, the samples were extruded into approximately 12 cm lengths of 1 mm diameter of either silicon (Grainger, Ill., USA, product number 2VLW4) or polytetrafluoroethylene (PTFE) tubing (from Van Waters and Rogers (VWR), PA, USA) The tubing was sealed with parafilm on both ends and left at 37° C. overnight to induce gelation. The tubing was then cut to the necessary size, typically 2 cm lengths. When the mixture was extruded from the tubing, the rods were found to hold their shape. The mixture was then frozen at −80° C. for at least four hours, either within or outside of the tubing. The resulting rods were then lyophilized for approximately 24 hours. Rods were removed from the tubing after lyophilization.

The rods are described in Table 2, alongside the concentration of silk solution used in their formulation, the total mass of silk fibroin used to formulate the rods, the total mass of CXB used to formulate the rods, and the theoretical loading percentages of the silk-fibroin and CXB in each sample. The term theoretical loading percentage refers to the assumed percentage of a component incorporated in a substance or product. The product may be an SBP. The component may be silk fibroin or CXB. The theoretical loading percentage may be in terms of either w/w percentage, w/v percentage, or v/v percentage. The samples were named by the process used to prepare and formulate each silk rod. For example, the sample named "480 mb; 1 mm; 20% st; 50mgsf; 150mgcxb; lyo; 25% sf; 75% cxb;" refers to a silk fibroin rod prepared from silk degummed with a 480-minute boil, an extrusion with a 1 mm diameter, a preparation from a 20% stock solution of silk fibroin, a preparation from 50 mg of silk fibroin, a preparation from 150 mg of celecoxib, lyophilization, a theoretical w/w percentage of 25% silk fibroin, and a theoretical w/w percentage of 75% celecoxib. The final rods contained trace amounts of potassium phosphate buffer (with potassium phosphate dibasic and potassium phosphate monobasic). The final concentration of phosphate buffer could be converted to (w/w) percentage by multiplying the concentration (in mM) by 0.0167.

TABLE 2

THEORETICAL SILK FIBROIN AND CELECOXIB PERCENTAGES FOR 1 MM SILK ROD SAMPLES

| Sample No. | Sample Name | Formulation Stock Silk Concentration (w/v %) | Silk-Fibroin Mass (mg) | CXB Mass (mg) | Silk-Fibroin Final % (w/w) | CXB Final % (w/w) | Phosphate Buffer Concentration (mM) |
|---|---|---|---|---|---|---|---|
| 8-58-1 | 480 mb; 1 mm; 20% st; 50 mgsf; 150 mgcxb; lyo; 25% sf; 75% cxb | 20 | 50 | 150 | 25 | 75 | 41.7 |
| 8-58-2 | 480 mb; 1 mm; 20% st; 50 mgsf; 200 mgcxb; lyo; 20% sf; 80% cxb | 20 | 50 | 200 | 20 | 80 | 37 |
| — | 480 mb; 1 mm; 20% st; 50 mgsf; 250 mgcxb; lyo; 16.7% sf; 83.3% cxb | 20 | 50 | 250 | 16.7 | 83.3 | 33.3 |

TABLE 2-continued

THEORETICAL SILK FIBROIN AND CELECOXIB
PERCENTAGES FOR 1 MM SILK ROD SAMPLES

| Sample No. | Sample Name | Formulation Stock Silk Concentration (w/v %) | Silk-Fibroin Mass (mg) | CXB Mass (mg) | Silk-Fibroin Final % (w/w) | CXB Final % (w/w) | Phosphate Buffer Concentration (mM) |
|---|---|---|---|---|---|---|---|
| 8-58-4 | 480 mb; 1 mm; 30% st; 75 mgsf; 150 mgcxb; lyo; 33.3% sf; 66.7% cxb | 30 | 75 | 150 | 33.3 | 66.7 | 62.5 |
| 8-58-5 | 480 mb; 1 mm; 30% st; 75 mgsf; 200 mgcxb; lyo; 27.3% sf; 72.2% cxb | 30 | 75 | 200 | 27.3 | 72.2 | 55.6 |
| 8-58-6 | 480 mb; 1 mm; 30% st; 75 mgsf; 250 mgcxb; lyo; 23% sf; 77% cxb | 30 | 75 | 250 | 23 | 77 | 50 |
| 8-58-7 | 480 mb; 1 mm; 40% st; 100 mgsf; 150 mgcxb; lyo; 40% sf; 60% cxb | 40 | 100 | 150 | 40 | 60 | 83.3 |
| 8-58-8 | 480 mb; 1 mm; 40% st; 100 mgsf; 200 mgcxb; lyo; 33.3% sf; 66.7% cxb | 40 | 100 | 200 | 33.3 | 66.7 | 74.1 |
| 8-58-9 | 480 mb; 1 mm; 40% st; 100 mgsf; 250 mgcxb; lyo; 28.6% sf; 71.4% cxb | 40 | 100 | 250 | 28.6 | 71.4 | 66.7 |

The resulting silk fibroin rods were imaged via scanning electron microscopy (SEM), seen in FIG. 1A, FIG. 1B, FIG. 1C, and FIG. 1D. The rods were approximately 1000 μm in diameter. The silk-fibroin-CXB-rods were densely packed. The outer surfaces and cross-sectional surfaces of the silk-fibroin-CXB rods had ridges that appeared approximately 15 μm in length. The cross-sectional images of the silk-fibroin-CXB rods contained pores ranging in size from approximately 10-75 μm in length.

In Vitro Release Experiments

The diameter of the silk-fibroin rods was measured using digital calipers. The rods were cut to 1 cm lengths to standardize release, and the weights of the rods were recorded. The density of the rods was calculated for each preparation. The rods from the tubing were placed into 45 mL of phosphate buffer (from Sigma Aldrich Fine Chemicals, St. Louis, Mo.), pH 7.4, 2% (v/v) Polysorbate-80 (from Croda, Snaith UK), and 0.05% (w/v) sodium azide (from Fisher Chemical, Waltham Mass.). This buffer ensured that the release was conducted under sink conditions (≥5× saturated solubility). The samples were incubated at 37° C. with gentle shaking. 1 mL of the release medium was taken at each timepoint (typically 1, 4, 7, 10, and 14 days and then weekly thereafter) and replaced with fresh media. The release medium was then analyzed via ultra-performance liquid chromatography (UPLC) to determine CXB concentration.

The silk fibroin rods demonstrated near zero-order kinetics for CXB release, with a low initial burst of 5-20%. The release rates of CXB were tuned by altering the density, CXB loading, and silk fibroin concentration. The CXB was released over the course of 1-3 months.

Example 3. In Vitro Release of Small Molecules from 0.5 mm Silk Fibroin Rods

The silk yarn was purchased from Jiangsu SOHO International Group (Jiangsu, China). Lithium bromide was purchased from Sigma Aldrich (St. Louis, Mo.). The potassium phosphate monobasic and potassium phosphate dibasic were purchased from Sigma Aldrich Fine Chemicals (SAFC) (St. Louis, Mo.). The sodium carbonate and the sodium azide were purchased from Fisher Chemical (Waltham, Mass.). The celecoxib (CXB) was purchased from Cipla (Miami, Fla.).

0.5 mm Silk Fibroin Rod Preparation

Silk-fibroin (from Jiangsu SOHO International Corporation) was isolated as described in the preparation of the silk fibroin rods with no additives. Briefly, silk yarn, purchased from Jiangsu SOHO International Group, was degummed to remove sericin. 30 grams of cut silk yarn were boiled at 100° C. in 3 L of deionized (DI) water with 0.02 M sodium carbonate with stirring. The yarn was then transferred to a new boiling 0.02 M sodium carbonate aqueous solution and boiled at 100° C. for additional time with stirring. The total boiling time was discussed in terms of minute boil, or "mb." The silk fibroin was boiled for either a total time of 480 or 120 minutes while being degummed. The total boiling time was discussed in terms of minute boil, or "mb." Longer boiling times produced silk fibroin with lower average molecular weights of approximately 5-60 kDa.

The fibroin was then placed in DI water at 60-70° C. for 20 minutes with stirring, and then rinsed with clean DI water. This process was repeated 3 times. The fibroin was placed in clean DI water, stirred for 20 minutes, then rinsed with clean DI water, and this process was repeated for a total of 3×20 min.-rinse cycles. The fibroin was dried overnight, weighed, and dissolved at 20% (w/v) in a 9.3 M aqueous solution of lithium bromide (from Sigma-Aldrich, St. Louis, Mo.) for 5 hours at 60° C. The resulting fibroin solution was dialyzed against water at 4° C. in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready. The silk fibroin solution was centrifuged for 20 minutes at 3,900 RPM and 4° C. to remove insoluble particles. Solutions were diluted to a final concentration of 3% (w/v) in 10 mM phosphate buffer, pH 7.4, filtered through a 0.22 μm filter, frozen in liquid nitrogen, and lyophilized for 72 hours.

Lyophilized silk-fibroin was dissolved with ultrapure water to obtain concentrations of 20, 30, and 40% (w/v). The relevant amount of CXB (from Cipla, Miami Fla.) was weighed into a 4 mL glass vial. 250 µL of the relevant silk-fibroin solution was then added to the dry CXB, and the vial was then briefly vortexed. A metal spatula was used to manually mix the suspension until it was homogeneous. Using the spatula, the viscous suspension was loaded into the back of a 1 cc. syringe. The viscous mixture was extruded out of the syringe into tubing with a variety of diameters, dependent on the indication. For this example, the samples listed in Table 3 were extruded into approximately 12 cm lengths of 0.508 mm diameter PEEK tubing (from Van Waters and Rogers (VWR), PA, USA, product 53500-690). The tubing was then sealed on both ends with parafilm and left at 37° C. for 24 hours or overnight for gelation. The tubing was cut to the necessary size, typically 2 cm lengths. Half of the samples were frozen to −80° C. for at least four hours and lyophilized, while half of the samples were oven dried at 60° C. for 16 hrs. The samples were named by the process used to prepare and formulate each silk rod. For example, the sample named "480 mb; 0.5 mm; 40% st; 100mgsf; 200mgcxb; lyo; 33.3% sf; 66.7% cxb" refers to a silk fibroin rod prepared from silk degummed with a 480-minute boil, an extrusion with a 0.5 mm diameter, a preparation from a 40% stock solution of silk fibroin, a preparation from 100 mg of silk fibroin, a preparation from 200 mg of celecoxib, lyophilization, a theoretical w/w percentage of 33.3% silk fibroin, and a theoretical w/w percentage of 66.7% celecoxib. The final rods contained trace amounts of potassium phosphate buffer (with potassium phosphate dibasic and potassium phosphate monobasic). The final concentration of phosphate buffer could be converted to (w/w) percentage by multiplying the concentration (in mM) by 0.0167.

the rods were calculated for each preparation. The rods were placed into 45 mL of phosphate buffer, pH 7.4, 0.3% (v/v) Polysorbate-80 (from Croda, Snaith UK), and 0.05% (w/v) sodium azide (from Fisher Chemical, Waltham Mass.). This buffer ensured that the release was conducted under sink conditions (≥5× saturated solubility). A suspension of CXB containing 800 µg CXB was used as a control. The samples were incubated at 37° C. with gentle shaking. 1 mL of the release medium was taken at each timepoint (typically 1, 4, 7, 10, and 14 days and then weekly thereafter) and replaced with fresh media. The release medium was then analyzed via UPLC at 260 nm to determine CXB concentration.

The silk fibroin rods demonstrated near zero-order kinetics for CXB release, with a low initial burst of 15%. The release rates of CXB could be modulated by altering the silk molecular weight, CXB loading, and the method of drying the silk fibroin rods. The CXB was released over the course of 1-3 months. The rods with the 0.5 mm diameter displayed a faster release, when compared to the 1 mm rods, due to the larger surface area to volume ratio of the smaller rods.

Example 4. In Vitro Release of Small Molecules from Silk Fibroin Gels

All formulations were prepared with silk yarn purchased from SOHO. The silk hydrogels were prepared with celecoxib (CXB) (from Cipla, Miami Fla.). The poloxamer-188 (P188), sodium chloride, and hydrochloric acid were from Sigma-Aldrich (St. Louis, Mo.), while the PEG4 kDa was from Clariant, Charlotte N.C. Polysorbate-80 was purchased from Croda (Snaith UK). Potassium phosphate monobasic and potassium phosphate dibasic were purchased from

TABLE 3

THEORETICAL SILK FIBROIN AND CELECOXIB PERCENTAGES FOR 0.5 MM SILK ROD SAMPLES

| Sample No. | Sample Name | Stock Concentration of Silk for Formulation (w/v %) | Silk Prep Boil Time (min) | Silk-Fibroin Mass (mg) | CXB Mass (mg) | Silk-Fibroin Final % (w/w) | CXB Final % (w/w) | Phosphate Buffer Conc. (mM) |
|---|---|---|---|---|---|---|---|---|
| — | — | — | 480 | 50 | 200 | 20 | 80 | 37 |
| — | — | — | 480 | 75 | 200 | 27.3 | 72.2 | 55.6 |
| — | — | — | 480 | 100 | 100 | 50 | 50 | 95.2 |
| — | — | — | 480 | 100 | 150 | 40 | 60 | 83.3 |
| 8-65-6 | 480 mb; 0.5 mm; 40% st; 100 mgsf; 200 mgcxb; lyo; 33.3% sf; 66.7% cxb | 40 | 480 | 100 | 200 | 33.3 | 66.7 | 74.1 |
| — | — | — | 480 | 100 | 250 | 28.6 | 71.4 | 66.7 |
| — | — | — | 120 | 50 | 200 | 20 | 80 | 37 |
| — | — | — | 120 | 75 | 200 | 27.3 | 72.2 | 55.6 |
| — | — | — | 120 | 100 | 150 | 40 | 60 | 83.3 |

Figure 2A:
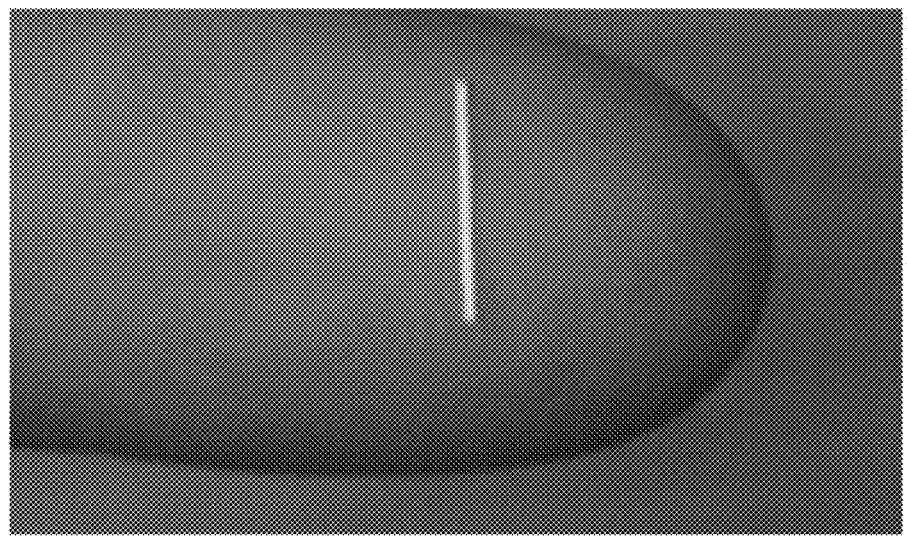
FIG. 2A is an image showing a silk fibroin rod formulated with celecoxib, with a diameter of 430 μm.
Figure 2B:
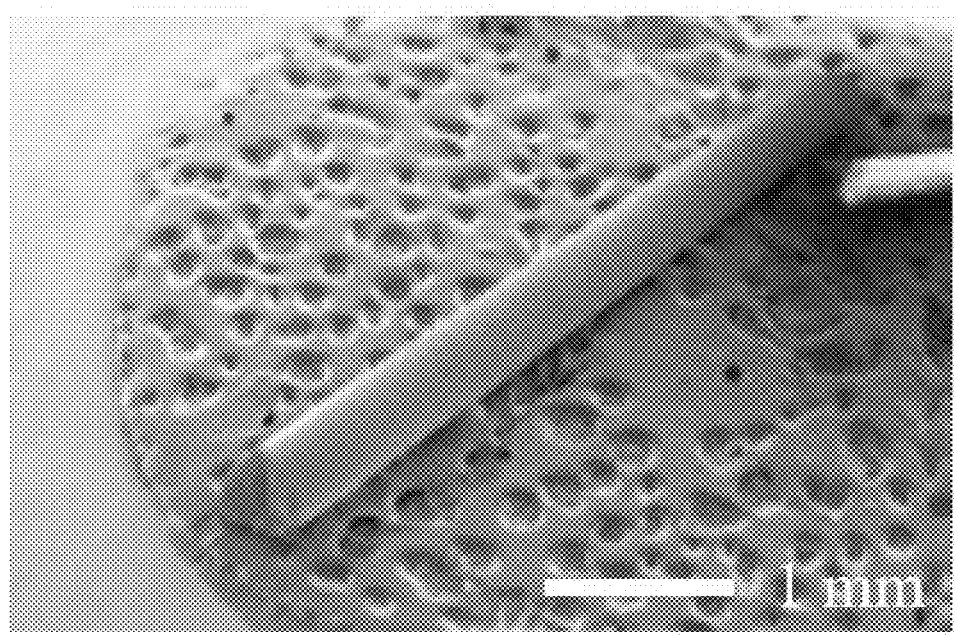
FIG. 2B is a SEM image showing a silk fibroin rod formulated with celecoxib, with a diameter of 430 μm.
Figure 2C:
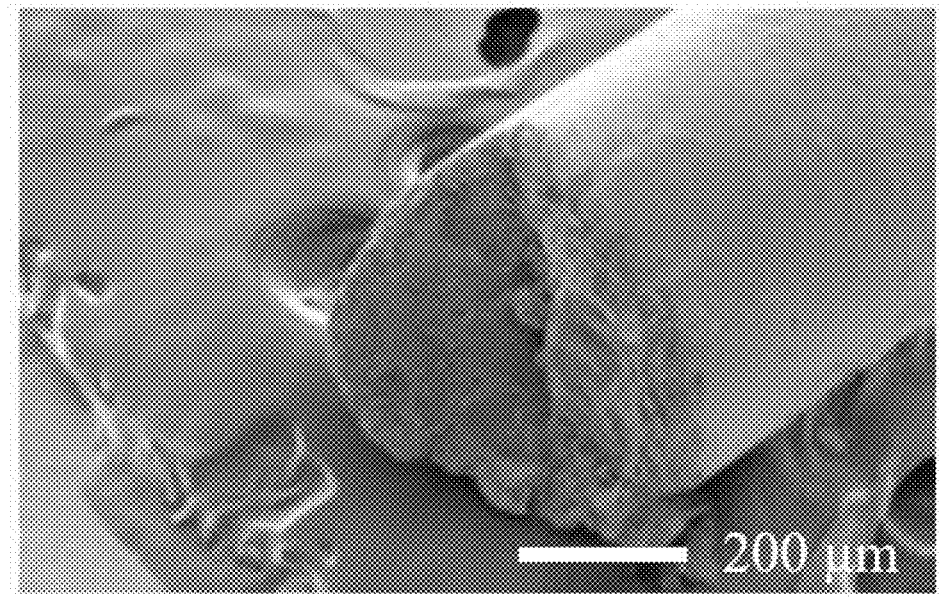
FIG. 2C is a SEM image showing a silk fibroin rod formulated with celecoxib, with a diameter of 430 μm.
Figure 2D:
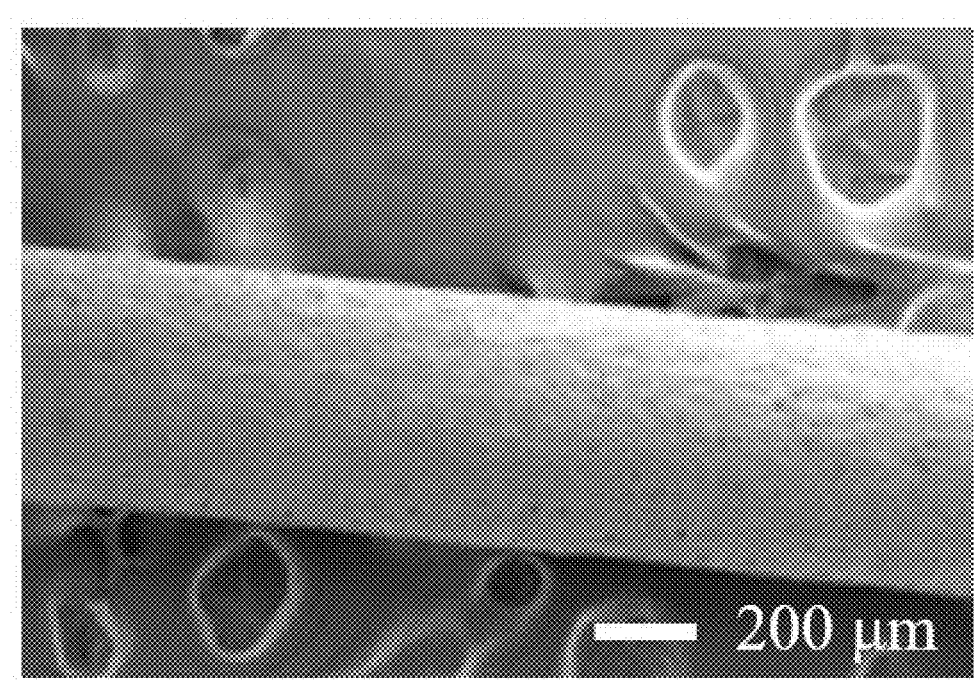
FIG. 2D is a SEM image showing a silk fibroin rod formulated with celecoxib, with a diameter of 430 μm.

The resulting lyophilized rods were photographed (see FIG. 2A) of imaged via SEM (see FIG. 2B, FIG. 2C, and FIG. 2D). The rods were approximately 400 µm in diameter, and the rod in FIG. 2A, FIG. 2B, FIG. 2C, and FIG. 2D had a diameter of 430 µm. The silk-fibroin rods were densely packed with an even distribution of the API. The outer surfaces and cross-sectional surfaces of the silk-fibroin rods loaded with CXB had ridges that appeared approximately 15 µm in length. Furthermore, the cross-sectional images of the silk-fibroin rods with celecoxib contained few small pores.

In Vitro Release Experiments

The rods were cut to 1 cm lengths to standardize release, and the weights of the rods were recorded. The densities of Sigma Aldrich Fine Chemical (SAFC, St. Louis Mo.). Phosphate buffered saline was purchased from Gibco (USA).

Formulation of Silk Fibroin Hydrogels

Silk fibroin hydrogels were formulated with poloxamer-188 (P188) (from Sigma, St. Louis, Mo.) or polyethylene glycol 4000 Da (PEG 4k) (from Clariant, Charlotte N.C.). These hydrogels were formulated with celecoxib, the delivery of which was monitored. To prepare the formulations, a 27.8% suspension of celecoxib (CXB) in 0.79% polysorbate 80 as well as a stock solution of phosphate buffer (315 mM, pH=7.4) was used to dissolve either 120 mb or 480 mb silk fibroin and added to a syringe. Excipient solutions were then prepared with varying combinations of sodium chloride, PEG4 kDa, P188, and/or hydrochloric acid and added to a second syringe. Excipient solutions were prepared so that a 0.75:1 mix of silk-fibroin solution:excipient solution would result in the desired final formulations, with an osmolarity of 280 mOsm. The two syringes were then connected via a B Braun fluid dispensing connector, and the contents of the two syringes were mixed back and forth until homogeneous (at least 25 times). The syringes were then capped with a sterile syringe cap and incubated on a rotator at 37° C. for 24 hours. Syringes were stored at 4° C. until analysis.

Formulations were prepared as described in Table 4A and Table 4B, with either high molecular weight (HMW or 120 mb, with an average molecular weight of 100-300 kDa) or low molecular weight (LMW or 480 mb, with an average molecular weight of about 30-60 kDa) silk fibroin. Longer boiling times, measured in "minute boil" or "mb", produced silk fibroin with smaller molecular weights. The samples in Table 4A and Table 4B are named by the process used to prepare and formulate each hydrogel. For example, in the sample named 120 mb; hyd; 27.8% cxbst; 5% SFf; 10% CXBf; 40% PEG4kf, "120 mb" refers to silk degummed with a 120-minute boil, "hyd" refers to the formulation of the sample as a hydrogel, "27.8% cxbst" refers to a preparation from a stock solution of 27.8% of celecoxib, "5% SFf" refers to a formulation with 5% (w/v) silk fibroin, "10% CXBf" refers to a formulation with 10% (w/v) celecoxib, and "40% PEG4kf" refers to a formulation with 40% PEG 4 kDa. Some hydrogels were prepared with P188 (% P188f). The hydrogels were injectable through a 27-gauge, ½ inch needle. The hydrogels were formulated with varying silk fibroin molecular weights, gelling excipients, and silk fibroin concentrations. The hydrogels were formulated under aqueous conditions, with tight control of osmolarity and pH. The pH was measured with a B30PCI Benchtop Multi Parameter Meter—pH, Conductivity, ISE (VWR Catalog #89231-696), with a glass probe (VWR Catalog #89231-592). All hydrogels had a final phosphate buffer concentration of 22 mM.

TABLE 4A

DESCRIPTIONS OF HYDROGELS PREPARED LOADED WITH CELECOXIB

| Sample No. | Sample name | Description | Min. Boil (mb) | Silk-fibroin Conc. % | Excipient | Excipient conc. % | CXB Conc. % | NaCl Conc. (mg/mL) | HCl Conc. (mM) |
|---|---|---|---|---|---|---|---|---|---|
| 168-1 | 120 mb; hyd; 27.8% cxbst; 5% SFf; 10% CXBf; 40% PEG4kf | 5% 120 mb with PEG 4k | 120 | 5 | PEG 4k | 40 | 10 | 2.95 | 15 |
| 168-2 | 120 mb; hyd; 27.8% cxbst; 3% SFf; 10% CXBf; 40% PEG4kf | 3% 120 mb with PEG 4k | 120 | 3 | PEG 4k | 40 | 10 | 2.95 | 15 |
| 168-3 | 120 mb; hyd; 27.8% cxbst; 5% SFf; 10% CXBf; 10% P188f | 5% 120 mb with P188 | 120 | 5 | P188 | 10 | 10 | 5.97 | 0 |
| 168-4 | 120 mb; hyd; 27.8% cxbst; 3% SFf; 10% CXBf; 10% P188f | 3% 120 mb with P188 | 120 | 3 | P188 | 10 | 10 | 5.99 | 0 |
| 168-5 | 480 mb; hyd; 27.8% cxbst; 5% SFf; 10% CXBf; 40% PEG4kf | 5% 480 mb with PEG 4k | 480 | 3 | PEG 4k | 40 | 10 | 2.87 | 15 |
| 168-6 | 480 mb; hyd; 27.8% cxbst; 3% SFf; 10% CXBf; 40% PEG4kf | 3% 480 mb with PEG 4k | 480 | 3 | PEG 4k | 40 | 10 | 2.91 | 15 |
| 168-7 | 480 mb; hyd; 27.8% cxbst; 5% SFf; 10% CXBf; 10% P188f | 5% 480 mb with P188 | 480 | 5 | P188 | 10 | 10 | 5.90 | 0 |
| 168-8 | 480 mb; hyd; 27.8% cxbst; 3% SFf; 10% CXBf; 10% P188f | 3% 480 mb with P188 | 480 | 3 | P188 | 10 | 10 | 5.94 | 0 |
| 168-9 | 480 mb; hyd; 27.8% cxbst; 2% SFf; 10% CXBf; 10% P188f | 2% 480 mb with P188 | 480 | 2 | P188 | 10 | 10 | 5.96 | 0 |

TABLE 4B

PROPERTIES OF THE HYDROGELS PREPARED LOADED WITH CELECOXIB

| Sample No. | Sample name | Actual CXB % (w/v) | Standard Deviation of Actual CXB % | pH | Replicate | Mass (mg) |
|---|---|---|---|---|---|---|
| 168-1 | 120 mb; hyd; 27.8% cxbst; 5% SFf; 10% CXBf; 40% PEG4kf | 9.5 | 0.8 | 6.78 | A<br>B<br>C | 49.78<br>54.35<br>53.45 |
| 168-2 | 120 mb; hyd; 27.8% cxbst; 3% SFf; 10% CXBf; 40% PEG4kf | 9.5 | 0.3 | 6.82 | A<br>B<br>C | 52.89<br>54.44<br>50.48 |
| 168-3 | 120 mb; hyd; 27.8% cxbst; 5% SFf; 10% CXBf; 10% P188f | 11.9 | 3.5 | 7.1 | A<br>B<br>C | 56.07<br>53.96<br>49.44 |
| 168-4 | 120 mb; hyd; 27.8% cxbst; 3% SFf; 10% CXBf; 10% P188f | 9.6 | 0.8 | 7.06 | A<br>B<br>C | 50.42<br>54.12<br>50.14 |
| 168-5 | 480 mb; hyd; 27.8% cxbst; 5% SFf; 10% CXBf; 40% PEG4kf | 9.3 | 0 | 7.15 | A<br>B<br>C | 51.75<br>49.55<br>55.33 |
| 168-6 | 480 mb; hyd; 27.8% cxbst; 3% SFf; 10% CXBf; 40% PEG4kf | 9.2 | 0.7 | 6.98 | A<br>B<br>C | 56.38<br>50.92<br>49.08 |
| 168-7 | 480 mb; hyd; 27.8% cxbst; 5% SFf; 10% CXBf; 10% P188f | 8.7 | 0.1 | 7.16 | A<br>B<br>C | 55.12<br>51.59<br>54.18 |
| 168-8 | 480 mb; hyd; 27.8% cxbst; 3% SFf; 10% CXBf; 10% P188f | 9.8 | 0.6 | 7.15 | A<br>B<br>C | 55.9<br>53.53<br>56.17 |
| 168-9 | 480 mb; hyd; 27.8% cxbst; 2% SFf; 10% CXBf; 10% P188f | 9.4 | 1.6 | 7.13 | A<br>B<br>C | 52.39<br>54.56<br>53.38 |

In Vitro Release Experiments

In triplicate, 50 mg of each formulation was weighed into half of a #4 gelatin capsule (MyHerbar, Dallas Tex.). It had previously been shown that the solubility of celecoxib in this release media was 850 µg/mL. 45 mL of this release media allowed for 38 mg CXB solubility. This media ensured sink conditions (greater than or equal to 5 times the CXB solubility) were maintained throughout the course of the study. The tubes were capped and incubated at 37° C. with shaking. 1 mL of the release media was collected from each sample at each timepoint and replaced with 1 mL fresh media. At each timepoint, the tubes were left to stand on end for at least 30 minutes to allow the formulation to settle prior to taking the sample. Release media was analyzed by HPLC-UV (Agilent 1290 HPLC system) at 260 nm. Controls were prepared at Day 0 by weighing 50 mg of each formulation in triplicate in separate 20 mL glass vials. Methanol was added to each sample to extract CXB. Samples were placed on a shaker at room temperature for 24 hours. The supernatant was analyzed by HPLC-UV to determine CXB loading. The results of the in vitro release experiments, seen in Table 5A, and Table 5B were consistent with first-order kinetics, with initial bursts from 25%-100%. All tested hydrogel formulations released the small molecule up to one month after the start of the experiment.

TABLE 5A

IN VITRO RELEASE KINETICS FOR HYDROGELS LOADED WITH CELECOXIB; AVERAGE CUMULATIVE PERCENTAGE OF API RELEASED

| Time (days) | Sample No. | | | | | | | | |
|---|---|---|---|---|---|---|---|---|---|
| | 168-1 | 168-2 | 168-3 | 168-4 | 168-5 | 168-6 | 168-7 | 168-8 | 168-9 |
| 0 | 0.00 | 0.00 | 0.00 | 0.00 | 0.00 | 0.00 | 0.00 | 0.00 | 0.00 |
| 1 | 24.59 | 42.53 | 51.15 | 42.75 | 30.64 | 96.24 | 43.26 | 27.68 | 46.90 |
| 4 | 50.91 | 67.96 | 73.54 | 69.47 | 56.39 | 96.99 | 73.38 | 51.56 | 74.89 |
| 7 | 67.59 | 81.51 | 79.05 | 82.51 | 75.78 | 96.32 | 87.00 | 66.01 | 87.51 |
| 14 | 79.43 | 86.60 | 75.51 | 88.35 | 86.61 | 94.02 | 94.64 | 80.88 | 93.81 |
| 25 | 96.86 | 98.22 | 85.72 | 104.14 | 102.82 | 105.89 | 110.51 | 100.24 | 105.61 |
| 29 | 95.90 | 96.43 | 82.39 | 99.86 | 102.21 | 100.32 | 105.56 | 95.38 | 102.51 |

TABLE 5B

STANDARD DEVIATIONS OF THE AVERAGE CUMULATIVE PERCENTAGE OF API RELEASED FROM THE IN VITRO RELEASE KINETICS EXPERIMENTS FOR HYDROGELS LOADED WITH CELECOXIB

| Time (days) | Sample No. | | | | | | | | |
|---|---|---|---|---|---|---|---|---|---|
| | 168-1 | 168-2 | 168-3 | 168-4 | 168-5 | 168-6 | 168-7 | 168-8 | 168-9 |
| 0 | 0.00 | 0.00 | 0.00 | 0.00 | 0.00 | 0.00 | 0.00 | 0.00 | 0.00 |
| 1 | 3.04 | 7.33 | 2.96 | 13.35 | 3.38 | 1.36 | 15.21 | 5.30 | 10.79 |
| 4 | 5.07 | 5.88 | 1.77 | 11.33 | 5.30 | 2.46 | 19.62 | 6.69 | 9.42 |
| 7 | 5.21 | 4.57 | 4.00 | 9.15 | 10.63 | 2.75 | 16.71 | 6.27 | 8.46 |
| 14 | 4.56 | 2.18 | 7.29 | 4.63 | 5.20 | 3.93 | 11.75 | 4.33 | 1.02 |
| 25 | 2.68 | 4.97 | 9.73 | 8.47 | 4.63 | 0.74 | 6.66 | 4.63 | 3.76 |
| 29 | 1.80 | 3.88 | 8.30 | 4.87 | 3.02 | 2.68 | 7.77 | 2.59 | 2.74 |

For the hydrogels prepared with P188, the initial burst was the highest for the hydrogel with 5% (w/v) high molecular weight silk fibroin, as seen in Table 5A. The hydrogel with 3% (w/v) low molecular weight silk fibroin had the lowest initial burst of therapeutic agent. The remaining hydrogels had initial bursts of a similar magnitude, the values of which were between those of the 5% (w/v) high molecular weight and the 3% (w/v) low molecular weight silk fibroin hydrogels. The hydrogels (with P188) with higher concentrations of silk fibroin demonstrated greater initial bursts of API in comparison with the corresponding hydrogels with lower concentrations of silk fibroin. In addition, the hydrogels (with P188) prepared from higher molecular weight silk fibroin also demonstrated greater initial bursts of API than the corresponding hydrogels with lower molecular weight silk fibroin.

For the hydrogels prepared with PEG4k, the initial burst was the highest for the hydrogel prepared with 3% (w/v) low molecular weight silk fibroin, followed by the hydrogel prepared with 3% (w/v) high molecular weight silk fibroin. The hydrogel prepared the with 5% (w/v) high molecular weight silk fibroin had the lowest initial burst, as seen in Table 5A. The hydrogels (with PEG4k) prepared from higher molecular weight silk fibroin demonstrated lower initial bursts of API than the hydrogels prepared from lower molecular weight silk fibroin. In addition, the hydrogel (with PEG4k) with a lower concentration of silk fibroin demonstrated a greater initial burst of API than the corresponding hydrogel with a higher concentration of silk fibroin.

The use of excipients with different molecular weights also revealed a pattern in the initial burst of therapeutic agent from the hydrogels. While both hydrogels were prepared at the same osmolarity, excipients used had different molecular weights. PEG4k had a molecular weight of 4 kDa, while P188 had a molecular weight of 8.4 kDa. The molecular weight of the excipient modulated the observed trends in the initial burst percentages. Hydrogels prepared from excipients with higher molecular weights demonstrated a direct relationship between the concentration of silk fibroin and the initial burst and a direct relationship between the molecular weight of the silk fibroin and the initial burst. Meanwhile, hydrogels prepared from excipients with lower molecular weights demonstrated an inverse relationship between the concentration of silk fibroin and the initial burst and an inverse relationship between the molecular weight of the silk fibroin and the initial burst.

Example 5. Biocompatibility of Silk Fibroin Rods and Hydrogels

Silk fibroin rods or silk fibroin hydrogels were formulated with a generic NSAID. The silk fibroin rods had a diameter of 430 μm and a length of 10 mm. Silk fibroin hydrogels were formulated with and without 100 mg/mL NSAID. The rods or hydrogels were administered to healthy rabbits as 100 μL injections in a 27-gauge needle. The rods were pre-loaded into sterile 21G, 1" needles with pieces of 28G wire were pre-cut, sterilized and placed into the needle from the hub. The needle was placed (as described below) and the formulation was pushed into the intravitreal space, 2 mm posterior to the limbus using the length of 28G wire. The wire extended past the end of needle 3-4 mm to ensure full injection. A lid speculum was inserted into the rabbit's left eye lid. The conjunctiva was drenched with BSS solution from a sterile dropper (3-5 drops). 1-2 drops of betadine solution was applied allowing 30 seconds after administration. One additional drop of betadine solution was applied followed by injection of the formulation using a double-plane tunnel technique (the sclera was penetrated at 15°-30°, then the needle is repositioned to a 45°-60° angle while the sclera was still engaged; the formulation was delivered and the needle removed at a 90° angle). Following injection, the central retinal artery was examined via indirect ophthalmoscopy to confirm perfusion and 1-2 drops of betadine solution were added to the conjunctiva prior to removal of the speculum. The silk fibroin compositions remained cohesive or in one piece in the intravitreal space. The subjects experienced normal intraocular pressures, no local inflammation, no hemorrhage, and no other complications. The silk fibroin rods and hydrogels were tolerated in the intravitreal space.

Example 6. Tolerability Studies

The tolerability of silk fibroin solutions, hydrogels, and rods was monitored in rabbits, rats, and dogs. All materials studied were well-tolerated clinically. The hydrogel material was observed to integrate into tissue with minimal inflammation, which was consistent with a transient local foreign body reaction. No adverse reactions were noted.

Example 7. Human Whole Blood Assay

Figure 3:
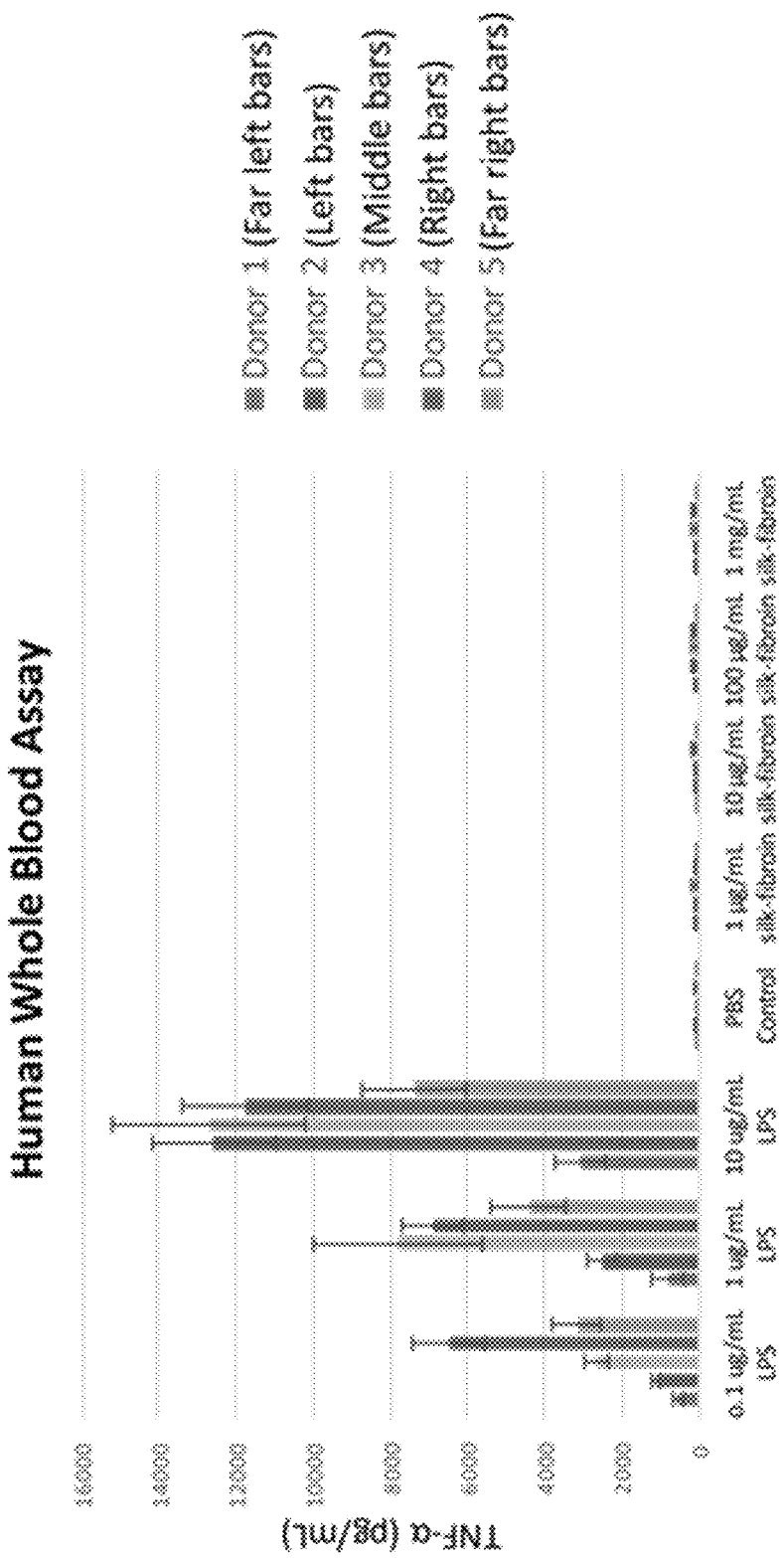
FIG. 3 is a graph showing TNF-α concentration in human whole blood after administration of various concentrations of lipopolysaccharide (LPS) or silk fibroin.

Whole human blood was exposed to soluble silk fibroin for 24 hours at 37° C. and assessed for inflammation. Lipopolysaccharide (LPS) was used as a positive stimulator of the inflammatory marker TNF-α, in whole blood. The experiments were conducted in the presence and absence of LPS to determine whether any formulation constituent had the activity of potentiating a known inflammatory signal. Plasma was collected at the end of the experiment and analyzed by enzyme-linked immunosorbent assay (ELISA) for TNF-α (FIG. 3). The experiments were performed with blood from 5 donors (FIG. 3) and repeated with 2 additional donors. The silk fibroin did not increase the release of TNF-α, and other inflammatory markers such as PGE2. The results were consistent with multiple silk fibroin formats, such as silk fibroin with different molecular weights, hydrogels, 3D fibroin scaffolds, and hydrogel extracts. No signs of local sensitization were detected after extended exposure.

Example 8. Measurements of Diameter, Density and In Vitro Experiments on 1 mm Celecoxib Loaded Silk Fibroin Rods The diameter of the silk-fibroin rods was measured using digital calipers. The rods were cut to 1 cm lengths to standardize release, and the weights of the rods were recorded. The density of the rods was calculated for each formulation. As seen in Table 6, the experimental data revealed that the samples generated at each theoretical w/w % formed silk rods with a diameter slightly below 1 mm, the theoretical silk rod diameter. In addition, most of the samples yielded silk rods with a density near 1 g/mL. In Table 6, "Std. Dev." Refers to standard deviation.

TABLE 6

OBSERVED DIAMETER AND DENSITY OF 1 MM SILK-FIBROIN RODS

| Sample No. | Sample Name | Diameter (mm) | Density (g/mL) | Density Std. Dev. (g/mL) |
|---|---|---|---|---|
| 8-58-1 | 480 mb; 1 mm; 20% st; 50 mgsf; 150 mgcxb; lyo; 25% sf; 75% cxb | 0.93 | 0.79 | 0.05 |
| 8-58-2 | 480 mb; 1 mm; 20% st; 50 mgsf; 200 mgcxb; lyo; 20% sf; 80% cxb | 0.95 | 0.83 | 0.08 |
| 8-58-4 | 480 mb; 1 mm; 30% st; 75 mgsf; 150 mgcxb; lyo; 33.3% sf; 66.7% cxb | 0.88 | 1.00 | 0.06 |
| 8-58-5 | 480 mb; 1 mm; 30% st; 75 mgsf; 200 mgcxb; lyo; 27.3% sf; 72.2% cxb | 0.92 | 1.09 | 0.14 |
| 8-58-6 | 480 mb; 1 mm; 30% st; 75 mgsf; 250 mgcxb; lyo; 23% sf; 77% cxb | 0.96 | 1.07 | 0.05 |
| 8-58-7 | 480 mb; 1 mm; 40% st; 100 mgsf; 150 mgcxb; lyo; 40% sf; 60% cxb | 0.88 | 1.19 | 0.07 |
| 8-58-8 | 480 mb; 1 mm; 40% st; 100 mgsf; 200 mgcxb; lyo; 33.3% sf; 66.7% cxb | 0.91 | 1.28 | 0.05 |
| 8-58-9 | 480 mb; 1 mm; 40% st; 100 mgsf; 250 mgcxb; lyo; 28.6% sf; 71.4% cxb | 0.92 | 1.30 | 0.11 |

Extraction controls were run to determine celecoxib (CXB) loading in the rods. Pre-weighed, 1 cm lengths of the rods were placed into 5 mL of 100% methanol, vortexed, and sonicated. The samples were left to shake overnight at room temperature. The methanol was then analyzed for CXB loading via UPLC. For most samples, the experimental loading percentage of CXB of the silk rods was lower than the theoretical loading percentage of CXB, as seen in Table 7. Many of the samples had actual CXB loadings around 8% lower than the theoretical CXB loading.

TABLE 7

CELECOXIB LOADING AFTER EXTRACTION FOR 1 MM RODS

| Sample No. | Sample Name | Theoretical CXB % (w/w) | Actual CXB % (w/w) | Standard Dev. of CXB % | Density (g/mL) |
|---|---|---|---|---|---|
| 8-58-1 | 480 mb; 1 mm; 20% st; 50 mgsf; 150 mgcxb; lyo; 25% sf; 75% cxb | 75 | 64.1 | 4.4 | 0.79 |
| 8-58-2 | 480 mb; 1 mm; 20% st; 50 mgsf; 200 mgcxb; lyo; 20% sf; 80% cxb | 80 | 70.4 | 0.8 | 0.83 |
| 8-58-4 | 480 mb; 1 mm; 30% st; 75 mgsf; 150 mgcxb; lyo; 33.3% sf; 66.7% cxb | 66.7 | 59.3 | 1.1 | 1.00 |
| 8-58-5 | 480 mb; 1 mm; 30% st; 75 mgsf; 200 mgcxb; lyo; 27.3% sf; 72.2% cxb | 72.2 | 65.6 | 4.1 | 1.09 |
| 8-58-6 | 480 mb; 1 mm; 30% st; 75 mgsf; 250 mgcxb; lyo; 23% sf; 77% cxb | 77 | 74.0 | 9.0 | 1.07 |
| 8-58-7 | 480 mb; 1 mm; 40% st; 100 mgsf; 150 mgcxb; lyo; 40% sf; 60% cxb | 60 | 59.7 | 15.7 | 1.19 |
| 8-58-8 | 480 mb; 1 mm; 40% st; 100 mgsf; 200 mgcxb; lyo; 33.3% sf; 66.7% cxb | 66.7 | 62.7 | 2.4 | 1.28 |
| 8-58-9 | 480 mb; 1 mm; 40% st; 100 mgsf; 250 mgcxb; lyo; 28.6% sf; 71.4% cxb | 71.4 | 65.9 | 4.5 | 1.30 |

For the release experiments, the rods were placed into 45 mL of phosphate buffer, pH 7.4, 2% (v/v) Polysorbate-80 (from Croda, Snaith UK), and 0.05% (w/v) sodium azide (from Fisher Chemical, Waltham Mass.). This buffer ensured that the release was conducted under sink conditions (≥5× saturated solubility). The samples were incubated at 37° C. with gentle shaking. 1 mL of the release medium was taken at each timepoint (typically 1, 4, and 7 days and then weekly thereafter). The release medium was then analyzed via ultra-performance liquid chromatography (UPLC) to determine CXB concentration. The results were shown in Table 8A and Table 8B.

TABLE 8A

IN VITRO RELEASE KINETICS OF CELECOXIB FROM 1 MM SILK-FIBROIN RODS; CUMULATIVE PERCENTAGE OF API RELEASED

| Day | 8-58-1 | 8-58-2 | 8-58-4 | 8-58-5 | 8-58-6 | 8-58-7 | 8-58-8 | 8-58-9 |
|---|---|---|---|---|---|---|---|---|
| 0 | 0 | 0.0 | 0.0 | 0 | 0.0 | 0.0 | 0.0 | 0.0 |
| 1 | 18.6 | 15.0 | 10.0 | 9.0 | 7.1 | 5.6 | 6.2 | 5.7 |
| 4 | 33.3 | 29.1 | 21.4 | 17.7 | 14.3 | 11.1 | 12.8 | 11.8 |
| 7 | 48.4 | 41.5 | 28.1 | 25.4 | 21.2 | 16.8 | 18.7 | 17.6 |
| 11 | 60.3 | 51.2 | 37.4 | 34.2 | 27.8 | 22.2 | 25.0 | 23.8 |
| 14 | 66.6 | 58.8 | 41.6 | 37.8 | 32.1 | 25.1 | 28.2 | 26.5 |
| 21 | 81.9 | 73.7 | 53.2 | 50.0 | 42.0 | 34.1 | 36.2 | 33.8 |
| 28 | 98.0 | 88.3 | 65.5 | 59.0 | 51.4 | 42.3 | 43.5 | 42.3 |
| 35 | 96.9 | 91.4 | 67.8 | 62.6 | 54.4 | 40.9 | 48.3 | 45.0 |
| 42 | 93.7 | 91.5 | 66.7 | 61.6 | 54.8 | 40.9 | 49.3 | 44.3 |
| 49 | 101.3 | 96.3 | 76.3 | 71.0 | 62.8 | 47.8 | 54.8 | 51.2 |
| 56 | 98.1 | 95.4 | 79.1 | 73.5 | 66.8 | 49.9 | 58.5 | 52.5 |
| 64 | 97.2 | 102.0 | 84.4 | 77.6 | 72.5 | 52.9 | 60.9 | 57.3 |
| 70 | — | — | 88.1 | 81.2 | 73.6 | 57.4 | 65.5 | 60.8 |
| 76 | — | — | 89.6 | 83.2 | 75.0 | 58.1 | 66.9 | 62.8 |
| 84 | — | — | 94.9 | 87.3 | 79.3 | 61.7 | 71.0 | 65.8 |
| 98 | — | — | 116.8 | 106.1 | 98.6 | 75.7 | 88.8 | 82.6 |
| 112 | — | — | 118.2 | 108.5 | 103.9 | 81.1 | 96.2 | 87.7 |
| 126 | — | — | 115.1 | 106.6 | 103.6 | 83.4 | 101.8 | 91.8 |
| 147 | — | — | — | — | — | 92.2 | 111.6 | 100.5 |
| 162 | — | — | — | — | — | 98.9 | 121.7 | 108.8 |
| 176 | — | — | — | — | — | 103.1 | 138.4 | 114.6 |
| 190 | — | — | — | — | — | 104.9 | 124.2 | 115.4 |
| 204 | — | — | — | — | — | 107.1 | 123.2 | 116.2 |

TABLE 8B

STANDARD DEVIATIONS OF THE DATA FROM THE IN VITRO RELEASE KINETICS OF CELECOXIB FROM 1 MM SILK-FIBROIN RODS; CUMULATIVE PERCENTAGE OF API RELEASED

| Day | 8-58-1 | 8-58-2 | 8-58-4 | 8-58-5 | 8-58-6 | 8-58-7 | 8-58-8 | 8-58-9 |
|---|---|---|---|---|---|---|---|---|
| 0 | 0 | 0.00 | 0.00 | 0 | 0.00 | 0.00 | 0.00 | 0.00 |
| 1 | 3.7 | 1.94 | 0.42 | 0.9 | 0.32 | 0.16 | 0.05 | 0.30 |
| 4 | 4.3 | 2.80 | 3.95 | 0.5 | 0.19 | 0.24 | 0.54 | 0.61 |
| 7 | 5.7 | 3.31 | 1.22 | 0.5 | 0.22 | 0.40 | 0.32 | 0.75 |
| 11 | 6.9 | 2.87 | 0.58 | 0.7 | 0.49 | 0.80 | 0.90 | 0.74 |
| 14 | 6.3 | 3.33 | 0.98 | 0.7 | 0.94 | 0.64 | 0.77 | 0.80 |
| 21 | 6.8 | 4.21 | 3.11 | 6.0 | 2.14 | 4.44 | 0.98 | 2.17 |
| 28 | 6.3 | 4.11 | 0.97 | 1.2 | 1.31 | 2.23 | 2.76 | 1.84 |
| 35 | 6.3 | 2.93 | 1.40 | 1.5 | 1.98 | 1.74 | 3.05 | 1.79 |
| 42 | 3.46 | 7.23 | 2.09 | 1.6 | 2.20 | 1.43 | 2.84 | 0.94 |
| 49 | 2.91 | 3.96 | 2.62 | 1.2 | 1.93 | 1.69 | 1.86 | 1.61 |
| 56 | 2.18 | 5.20 | 2.95 | 1.0 | 3.00 | 2.08 | 2.12 | 1.43 |
| 64 | 5.31 | 7.87 | 8.65 | 1.1 | 7.93 | 3.39 | 1.80 | 1.47 |
| 70 | — | — | 2.85 | 1.6 | 2.52 | 2.28 | 3.04 | 2.64 |
| 76 | — | — | 3.28 | 0.8 | 1.93 | 3.36 | 3.57 | 3.01 |
| 84 | — | — | 3.93 | 1.9 | 2.43 | 3.68 | 4.64 | 3.83 |
| 98 | — | — | 6.36 | 0.8 | 3.45 | 4.39 | 7.17 | 4.62 |
| 112 | — | — | 8.59 | 1.5 | 3.88 | 5.16 | 7.89 | 4.77 |
| 126 | — | — | 7.38 | 1.3 | 3.87 | 6.56 | 11.24 | 5.32 |
| 147 | — | — | — | — | — | 8.93 | 16.8 | 8.89 |
| 162 | — | — | — | — | — | 9.82 | 20.4 | 7.60 |
| 176 | — | — | — | — | — | 10.41 | 12.5 | 8.53 |
| 190 | — | — | — | — | — | 9.85 | 16.7 | 10.83 |
| 204 | — | — | — | — | — | 9.42 | 10.6 | 9.36 |

The data demonstrated near-zero-order release kinetics. Each silk fibroin rod sample experienced an initial burst of API release as seen in Table 9, followed by the continued gradual release of the therapeutic agent at a slower rate. The initial burst of API release from the rods ranged from about 5-20% of the API loaded into the rods by mass. The theoretical loading percentage of CXB affected the initial burst of API release. Higher percentages of silk fibroin in the theoretical loading (w/w) percentages of silk fibroin correlated with lower initial burst rates. This inverse relationship between the amount of silk fibroin in the rods and the initial burst rate was evident across all samples. Sample 8-58-1 reached complete release by day 35, and 8-58-2 reached completion by day 64. Samples 8-58-4 and 8-58-5, reached complete release by day 98. Sample 8-58-6 reached complete release by day 112.

TABLE 9

CELECOXIB RELEASE RATES FOR 1 MM RODS

| Sample No. | Ratio CXB:SF Theoretical | Ratio CXB:SF Actual | Initial Burst % | Daily Release % (at 64 days) | Initial burst:Daily release (at 64 days) | Density (g/mL) |
|---|---|---|---|---|---|---|
| 8-58-1 | 3.0 | 1.8 | 18.6 | 1.34 | 13.9 | 0.79 |
| 8-58-2 | 4.0 | 2.4 | 15.0 | 1.42 | 10.6 | 0.83 |
| 8-58-4 | 2.0 | 1.5 | 10.0 | 1.19 | 8.4 | 1.00 |
| 8-58-5 | 2.6 | 1.9 | 9.0 | 1.11 | 8.1 | 1.09 |
| 8-58-6 | 3.3 | 2.8 | 7.1 | 1.04 | 6.8 | 1.07 |
| 8-58-7 | 1.5 | 1.5 | 5.6 | 0.76 | 7.4 | 1.19 |
| 8-58-8 | 2.0 | 1.7 | 6.2 | 0.90 | 6.9 | 1.28 |
| 8-58-9 | 2.5 | 1.9 | 5.7 | 0.82 | 6.9 | 1.30 |

The kinetics data demonstrated the possible existence of a relationship between the rate of API release and the (w/w) ratio of API to silk fibroin for the 1 mm silk fibroin rods. These ratios were calculated for both the theoretical loading and the actual loading of the rods. The use of each formulation in a device or product might depend on the desired amount of API released in the time frame of interest. For example, if a smaller amount of the API needed to be released in the designated time frame, the formulations from Samples 8-58-7 through 8-58-9 would be most effective. As seen in Table 8A and Table 9, the release duration of CXB was related to the rod density, with increased density resulting in longer release times and slower release rates. The rods with a higher density also demonstrated a lower daily release percentage and lower initial burst percentages. Daily release percentage was defined as the weight percent of the total API released per day, and it was calculated as the slope of the plot of cumulative release over time. We have shown the daily release percentages calculated for the first 64 days of the study. The rod density was tuned by varying the starting concentration of the silk-fibroin used during formulation. For example, the formulations prepared with 40% (w/v) silk-fibroin solution had the highest densities of 1.30, 1.28, and 1.19 g/mL, while the formulations prepared with 20% (w/v) silk-fibroin had the lowest densities of 0.83 and 0.79 g/mL. The initial burst and release rate decreased with increasing density. Ultimately, the samples with a density below 1.0 g/mL reached complete release about 64 days or less, the samples with a density between 1.0 g/mL and 1.1 g/mL reached complete release in about 98 days, and the samples with a density above 1.1 g/mL reached complete release in greater than 98 days. The higher density rods represented a more tightly packed CXB/fibroin formulation. Since both the CXB as well as the formulated silk-fibroin were hydrophobic, this lead to the prevention of water uptake into the rod. The more tightly packed rods also slowed the diffusion of CXB from the formulation by creating locally saturated regions of CXB within the rod, slowing the dissolution and release.

Example 9. Measurements of Diameter, Density and In Vitro Experiments on 0.5 mm Celecoxib Loaded Silk Fibroin Rods As seen in the experiments on the 1 mm silk rods, the diameter of the 0.5 mm silk-fibroin rods was measured using digital calipers. The rods were cut to 1 cm lengths to standardize release, and the weights of the rods were recorded. The densities of the rods were calculated for each formulation. The rods were placed into 45 mL of 1× phosphate buffer, pH 7.4, 0.3% (v/v) Polysorbate-80 (from Croda, Snaith UK), and 0.05% (w/v) sodium azide (from Fisher Chemical, Waltham Mass.). This buffer ensured that the release was conducted under sink conditions (≥5× saturated solubility). A suspension of celecoxib (CXB) (from Cipla, Miami Fla.) containing 800 µg CXB was used as a control. The samples were incubated at 37° C. with gentle shaking. 1 mL of the release medium was taken at each timepoint (typically 1, 4, and 7 days and then weekly thereafter). The release medium was then analyzed via UPLC at 260 nm to determine CXB concentration. The data from the experiment was summarized in Table 10. Extraction controls were run to determine CXB loading in the rods. Pre-weighed, 1 cm lengths of the rods were placed into 2 mL of 100% methanol, vortexed, and sonicated. The samples were left to shake overnight at room temperature. The methanol was then analyzed for CXB loading via HPLC.

TABLE 10

PRECISE DIAMETER, DENSITY, AND LOADING PERCENTAGES OF 0.5 MM SILK-FIBROIN RODS (480 MB; 0.5 MM; 40% ST; 100 MGSF; 200 MGCXB; LYO; 33.3% SF; 66.7% CXB)

| Sample No. | Ratio CXB:SF Theoretical | Ratio CXB:SF Actual | Diameter (mm) | Density (g/mL) | Theoretical CXB % (w/w) | Actual CXB % (w/w) | Standard Dev. of CXB % |
|---|---|---|---|---|---|---|---|
| 8-65-6 | 2 | 1.0 | 0.43 | 1.2 | 66.7 | 48.9 | 3.2 |

The release of CXB was monitored as described over a period of 77 days, as seen in Table 11 and Table 12. The data demonstrated near-zero-order release kinetics. The CXB suspension was completely released after 1 day. The rod formulation, however, displayed very extended release. The initial burst from the rod was only 12.9% with near zero-order release out to 21 days. After 21 days, the release rate slowed even more, allowing for a second zero-order segment of release out to completion at about 70 days. After day 70, no additional API was released. In Table 11, "Std. Dev." refers to standard deviation.

TABLE 11

IN VITRO RELEASE KINETICS OF CELECOXIB
FROM 0.5 MM SILK-FIBROIN RODS; AVERAGE
CUMULATIVE PERCENTAGE OF API RELEASED

| | | | Average Cumulative % Released | |
|---|---|---|---|---|
| Day | CXB Suspension | Std. Dev. suspension | 8-65-6 | 8-65-6 Std. Dev. |
| 0 | 0 | 0 | 0 | 0 |
| 1 | 111.8 | 0.8 | 12.9 | 1.3 |
| 2 | 110.9 | 0.7 | 18.7 | 1.3 |
| 7 | 113.8 | 0.8 | 43.7 | 2.4 |
| 10 | — | — | 57.9 | 2.7 |
| 14 | — | — | 65.4 | 2.9 |
| 21 | — | — | 84.7 | 4.9 |
| 28 | — | — | 92.5 | 5.3 |
| 35 | — | — | 95.1 | 5.4 |
| 42 | — | — | 102.1 | 5.5 |
| 49 | — | — | 113.9 | 5.9 |
| 56 | — | — | 118.9 | 5.6 |
| 63 | — | — | 124.0 | 5.0 |
| 70 | — | — | 117.8 | 4.7 |
| 77 | — | — | 117.2 | 4.4 |

TABLE 12

DAILY PERCENTAGE OF CELECOXIB RELEASED
FOR RODS OF DIFFERENT DIAMETERS

| Sample No. | Sample Name | Initial Burst % | Daily % Released | Initial burst:Daily release | Measured rod diameter (mm) |
|---|---|---|---|---|---|
| 8-65-6 | 480 mb; 0.5 mm; 40% st; 100 mgsf; 200 mgcxb; lyo; 33.3% sf; 66.7% cxb | 12.9 | 1.8 | 7.2 | 0.43 |
| 8-58-8 | 480 mb; 1 mm; 40% st; 100 mgsf; 200 mgcxb; lyo; 33.3% sf; 66.7% cxb | 6.2 | 0.9 | 6.9 | 0.91 |

The data from this experiment suggested that the rate of release of therapeutic, CXB, was inversely related to the diameter of the silk rods. The daily release percentage of CXB, as well as the ratio of the initial burst to the daily release percentage and other rod parameters, is shown in Table 12. The daily percentage of CXB released for sample 8-65-6, which was calculated for 63 days, was 1.8%. The corresponding 1 mm silk rods (Sample 8-58-8), as seen in 1 mm silk rod experiments, were 33.3% (w/w) SF, 66.7% (w/w) CXB, and had a 480-minute boil. These 1 mm silk rods released 0.9% of the loaded CXB per day. The almost two-fold difference between the 1 mm and 0.5 mm silk rods suggested that the therapeutics were released more quickly from rods with a smaller diameter. This difference was also observed in the initial burst of drug release; however, the ratio between the initial burst and the daily release percentage remained consistent regardless of rod diameter. The 1 mm silk rods had an initial burst of 6.2%, while the corresponding 0.5 mm rods had an initial burst of 12.9%. The changes in initial burst and daily release percentage were likely due to the greater surface area to volume ratio in the rods of smaller diameter. In the narrower rods, water penetration and diffusion lengths were shorter, which lead to the faster releasing effect. These narrower rods could be injected through a 21-22G needle (standard for intravitreal injection devices), making them appropriate for intraocular delivery.

It should be noted that the actual CXB loading of 1 mm rods was higher than that of the 0.5 mm silk rods. This higher loading could alter the rate of CXB release between rods of the same theoretical formulation. Furthermore, the experiments for the 1 mm silk rods were carried out over a period of 126 days, which was longer than the experiments for the 0.5 mm rods. The release of CXB may decrease over longer periods of time, and the potential change in rate over time may alter the average daily percentage released.

Example 10. Comparison of Silk Fibroin Rods Prepared Via Lyophilization Vs Oven Drying The silk yarn was purchased from Jiangsu SOHO International Group (Jiangsu, China). Lithium bromide and phosphate buffer saline were purchased from Sigma Aldrich (St. Louis, Mo.). The potassium phosphate monobasic and potassium phosphate dibasic were purchased from Sigma Aldrich Fine Chemicals (SAFC) (St. Louis, Mo.). The sodium carbonate and the sodium azide were purchased from Fisher Chemical (Waltham, Mass.). The celecoxib (CXB) was purchased from Cipla (Miami, Fla.).

Silk Fibroin Isolation

The silk yarn was degummed at 100° C. for either 120 or 480 minutes in 0.02 M sodium carbonate solution to remove sericin and modify the molecular weight. The total boiling time was discussed in terms of minute boil, or "mb." Longer boiling times produced silk fibroin with lower average molecular weights. The objective of this experiment was to determine any difference in the release rate of the API between the silk rods prepared via lyophilization and the silk rods prepared via oven drying. Silk-fibroin (Jiangsu SOHO) was isolated as described in the preparation of the silk fibroin rods with no additives. Briefly, Silk yarn, purchased from Jiangsu SOHO International Group, was degummed to remove sericin. 30 grams of cut silk yarn were boiled at 100° C. in 3 L of deionized (DI) water with 0.02 M sodium carbonate with stirring. The yarn was then transferred to a new boiling 0.02 M sodium carbonate aqueous solution and boiled at 100° C. for additional time with stirring. The fibroin was then placed in DI water at 60-70° C. for 20 minutes with stirring, and then rinsed with clean DI water. This process was repeated 3 times. The fibroin was placed in clean DI water, stirred for 20 minutes, then rinsed with clean DI water, and this process was repeated for a total of 3×20 min.-rinse cycles.

The fibroin was dried overnight, weighed, and dissolved at 20% (w/v) in a 9.3 M aqueous solution of lithium bromide (from Sigma-Aldrich, St. Louis, Mo.) for 5 hours at 60° C. The resulting fibroin solution was dialyzed against water at 4° C. in a 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready. The solution was then centrifuged for 20 minutes at 9,000 RPM and 4° C. to remove insoluble particles. Solutions were diluted to a final concentration of 3% (w/v) in 10 mM phosphate buffer, pH 7.4, filtered through a 0.22 µm filter, frozen in liquid nitrogen, and lyophilized for 72 hours.

Silk Fibroin Rod Preparation

Lyophilized silk fibroin was reconstituted to either 20, 30, or 40% (w/v) with DI water. The desired amount of CXB was weighed into 4 mL glass vials. 250 µL of stock fibroin solution was then added to each vial accordingly. The fibroin and CXB was mixed both manually using a spatula and with a vortex. This mixture was then transferred to a 1 mL syringe using the spatula and extruded into 2×10 cm lengths of 500 µm ID polytetrafluoroethylene (PTFE) tubing (from Van Waters and Rogers (VWR), PA, USA). The tubing was then sealed on both ends using Parafilm and incubated at 37° C. to induce gelation. The lengths of tubing were cut into 2 cm sections. Half of the sections were dried for 48 hours in an oven at 60° C. The other half were frozen at −80° C. and lyophilized. Rods were stored at 4° C. prior to use.

The samples, shown in Table 13, are named by the process used to prepare and formulate each silk rod. For example, the sample named "480 mb; 0.5 mm; 40% st; 100mgsf; 100mgcxb; lyo; 50% sf; 50% cxb" refers to a silk fibroin rod prepared from silk degummed with a 480-minute boil, an extrusion with a 0.5 mm diameter, a preparation from a 40% stock solution of silk fibroin, a preparation from 100 mg of silk fibroin, a preparation from 100 mg of celecoxib, lyophilization, a theoretical w/w percentage of 50% silk fibroin, and a theoretical w/w percentage of 50% celecoxib. Samples prepared via oven drying were labeled with "oven". Some samples were prepared with silk fibroin degummed with a 120-minute boil (120 mb). The final rods contained trace amounts of potassium phosphate buffer (with potassium phosphate dibasic and potassium phosphate buffer monobasic). In Table 13, "Std. Dev." refers to standard deviation.

TABLE 13

THEORETICAL AND EXPERIMENTAL LOADING PERCENTAGES FOR OVEN-DRIED AND LYOPHILIZED 0.5 MM SILK-FIBROIN RODS

| Sample No. | Sample Name | Stock Conc. of Silk for Formulation (w/v %) | Drying Method | Actual Silk-Fibroin Final % (w/w) | Actual CXB Final % (w/w) | Std. Dev. of CXB Final % (w/w) | Silk Prep Boil Time (min) | Phosphate Buffer Conc. (mM) |
|---|---|---|---|---|---|---|---|---|
| 177-1A | 480 mb; 0.5 mm; 40% st; 100 mgsf; 100 mgcxb; lyo; 50% sf; 50% cxb | 40 | Lyophilized | 62.30 | 37.70 | 0.52 | 480 | 95.2 |
| 177-1B | 480 mb; 0.5 mm; 40% st; 100 mgsf; 100 mgcxb; oven; 50% sf; 50% cxb | 40 | Oven | 61.54 | 38.46 | 0.08 | 480 | 95.2 |
| 177-2A | 480 mb; 0.5 mm; 40% st; 100 mgsf; 150 mgcxb; lyo; 40% sf; 60% cxb | 40 | Lyophilized | 53.14 | 46.86 | 0.70 | 480 | 83.3 |
| 177-2B | 480 mb; 0.5 mm; 40% st; 100 mgsf; 150 mgcxb; oven; 40% sf; 60% cxb | 40 | Oven | 53.27 | 46.73 | 1.19 | 480 | 83.3 |
| 177-4A | 480 mb; 0.5 mm; 40% st; 100 mgsf; 250 mgcxb; lyo; 28.6% sf; 71.4% cxb | 40 | Lyophilized | 45.61 | 54.39 | 0.92 | 480 | 66.7 |
| 177-4B | 480 mb; 0.5 mm; 40% st; | 40 | Oven | 45.72 | 54.28 | 0.93 | 480 | 66.7 |

TABLE 13-continued

THEORETICAL AND EXPERIMENTAL LOADING PERCENTAGES FOR
OVEN-DRIED AND LYOPHILIZED 0.5 MM SILK-FIBROIN RODS

| Sample No. | Sample Name | Stock Conc. of Silk for Formulation (w/v %) | Drying Method | Actual Silk-Fibroin Final % (w/w) | Actual CXB Final % (w/w) | Std. Dev. of CXB Final % (w/w) | Silk Prep Boil Time (min) | Phosphate Buffer Conc. (mM) |
|---|---|---|---|---|---|---|---|---|
| 177-6A | 100 mgsf; 250 mgcxb; oven; 28.6% sf; 71.4% cxb 480 mb; 0.5 mm; 30% st; 75 mgsf; 200 mgcxb; lyo; 27.3% sf; 72.7% cxb | 30 | Lyophilized | 46.03 | 53.97 | 1.82 | 480 | 55.6 |
| 177-6B | 480 mb; 0.5 mm; 30% st; 75 mgsf; 200 mgcxb; oven; 27.3% sf; 72.7% cxb | 30 | Oven | 45.27 | 54.73 | 1.01 | 480 | 55.6 |
| 177-7A | 120 mb; 0.5 mm; 20% st; 50 mgsf; 200 mgcxb; lyo; 20% sf; 80% cxb | 20 | Lyophilized | 43.35 | 56.65 | 2.97 | 120 | 37 |
| 177-7B | 120 mb; 0.5 mm; 20% st; 50 mgsf; 200 mgcxb; oven; 20% sf; 80% cxb | 20 | Oven | 39.71 | 60.29 | 0.26 | 120 | 37 |
| 177-8A | 120 mb; 0.5 mm; 30% st; 75 mgsf; 200 mgcxb; lyo; 27.3% sf; 72.7% cxb | 30 | Lyophilized | 42.23 | 57.77 | 4.08 | 120 | 55.6 |
| 177-8A | 120 mb; 0.5 mm; 30% st; 75 mgsf; 200 mgcxb; oven; 27.3% sf; 72.7% cxb | 30 | Oven | 42.25 | 57.75 | 3.87 | 120 | 55.6 |
| 177-9A | 120 mb; 0.5 mm; 40% st; 100 mgsf; 200 mgcxb; lyo; 33.3% sf; 66.7% cxb | 40 | Lyophilized | 48.46 | 51.54 | 0.48 | 120 | 74.1 |
| 177-9B | 120 mb; 0.5 mm; 40% st; 100 mgsf; 200 mgcxb; oven; 33.3% sf; 66.7% cxb | 40 | Oven | 48.93 | 51.07 | 3.46 | 120 | 74.1 |

In Vitro Release

The rods were cut to 1 cm lengths to standardize release, and the weights of the rods were recorded. In triplicate, a 1 cm segment of rod was weighed into a 50 mL conical tube. 45 mL of release medium (phosphate buffered saline, 0.3% Polysorbate-80, and 0.05% sodium azide) was added to each tube. We had previously shown that this media would ensure sink conditions (≥5×CXB solubility) are maintained throughout the study. The tubes were incubated at 37° C. with shaking. 1 mL of the release media was collected from each sample at days 1, 4, 7, 10, 14, and weekly thereafter and replaced with fresh media. Release media was analyzed for CXB concentration by HPLC-UV at 260 nm.

Controls were prepared by weighing 1 cm of each formulation in triplicate in separate glass vials. Methanol was added to each vial. Samples were vortexed, sonicated, and placed on a shaker at room temperature for 24 hours. The supernatant was analyzed by HPLC to determine CXB loading (mg/g), as seen in Table 13. CXB loaded silk-fibroin rods were prepared with loadings ranging from 38-60% (w/w). Drying method did not have an impact on the drug loading, suggesting that the drug was stable through the 60° C. treatment. The release kinetics of both the lyophilized and the oven dried silk rods were shown in Table 14A, Table 14B, and Table 15. All samples showed zero percent (%) API release on day zero. The rods demonstrated near zero-order kinetics of API release.

TABLE 14A

IN VITRO RELEASE KINETICS OF CELECOXIB FROM 0.5 MM SILK-FIBROIN RODS, LYOPHILIZED VS. OVEN DRIED; AVERAGE CUMULATIVE PERCENTAGE OF API RELEASED

| Lot No. | Day | | | | | | | | | | | |
|---|---|---|---|---|---|---|---|---|---|---|---|---|
| | 1 | 3 | 7 | 10 | 14 | 21 | 28 | 35 | 42 | 49 | 56 | 63 |
| 177-1A | 13.6 | 27.8 | 51.5 | 58.9 | 70.5 | 80.2 | 92.2 | 105.9 | 112.3 | 110.7 | 114.8 | — |
| 177-1B | 10.1 | 21.6 | 41.0 | 47.4 | 57.2 | 66.3 | 77.3 | 90.3 | 97.6 | 99.8 | 108.9 | 112.2 |
| 177-2A | 15.4 | 32.2 | 59.6 | 66.9 | 78.7 | 87.9 | 97.3 | 105.9 | 108.0 | 104.8 | — | — |
| 177-2B | 12.1 | 25.4 | 47.4 | 54.7 | 64.8 | 73.6 | 83.5 | 95.0 | 100.6 | 99.9 | 106.0 | — |
| 177-4A | 13.0 | 75.8 | 50.0 | 55.7 | 66.4 | 75.3 | 87.5 | 97.8 | 106.9 | 106.7 | 110.7 | — |
| 177-4B | 14.2 | 30.5 | 57.6 | 65.2 | 76.9 | 85.9 | 96.1 | 108.1 | 112.4 | 108.2 | — | — |
| 177-6A | 18.4 | 35.7 | 63.3 | 70.9 | 82.6 | 90.4 | 96.0 | 102.9 | 103.5 | 99.5 | — | — |
| 177-6B | 16.2 | 33.8 | 66.2 | 72.8 | 85.7 | 94.4 | 100.0 | 107.4 | 108.4 | 104.1 | — | — |
| 177-7A | 23.7 | 46.6 | 83.6 | 93.7 | 108.5 | 112.3 | 111.0 | — | — | — | — | — |
| 177-7B | 15.7 | 34.3 | 67.3 | 76.6 | 90.9 | 100.4 | 104.9 | 108.8 | 108.6 | 104.3 | — | — |
| 177-8A | 14.5 | 31.6 | 57.7 | 66.3 | 78.5 | 87.8 | 97.2 | 106.3 | 106.5 | 102.4 | — | — |
| 177-8B | 15.8 | 31.9 | 58.5 | 66.2 | 77.9 | 87.1 | 96.8 | 106.2 | 106.8 | 102.4 | — | — |
| 177-9A | 14.1 | 28.8 | 51.6 | 58.1 | 68.6 | 76.5 | 86.0 | 97.3 | 102.2 | 99.5 | — | — |
| 177-9B | 13.4 | 27.4 | 48.9 | 54.8 | 64.7 | 72.2 | 81.4 | 92.5 | 97.9 | 97.6 | 101.9 | — |
| 177-10 | 106.2 | 106.2 | 110.9 | — | — | — | — | — | — | — | — | — |

TABLE 14B

STANDARD DEVIATION OF THE IN VITRO RELEASE KINETICS OF CELECOXIB FROM 0.5 MM SILK-FIBROIN RODS, LYOPHILIZED VS. OVEN DRIED; CUMULATIVE PERCENTAGE OF API RELEASED

| Lot No. | Day | | | | | | | | | | | | |
|---|---|---|---|---|---|---|---|---|---|---|---|---|---|
| | 0 | 1 | 3 | 7 | 10 | 14 | 21 | 28 | 35 | 42 | 49 | 56 | 63 |
| 177-1A | 0 | 1.1 | 2.2 | 4.0 | 4.9 | 5.5 | 6.9 | 8.2 | 10.2 | 11.2 | 10.3 | 8.0 | — |
| 177-1B | 0 | 0.5 | 1.2 | 1.7 | 2.0 | 2.1 | 2.3 | 2.6 | 4.2 | 4.3 | 4.1 | 4.2 | 4.1 |
| 177-2A | 0 | 3.0 | 5.6 | 9.6 | 10.2 | 11.3 | 11.8 | 12.1 | 10.3 | 7.6 | 6.3 | — | — |
| 177-2B | 0 | 2.6 | 3.9 | 6.2 | 6.9 | 7.4 | 7.8 | 8.0 | 7.8 | 5.7 | 2.7 | 1.0 | — |
| 177-4A | 0 | 0.3 | 0.8 | 0.9 | 1.0 | 1.2 | 1.7 | 1.6 | 2.6 | 1.9 | 1.6 | 1.5 | — |
| 177-4B | 0 | 0.7 | 1.2 | 2.6 | 3.2 | 3.9 | 3.5 | 3.7 | 4.3 | 4.4 | 3.9 | — | — |
| 177-6A | 0 | 4.1 | 7.2 | 10.3 | 10.2 | 10.7 | 9.0 | 6.6 | 8.1 | 8.9 | 8.4 | — | — |
| 177-6B | 0 | 2.8 | 6.7 | 12.4 | 13.1 | 14.8 | 13.3 | 7.7 | 4.2 | 3.2 | 3.3 | — | — |
| 177-7A | 0 | 4.7 | 5.4 | 7.7 | 7.2 | 6.7 | 3.9 | 4.0 | — | — | — | — | — |
| 177-7B | 0 | 0.3 | 1.2 | 3.1 | 3.4 | 4.1 | 3.6 | 2.7 | 2.4 | 2.4 | 2.4 | — | — |
| 177-8A | 0 | 0.1 | 2.2 | 3.4 | 3.8 | 3.9 | 3.5 | 3.1 | 2.9 | 2.9 | 2.7 | — | — |
| 177-8B | 0 | 1.6 | 3.1 | 3.3 | 2.9 | 3.2 | 3.0 | 3.7 | 5.1 | 5.5 | 5.1 | — | — |
| 177-9A | 0 | 1.7 | 3.1 | 4.5 | 4.5 | 5.0 | 5.0 | 4.2 | 3.4 | 1.9 | 1.0 | — | — |
| 177-9B | 0 | 0.7 | 1.0 | 1.9 | 1.9 | 1.5 | 1.5 | 0.9 | 0.6 | 0.3 | 1.0 | 2.3 | — |
| 177-10 | 0.0 | 0.4 | 0.3 | 0.4 | — | — | — | — | — | — | — | — | — |

All CXB loaded rod formulations exhibited biphasic release. Initial zero-order release from 1-10 days and a second zero-order profile from 10 days to completion. The rods reached complete release between 14 and 56 days.

In many of the samples subjected to the 480 mb degumming process, the initial burst of API release, determined as the total w/w percentage of CXB released in one day, was smaller for the oven dried silk rods than the lyophilized silk rods. For many rods prepared under identical conditions except for drying, the oven dried rods released between 5 and 35% less API during the initial burst than their lyophilized counterparts. This difference, shown in Table 15, was determined as the percent error between the initial bursts of the oven dried and lyophilized rods prepared under otherwise identical conditions.

TABLE 15

ANALYSIS OF INITIAL BURST PERCENTAGES OF OVEN DRIED AND FREEZE DRIED 0.5 MM RODS

| Sample No. | Sample Name | Initial burst (% API released by mass) | Difference by % |
|---|---|---|---|
| 177-1A | 480 mb; 0.5 mm; 40% st; 100 mgsf; 100 mgcxb; lyo; 50% sf; 50% cxb | 13.6 | 25.8 |
| 177-1B | 480 mb; 0.5 mm; 40% st; 100 mgsf; 100 mgcxb; oven; 50% sf; 50% cxb | 10.1 | — |
| 177-2A | 480 mb; 0.5 mm; 40% st; 100 mgsf; 150 mgcxb; lyo; 40% sf; 60% cxb | 15.4 | 21.4 |
| 177-2B | 480 mb; 0.5 mm; 40% st; 100 mgsf; 150 mgcxb; oven; 40% sf; 60% cxb | 12.1 | — |
| 177-4A | 480 mb; 0.5 mm; 40% st; 100 mgsf; 250 mgcxb; lyo; 28.6% sf; 71.4% cxb | 13.0 | -9.6 |
| 177-4B | 480 mb; 0.5 mm; 40% st; 100 mgsf; 250 mgcxb; oven; 28.6% sf; 71.4% cxb | 14.2 | — |
| 177-6A | 480 mb; 0.5 mm; 30% st; 75 mgsf; 200 mgcxb; lyo; 27.3% sf; 72.7% cxb | 18.4 | 12.0 |
| 177-6B | 480 mb; 0.5 mm; 30% st; 75 mgsf; 200 mgcxb; oven; 27.3% sf; 72.7% cxb | 16.2 | — |
| 177-7A | 120 mb; 0.5 mm; 20% st; 50 mgsf; 200 mgcxb; lyo; 20% sf; 80% cxb | 23.7 | 33.8 |
| 177-7B | 120 mb; 0.5 mm; 20% st; 50 mgsf; 200 mgcxb; oven; 20% sf; 80% cxb | 15.7 | — |
| 177-8A | 120 mb; 0.5 mm; 30% st; 75 mgsf; 200 mgcxb; lyo; 27.3% sf; 72.7% cxb | 14.5 | -8.9 |
| 177-8B | 120 mb; 0.5 mm; 30% st; 75 mgsf; 200 mgcxb; oven; 27.3% sf; 72.7% cxb | 15.8 | — |
| 177-9A | 120 mb; 0.5 mm; 40% st; 100 mgsf; 200 mgcxb; lyo; 33.3% sf; 66.7% cxb | 14.1 | 5.2 |
| 177-9B | 120 mb; 0.5 mm; 40% st; 100 mgsf; 200 mgcxb; oven; 33.3% sf; | 13.4 | — |
| 177-10 | CXB suspension | 106.2 | N/A |

Samples 177-6 (A and B, both oven dried and lyophilized), were prepared in a manner identical to that of samples 177-8 (A and B, both oven dried and lyophilized), except for the boiling time of the silk fibroin. As previously stated, an increase in the boiling time reduces the molecular weight of the silk fibroin. Consequently, these samples allowed for the direct comparison of rods prepared identically with different molecular weights of silk fibroin. The lyophilized samples with a higher molecular weight (120 mb) exhibited an initial burst that was 21.1% less than the lyophilized samples prepared with a lower molecular weight (480 mb). Meanwhile, the oven dried samples with a higher molecular weight (120 mb) exhibited an initial burst that was 2.5% less than the oven dried samples prepared with a lower molecular weight (480 mb).

The daily release percentages were also compared to the initial burst percentages. The daily release percentages, as well as the ratio of the initial burst percentages to the daily release percentages, were calculated from the data from the in vitro release experiments, and these data were displayed in Table 16. The daily release percentages were calculated for the first 49 days of the study.

TABLE 16

DAILY PERCENTAGE OF CELECOXIB RELEASE FOR RODS OF DIFFERENT DRYING METHODS AND DIFFERENT BOILING TIMES

| Lot | Sample Name | Initial Burst % | Daily Release % | Initial burst:Daily release | Ratio CXB:SF Theoretical | Ratio CXB:SF Actual |
|---|---|---|---|---|---|---|
| 177-1A | 480 mb; 0.5 mm; 40% st; 100 mgsf; 100 mgcxb; lyo; 50% sf; 50% cxb | 13.6 | 2.1 | 6.3 | 1.0 | 0.6 |
| 177-1B | 480 mb; 0.5 mm; 40% st; 100 mgsf; 100 mgcxb; oven; 50% sf; 50% cxb | 10.1 | 1.9 | 5.2 | 1.0 | 0.6 |

TABLE 16-continued

DAILY PERCENTAGE OF CELECOXIB RELEASE FOR RODS OF DIFFERENT DRYING METHODS AND DIFFERENT BOILING TIMES

| Lot | Sample Name | Initial Burst % | Daily Release % | Initial burst:Daily release | Ratio CXB:SF Theoretical | Ratio CXB:SF Actual |
|---|---|---|---|---|---|---|
| 177-2A | 480 mb; 0.5 mm; 40% st; 100 mgsf; 150 mgcxb; lyo; 40% sf; 60% cxb | 15.4 | 2.0 | 7.9 | 1.5 | 0.9 |
| 177-2B | 480 mb; 0.5 mm; 40% st; 100 mgsf; 150 mgcxb; oven; 40% sf; 60% cxb | 12.1 | 1.9 | 6.4 | 1.5 | 0.9 |
| 177-4A | 480 mb; 0.5 mm; 40% st; 100 mgsf; 250 mgcxb; lyo; 28.6% sf; 71.4% cxb | 13.0 | 2.0 | 6.4 | 2.5 | 1.2 |
| 177-4B | 480 mb; 0.5 mm; 40% st; 100 mgsf; 250 mgcxb; oven; 28.6% sf; 71.4% cxb | 14.2 | 2.1 | 6.9 | 2.5 | 1.2 |
| 177-6A | 480 mb; 0.5 mm; 30% st; 75 mgsf; 200 mgcxb; lyo; 27.3% sf; 72.7% cxb | 18.4 | 1.8 | 10.3 | 2.7 | 1.2 |
| 177-6B | 480 mb; 0.5 mm; 30% st; 75 mgsf; 200 mgcxb; oven; 27.3% sf; 72.7% cxb | 16.2 | 1.9 | 8.5 | 2.7 | 1.2 |
| 177-7A | 120 mb; 0.5 mm; 20% st; 50 mgsf; 200 mgcxb; lyo; 20% sf; 80% cxb | 23.7 | 3.7 | 6.4 | 4.0 | 1.3 |
| 177-7B | 120 mb; 0.5 mm; 20% st; 50 mgsf; 200 mgcxb; oven; 20% sf; 80% cxb | 15.7 | 1.9 | 8.2 | 4.0 | 1.5 |
| 177-8A | 120 mb; 0.5 mm; 30% st; 75 mgsf; 200 mgcxb; lyo; 27.3% sf; 72.7% cxb | 14.5 | 1.9 | 7.5 | 2.7 | 1.4 |
| 177-8B | 120 mb; 0.5 mm; 30% st; 75 mgsf; 200 mgcxb; oven; 27.3% sf; 72.7% cxb | 15.8 | 1.9 | 8.2 | 2.7 | 1.4 |
| 177-9A | 120 mb; 0.5 mm; 40% st; 100 mgsf; 200 mgcxb; lyo; 33.3% sf; 66.7% cxb | 14.1 | 1.9 | 7.5 | 2.0 | 1.1 |
| 177-9B | 120 mb; 0.5 mm; 40% st; 100 mgsf; 200 mgcxb; oven; 33.3% sf; 66.7% cxb | 13.4 | 1.8 | 7.4 | 2.0 | 1.0 |
| 177-10 | CXB Suspension | 106.2 | N/A | N/A | N/A | N/A |

Oven dried rods showed slower release than the lyophilized rods, with lower initial burst percentages, however they also showed similar biphasic release profiles. The second phase of release, however, was delayed from 10 to 14 days when the rods were oven dried. The complete release of CXB ranged from 35 to greater than 63 days and followed the same trends as the lyophilized rods (rates increasing with increasing CXB:silk ratio). This slower release of the oven-dried rods was most likely due to increased beta-sheet content of the silk-fibroin as well as decreased porosity of the rods. Both factors would make the rods more hydrophobic, slowing water uptake and decreasing diffusion of CXB.

The data also revealed that the (w/w) ratio of API to silk fibroin was directly proportional to the initial burst percentage. In the context of the 0.5 mm silk fibroin rods, lower initial burst percentages corresponded with lower ratios of CXB to silk fibroin, while higher initial burst percentages corresponded to higher ratios of CXB to silk fibroin. The daily release percentage of the 0.5 mm rods also increased as the ratio of CXB to silk fibroin increased. As the drug loading increased and silk-fibroin concentration decreased, the release rates increased. This suggested that the silk-fibroin was controlling release and that release rates could be tuned using this variable.

The measured and calculated parameters of the rods were also examined in the context of silk fibroin boiling time and molecular weight, by comparing the experimental results from rods of lot numbers 177-6 (A and B) and 177-8 (A and B). As stated previously, the rods from these preparations were identical except for the boiling time, and therefore the molecular weight, of the silk fibroin. The ratio of the initial burst percentages to the daily release percentages was lower for rods prepared from higher molecular weight silk fibroin; this result was likely due to the observed lower initial burst percentage with silk rods of higher molecular weight silk fibroin. Meanwhile, the daily release percentages differed by only 0.1% between the freeze-dried rods with lower and higher molecular weights; the daily release percentages of these samples were 1.8% and 1.9% respectively. The daily release percentages did not change between oven dried samples of lower and higher molecular weight; the daily release percentage for those samples was 1.9%. As a result, it was concluded that the boiling time, and consequently the molecular weight, of the silk fibroin did not affect the daily release percentages of the silk fibroin rods. These in vitro characterizations displayed that release from these formulations was independent of the silk-fibroin molecular weights assessed.

Example 11. In Vivo Study of Silk Fibroin Rods with Celecoxib in an Animal Model As with the hydrogels without celecoxib (CXB), all buffers and stock solutions were prepared under sterile conditions unless otherwise indicated. All formulations were prepared with SOHO silk yarn. The poloxamer-188 was from Sigma-Aldrich (St. Louis, Mo.), while the PEG4 kDa was from Clariant, Charlotte N.C. Multiple preparations of the same formulations may be used in the study and overall analysis.

Preparation of Celecoxib Experimental Controls

As seen in the hydrogels formulated with CXB, a 27.8% suspension of celecoxib (CXB) was prepared from 4.15 g dry heat treated (DHT) CXB (from Cipla, Miami Fla.) in 10.78 mL of 0.79% Polysorbate-80 (from Croda, Snaith UK) and mixed until homogenous. To prepare the 10% CXB suspension as a control, a 1.789 mL fraction of the 27.8% CXB suspension was diluted to 5 mL via the addition of 0.349 mL 315 mM PB (pH=7.4), 0.158 mL of 200 mg/mL NaCl, and DI water. The resulting 10% CXB suspension was immediately aliquoted into 0.2 mL fractions in 1 cc syringes so that it remained homogenous, and the fractions were stored on ice until subsequent injection. To prepare the 0.2% CXB suspension as an additional control, a 0.18 mL fraction of the 10% CXB solution was diluted with 0.686 mL of 315 mM PB (pH=7.4), 0.31 mL of 200 mg/mL NaCl, 2.468 mL of 0.79% Polysorbate-80, and DI water to a final volume of 10 mL. The suspension was mixed until homogenous, aliquoted into 0.2 mL fractions, and stored on ice until use.

Preparation of Silk Fibroin Materials for Injection

The efficacy of the silk rods was compared to that of silk fibroin hydrogels. Both unadulterated silk fibroin hydrogels and silk fibroin hydrogels with 10% CXB were prepared as experimental controls. All processes were performed under aseptic conditions using pre-sterilized materials. To prepare the unadulterated silk fibroin hydrogel (sample 3B) 300 mg of 480 mb silk fibroin were brought up in 3.342 mL 0.6% Polysorbate-80, 0.383 mL of 315 mM phosphate buffer (pH=7.4), and 0.246 mL DI water. To prepare the 10% CXB hydrogel (sample 4B), 300 mg of 480 mb silk fibroin were brought up in 3.589 mL of the 27.8% CXB suspension and 0.381 mL of 315 mM PB (pH=7.4). Both the solutions for the hydrogel samples were incubated at room temperature and mixed for 30 minutes until homogenous. Each mixture was then aliquoted into 3.41 mL fractions in 10 cc syringes. The samples in Table 17 are named by the process used to prepare and formulate each hydrogel. For example, in the sample named 480 mb; hyd; 27.8% cxbst; 3% SFf; 10% CXBf; 10% P188f, "480 mb" refers to silk degummed with a 480-minute boil, "hyd" refers to the formulation of the sample as a hydrogel, "27.8% cxbst" refers to a preparation from a stock solution of 27.8% of celecoxib, "3% SFf" refers to a formulation with 3% (w/v) silk fibroin, "10% CXBf" refers to a formulation with 10% (w/v) celecoxib, and "10% P188f" refers to a formulation with 10% (w/v) poloxamer 188. The sample named "480 mb; 0.5 mm; 40% st; 100mgsf; 200mgcxb; lyo; 33.3% sf; 66.7% cxb" refers to a silk fibroin rod prepared from silk degummed with a 480-minute boil, an extrusion with a 0.5 mm diameter, a preparation from a 40% stock solution of silk fibroin, a preparation from 100 mg of silk fibroin, a preparation from 200 mg of celecoxib, lyophilization, a theoretical w/w percentage of 33.3% silk fibroin, and a theoretical w/w percentage of 66.7% celecoxib. All suspension and gel formulations contained 0.2% polysorbate-80 and 22 mM phosphate buffer. The 1.4% CXB suspension contained 6.34 mg/mL NaCl. The 10% CXB suspension contained 6.32 mg/mL NaCl. Both hydrogels contained 5.94 mg/mL NaCl. The rods contained 74.1 mM phosphate buffer.

TABLE 17

DESCRIPTIONS OF SAMPLES FOR IN VIVO EXPERIMENTS OF SILK FIBROIN RODS WITH CELECOXIB

| Sample Name | Description | Silk-Fibroin Boil Time | Silk-Fibroin Conc. (%) | Excipient | Excipient Conc. (%) |
|---|---|---|---|---|---|
| 1.4% CXB control | 1.4% CXB Suspension | — | — | — | — |
| 10% CXB control | 10% CXB Suspension | — | — | — | — |
| 480 mb; hyd; 0% cxbst; 3% SFf; 0% CXBf; 10% P188f | 3% 480 mb; 10% P188 | 480 | 3 | P188 | 10 |
| 480 mb; hyd; 27.8% cxbst; 3% SFf; 10% CXBf; 10% P188f | 3% 480 mb; 10% P188; 10% CXB | 480 | 3 | P188 | 10 |
| 480 mb; 0.5 mm; 40% st; 100 mgsf; 200 mgcxb; lyo; 33.3% sf; 66.7% cxb | 20% 480 mb; 40% CXB Rods | 480 | 20 | — | — |

An excipient solution was prepared from 13.05 mL of stock 20% P188, 0.777 mL of 200 mg/mL NaCl, and 1.173 mL of DI water. This excipient solution was prepared in 10 cc syringes in 4.59 mL aliquots. For each sample, the syringe of the representative silk fibroin solution was connected to a syringe of its designated excipient solution via a B Braun fluid dispensing connector. The contents of the syringes were then mixed until homogenous. The resulting samples were incubated on a rotator for 24 hours at 37° C. and then separated into 0.2 mL aliquots in 1 cc syringes. The pH values of the samples were measured with a glass pH probe. Samples were stored at 4° C., as needed. Formulations of the hydrogels contained 1.04% (w/v) sodium chloride, 0.2% (w/v) Polysorbate-80, and 22 mM phosphate buffer at pH=7.4 for the P188-containing hydrogels. Some formulations comprised 10% P188, 10% CXB, and 10.4 mg/mL sodium chloride at a pH of 7.4.

The silk fibroin rods were prepared as described in the preparation of 0.5 mm silk fibroin rods. Briefly, 600 mg of 480 mb silk fibroin were dissolved in 0.900 mL of DI water. 0.591 mL of the resulting solution was then used to bring up 473 mg of CXB, vortexed, and mixed. The mixture of silk fibroin and CXB was further mixed back and forth through a syringe connector until the mixture was homogenous. The mixture was then capped with a 27-gauge, 0.5 inch, needle and extruded into 10 cm lengths of 0.02" ID PEEK tubing.

The tubing was cut into 2 cm pieces and incubated overnight at 37° C. under sterile conditions. The rods were then removed from the tubing, frozen, and lyophilized overnight. Lyophilized rods were stored at 4° C. until injection. The rod-containing sample is named by the process used to prepare and formulate each silk rod. For example, the sample named "480 mb; 0.5 mm; 40% st; 100mgsf; 200mgcxb; lyo; 33.3% sf; 66.7% cxb" refers to a silk fibroin rod prepared from silk degummed with a 480-minute boil, an extrusion with a 0.5 mm diameter, a preparation from a 40% stock solution of silk fibroin, a preparation from 100 mg of silk fibroin, a preparation from 200 mg of celecoxib, lyophilization, a theoretical w/w percentage of 33.3% silk fibroin, and a theoretical w/w percentage of 66.7% silk fibroin. CXB loaded rods were cut to 1 cm lengths and preloaded into 21G, 1" needles. The final formulations of the rods also contained trace amounts of potassium phosphate buffer (phosphate buffer monobasic and phosphate buffer dibasic).

In Vitro Release Profile of Hydrogel for In Vivo Experiments

The silk fibroin hydrogels were subject to the in vitro release experiments used to analyze silk hydrogels of varying concentration and silk fibroin boiling time. Briefly, In triplicate, 50 mg of each formulation were weighed into half of a #4 gelatin capsule (MyHerbar, Dallas Tex.). Capsules were added to 45 mL of release medium (lx phosphate buffered saline, 2% polysorbate-80, and 0.05% sodium azide). It had previously been shown that the solubility of celecoxib in this release media is 850 µg/mL. 45 mL of this release media allowed for 38 mg CXB solubility. This media will ensure sink conditions (greater than or equal to 5 times the CXB solubility) are maintained throughout the study. The tubes were incubated at 37° C. with shaking. 1 mL of the release media was collected from each sample at days 1, 4, 7, 10, 14 and weekly thereafter and replaced with fresh media. At each timepoint, the tubes were placed upright for at least 15 minutes to allow the formulation to settle prior to taking the sample. Release media was analyzed by HPLC (Agilent 1290 HPLC system) at 260 nm Controls were prepared at Day 0 by weighing 50 mg of each formulation in triplicate in separate glass vials. Methanol was added to each sample to extract CXB. Samples were placed on a shaker at room temperature for 24 hrs. The supernatant was analyzed by HPLC to determine CXB loading.

Figure 4:
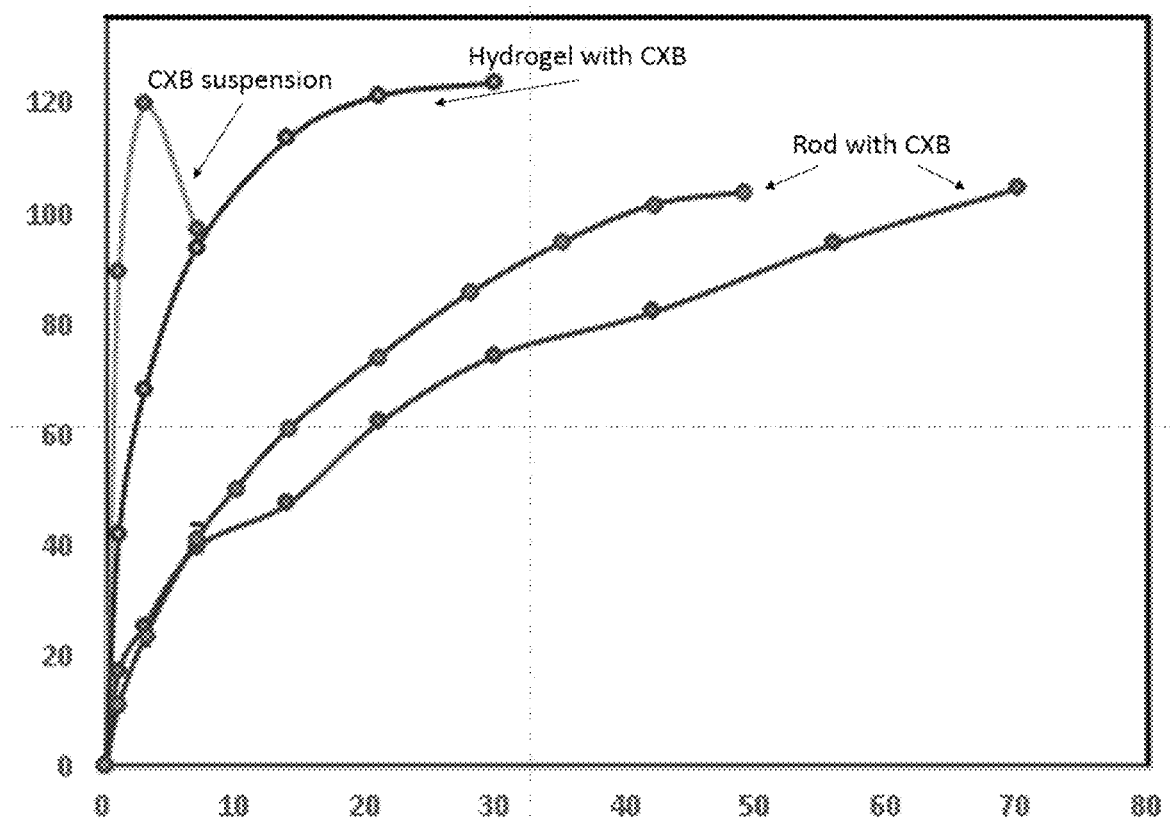
FIG. 4 is a plot of the cumulative release percentage of an API, celecoxib, over time for a hydrogel and a suspension of celecoxib.

The plot of the cumulative percentage of API released over time can be seen in FIG. 4. The release of the API from the hydrogel was much slower than the CXB suspension, which served as a control. The release of API from the hydrogel followed first order kinetics, and it occurred over the span of 1 month. The initial burst was approximately 40%.

In Vitro Release Profile of Rods for In Vivo Experiments

The silk fibroin rods were subject to the in vitro release experiments used to analyze silk fibroin rods of both 1 mm and 0.5 mm diameter loaded with CXB. Briefly, 1 cm segments of rod were weighed into 50 mL conical tubes. 45 mL of release medium (phosphate buffered saline, 0.3% polysorbate-80, and 0.05% sodium azide) was added to each tube. It had previously been shown that this media would ensure sink conditions (greater than or equal to 5 times CXB solubility) were maintained throughout the study. The tubes were incubated at 37° C. with shaking. 1 mL of the release media was collected from each sample at days 1, 4, 7, 10, 14 and weekly thereafter and replaced with fresh media.

Controls were prepared by weighing 1 cm of each formulation in triplicate in separate glass vials. Methanol was added to each vial. Samples were vortexed, sonicated, and placed on a shaker at RT for 24 hrs. The supernatant was analyzed by HPLC to determine CXB loading (mg/g).

Release media was analyzed for CXB concentration by HPLC-UV (Agilent 1290 HPLC system) 260 nm. The average cumulative percentage of API released over time was listed in Table 18 and FIG. 4. The release of CXB followed near zero-order kinetics. Cumulative percent released was calculated with a daily standard curve unless otherwise indicated. In Table 18, "Std. Dev." refers to standard deviation.

TABLE 18

IN VITRO RELEASE KINETICS OF CELECOXIB FROM 480 MB; 0.5 MM; 40% ST; 100 MGSF; 200 MGCXB; LYO; 33.3% SF; 66.7% CXB

| Day | Average Cumulative % Released | Std. Dev. | Average Cumulative % Released (Calculated with single standard) | Std. Dev. (Calculated with single standard) |
|---|---|---|---|---|
| 0 | 0.0 | 0 | 0.0 | 0 |
| 1 | 12.5 | 1.2 | 11.1 | 1.0 |
| 3 | 26.4 | 2.0 | 23.4 | 1.4 |
| 7 | 50.4 | 3.0 | 41.0 | 2.4 |
| 10 | 58.0 | 4.2 | 50.1 | 3.5 |
| 14 | 69.5 | 5.0 | 60.8 | 4.4 |
| 21 | 79.0 | 5.7 | 74.0 | 5.1 |
| 28 | 90.4 | 5.5 | 85.4 | 5.4 |
| 35 | 105.2 | 5.7 | 94.4 | 5.2 |
| 42 | 112.1 | 5.3 | 101.2 | 4.3 |
| 49 | 119.7 | 4.7 | 103.5 | 4.0 |
| 56 | — | — | 102.9 | 3.4 |
| 63 | — | — | 102.3 | 3.2 |

Additional parameters of the silk fibroin rods were also explored in Table 19. First the actual loading of CXB was determined by UPLC to be 48.4%, which was slightly higher than the theoretical loading percentage. The initial burst percentage, 11.1%, was then analyzed in comparison with the daily release percentage, 1.6%. The ratio of the initial burst percentage to the daily release percentage was determined to be 7.1. Overall, the rods were demonstrated to be capable of releasing the API, CXB, over a period of 49 days, and this gradual release rendered these rods acceptable candidates for in vivo studies. In Table 19, "Std. Dev." refers to standard deviation.

TABLE 19

EXAMINING THE LOADING AND KINETICS OF 480 MB; 0.5 MM; 40% ST; 100 MGSF; 200 MGCXB; LYO; 33.3% SF; 66.7% CXB

| | |
|---|---|
| Sample No. | 179 |
| Sample Name | 480 mb; 0.5 mm; 40% st; 100 mgsf; 200 mgcxb; lyo; 33.3% sf; 66.7% cxb |
| Theoretical % CXB (w/w) | 66.7 |
| Actual % CXB (w/w) | 48.4 |
| Std. Dev. of actual CXB % (w/w) | 0.6 |
| Initial Burst % | 12.5 |
| Initial Burst % (single standard) | 11.1 |
| Daily release % | 2.2 |
| Daily release % (single standard) | 1.6 |
| Initial Burst:Daily release | 5.6 |
| Initial Burst:Daily release (single standard) | 7.1 |

Administration of 0.5 mm Rods with Celecoxib

New Zealand adult white rabbits were prepared and draped in the usual sterile fashion. Intravitreal injections were made into the left eye (OS) of all rabbits. Right eyes remained as naïve controls. Animals were given a pre-anesthetic (Xylazine 1.1 mg/kg IM, Buprenorphine HCl 2-6 mcg/kg IM). Animals were then anesthetized with ketamine 22 mg/kg IM. The animals were placed on a heating pad and their vitals were monitored. The animals were put on inhalation anesthesia (Isoflurane at 1.5-2%) with 02 supplement.

To administer the hydrogels into the intravitreal space, a lid speculum was inserted into the rabbit's left eye. The conjunctiva was rinsed with BSS solution. Then, the conjunctival sac was prepped with a 5% ophthalmic betadine solution. The hydrogel was then injected into the intravitreal space using a double-plane injection technique. The sclera was penetrated at 15°-30°, then the needle was repositioned to a 45°-60° angle while the sclera was still engaged; the formulation was delivered and the needle was removed at a 90° angle. Following injection, the central retinal artery was examined via indirect ophthalmoscopy to confirm perfusion and 1-2 drops of betadine solution were added to the conjunctiva prior to removal of the speculum.

To administer the rods, formulations were pre-loaded into sterile 21 g, 1" needle cannulas. Intracannular plungers were fashioned with 28G wire which were pre-cut, sterilized, and placed into the needle from the hub. The same sterile and double-plane injection technique was used as for the hydrogels. The sclera was penetrated at 15°-30°, then the needle was repositioned to a 45°-60° angle while the sclera was still engaged; the formulation was delivered. The plunger was depressed, resulting in complete delivery of the rod into the eye into the intravitreal space. The wire could be pushed until it extended beyond the needle or cannula to ensure complete delivery. The needle was removed at a 90° angle. Following injection, the central retinal artery was examined via indirect ophthalmoscopy to confirm perfusion and 1-2 drops of betadine solution were added to the conjunctiva prior to removal of the speculum. When fully injected, the rod was clear from the wall of the eye.

Intraocular Pressure and Biocompatibility after Rod Administration

Intraocular pressure was measured with a Tono-Pen. 7 days after rod administration, there were no obvious signs of inflammation. No elevation in intraocular pressure was detected as compared to the naïve contralateral eyes. There were slightly lower intraocular pressures detected in the eyes treated with celecoxib, as seen in Table 20. As a result, the celecoxib loaded rods reduced the intraocular pressure of the treated eye. The analysis of the intraocular pressure was continued over the course of the study, as seen in Table 20, and multiple preparations of the same rod formulations were used. The intraocular pressure in the eyes containing the silk fibroin rod did not increase over the time evaluated.

No adverse clinical findings were noted throughout the course of the study. Mild-vitreous hemorrhage was sometimes observed following rod injection. Similar findings were seen previously with silk-fibroin solutions and hydrogels with CXB. Additionally, the histopathology report indicated that the rods did not induce any inflammation in the vitreous. There was slight infiltration of macrophages into the silk-fibroin rods, but there were no signs of inflammation or damage in the remainder of the eye. In addition, normal or lower intraocular pressure was measured 4 months after rod administration. No local inflammation, hemorrhage, or other complications were detected 4 months after administration. Based on these results, intravitreal injections of silk-fibroin rods were determined to be well tolerated in rabbits.

TABLE 20

INTRAOCULAR PRESSURE MEASUREMENTS AT EXAMS WITH SILK FIBROIN RODS (480 MB; 0.5 MM; 40% ST; 100 MGSF; 200 MGCXB; LYO; 33.3% SF; 66.7% CXB)

| Group | Day | Left Eye (Injected) | | Right Eye (Naïve) | | Fold change in IOP (Injected/Naïve) |
| --- | --- | --- | --- | --- | --- | --- |
| | | Average IOP (mmHg) | Standard Deviation | Average IOP (mmHg) | Standard Deviation | |
| 1 | 47 | 9.00 | 2.00 | 12.00 | 0.00 | 0.75 |
| | 30 | 12.33 | 4.04 | 11.67 | 5.86 | 1.06 |
| | 88 | 10.75 | 3.10 | 11.75 | 1.50 | 0.91 |
| | 111 | 12.33 | 4.04 | 11.00 | 5.20 | 1.12 |
| | 126 | 8.00 | 4.08 | 10.00 | 4.90 | 0.80 |
| | 169 | 10.00 | 1.41 | 10.50 | 2.12 | 0.95 |
| Control (1.4% CXB solution) | 30 | 5.33 | 3.51 | 11.33 | 1.15 | 0.47 |

Example 12. In Vivo Study of Silk Fibroin Hydrogels in an Animal Model

All buffers and stock solutions were prepared under sterile conditions unless otherwise indicated. All formulations were prepared with silk yarn purchased from SOHO. The silk rods were prepared with a dose of 750 µg of celecoxib (CXB) (from Cipla, Miami Fla.). The poloxamer-188, sodium chloride, and hydrochloric acid were from Sigma-Aldrich (St. Louis, Mo.), while the PEG4 kDa was from Clariant, Charlotte N.C. Polysorbate-80 was purchased from Croda (Snaith UK). Potassium phosphate monobasic and potassium phosphate dibasic were purchased from Sigma Aldrich Fine Chemical (SAFC, St. Louis Mo.). Phosphate buffered saline was purchased from Gibco (USA). Multiple preparations of the same formulations were used.

Preparation of Silk Fibroin Experimental Controls

A phosphate buffer (PB) control was prepared for the in vivo experiments. PB was aliquoted into 0.4 mL fractions and stored in 1 cc syringes. The PBS controls were stored at 4° C. until time of injection.

A CXB suspension was also prepared as an experimental control. CXB was suspended in an aqueous solution of sodium chloride (Sigma-Aldrich, St. Louis, Mo.), Polysorbate-80 (Croda, Snaith UK), and phosphate buffer. The CXB was homogeneously dispersed using ultrasonication and stored at 4° C. prior to injection. The suspension drawn up into 1 cc. syringes just prior to injection to avoid settling.

Silk fibroin solutions were prepared by boiling raw silk (from Jiangsu SOHO) for 120 minutes (herein referred to as "120 mb") or by boiling for 480 minutes (herein referred to as "480 mb"). 120-minute boil results in silk fibroin with a higher molecular weight than the 480-minute boil. Lyophilized silk-fibroin was reconstituted with an aqueous solution of sodium chloride, Tween-80, and phosphate buffer. The fibroin was allowed to fully reconstitute prior to being drawn into a 6 cc. syringe. Sodium chloride concentration was adjusted to ensure a final osmolarity of 280 mOsm. During preparations, 300 mg of 120 mb silk fibroin was brought up in 3.33 mL of 0.6% Polysorbate-80, 0.317 mL of 200 mg/mL NaCl, and 5.672 mL of DI water. Concurrently, 40% PEG4kf, "120 mb" refers to silk degummed with a 120-minute boil, "hyd" refers to the formulation of the sample as a hydrogel, "0% cxbst" refers to a preparation from a stock solution of 0% of celecoxib, "3% SFf" refers to a formulation with 3% (w/v) silk fibroin, "0% CXBf" refers to a formulation with 0% (w/v) celecoxib, and "40% PEG4kf" refers to a formulation with 40% (w/v) PEG4k. Some samples were prepared with P188 (% P188f). Some samples were prepared with silk fibroin degummed with a 120-minute boil (120 mb). The 120 mb solution control contained 0.2% Polysorbate-80, 22 mM phosphate buffer, and 6.34 mg/mL NaCl. The 480 mb solution control contained 0.2% Polysorbate-80, 22 mM phosphate buffer, and 6.28 mg/mL NaCl. The 120 mb hydrogel with PEG4k contained 0.2% Polysorbate-80, 22 mM phosphate buffer, 2.97 mg/mL NaCl, and 15 mM HCl. The 120 mb hydrogel with P188 contained 0.2% Polysorbate-80, 22 mM phosphate buffer, and 5.99 mg/mL NaCl. The 480 mb hydrogel with P188 contained 0.2% Polysorbate-80, 22 mM phosphate buffer, and 5.95 mg/mL NaCl.

TABLE 21

DESCRIPTIONS OF SAMPLES FOR IN VIVO SILK FIBROIN HYDROGEL EXPERIMENTS

| Sample name | Description | Silk-Fibroin Boil Time | Silk-Fibroin Conc. (%) | Excipient | Excipient Conc. (%) | Ratio SF to Excipient |
|---|---|---|---|---|---|---|
| PBS control | PBS | — | — | — | — | — |
| 120 mb control | 120 mb Solution | 120 | 3 | — | — | — |
| 480 mb control | 480 mb Solution | 480 | 3 | — | — | — |
| 120 mb; hyd; 0% cxbst; 3% SFf; 0% CXBf; 40% PEG4kf | 3% 120 mb; 40% PEG 4 kDa | 120 | 3 | PEG 4 kDa | 40 | 0.075 |
| 120 mb; hyd; 0% cxbst; 3% SFf; 0% CXBf; 10% P188f | 3% 120 mb; 10% P188 | 120 | 3 | P188 | 10 | 0.3 |
| 480 mb; hyd; 0% cxbst; 3% SFf; 0% CXBf; 10% P188f | 3% 480 mb; 10% P188 | 480 | 3 | P188 | 10 | 0.3 |

300 mg of 480 mb silk fibroin was brought up in 3.33 mL 0.6% Polysorbate-80, 0.381 mL of 200 mg/mL NaCl, and 5.675 mL DI water. Each individual solution was mixed and incubated at room temperature for 30 minutes to dissolve the silk fibroin. The resulting solutions were stored at 4° C. and aliquoted into 1 cc. syringes prior to injection.

Preparation of Hydrogels

The hydrogel samples were prepared as described below. The lyophilized silk fibroin was allowed to fully reconstitute prior to being drawn into a 6 cc. syringe. During preparation, 300 mg of 120 mb silk fibroin or 480 mb silk fibroin were brought up in 3.342 mL 0.6% Polysorbate-80, 0.383 mL of 315 mM PB (pH=7.4), and 0.246 mL DI water. Each solution was mixed and incubated at room temperature for 30 minutes to dissolve the silk fibroin. The mixtures were aliquoted into 2.13 mL fractions in 3, 6 cc. syringes. The samples in Table 21 were named by the process used to prepare and formulate each hydrogel. For example, in the sample named 120 mb; hyd; 0% cxbst; 3% SFf; 0% CXBf;

Excipient solutions were prepared so that a 0.75:1 mix of silk-fibroin solution:excipient solution would result in the desired final formulations. The pH of polyethylene glycol (PEG) hydrogels was adjusted using hydrochloric acid (from Sigma, St. Louis, Mo.) to account for the changes in pH observed when mixing phosphate buffer and PEG. The excipient solutions were drawn up into a second 6 mL. syringe. The corresponding solutions of excipients were prepared as described in Table 22. A 2.87 mL volume of each excipient was aliquoted into a syringe for subsequent mixing with the silk fibroin to generate the desired formulation. Excipients included NaCl, polyethylene glycol (PEG), and poloxamer 188 (P188). For each sample, the syringe of the representative silk fibroin solution was connected to a syringe of its designated excipient solution via a B Braun fluid dispensing connector. The contents of the syringes were then mixed until homogenous. The hydrogels had an osmolarity of 280 mOsm. The resulting samples were incubated on a rotator for 24 hours at 37° C. The pH values of the samples were measured with a glass pH probe, and they were adjusted with hydrochloric acid. The samples had a final (w/v) ratio of silk fibroin to excipient of between 0.01 and 0.5. The samples were then separated into 0.4 mL aliquots in 1 cc syringes, and they were stored at 4° C. until time of injection. Formulations of the hydrogels contained sodium chloride, 0.2% (w/v) Polysorbate-80, and 22 mM phosphate buffer at pH=7.4 for the P188-containing hydrogels. Some hydrogel formulations comprised 10% P188 and 10.4 mg/mL sodium chloride with a pH of 7.4. Formulations contained hydrochloric acid, sodium chloride, 0.2% (w/v) Polysorbate-80, and 22 mM phosphate buffer at pH=7.4 for the PEG 4 kDa-containing hydrogels. Some formulations contained 40% PEG 4 kDa, 5.2 mg/mL sodium chloride, and 22 mM hydrochloric acid, with a pH of 7.4.

TABLE 22

SOLUTION PREPARATIONS FOR EXCIPIENTS

| Sample | NaCl mg/mL needed in exc. | mL to make | mL stock PEG | mL stock P188 | uL 200 mg/mL NaCl | uL DI Water | uL 1N HCl |
|---|---|---|---|---|---|---|---|
| 120 mb; hyd; 0% cxbst; 3% SFf; 0% CXBf; 40% PEG4kf | 5.17 | 4 | 3.72 | 0 | 103 | 69 | 108 |
| 120 mb; hyd; 0% cxbst; 3% SFf; 0% CXBf; 10% P188f | 10.43 | 4 | 0 | 3.48 | 208.6 | 311 | 0 |
| 480 mb; hyd; 0% cxbst; 3% SFf; 0% CXBf; 10% P188f | 10.36 | 4 | 0 | 3.48 | 207.2 | 313 | 0 |

Administration of Hydrogels

The subjects were New Zealand white rabbits with a mass of 3-4 kg. The rabbits were separated into six groups, with three rabbits in each group. Each group was given an intravitreal injection with the formulation as described in Table 23. All injections were performed in the left eye, with the right eye remaining naïve to serve as an intra-animal control.

TABLE 23

EXPERIMENTAL GROUPS OF RABBITS FOR THE STUDY OF SILK FIBROIN HYDROGELS

| Group | Description | Name of Samples Administered |
|---|---|---|
| 1 | PBS | PBS control |
| 2 | 120 mb Solution | 120 mb control |
| 3 | 480 mb Solution | 480 mb control |
| 4 | 3% 120 mb; 40% PEG 4 kDa | 120 mb; hyd; 0% cxbst; 3% SFf; 0% CXBf; 40% PEG4kf |
| 5 | 3% 120 mb; 10% P188 | 120 mb; hyd; 0% cxbst; 3% SFf; 0% CXBf; 10% P188f |
| 6 | 3% 480 mb; 10% P188 | 480 mb; hyd; 0% cxbst; 3% SFf; 0% CXBf; 10% P188f |

All silk fibroin hydrogel formulations were pre-loaded into sterile 1 cc syringes, with 0.4 mL in each syringe. Prior to injection, the syringe cap was removed, and a sterile 27-gauge, ½" needle was attached. The volume was adjusted to 0.1 mL, and the formulation was injected into the intravitreal space, 2 mm posterior to the limbus.

All procedures were performed under general anesthesia. Animals were given a pre-anesthetic (Xylazine 1.1 mg/kg IM, Buprenorphine HCl 2-6 mcg/kg IM). Animals were then anesthetized with ketamine 22 mg/kg IM. Animals were placed on a heating pad, and vitals were monitored. Animals were put on inhalation anesthesia (Isoflurane at 1.5-2%) with O2 supplement.

All rabbits had their peri-ocular fur of the left eye trimmed prior to the procedure. A wire lid speculum was used to hold the eye open. The eye was rinsed with balanced salt solution (BSS), followed by a rinse with 5% ophthalmic betadine. The betadine was applied again, immediately prior to the injection and post-injection. All rabbits received gentamycin ophthalmic ointment to the operative (left) eye in the recovery area post-procedure.

To administer the hydrogels into the intravitreal space, a lid speculum was inserted into the rabbit's left eye. The conjunctiva was rinsed with BSS solution. Then, the conjunctival sac was prepped with a 5% ophthalmic betadine solution. The hydrogel was then injected into the intravitreal space using standard the double panel technique described in the earlier in vivo studies of rods and gels. The formulation was delivered to the intravitreal space, and the needle was removed. Following injection, the central retinal artery was examined via indirect ophthalmoscopy to confirm perfusion and 1-2 drops of betadine solution were added to the conjunctiva prior to removal of the speculum.

Intraocular Pressure and Biocompatibility after Hydrogel Injection

Immediately following the injection, it was noted that the smaller size of the animals used in the study lead to hypoperfusion upon injection of 0.1 mL of material. The rabbits had a mass of approximately 3 kg. The hydrogels injected into animals from groups 4-6 formed well defined, cohesive, spherical depots upon injection. These opaque formulations were easily visualized. The hydrogels for the experiments on the rabbits in group 4 (120 mb; hyd; 0% cxbst; 3% SFf; 0% CXBf; 40% PEG4kf) were too difficult to inject. The injection of this formulation was concluded to not be feasible without the use of an auto-injector. In addition, the low molecular weight silk hydrogels, used in the formulations for group 6, were less opaque than the formulations with high molecular weight silk, used on groups 4 and 5.

48 hours after injection, 8 days after injection, and 9 days after injection the intraocular pressure was measured with a Tono-Pen (see Table 24 for results). Anterior penlight exams and posterior dilated fundus exams were also performed at these times. 48 hours after the injection, all animals exhibited slight conjunctival irritation. This result was attributed to the betadine solution used during the procedure. All silk hydrogel formulations, as seen in groups 4-6, were unchanged. The depots were located at the base of the eye, out of the visual field, and they were cohesive and opaque. The depots from the formulations used in group 6 (480 mb; hyd; 0% cxbst; 3% SFf; 0% CXBf; 10% P188f) were less opaque than those of the other hydrogels. The standard deviation of the intraocular pressure of the right eye for 5 subjects in group 4 (noted by "*") was not calculable because only one animal had the IOP of the right eye measured with a method identical to the rest, rendering n=1 for direct comparisons.

With the exception of the PBS control, i.e., group 1, in all instances the fold change in the TOP between the injected and the naïve eye in each group was less than one, which indicated that all formulations with silk reduced intraocular pressure. Group 4, where the silk was formulated with 40% PEG (4 kDa), showed the lowest fold change value, which indicated that this formulation was the most effective in reducing the intraocular pressure.

TABLE 24

INTRAOCULAR PRESSURE MEASUREMENTS AT 48 HOUR EXAM WITH SILK FIBROIN HYDROGELS

| | | Left Eye (Injected) | | Right Eye (Naïve) | | |
|---|---|---|---|---|---|---|
| Group | Sample Name | Average IOP (mmHg) | Standard Deviation | Average IOP (mmHg) | Standard Deviation | Fold change in IOP (Injected/Naïve) |
| 1 | PBS control | 11.33 | 0.58 | 11 | 2.65 | 1.03 |
| 2 | 120 mb control | 11.33 | 2.08 | 11.5 | 0.71 | 0.99 |
| 3 | 480 mb control | 10.33 | 1.53 | 12 | 1.41 | 0.86 |
| 4 | 120 mb; hyd; 0% cxbst; 3% SFf; 0% CXBf; 40% PEG4kf | 16.33 | 3.21 | 20 | 0.00* | 0.82 |
| 5 | 120 mb; hyd; 0% cxbst; 3% SFf; 0% CXBf; 10% P188f | 14.67 | 2.52 | 16.33 | 4.04 | 0.90 |
| 6 | 480 mb; hyd; 0% cxbst; 3% SFf; 0% CXBf; 10% P188f | 15.5 | 2.12 | 17 | 2.65 | 0.91 |

All silk solutions were determined to be well tolerated via the pen light exam at this timepoint. There were no signs of intraocular inflammation or irritation. Any slight hypoperfusion due to the volume of the injection had been resolved by this time. Compared to the naïve contralateral eyes (the right eyes), no elevation in intraocular pressure (TOP) was measured with the Tono-Pen. The fold change in TOP between the average TOP of injected (left) eye and the average TOP of naïve (right) eye for each group was also calculated. In most cases, the TOP of the left eye was measured to be slightly lower than that of the right eye (the control).

8 to 9 days after the injection, all conjunctival irritation had subsided. All silk hydrogel formulations (groups 4-6) were mainly unchanged since the 48 hour examination. The depots were still present at the base of the eye, out of the visual field, and they were still cohesive and opaque. The depots from the formulations used in group 6 (480 mb; hyd; 0% cxbst; 3% SFf; 0% CXBf; 10% P188f) were still less opaque than those of the other hydrogels. The intraocular pressure measurements using a Tono-Pen were also made at day 8/9 following the hydrogel injection. The results were shown in Table 25.

TABLE 25

INTRAOCULAR PRESSURE MEASUREMENTS AT 8 OR 9 DAY EXAM WITH SILK FIBROIN HYDROGELS

| | | Left Eye (Injected) | | Right Eye (Naïve) | | |
|---|---|---|---|---|---|---|
| Group | Sample name | Average Left Eye IOP (mmHg) | Standard Deviation | Average Right Eye IOP (mmHg) | Standard Deviation | Fold change in IOP (Injected/Naïve) |
| 1 | PBS control | 8.00 | 4.00 | 13.00 | 3.61 | 0.62 |
| 2 | 120 mb control | 11.67 | 0.58 | 13.67 | 2.08 | 0.85 |
| 3 | 480 mb control | 13.00 | 2.65 | 14.33 | 2.52 | 0.91 |
| 4 | 120 mb; hyd; 0% cxbst; 3% SFf; 0% CXBf; 40% PEG4kf | 15.67 | 1.53 | 17.33 | 4.93 | 0.90 |
| 5 | 120 mb; hyd; 0% cxbst; 3% SFf; 0% CXBf; 10% P188f | 16.00 | 10.44 | 10.33 | 3.79 | 1.55 |
| 6 | 480 mb; hyd; 0% cxbst; 3% SFf; 0% CXBf; 10% P188f | 12.00 | 3.61 | 24.33 | 10.41 | 0.49 |

All hydrogel formulations, silk solutions, and PBS solutions were determined to be well tolerated via clinical examination. There were no signs of intraocular inflammation or irritation. Compared to the naïve contralateral eyes (the right eyes), no elevation in intraocular pressure (TOP) was measured with the Tono-Pen. Animals in groups 1–4 were sacrificed 9 days post-injection. Animals in groups 4-6 were sacrificed 8 days post-injection After 8-9 days, the fold change of the intraocular pressures between the injected eye and the naïve eye changed more drastically. Almost every group experienced a decrease in the fold change, which indicated that these formulations with silk reduced intraocular pressure more drastically over time. Group 6 (480 mb; hyd; 0% cxbst; 3% SFf; 0% CXBf; 10% P188f) showed the lowest fold change value, which indicated that this formulation was the most effective in reducing the intraocular pressure. Meanwhile, group 5 (120 mb; hyd; 0% cxbst; 3% SFf; 0% CXBf; 10% P188f), the hydrogels of which were formulated with a higher molecular weight silk fibroin, experienced an increase in the fold change, which indicated that this formulation increased intraocular pressure over time.

Example 13. In Vivo Study of Silk Fibroin Hydrogels with Celecoxib in an Animal Model As seen in the studies of silk fibroin hydrogels formulated without a therapeutic agent, all buffers and stock solutions were prepared under sterile conditions unless otherwise indicated. All formulations were prepared with SOHO silk yarn. The poloxamer-188, sodium chloride, and hydrochloric acid were from Sigma-Aldrich (St. Louis, Mo.), the PEG4 kDa was from Clariant, Charlotte N.C., and the celecoxib (CXB) was from Cipla, Miami Fla. Polysorbate-80 was purchased from Croda (Snaith UK). Potassium phosphate monobasic and potassium phosphate dibasic were purchased from Sigma Aldrich Fine Chemical (SAFC, St. Louis Mo.). Phosphate buffered saline was purchased from Gibco (USA). Multiple preparations of the same formulations were used.

Preparation of Celecoxib Experimental Controls

All controls were prepared as described for the in vivo experiments of silk fibroin hydrogels with no therapeutic agent. Briefly, a 27.8% suspension of celecoxib (CXB) was prepared from 4.15 g dry heat treated (DHT) CXB in 10.78 mL of 0.79% Polysorbate-80 and mixed until homogenous. 1.789 mL of the 27.8% CXB suspension was diluted to 5 mL via the addition of 0.349 mL 315 mM PB (pH=7.4), 0.158 mL of 200 mg/mL NaCl, and DI water. The resulting 10% CXB suspension was immediately aliquoted into 0.4 mL fractions in 1 cc syringes so that it remained homogenous, and the fractions were stored on ice until injection.

Preparation of Silk Fibroin Hydrogels with 10% Celecoxib

The hydrogel samples were prepared as described in the experiments on hydrogels without a therapeutic agent. Hydrogels were prepared from both high molecular weight (120 mb) and low molecular weight (480 mb) silk fibroin. 300 mg of either 120 mb or 480 mb silk fibroin were brought up in 3.589 mL of the 27.8% CXB suspension and 0.381 mL of 315 mM PB (pH=7.4). The resulting solutions were incubated at room temperature and mixed for 30 minutes until homogenous. The silk fibroin solutions were then aliquoted into 2.13 mL fractions in 5 cc syringes. The samples in Table 26 are named by the process used to prepare and formulate each hydrogel. For example, in the sample named 120 mb; hyd; 27.8% cxbst; 3% SFf; 10% CXBf; 10% P188f, "120 mb" refers to silk degummed with a 120-minute boil, "hyd" refers to the formulation of the sample as a hydrogel, "27.8% cxbst" refers to a preparation from a stock solution of 27.8% of celecoxib, "3% SFf" refers to a formulation with 3% (w/v) silk fibroin, "10% CXBf" refers to a formulation with 10% (w/v) celecoxib, and "10% P188f" refers to a formulation with 10% (w/v) poloxamer 188. Some samples were prepared with silk fibroin degummed with a 120-minute boil (120 mb). The 10% CXB suspension contained 0.2% Tween-80, 22 mM phosphate buffer, and 6.32 mg/mL NaCl. The 120 mb hydrogel contained 0.2% Tween-80, 22 mM phosphate buffer, and 5.99 mg/mL NaCl. The 480 mb hydrogel contained 0.2% Tween-80, 22 mM phosphate buffer, and 5.95 mg/mL NaCl.

TABLE 26

DESCRIPTIONS OF SAMPLES FOR IN VIVO EXPERIMENTS WITH 3% (W/V) SILK FIBROIN (SF) HYDROGELS FORMULATED WITH 10% (W/V) CELECOXIB AND 10% P188

| Sample Name | Description | SF Boil Time | SF Conc. (%) | P188 Conc. (%) | Ratio SF to Excipient (P188) | Ratio CXB to SF | Ratio CXB to Excipient (P188) | CXB:SF:P188 |
|---|---|---|---|---|---|---|---|---|
| 10% CXB control | 10% CXB Suspension | — | — | — | — | — | — | — |
| 120 mb; hyd; 27.8% cxbst; 3% SFf; 10% CXBf; 10% P188f | 3% 120 mb; 10% P188; 10% CXB | 120 | 3 | 10 | 0.3 | 3.33 | 1 | 10:3:10 |
| 480 mb; hyd; 27.8% cxbst; 3% SFf; 10% CXBf; 10% P188f | 3% 480 mb; 10% P188; 10% CXB | 480 | 3 | 10 | 0.3 | 3.33 | 1 | 10:3:10 |

The corresponding solutions of excipients were prepared as described in Table 27. As with the hydrogels without CXB, a 2.87 mL volume of each excipient was aliquoted into a 3 cc syringe for subsequent mixing with the silk fibroin to generate the described formulation. For each sample, the syringe of the representative silk fibroin solution was connected to a syringe of its designated excipient solution via a B Braun fluid dispensing connector. The contents of the syringes were then mixed until homogenous. The resulting samples were incubated on a rotator for 24 hours at 37° C. and then separated into 0.4 mL aliquots in 1 cc syringes. The pH values of the samples were measured with a glass pH probe, and they were adjusted with hydrochloric acid. The resulting hydrogels had a ratio of silk fibroin to excipient of between 0.01 and 0.5, a ratio of celecoxib to silk fibroin of between 0.1 and 5, and a ratio of celecoxib to excipient of 1. The ratio of celecoxib to silk fibroin to excipient was 10:3:10. Formulations of the hydrogels contained sodium chloride, 0.2% (w/v) Polysorbate-80, and 22 mM phosphate buffer at pH=7.4 for the P188-containing hydrogels. Some formulations comprised 10% P188, 10% CXB, and 10.4 mg/mL sodium chloride at a pH of 7.4.

TABLE 27

EXCIPIENT SOLUTION PREPARATIONS FOR HYDROGELS WITH CELECOXIB.

| Sample Name | NaCl mg/mL needed in exc. | mL to make | mL stock P188 | µL 200 mg/mL NaCl | µL DI Water |
|---|---|---|---|---|---|
| 120 mb; hyd; 27.8% cxbst; 3% SFf; 10% CXBf; 10% P188f | 10.44 | 4 | 3.48 | 208.8 | 311.2 |
| 480 mb; hyd; 27.8% cxbst; 3% SFf; 10% CXBf; 10% P188f | 10.36 | 4 | 3.48 | 207.2 | 312.8 |

Administration of Hydrogels

The methods of administration of silk fibroin hydrogels with celecoxib were identical to those used to administer the hydrogels without celecoxib. Briefly, the subjects were New Zealand white rabbits with a mass of 4 kg. The rabbits were separated into three groups, with three rabbits in each group. Each group was injected with the formulation as described in Table 28. All injections were performed in the left eye, with the right eye remaining naïve to serve as an intra-animal control.

TABLE 28

EXPERIMENTAL GROUPS OF RABBITS FOR THE STUDY OF SILK FIBROIN HYDROGELS FORMULATED WITH CELECOXIB.

| Group | Description | Name of Sample Administered |
|---|---|---|
| 1 | 10% CXB Suspension | 10% CXB control |
| 2 | 3% HMW (120 mb) Silk; 10% Poloxamer-188; 10% CXB | 120 mb; hyd; 27.8% cxbst; 3% SFf; 10% CXBf; 10% P188f |
| 3 | 3% LMW (480 mb) Silk; 10% Poloxamer-188; 10% CXB | 480 mb; hyd; 27.8% cxbst; 3% SFf; 10% CXBf; 10% P188f |

All silk fibroin hydrogel formulations were pre-loaded into sterile 1 cc syringes, with 0.4 mL in each syringe. Prior to injection, the syringe cap was removed, and a sterile 27-gauge, ½" needle was attached. The volume was adjusted to 0.1 mL, and the formulation was injected into the intravitreal space, 2 mm posterior to the limbus. The method of injection was as described for the in vivo studies of silk fibroin hydrogels without celecoxib. Briefly, a lid speculum was inserted into the rabbit's left eye. The conjunctiva was rinsed with BSS solution. Then, the conjunctival sac was prepped with a 5% ophthalmic betadine solution. The hydrogel was then injected into the intravitreal space using the double panel technique described in the earlier in vivo studies of rods and gels. The formulation was delivered, and the needle was removed. Following injection, the central retinal artery was examined via indirect ophthalmoscopy to confirm perfusion and 1-2 drops of betadine solution were added to the conjunctiva prior to removal of the speculum.

All procedures were performed under general anesthesia. All rabbits had their pen-ocular fur of the left eye trimmed prior to the procedure. All rabbits received gentamycin ophthalmic ointment to the operative (left) eye in the recovery area post-procedure.

Intraocular Pressure and Biocompatibility after Injection of Hydrogels with Celecoxib 24 hours after the injection, and 7 days after the injection, the intraocular pressure was measured with a Tono-Pen, as shown in Table 29. Anterior penlight exams and posterior dilated fundus exams were also performed at these times. Even though larger animals, with a mass of approximately 4 kg, were used for this study than those used for the study of hydrogels without therapeutics, it was noted that hypoperfusion still occurred upon injection of 0.1 mL. This was expected as this volume was likely the largest volume that could be well-tolerated. Animal CCN-23 only received a half-volume injection and was therefore considered not usable for the current study. However, the injection did seem well-tolerated, and may be a suitable volume for injection in future studies. All hydrogel groups were more difficult to inject than their corresponding controls without drug. The hydrogels formed well defined, cohesive depots upon injection. These opaque formulations were easily visualized. Furthermore, the suspension, rather than immediately dispersing, stayed together well in the vitreous space.

TABLE 29

INTRAOCULAR PRESSURE MEASUREMENTS AT 24 HOUR EXAM WITH SILK FIBROIN HYDROGELS WITH CELECOXIB

| | | Left Eye (Injected) | | Right Eye (Naïve) | | |
|---|---|---|---|---|---|---|
| Group | Sample Name | Average Left Eye IOP (mmHg) | Standard Deviation | Average Right Eye IOP (mmHg) | Standard Deviation | Fold change in IOP (Injected/Naïve) |
| 1 | 10% CXB control | 10.00 | 4.58 | 11.33 | 1.53 | 0.88 |
| 2 | 120 mb; hyd; 27.8% cxbst; 3% SFf; 10% CXBf; 10% P188f | 8.00 | 2.65 | 13.33 | 4.16 | 0.60 |
| 3 | 480 mb; hyd; 27.8% cxbst; 3% SFf; 10% CXBf; 10% P188f | 7.67 | 0.58 | 13.00 | 1.00 | 0.59 |

24 hours after the injection, all animals exhibited slight conjunctival irritation. This result was attributed to the betadine solution used during the procedure. All silk hydrogel formulations, as well as the suspension, were physically unchanged. All formulations were determined to be well-tolerated via ocular examination. There were no observed signs of intraocular inflammation or irritation. Any slight hypoperfusion due to injection had resolved. Compared to the naïve contralateral eyes (the right eyes), no elevation in intraocular pressure (TOP) was measured with the Tono-Pen. In most cases, the TOP of the injected left eye was measured to be lower than that of the right eye (the control). The fold change of the intraocular pressure between the injected eye and the naïve eye decreased for all silk fibroin formulations relative to the CXB suspension control.

The eyes were examined again during a 7-day exam. The intraocular pressure was also measured at this timepoint, seen in Table 30A.

By the 7-day examination, all conjunctival irritation had subsided. The materials were concluded to be tolerated at 7 days. There were no obvious signs of inflammation. The hydrogels and the suspensions were cohesive at the 7-day timepoint. No elevation was detected in intraocular pressure compared to the naïve contralateral eyes. There was a slight trend toward lower intraocular pressures in the CXB-treated eyes. The fold change in the TOP between the injected and the naïve eye in each group was less than one, which indicated that all formulations reduced intraocular pressure. The fold change also revealed that the formulations with silk reduced the intraocular pressure to a lesser extent than the CXB suspension.

The analysis of the intraocular pressure was continued, as seen in Table 30B. At 4.5 months after administration, the CXB-containing hydrogels showed a slight decrease in intraocular pressure, similar to that of the CXB suspension. In addition, the intraocular pressure was measured to be the same as the untreated eye at 7 months after administration of hydrogel with no CXB. No local inflammation, hemorrhage, or other complications were detected 7 months after administration.

TABLE 30A

INTRAOCULAR PRESSURE MEASUREMENTS AT 7-DAY EXAM WITH SILK FIBROIN HYDROGELS WITH CELECOXIB

| | | Left Eye (Injected) | | Right Eye (Naïve) | | |
|---|---|---|---|---|---|---|
| Group | Sample Name | Average Left Eye IOP (mmHg) | Standard Deviation | Average Right Eye IOP (mmHg) | Standard Deviation | Fold change in IOP (Injected/Naïve) |
| 1 | 10% CXB control | 6.67 | 0.58 | 13.33 | 0.58 | 0.50 |
| 2 | 120 mb; hyd; 27.8% cxbst; 3% SFf; 10% CXBf; 10% P188f | 7.67 | 2.31 | 10.00 | 4.36 | 0.77 |
| 3 | 480 mb; hyd; 27.8% cxbst; 3% SFf; 10% CXBf; 10% P188f | 8.67 | 4.04 | 11.67 | 2.89 | 0.74 |

TABLE 30B

CONTINUED MEASUREMENTS OF INTRAOCULAR PRESSURE OF
SILK FIBROIN HYDROGELS WITH AND WITHOUT CELECOXIB

| | | Left Eye (Injected) | | Right Eye (Naïve) | | |
|---|---|---|---|---|---|---|
| Sample Name | Days | Average Left Eye IOP (mmHg) | Standard Deviation | Average Right Eye IOP (mmHg) | Standard Deviation | Fold change in IOP (Injected/Naïve) |
| 10% CXB control | 127 | 7.00 | 2.58 | 9.25 | 2.22 | 0.76 |
| 480 mb; hyd; 27.8% ccxbst; 3% SFf; 10% CXBf; 10% P188f | 127 | 6.00 | 2.16 | 7.75 | 3.30 | 0.77 |
| 480 mb; hyd; 27.8% cxbst; 3% SFf; 0% CXBf; 10% P188f | 197 | 10.33 | 3.21 | 10.67 | 3.21 | 0.97 |

Example 14. Histopathology Studies of Rabbit Eyes with Hydrogels

Following the experiments on intraocular pressure and biocompatibility, the animals were sacrificed, and both eyes were immediately enucleated and placed into a solution of 10% formalin. After 24 hours, the eyes were transferred to a solution of 70% ethanol for subsequent histopathology studies. Thirty-two rabbit eyes were submitted for the study. The eyes were processed into two blocks per sample. One slide per block was sectioned and stained with hematoxylin and eosin (H&E). The glass slides were evaluated by a board-certified veterinary pathologist via light microscopy. Histologic legions were graded for severity (0=absent; 1=minimal; 2=mild; 3=moderate; 4=marked; 5=severe).

Histologic findings in this study consisted of an infiltration of mixed inflammatory cells into the vitreous chamber, including heterophils (neutrophils), lymphocytes, plasma cells, macrophages and rare multinucleated giant cells. Inflammatory cells were primarily present in the region of the ora ciliaris retinae and variably surrounded presumed injected material within the vitreous chamber. This material ranged from basophilic flocculent to granular material, to more discrete, non-staining slightly refractile material less than 10 μm in diameter, to non-staining cleft-shaped material (resembling cholesterol clefts). Similar inflammatory cells infrequently extended into the adjacent ciliary body epithelium or retina. A granuloma, characterized by aggregation of macrophages and multinucleated giant cells, surrounding non-staining cholesterol cleft-like material and phagocytized debris, was present in the conjunctiva of one animal. Mononuclear inflammatory infiltrate was characterized by infiltration or aggregation of lymphocytes and plasma cells, with rare heterophils, in the conjunctiva. Infiltration of similar mononuclear cells into the iris was observed in one animal. Elevation of the retina from the retinal pigmented epithelium, present in many samples, was not associated with other features supportive of true retinal separation and this finding was therefore considered an artifact.

Means of the grades of the histologic lesions were examined, as well as the standard error of the mean (SEM), shown in Table 31. Mean scores for mixed inflammatory cell infiltration into the vitreous chamber were only observed in samples with intravitreal injections containing 10% celecoxib (CXB) (Groups 8-10). The highest mean score was observed in the 10% CXB suspension alone group (Group 8). The animal with a conjunctival granuloma was also in this group. Mean scores for conjunctival mononuclear cell infiltration severity were similar among all groups, regardless of injection status or injection material. Focal iris infiltration of inflammatory cells was only present in one animal, which had been from the low molecular weight (MW) solution group.

TABLE 31

H&E GRADES OF THE RABBIT EYE HISTOPATHOLOGY DATA OF ANIMALS TREATED
WITH SILK FIBROIN COMPOSITIONS (STANDARD ERROR OF THE MEAN)

| Group | Name of injected sample | Inflammation, mixed, vitreous chamber | Infiltrate, mononuclear, iris | Granuloma, conjunctiva | Infiltrate, mononuclear, conjunctiva |
|---|---|---|---|---|---|
| Group 1 (Untreated) | Untreated | 0 (±0.00) | 0 (±0.00) | 0 (±0.00) | 0.50 (±0.50) |
| Group 2 (PBS) | PBS | 0 (±0.00) | 0 (±0.00) | 0 (±0.00) | 0.33 (±0.33) |
| Group 3 (HMW Solution) | 120 mb control | 0 (±0.00) | 0 (±0.00) | 0 (±0.00) | 0.67 (±0.33) |
| Group 4 (LMW Solution) | 480 mb control | 0 (±0.00) | 0.33 (±0.33) | 0 (±0.00) | 0 (±0.00) |
| Group 5 (3% HMW SF; 40% 4 kDa PEG) | 120 mb; hyd; 0% cxbst; 3% SFf; 0% CXBf; 40% PEG4kf | 0 (±0.00) | 0 (±0.00) | 0 (±0.00) | 1 (±0.00) |

TABLE 31-continued

H&E GRADES OF THE RABBIT EYE HISTOPATHOLOGY DATA OF ANIMALS TREATED
WITH SILK FIBROIN COMPOSITIONS (STANDARD ERROR OF THE MEAN)

| Group | Name of injected sample | Inflammation, mixed, vitreous chamber | Infiltrate, mononuclear, iris | Granuloma, conjunctiva | Infiltrate, mononuclear, conjunctiva |
|---|---|---|---|---|---|
| Group 6 (3% HMW SF, 10% P188) | 120 mb; hyd; 0% cxbst; 3% SFf; 0% CXBf; 10% P188f | 0 (±0.00) | 0 (±0.00) | 0 (±0.00) | 1.33 (±0.33) |
| Group 7 (3% LMW SF, 10% P188) | 480 mb; hyd; 0% cxbst; 3% SFf; 0% CXBf; 10% P188f | 0 (±0.00) | 0 (±0.00) | 0 (±0.00) | 1 (±0.00) |
| Group 8 (10% CXB Suspension) | 10% CXB control | 2 (±0.00) | 0 (±0.00) | 0.67 (±0.67) | 1 (±0.00) |
| Group 9 (3% HMW SF, 10% P188, 10% CXB Suspension) | 120 mb; hyd; 27.8% cxbst; 3% SFf; 10% CXBf; 10% P188f | 0.75 (±0.48) | 0 (±0.00) | 0 (±0.00) | 0.75 (±0.25) |
| Group 10 (3% LMW SF, 10% P188, 10% CXB Suspension) | 480 mb; hyd; 27.8% cxbst; 3% SFf; 10% CXBf; 10% P188f | 0.67 (±0.33) | 0 (±0.00) | 0 (±0.00) | 0.67 (±0.33) |

Imaging of an untreated eye displayed no lesions at the ora ciliaris retinae. The normal vitreous humor was visible as an acellular, slightly eosinophilic wispy material in the vitreous chamber. The ciliary body, retina, and sclera were also visible in the images. Imaging of an eye treated with a 10% CXB suspension demonstrated inflammatory infiltration into the vitreous chamber. There were more abundant heterophils, lymphocytes, and macrophages. Inflammatory cells were also rarely present in the retina.

Imaging of an eye treated with 120 mb; hyd; 0% cxbst; 3% SFf; 0% CXBf; 10% P188f showed that there was a mild infiltration of lymphocytes and mononuclear plasma cells within the conjunctiva.

Imaging of an eye treated with an intravitreal injection of 120 mb; hyd; 27.8% cxbst; 3% SFf; 10% CXBf; 10% P188f demonstrated that the injected vitreous material was more basophilic and granular compared to the normal vitreous humor. Macrophages, and fewer lymphocytes and heterophils, surrounded and infiltrated this material.

The major finding associated with intravitreal injections in this study was vitreous chamber mixed inflammation, limited to the eyes receiving injections containing 10% CXB. Mixed inflammatory cell infiltration in the vitreous chamber was only observed in groups receiving 10% CXB, with a 3-fold increase in the scores in the 10% CXB suspension group compared to groups 9 and 10 where the CXB was formulated with silk. This result showed that CXB silk formulations can potentially reduce the inflammatory responses seen with CXB only injections.

The observed inflammation was likely due to the presence of CXB. It is possible that the inflammation is a result of slight toxicity due to high initial levels of CXB in the vitreous. In the silk fibroin formulations, the initial levels of CXB in the vitreous were lower likely due to the slower release of the therapeutic agent. The inflammation might also have been caused by the suspension form of CXB. The smaller particles could induce a macrophage response; they could be engulfed by macrophages and ultimately lead to inflammation. By contrast, the hydrogel would contain these particles and reduce the resulting inflammation.

In most groups, there was minimal to mild conjunctival mononuclear infiltration. This inflammatory infiltrate typically targeted presumptive injected material, with a range in inflammatory response from primarily acute (heterophilic/neutrophilic) to a more foreign body-type reaction with more numerous macrophages ingesting the injected material. Extension of inflammatory cells into the surrounding tissues was infrequently present and was not associated with ciliary epithelial or retinal degeneration. The granuloma present in the conjunctiva of one eye (10% CXB Suspension group) was considered secondary to the injection procedure. Conjunctival and iridal mononuclear inflammatory cell infiltration was present in numerous eyes from both untreated and treated groups; these findings were considered background lesions that were unrelated to treatment. The retinal tissue was considered normal.

Additional histopathology studies were performed on animals sacrificed 6 and 7 months after administration of the silk fibroin hydrogels (480 mb; hyd; 0% cxbst; 3% SFf; 0% CXBf; 10% P188f). At 6 and 7 months after administration, the injected material was free of cellular infiltrate. No other histologic findings were observed. No local inflammation, hemorrhage, or other complications were observed. Ultimately the hydrogels were determined to be biocompatible and well-tolerated in the intravitreal space for at least 7 months after administration.

Example 15. Histopathology Studies of Rabbit Eyes with Silk Rods

Following the experiments on intraocular pressure and biocompatibility, the animals were sacrificed, and both eyes were immediately enucleated and placed into a solution of 10% formalin. After 24 hours, the eyes were transferred to a solution of 70% ethanol for shipment and subsequent histopathology studies. The eyes were from animals sacrificed 1 week after administration of the silk rods. Four formalin-fixed rabbit eyes were processed into two blocks per sample. One slide per block was sectioned and stained with hematoxylin and eosin (H&E). The glass slides were evaluated by a board-certified veterinary pathologist, using light microscopy. Histologic lesions were graded for severity (0=absent; 1=minimal; 2=mild; 3=moderate; 4=marked; 5=severe), as seen in Table 32. L denoted the left eye, while R denoted the right eye.

TABLE 32

H&E GRADES OF THE RABBIT EYE HISTOPATHOLOGY DATA
OF ANIMALS TREATED WITH SILK FIBROIN ROD COMPOSITIONS;
P = PRESENT, NP = NOT PRESENT

| Treatment | Sample Name | Eye | Block | Foreign material, vitreous chamber (presumptive rod) | Mixed infiltrate, vitreous chamber (surrounding foreign material) | Degeneration, lens fiber | Mixed inflammation, conjunctiva |
|---|---|---|---|---|---|---|---|
| Silk-Fibroin/CXB Rod | 480 mb; 0.5 mm; 40% st; 100 mgsf; 200 mgcxb; lyo; 33.3% sf; 66.7% cxb | 56L | 1 | NP | 0 | 0 | 0 |
| | | | 2 | P | 1 | 0 | 0 |
| | | 58L | 1 | P | 1 | 0 | 2 |
| | | | 2 | P | 0 | 0 | 1 |
| | | 59L | 1 | NP | 0 | 2 | 0 |
| | | | 2 | NP | 0 | 0 | 0 |
| Untreated | — | 56R | 1 | NP | 0 | 0 | 0 |
| | | | 2 | NP | 0 | 0 | 0 |

Foreign material, presumably the injected celecoxib (CXB) rod, was present in the vitreous chamber of two eyes, near the ora ciliaris retinae. This material was a solid mass of amphophilic material, approximately 500 μm in diameter, containing non-staining clefts and vacuoles. This material was variably loosely surrounded or minimally infiltrated by low numbers of macrophages, rare heterophils and scant hemorrhage. Inflammation was not observed in other areas of the vitreous chamber or within the adjacent ciliary body/uveal tract or retina. In one eye, slight lens fiber degeneration was present. This finding might be associated with the injection procedure. Mixed inflammatory cell infiltration was observed in the conjunctiva from one eye. This finding was determined to be a background lesion, and it was unlikely to be associated with test article administration. Ultimately, histopathologic evaluation revealed minimal infiltration of low numbers of macrophages and rare heterophils. No other inflammation of note within the vitreous cavity, adjacent ciliary body, or retina, was detected. The silk rods were well tolerated in the intravitreal space.

Additional histopathology studies were performed on animals sacrificed 4 months after administration of the silk fibroin rods. The studies determined 2 out of the 3 rods to be acellular with visible implant. In 1 of the 3 rods the implant was surrounded and infiltrated by lymphocytes, macrophages, and multinucleated giant cells. Most of the samples did not illicit a significant inflammatory response. Ultimately the rods were determined to be biocompatible and well-tolerated in the intravitreal space for at least 4 months after administration.

Example 16. Release of Protein Cargo and Relation of Release Kinetics to Protein Molecular Weight in Silk Fibroin Rods Silk fibroin rods were prepared from silk fibroin degummed with a 480 mb or a 120 mb. Sodium chloride was purchased from Chemsavers (Bluefield Va.). Polysorbate-80 was purchased from Croda (Snaith, United Kingdom). Phosphate buffered saline (10×PBS) was purchased from Gibco (USA). Sodium phosphate dibasic, sodium phosphate monobasic, human lysozyme, sucrose, Bovine Serum Albumin (BSA), trehalose, and poloxamer-188 (P188) were purchased from Sigma-Aldrich (St. Louis, Mo.). Sodium azide and glycerol were purchased from Fisher Chemical (Waltham, Mass.). Bevacizumab was purchased from Genentech Inc. (San Francisco, Calif.). Human immunoglobulin G (IgG) was purchased from Innovative Research (Novi, Mich.).

Preparation of Silk Fibroin Rods with Proteins

Silk fibroin rods were formulated with proteins, and the controlled release of said proteins were monitored in vitro. Silk fibroin rods were formulated with lysozyme (molecular weight=14 kDa; Sigma-Aldrich, St. Louis, Mo.), bovine serum albumin (BSA) (molecular weight=67 kDa; Sigma-Aldrich, St. Louis, Mo.), bevacizumab (molecular weight=150 kDa; Genentech Inc., San Francisco, Calif.), and Immunoglobulin G (IgG) as described in Table 33. The aqueous processing of the silk fibroin rods was amenable to aseptic conditions. Some of the silk fibroin rods were 5% (w/w) of the respective protein. The silk fibroin rods are named by the process used to prepare and formulate each rod. For example, the rod named "480 mb; 1 mm; 5% bevst; lyo; 75% sf; 3% bevacizumab; 22% sucrose" refers to a rod prepared from silk degummed with a 480-minute boil (480 mb), a 1 mm diameter (1 mm), prepared from a 5% w/v bevacizumab stock solution (5% bevst), lyophilization (lyo), a theoretical w/w percentage of 75% silk fibroin (75% sf), a theoretical w/w percentage of 3% bevacizumab (3% bevacizumab), and a theoretical w/w percentage of 22% sucrose (22% sucrose). Other potential components of the rods described in the name included gelation at 4° C. (4° C.), a preparation from a stock solution of silk fibroin (e.g. 40% st), a theoretical w/w percentage of IgG (% igg), a theoretical w/w percentage of lysozyme (% lysozyme), a preparation from silk fibroin degummed with a 120-minute boil (120 mb), a preparation from silk fibroin degummed with a 90-minute boil (90 mb), a theoretical w/w percentage of bovine serum albumin (% bsa), and a theoretical w/w percentage of trehalose (% trehalose). Sample 205-1 contained 133.3 mM phosphate buffer. 205-2 contained 133.3 mM phosphate buffer. 205-5 contained 133.3 mM phosphate buffer. Rods with bevacizumab also contained small amounts of the buffer that the product was provided in (trehalose, a sodium phosphate buffer, and polysorbate-20).

TABLE 33

SILK RODS FORMULATED WITH PROTEINS

| Sample No. | Sample Name | Time of heating (mb) | Silk-fibroin Conc. % | Protein | Protein conc. % | Excipient | Excipient Conc. % | Sample mass of each replicate (mg) |
|---|---|---|---|---|---|---|---|---|
| 204-05 | 480 mb; 1 mm; 5% bevst; lyo; 75% sf; 3% bevacizumab; 2.2% sucrose | 480 | 75 | Bevacizumab | 3 | Sucrose | 22 | 10.07<br>9.82<br>9.74 |
| 205-01 | 480 mb; 1 mm; 5% bevst; lyo; 85% sf; 5% bevacizumab; 10% sucrose | 480 | 85 | Bevacizumab | 5 | Sucrose | 10 | 9.71<br>10.17<br>10.05 |
| 205-02 | 480 mb; 1 mm; 5% bevst; lyo; 73% sf; 5% bevacizumab; 22% sucrose | 480 | 73 | Bevacizumab | 5 | Sucrose | 22 | 10.6<br>9.87<br>10.36 |
| 202-03 | 480 mb; 1 mm; 30% st; 5% bevst; lyo; 95% sf; 5% bevacizumab | 480 | 95 | Bevacizumab | 5 | — | — | 6.18<br>7.16<br>6.93 |
| 205-04 | 480 mb; 1 mm; 40% st; 4° C.; lyo; 85% sf; 5% igg; 10% sucrose | 480 | 85 | IgG | 5 | Sucrose | 10 | 7.64<br>8.3<br>7.7 |
| 205-05 | 480 mb; 1 mm; lyo; 95% sf; 5% lysozyme | 480 | 95 | Lysozyme | 5 | — | — | 6.68<br>7.8<br>6.22 |
| 205-06 | 480 mb; 1 mm; lyo; 85% sf; 5% lysozyme; 10% sucrose | 480 | 85 | Lysozyme | 5 | Sucrose | 10 | 8.66<br>7.94<br>9.23 |
| 205-07 | 480 mb; 1 mm; lyo; 75% sf; 25% lysozyme | 480 | 75 | Lysozyme | 25 | — | — | 8.3<br>9.64<br>— |
| 205-08 | 480 mb; 1 mm; lyo; 65% sf; 25% lysozyme; 10% sucrose | 480 | 65 | Lysozy me | 25 | Sucrose | 10 | 10.4<br>10.02<br>7.98 |
| 205-A | 120 mb; 1 mm; lyo; 95% sf; 5% lysozyme | 120 | 95 | Lysozyme | 5 | — | — | 6.36<br>5.99<br>5.58 |
| 197-09 | 480 mb; 1 mm; 40% st; lyo; 96.5% sf; 2.5% bsa; 1% trehalose | 480 | 96.5 | BSA | 2.5 | Trehalose | 1 | 9.24<br>8.27<br>8.11 |
| 197-11 | 120 mb; 1 mm; 30% st; lyo; 96.5% sf; 2.5% bsa; 1% trehalose | 120 | 96.5 | 13 SA | 2.5 | Trehalose | 1 | 4.89<br>4.89<br>5.29 |
| 197-12 | 120 mb; 1 mm; 30% st; lyo; 94% sf; 5% bsa; 1% trehalose | 120 | 94 | BSA | 5 | Trehalose | 1 | 6.59<br>6<br>6.02 |
| 201-04 | 480 mb; 1 mm; 5% bevst; 4° C.; lyo; 95% sf; 5% bevacizumab | 480 | 95 | Bevacizumab | 5 | — | — | 8.45<br>8<br>7.89 |
| 209-05 | 90 mb; 1 mm; 30% st; 4° C.; lyo; 97.5% sf; 2.5% igg | 90 | 97.5 | IgG | 2.5 | — | — | —<br>—<br>— |
| 209-A | 480 mb; 1 mm; 40% st; 4° C.; lyo; 85% sf; 5% igg; 10% sucrose | 480 | 85 | IgG | 5 | Sucrose | 10 | —<br>—<br>— |
| 191-01 | 480 mb; 1 mm; 40% st; lyo; 94% sf; 5% bsa; 1% trehalose | 480 | 94 | BSA | 5 | Trehalose | 1 | —<br>—<br>— |

TABLE 33-continued

SILK RODS FORMULATED WITH PROTEINS

| Sample No. | Sample Name | Time of heating (mb) | Silk-fibroin Conc. % | Protein | Protein conc. % | Excipient | Excipient Conc. % | Sample mass of each replicate (mg) |
|---|---|---|---|---|---|---|---|---|
| 191-02 | 480 mb; 1 mm; 40% st; lyo; 96.5% sf; 2.5% bsa; 1% trehalose | 480 | 96.5 | BSA | 2.5 | Trehalose | 1 | — — — |

To prepare the silk fibroin rods with lysozyme, silk fibroin was dissolved in lysozyme stock solution to reach the final desired silk/lysozyme concentrations. Sucrose (Sigma Aldrich, St. Louis Mo.) was dissolved in this solution when necessary. Formulations were injected into 1.0 mm diameter PTFE tubing. The tubing was capped with Parafilm® and allowed to gel at 37° C. overnight. Once gelling was achieved, the tubing was frozen and lyophilized.

To prepare the silk fibroin rods with BSA, silk fibroin was reconstituted in sufficient deionized water to reach a final concentration of 30 or 40% (w/v). BSA solutions were prepared, from a stock solution of 40 mg/mL BSA, with or without trehalose (Sigma Aldrich, St. Louis Mo.) and/or polysorbate-80 (Sigma Aldrich, St. Louis Mo.). Solutions were mixed between two syringes and extruded into 1.0 mm inner diameter PTFE tubing (Grainger, Ill., USA). The tubing was capped with Parafilm® and allowed to gel at 4° C. overnight. Once gelling was achieved, the tubes were frozen and lyophilized. Samples 191-01 and 191-02 had 0.1% Tween-80 in the final formulation.

To prepare the silk fibroin rods with bevacizumab, silk fibroin was reconstituted in sufficient deionized water to reach a final concentration of 30% (Sample 202-03) or 40% (remaining samples) (w/v). The reconstituted fibroin was added to a concentrated solution of bevacizumab (50 mg/mL) to achieve the desired final ratio of bevacizumab: silk. Rods containing sucrose were prepared from silk fibroin lyophilized with sucrose. Solutions were mixed using two linked syringes and then injected into 1.0 mm diameter PTFE tubing. The rods were capped with Parafilm® and allowed to gel at 4° C. (Sample 201-4 only) or 37° C. overnight. Once gelling was achieved, the tubes were lyophilized overnight.

To prepare silk fibroin rods with immunoglobulin G (IgG), silk fibroin degummed with a 480 mb or a 90 mb, was reconstituted in sufficient deionized water to reach a final concentration of 30 or 40% (w/v). Rods containing sucrose were prepared from silk-fibroin lyophilized with sucrose as an additive. Solutions were mixed between two syringes and injected into 1.0 mm diameter PTFE tubing. The rods were capped with Parafilm® and allowed to gel at 4° C. overnight. Once gelling was achieved, the tubes were frozen and lyophilized.

In Vitro Release Profile of Silk Fibroin Rods Formulated with Protein Apis

Silk fibroin rods were cut into 1 cm sections and two sections were placed, in triplicate, into 4 mL glass vials. 1 mL of release media (PBS, 0.01% polysorbate-80 (PS80), 0.05% sodium azide) was added to each vial. Samples were incubated with gentle shaking at 37° C. At 2 hours, 1, 2, 3, 7, 10, 14, 21, and 28 days, 100 µL of release media was removed and replaced with 100 µL of fresh release media. Total protein released was quantified via size-exclusion chromatography (SEC) using a Waters X-Bridge Protein BEH SEC, 200 Å, 3.5 µm column. An isocratic flow of mobile phase (100 mM sodium phosphate (Sigma Aldrich, St. Louis Mo.), 200 mM NaCl (Chemsavers, Bluefield Va.) pH 6.8) was run at 0.80 mL/min to elute protein. Protein elution was monitored at 280 and 214 nm using an Agilent 1290 HPLC system with a photodiode array (PDA) detector. Cumulative percentage of protein released was calculated using theoretical loading of the silk fibroin rods.

The average cumulative release percentage of each protein was monitored over time, as seen in Table 34A and Table 34B. The data suggested that release was related to size-dependent diffusion through the silk fibroin matrix. The release kinetics and the cumulative release percentages decreased with increased molecular weight of the protein to be released. Silk fibroin rods formulated with lysozyme had the highest initial burst percentage, while rods formulated with bevacizumab had the lowest initial burst percentage. The initial burst percentages ranged from 1-85% over the first 24 hours of the experiment. The cumulative release percentage of protein released from each rod were measured in triplicate, except for the specific measurements marked with "*", which were measured in singlicate. Sample 205-07 and sample 197-12, marked with "***", were tested in duplicate.

TABLE 34A

IN VITRO RELEASE OF PROTEINS FROM SILK-FIBROIN RODS; CUMULATIVE PERCENTAGE (%) OF API RELEASED

| Sample No. | Sample Name | Days | | | | | |
|---|---|---|---|---|---|---|---|
| | | 0 | 0.083 | 1 | 2 | 3 | 7 |
| 204-05 | 480 mb; 1 mm; 5% bevst; lyo; 75% sf; 3% bevacizumab; 22% sucrose | 0.0 | 0.5 | 0.7 | — | — | — |
| 205-01 | 480 mb; 1 mm; 5% bevst; lyo; 85% sf; 5% bevacizumab; 10% sucrose | 0.0 | 6.6 | 6.9 | — | — | — |

TABLE 34A-continued

IN VITRO RELEASE OF PROTEINS FROM SILK-FIBROIN RODS; CUMULATIVE PERCENTAGE (%) OF API RELEASED

| Sample No. | Sample Name | Days | | | | | |
|---|---|---|---|---|---|---|---|
| | | 0 | 0.083 | 1 | 2 | 3 | 7 |
| 205-02 | 480 mb; 1 mm; 5% bevst; lyo; 73% sf; 5% bevacizumab; 22% sucrose | 0.0 | 2.2 | 2.7 | — | — | — |
| 202-03 | 480 mb; 1 mm; 30% st; 5% bevst; lyo; 95% sf; 5% bevacizumab | 0.0 | 3.2 | — | — | — | — |
| 205-04 | 480 mb; 1 mm; 40% st; 4° C.; lyo; 85% sf; 5% igg; 10% sucrose | 0.0 | 5.7 | 19.4 | 20.2 | — | — |
| 205-05 | 480 mb; 1 mm; lyo; 95% sf; 5% lysozyme | 0.0 | 18.7 | 27.2 | 32.4 | 7.2 | 7.6 |
| 205-06 | 480 mb; 1 mm; lyo; 85% sf; 5% lysozyme; 10% sucrose | 0.0 | 19.4 | 29.4 | 34.8 | *29.5 | 10.3 |
| 205-07*** | 480 mb; 1 mm; lyo; 75% sf; 25% lysozyme | 0.0 | 17.5 | 22.4 | 35.0 | 37.1 | 39.7 |
| 205-08 | 480 mb; 1 mm; lyo; 65% sf; 25% lysozyme; 10% sucrose | 0.0 | 48.7 | 75.0 | 83.3 | 71.1 | 73.9 |
| 205-A | 120 mb; 1 mm; lyo; 95% sf; 5% lysozyme | 0.0 | 11.6 | 12.8 | 14.2 | 10.3 | — |
| 197-09 | 480 mb; 1 mm; 40% st; lyo; 96.5% sf; 2.5% bsa; 1% trehalose | 0.0 | 0.0 | 0.0 | 0.0 | 0.0 | — |
| 197-11 | 120 mb; 1 mm; 30% st; lyo; 96.5% sf; 2.5% bsa; 1% trehalose | 0.0 | 13.7 | 21.3 | 21.6 | 26.1 | — |
| 197-12*** | 120 mb; 1 mm; 30% st; lyo; 94% sf; 5% bsa; 1% trehalose | 0.0 | 9.1 | 14.2 | 16.0 | 17.9 | — |
| 201-04 | 480 mb; 1 mm; 5% bevst; 4° C.; lyo; 95% sf; 5% bevacizumab | 0.0 | 56.0 | 84.5 | 73.8 | 58.3 | 66.8 |

TABLE 34B

STANDARD DEVIATIONS (%) OF THE CUMULATIVE PERCENTAGE OF API RELEASED FOR THE IN VITRO RELEASE OF PROTEINS FROM SILK RODS

| Sample No. | Sample Name | Day | | | | | |
|---|---|---|---|---|---|---|---|
| | | 0 | 0.083 | 1 | 2 | 3 | 7 |
| 204-05 | 480 mb; 1 mm; 5% bevst; lyo; 75% sf; 3% bevacizumab; 22% sucrose | 0.0 | 0.1 | 0.2 | — | — | — |
| 205-01 | 480 mb; 1 mm; 5% bevst; lyo; 85% sf; 5% bevacizumab; 10% sucrose | 0.0 | 2.7 | 2.9 | — | — | — |
| 205-02 | 480 mb; 1 mm; 5% bevst; lyo; 73% sf; 5% bevacizumab; 22% sucrose | 0.0 | 0.6 | 1.0 | — | — | — |
| 202-03 | 480 mb; 1 mm; 30% st; 5% bevst; lyo; 95% sf; 5% bevacizumab | 0.0 | 0.4 | — | — | — | — |
| 205-04 | 480 mb; 1 mm; 40% st; 4° C.; lyo; 85% sf; 5% igg; 10% sucrose | 0.0 | 0.3 | 0.9 | 0.8 | — | — |
| 205-05 | 480 mb; 1 mm; lyo; 95% sf; 5% lysozyme | 0.0 | 3.3 | 1.2 | 2.6 | 0.6 | 0.7 |
| 205-06 | 480 mb; 1 mm; lyo; 85% sf; 5% lysozyme; 10% sucrose | 0.0 | 1.0 | 1.6 | 1.1 | *0.0 | 1.2 |
| 205-07*** | 480 mb; 1 mm; lyo; 75% sf; 25% lysozyme | 0.0 | 2.9 | 3.0 | 2.5 | 2.9 | 4.5 |
| 205-08 | 480 mb; 1 mm; lyo; 65% sf; 25% lysozyme; 10% sucrose | 0.0 | 1.1 | 2.6 | 2.8 | 6.1 | 1.8 |
| 205-A | 120 mb; 1 mm; lyo; 95% sf; 5% lysozyme | 0.0 | 1.1 | 1.1 | 0.3 | 0.1 | — |
| 197-09 | 480 mb; 1 mm; 40% st; lyo; 96.5% sf; 2.5% bsa; 1% trehalose | 0.0 | 0.0 | 0.0 | 0.0 | 0.0 | — |
| 197-11 | 120 mb; 1 mm; 30% st; lyo; 96.5% sf; 2.5% bsa; 1% trehalose | 0.0 | 1.8 | 3.0 | 8.6 | 5.6 | — |
| 197-12*** | 120 mb; 1 mm; 30% st; lyo; 94% sf; 5% bsa; 1% trehalose | 0.0 | 0.5 | 0.2 | 2.2 | 1.1 | — |
| 201-04 | 480 mb; 1 mm; 5% bevst; 4° C.; lyo; 95% sf; 5% bevacizumab | 0.0 | 2.5 | 3.4 | 2.3 | 3.0 | 2.5 |

Silk fibroin molecular weight seemed to play a role in release of lysozyme from silk fibroin rods. Increasing the silk fibroin molecular weight from low molecular weight silk fibroin (480 mb) to relatively higher molecular weight silk fibroin (120 mb), with 5% lysozyme loading as seen in samples 205-05 and 205-A respectively, decreased the initial burst and cumulative release percentage over 3 days.

BSA-containing rods with lower molecular weight silk fibroin (480 mb) showed a protein-loading dependent release. Rods prepared from 480 mb silk fibroin with 2.5% BSA showed release below detectable levels (BDL) out to 3 days (197-09). Rods prepared from 120 mb silk fibroin with low loading (2.5% BSA, sample 197-11) showed faster release kinetics in comparison with the corresponding rods with higher BSA loading (197-12). The lower loaded 120 mb rods (197-11) initial burst at 2 hours of 13.7% and a cumulative release of 26.1% by day 3. 120 mb silk fibroin rods showed faster release of BSA than the comparable formulation made with 480 mb silk fibroin (which showed no release). The results suggested a relationship between the BSA:silk fibroin ratio and the release kinetics of the protein from the rod.

For the silk fibroin rods prepared with bevacizumab, all formulations showed very little burst (less than or equal to 7%) with no continued release, with the exception of the rod formulation prepared at 4° C. (201-04). This low temperature rod had a burst at 2 hours of 56.0% of the loaded protein, with 84.5% of the protein released after 1 day This formulation temperature-dependent release could be caused by an increase in non-specific or hydrophobic binding of silk fibroin and bevacizumab at elevated temperatures. The lower temperature might also effect the tightness and size of the silk fibroin network within the rod formulation.

The silk fibroin rod with IgG subject to the in vitro experiments (205-04, 480 mb; 1 mm; 40% st; 4° C.; lyo; 85% sf; 5% igg; 10% sucrose) showed a lower burst and release out to 2 days. 2 hours into the experiment, 5.7% of the protein was released, and the cumulative release percentage leveled after 1 day at about 19.4%. This rod released more protein than similar rods with 5% bevacizumab (205-01), but it released less protein than similar rods with 5% lysozyme (205-06).

The release data from 5% analyte rod formulations for lysozyme (205-05), BSA (197-12), and bevacizumab (202-03 and 205-01) demonstrated a trend. The smaller proteins, lysozyme and BSA, had higher burst releases from the rods and faster release kinetics than bevacizumab. Additionally, the rods formulated with smaller proteins seemed to release protein over several days, whereas release of bevacizumab (a larger molecule) for the rod formulation plateaued after 1 day of release.

Example 17. Excipient Effects on Release Kinetics of Protein Cargo

Silk fibroin rods were formulated with proteins, and the controlled release of said proteins were monitored in vitro. Silk fibroin rods were formulated with 5 or 25% (w/w) lysozyme (molecular weight=14 kDa). Some silk fibroin rods were formulated with 5 or 25% (w/w) lysozyme, and with 10% (w/w) sucrose as an excipient. The excipient was added to reduce the silk concentration, while increasing the size of the silk fibroin network and tuning the release kinetics.

Silk fibroin rods were prepared from silk fibroin degummed with a 480 mb. Sodium chloride was purchased from Chemsavers (Bluefield Va.). Polysorbate-80 was purchased from Croda (Snaith, United Kingdom). Phosphate buffered saline (10×PBS) was purchased from Gibco (USA). Sodium phosphate dibasic, sodium phosphate monobasic, human lysozyme, sucrose, were purchased from Sigma-Aldrich (St. Louis, Mo.). Sodium azide and glycerol were purchased from Fisher Chemical (Waltham, Mass.).

Preparation of Silk Fibroin Rods with Proteins and Other Excipients

To prepare the silk fibroin rods with lysozyme, silk fibroin was dissolved in lysozyme stock solution to reach the final desired silk/lysozyme concentrations. Sucrose (Sigma Aldrich, St. Louis Mo.) was dissolved in this solution when necessary. Formulations were injected into 1.0 mm diameter PTFE tubing. The tubing was capped with Parafilm® and allowed to gel at 37° C. overnight. Once gelling was achieved, the tubing was frozen and lyophilized. The formulations were prepared as described in Table 35. The silk fibroin rods are named by the process used to prepare and formulate each rod. For example, the rod named 480 mb; 1 mm; lyo; 85% sf; 5% lysozyme; 10% sucrose refers to a rod prepared with silk degummed with a 480-minute boil (480 mb), a 1 mm diameter (1 mm), lyophilization (lyo), a theoretical w/w percentage of 85% silk fibroin (85% sf), a theoretical w/w percentage of 5% lysozyme (5% lysozyme), and a theoretical w/w percentage of 10% sucrose (10% sucrose). Sample 205-05 also contained 133.3 mM phosphate buffer.

TABLE 35

SILK RODS FORMULATED WITH PROTEINS AND EXCIPIENTS

| Sample No. | Sample name | Time of heating (mb) | Silk-fibroin Conc. % | Protein | Protein conc. % | Excipient | Excipient conc. % |
|---|---|---|---|---|---|---|---|
| 205-05 | 480 mb; 1 mm; lyo; 95% sf; 5% lysozyme | 480 | 95 | Lysozyme | 5 | — | — |
| 205-06 | 480 mb; 1 mm; lyo; 85% sf; 5% lysozyme; 10% sucrose | 480 | 85 | Lysozyme | 5 | Sucrose | 10 |
| 205-07 | 480 mb; 1 mm; lyo; 75% sf; 25% lysozyme | 480 | 75 | Lysozyme | 25 | — | — |
| 205-08 | 480 mb; 1 mm; lyo; 65% sf; 25% lysozyme; 10% sucrose | 480 | 65 | Lysozyme | 25 | Sucrose | 10 |

In Vitro Release Profile of Silk Fibroin Rods Formulated with Protein Apis and Other Excipients Silk fibroin rods were cut into 1 cm sections and two sections were placed, in triplicate, into 4 mL glass vials. 1 mL of release media was added to each vial. Samples were incubated with gentle shaking at 37° C. At 2 hours, 1, 2, 3, 7, 10, 14, 21, and 28 days, 100 µL of release media was removed and replaced with 100 µL of fresh release media. Total protein released was quantified via size-exclusion chromatography (SEC) using a Waters X-Bridge Protein BEH SEC, 200 Å, 3.5 µm column. An isocratic flow of mobile phase (100 mM sodium phosphate (Sigma Aldrich, St. Louis Mo.), 200 mM NaCl (Chemsavers, Bluefield Va.) pH 6.8) was run at 0.80 mL/min to elute protein. Protein elution was monitored at 280 and 214 nm using an Agilent 1290 HPLC system with a PDA detector. Cumulative percentage of protein released was calculated using theoretical loading of the silk fibroin rods.

The cumulative release percentage of each protein was monitored over time, as seen in Table 36A and Table 36B. The incorporation of sucrose in the silk fibroin rods resulted in a faster release of lysozyme for some of the rod formulations. The initial burst of lysozyme release was at least two-fold greater for the rods formulated with sucrose and 25% lysozyme. Furthermore, the cumulative release percentage of lysozyme was at least about two-fold greater over time when the rods were formulated with sucrose and 25% lysozyme. The cumulative release percentage of protein released from each rod were measured in triplicate, except for the specific measurements marked with "*", which were measured in singlicate. Sample 205-07, marked with "***", was tested in duplicate.

TABLE 36A

IN VITRO RELEASE OF LYSOZYME FROM SILK-FIBROIN RODS WITH AND WITHOUT AN EXCIPIENT; CUMULATIVE PERCENTAGE (%) OF API RELEASED

| Sample No. | Day | | | | | |
|---|---|---|---|---|---|---|
| | 0 | 0.083 | 1 | 2 | 3 | 7 |
| 205-05 | 0.00 | 18.74 | 27.19 | 32.43 | 7.21 | 7.64 |
| 205-06 | 0.00 | 19.42 | 29.37 | 34.84 | *29.54 | 10.29 |
| 205-07*** | 0.00 | 17.50 | 22.42 | 35.04 | 37.12 | 39.75 |
| 205-08 | 0.00 | 48.69 | 74.98 | 83.25 | 71.14 | 73.94 |

TABLE 36B

STANDARD DEVIATION OF IN VITRO RELEASE OF LYSOZYME FROM SILK-FIBROIN RODS WITH AND WITHOUT AN EXCIPIENT; IN TERMS OF CUMULATIVE PERCENTAGE (%) OF API RELEASED

| Sample No. | Day | | | | | |
|---|---|---|---|---|---|---|
| | 0 | 0.083 | 1 | 2 | 3 | 7 |
| 205-05 | 0.00 | 3.25 | 1.24 | 2.63 | 0.56 | 0.71 |
| 205-06 | 0.00 | 1.00 | 1.61 | 1.09 | 0.00* | 1.24 |
| 205-07*** | 0.00 | 2.85 | 2.98 | 2.47 | 2.87 | 4.52 |
| 205-08 | 0.00 | 1.13 | 2.60 | 2.80 | 6.11 | 1.85 |

Silk fibroin rods loaded with 5% lysozyme (sample 205-05) had similar release profiles to rods loaded with 25% lysozyme (205-07). However, the addition of sucrose affected these formulations very differently. Replacing 10% silk fibroin with sucrose did not change the 5% lysozyme loaded formulation release, while it increased the initial burst (measured at 2 hours) of the 25% lysozyme rod from 17.5% to 48.7%. This result suggested a critical silk fibroin: lysozyme ratio that needed to be maintained to reduce the initial burst. Adding sucrose in place of silk fibroin reduced this ratio enough in the higher loaded lysozyme rods, but not in the rods with lower loading.

Example 18. In Vivo Ocular Pharmacokinetic Studies with Silk Fibroin Rods and Hydrogels with Celecoxib Silk fibroin platforms were evaluated for delivery of celecoxib (CXB) to the intraocular tissues. Both the hydrogel and rod formulations were well tolerated, showing no negative clinical symptoms, rise in intraocular pressure (IOP), or adverse histological findings over 6 months. After the silk fibroin rods or 0.050 mL samples of hydrogels were administered, the SBPs were subject to pharmacokinetic studies. Multiple preparations of the same formulations were used. The average calculated CXB dose for the hydrogels comprised 3.5-3.6 mg, while the average calculated CXB dose comprised 0.59 to 0.75 mg for the rods. Clinical exams, intraocular pressure (IOP), and histological assessment were performed to determine local tolerability. Vitreous humor (VH) and retina/choroid (RC) tissues were collected and analyzed for CXB concentration over 6 months. Animals had gross examinations of the eye as well as slit-lamp fundus examinations. For slit-lamp exams, a hand-held slit-lamp (Koma or similar) were used.

Briefly, the concentration of API in the vitreous humor was determined after the administration of CXB via silk fibroin rod. After the in vivo silk rods experiments, the vitreous humor of the subjects of the experiments was analyzed for the concentration of celecoxib present. The silk fibroin rods (480 mb; 0.5 mm; 40% st; 100mgsf; 200mgcxb; lyo; 33.3% sf; 66.7% cxb) and silk fibroin hydrogels were administered to the left eye of New Zealand white rabbits, with a total celecoxib dose of 640-750 µg. Two to three animals were used in each group for each time point. The rabbits were sacrificed at about 2 weeks, 1 month 2 months, 3 months, 4.5 months, and 6 months after injection.

Formulation Residence Time

The formulations containing celecoxib were still clinically visible at 6 months post injection (10% CXB suspension, 10% CXB hydrogel, and CXB rod). All hydrogel and suspension groups had reduced in size over time. Additionally, the 1.4% CXB suspension was visible clinically out to 3 months. A blank hydrogel formulation was evaluated out to 7 months, and although it decreased in size, it was still clinically present at the time of sacrifice. Formulations had no adverse clinical findings for the duration of the study.

Celecoxib Detection in Aqueous Humor

The concentration of API in the aqueous humor was determined after the administration of CXB with different API delivery media. To collect the aqueous humor, the animals were anesthetized. Approximately 50-100 µL aqueous humor was removed from the anterior chamber at the limbus by a 31G needle attached to a 1 mL insulin syringe. Samples of the aqueous humor were prepared in a 50/50 Acetonitrile/50 mM Ammonium Formate, pH 4.0 buffer and analyzed via HPLC. The results of the in vivo administration of celecoxib through the eye were shown in Table 37. As seen in the Table 37, at least 50% of the animals subject to experiments with silk fibroin rods had detectable amounts of CXB in the aqueous humor after 7 days. 100% of the animals tested with silk fibroin rods had detectable levels of CXB in the aqueous humor after 28 days.

TABLE 37

DETECTION AND CONCENTRATION OF
CELECOXIB IN THE AQUEOUS HUMOR
AFTER INTRAOCULAR ADMINISTRATION

| Sample Name | CXB Dose | Day | Average Concentration (ng/mL) | St. Dev. | % of Animals with Detectable CXB |
|---|---|---|---|---|---|
| 10% CXB Control | 5 mg | 7 | 0.43 | 0.45 | 100 |
|  |  | 28 | 1.25 | 1.09 | 100 |
|  |  | 56 | 0.58 | 0.40 | 100 |
| 480 mb; hyd; 27.8% cxbst; 3% SFf; 10% CXBf; 10% P188f | 5 mg | 7 | 1.03 | 1.66 | 83.3 |
|  |  | 28 | 1.17 | 0.49 | 100 |
|  |  | 56 | 1.62 | 0.40 | 100 |
| 480 mb; 0.5 mm; 40% st; 100 mgsf; 200 mgcxb; lyo; 33.3% sf; 66.7% cxb | 0.7 mg | 7 | 0.27 | 0.15 | 50 |
|  |  | 28 | 0.38 | 0.30 | 100 |
|  |  | 56 | 0.30 | 0.07 | 100 |

Celecoxib Detection in Whole Eye

The animals were euthanized, and eyes were enucleated and immediately snap frozen in liquid nitrogen. position of the implant/formulation was visualized and recorded to ensure that each eye was oriented appropriately during freezing and dissection. The eyes were then bisected ensuring that the implant/formulation was completely retained in one half of vitreous. The eyes were then thawed, and both vitreous hemispheres (formulation and no formulation) were collected. The vitreous with no formulation was analyzed for CXB concentration via HPLC-MS. The vitreous containing the formulation was centrifuged at 10,000×g for 10 minutes. The supernatant was removed and analyzed for CXB concentration via HPLC-MS. Samples of the vitreous humor were prepared in a 50/50 Acetonitrile/50 mM Ammonium Formate, pH 4.0 buffer prior to analysis via HPLC. The formulation pellet collected after centrifugation was frozen and lyophilized. CXB was extracted from the formulations using acetonitrile and analyzed via HPLC-UV.

Furthermore, the retina and choroid were dissected from both hemispheres for extraction and analysis via HPLC-MS. Samples of retinoid were initially wetted with acetonitrile and dried prior to sample preparation. The retinoid samples were finely cut with a scissors and mixed into a uniform paste. 10 times the weight of 50/50 Acetonitrile/50 mM ammonium formate pH 4 was added to every sample. The samples were then vortexed for 2 minutes, sonicated for 15 minutes, and refrigerated overnight. The samples were then sonicated for an additional 15 minutes, then centrifuged for 8 minutes and then processed per the same test procedures used for the aqueous and vitreous humors.

The concentration of celecoxib in the vitreous humor from each bisected half (with and without the implanted silk fibroin rod) was analyzed, as seen in Table 38A and Table 38B. At each timepoint, the concentration of celecoxib in the vitreous humor, with and without the implant, was determined to be greater than or equal to the $IC_{50}$, the half-maximal inhibitory concentration, of celecoxib, which was 40 nM (15.3 ng/mL). The silk fibroin rods showed near steady state drug concentrations, with concentrations in the vitreous humor greater than or equal to the $IC_{50}$ for three months. Controls of celecoxib suspensions were also analyzed, with an approximate dosage of 5 mg celecoxib.

TABLE 38A

DESCRIPTIONS OF SAMPLES ANALYZED FOR CONCENTRATIONS OF CELECOXIB IN WHOLE EYE

| Sample | Sample Name | CXB Theoretical Dose | CXB Average Dose | CXB Theoretical loading | CXB Average Loading |
|---|---|---|---|---|---|
| Low CXB control | 1.4% CXB Suspension | 0.7 mg (14 mg/mL) | 0.65 mg | 1.4% | 1.3% |
| High CXB control | 10% CXB Suspension | 5 mg (100 mg/mL) | 4.0-4.3 mg | 10% | 8.0-8.5% |
| 10% CXB hydrogel | 480 mb; 27.8% cxbst; 3% SFf; 10% CXBf; 10% P188f | 5 mg (100 mg/mL) | 3.5-3.6 mg | 10% | 6.9-7.2% |
| CXB rods | 480 mb; 0.5 mm; 40% st; 100 mgsf; 200 mgcxb; lyo; 33.3% sf; 66.7% cxb | 0.7 mg (N/A) | 0.59-0.75 mg | 66.7% | 44.7-52.5% |

TABLE 38B

DETECTION AND CONCENTRATION OF CELECOXIB IN THE VITREOUS
HUMOR (VH) AND RETINA AFTER INTRAOCULAR ADMINISTRATION

| Sample | Sample Name | CXB Dose | Day | VH No Implant (ng/mL) | Std Dev. | VH Implant (ng/mL) | Std Dev. | Retina/ Choroid (ng/mL) | Std Dev. |
|---|---|---|---|---|---|---|---|---|---|
| Low CXB control | 1.4% CXB Suspension | 0.7 mg (14 mg/mL) | 14 | 817 | 690 | 17733 | 29503 | 4190 | 4587 |
|  |  |  | 29 | 100 | 129 | 28806 | 39590 | 65 | 15 |
|  |  |  | 84 | 17 | 12 | 3445 | 4992 | 55 | 48 |
| High | 10% CXB | 45 mg (100 | 14 | 491 | 787 | 434 | 665 | 36338 | 53177 |

TABLE 38B-continued

DETECTION AND CONCENTRATION OF CELECOXIB IN THE VITREOUS
HUMOR (VH) AND RETINA AFTER INTRAOCULAR ADMINISTRATION

| Sample | Sample Name | CXB Dose | Day | VH No Implant (ng/mL) | Std Dev. | VH Implant (ng/mL) | Std Dev. | Retina/Choroid (ng/mL) | Std Dev. |
|---|---|---|---|---|---|---|---|---|---|
| CXB control | Suspension | mg/mL) | 86 | 11 | 2 | 7125 | 7036 | 131 | 37 |
| | | | 127 | 133 | 161 | 1173 | 462 | 141 | 37 |
| | | | 170 | 1998 | 2760 | 834 | 914 | 1194 | 154 |
| 10% CXB hydrogel | 480 mb; hyd; 27.8% cxbst; 3% SFf; 10% CXBf; 10% P188f | 5 mg (100 mg/mL) | 14 | 4663 | 7314 | 12167 | 12262 | 7349 | 11480 |
| | | | 86 | 3807 | 5124 | 18050 | 3182 | 60400 | 27153 |
| | | | 127 | 125 | 144 | 708 | 165 | 344 | 161 |
| | | | 170 | 24 | 4 | 1314 | 1353 | 122 | 81 |
| CXB rods | 480 mb; 0.5 mm; 40% st; 100 mgsf; 200 mgcxb; lyo; 33.3% sf; 66.7% cxb | 0.7 mg (N/A) | 14 | 70 | 91 | 413 | 441 | 133 | 99 |
| | | | 29 | 11832 | 16501 | 220 | 13 | 1254 | 1635 |
| | | | 58 | 25 | 21 | 317 | 80 | 1493 | 986 |
| | | | 86 | 31 | 18 | 783 | 774 | 60 | 46 |
| | | | 126 | 30 | 24 | 170 | 97 | 79 | 39 |
| | | | 169 | 45 | 1 | 234 | 4 | 159 | 11 |

At 14 days, the low concentration suspension formulations exhibited comparatively lower CXB concentrations in the vitreous with no formulation, while the vitreous with formulation as well as the retina/choroid had higher concentrations of CXB. This may have been due to the nature of the suspension formulations, which are more diffuse within the vitreous humor and more difficult to separate than the silk fibroin formulations. The vitreous humor containing the formulation ranged from 28806 ng/mL to 3445 ng/mL CXB, maintaining levels well above the estimated $EC_{80}$ for celecoxib (1-3 µM; 381-1143 ng/mL). The vitreous humor with no formulation as well as the retina/choroid showed very similar trends of high concentration at 14 days followed by a dramatic drop by 30 days. This low level was decreased further out to 90 days. The intravitreal concentration of CXB generally decreased over the 84 day time frame with the administration of the 1.4% CXB suspension. CXB concentrations in multiple tissues fell below the $EC_{80}$ by 29 days and approached the reported biochemical inhibitory concentration (IC50; 40 nM; 15 ng/mL) by 90 days post injection.

The intravitreal injection of a 10% CXB suspension showed decreasing retinal tissue concentrations from 14 to 86 days (36338 ng/mL to 131 ng/mL). This concentration was then maintained in the retina/choroid over 6 months at 130-200 ng/mL (below the $EC_{80}$ for celecoxib). Vitreous humor CXB concentrations displayed differences over time which seemed to be dependent on the hemisphere. Over the 170 day experiment, the concentration of CXB delivered by the 10% CXB suspension, was variable amongst the tissues. After injection of the 10% CXB suspension, both vitreous halves had similar CXB concentrations at 14 days (491 ng/mL and 433 ng/mL for no formulation and formulation vitreous respectively); however, these two locations varied more noticeably at the later timepoints (86 days or longer). The vitreous humor containing the formulation showed a maximum CXB concentration of 7125 ng/mL at 3 months, which then decreased to approximately 1000 ng/mL after 127 days. The vitreous humor from the hemisphere containing no formulation dropped to a concentration of only 11 ng/mL at about 3 months, then increased at 127 and 170 days to 133 ng/mL and 1998 ng/mL. This variability, similar to the lower concentration suspension group, may have been due to the dispersity of the suspension and inefficient removal of undissolved CXB during extraction. Although all of the tissues displayed levels at or above the $EC_{80}$ for CXB at 14 days, only the vitreous humor containing the formulation maintained concentrations in this range over the 6 months of the study. CXB concentrations in the other tissues fell well below this concentration by 3 months.

The silk-fibroin hydrogel formulation containing 10% CXB (5 mg dose) displayed elevated, steady-state concentrations in both vitreous samples as well as retina/choroid tissue over 86 days, which decreased slightly thereafter. The retina/choroid showed CXB levels of 7349 ng/mL and 60400 ng/mL (7 times and 60 times the $EC_{80}$ for CXB) at 14 days and 86 days, respectively. Concentrations decreased to 344 ng/mL at 127 days (within the $EC_{80}$) and further to 122 ng/mL at about 6 months. Vitreous humor containing the formulation maintained levels at or above the $EC_{80}$ for the duration of the study. Over the first 3 months, concentrations ranged slightly from 12167-18050 ng/mL CXB. These concentrations decreased to 708 ng/mL and 1314 ng/mL at 127 and 170 days. The vitreous humor with no formulation was also well above the $EC_{80}$ over the first 3 months with concentrations in the range of 3807-4663 ng/mL. Similar to the other tissues, CXB concentrations decreased at about 4.5 and 6 months, however these CXB levels fell below the $EC_{80}$. The hydrogels maintained higher local levels of CXB over the course of the study. These concentrations were above the $IC_{50}$ for CXB to COX-2, as described in Table 39. During the 6 months of the study all tissue concentrations for the hydrogel formulation were maintained well above the $IC_{50}$ for CXB.

Silk-fibroin rod implant formulations loaded with CXB exhibited steady-state drug levels in the vitreous as well as retina/choroid above the $IC_{50}$ for CXB to COX-2 for greater than 3 months, and at least 169 days. Silk-fibroin rod implant formulations loaded with CXB exhibited steady-state drug levels in the vitreous humor as well as retina/choroid above the $IC_{50}$ for CXB to COX-2 for 6 months. Data showed that the CXB concentration in the two vitreous humor samples trended together with the same steady-state. However, in most cases there was 5-10 times higher CXB concentration throughout the study in the hemisphere containing the implant, displaying a CXB concentration gradient. Individual timepoints at 14 days, about 2, about 3, about 4, and about 6 months indicated that the CXB concentration in vitreous humor was higher in the hemisphere containing the implant. In the vitreous humor containing the implant, CXB levels ranged from 170 ng/mL to 783 ng/mL over the 6 months evaluated, with the highest concentration recorded at 86 days. These concentrations were very close to the expected $EC_{80}$ for CXB. Drug levels in the opposing vitreous humor hemisphere, however, dipped below this mark and ranged from 25 ng/mL to 70 ng/mL, with an exception of 11832 ng/mL at about 1 month. Retina/choroid tissue showed a spike in CXB concentration of 1254 and 1493 ng/mL at 29 and 58 days respectively, bringing the levels above the efficacious range ($EC_{80}$). CXB concentrations in the retina/choroid at 14 days and about 3-6 months were lower and very steady, ranging from only 60 ng/mL to 159 ng/mL.

TABLE 39

FOLD INCREASE OF CONCENTRATION OF CELECOXIB IN THE EYE OVER $IC_{50}$ OF CELECOXIB WITH COX-2 (IN VIVO API CONCENTRATION/$IC_{50}$ OF CELECOXIB)

| Sample | Sample Name | CXB Dose | Day | Fold over IC50 (15 ng/mL) (API concentration/IC50 of API with COX-2) | | |
|---|---|---|---|---|---|---|
| | | | | VH No Implant | VH Implant | Retina/Choroid |
| Low CXB control | 1.4% CXB Suspension | 0.7 mg | 14 | 54.5 | 1182.2 | 279.3 |
| | | | 29 | 6.6 | 1920.4 | 4.4 |
| | | | 84 | 1.2 | 229.6 | 3.7 |
| High CXB control | 10% CXB Suspension | 4 mg | 14 | 32.7 | 28.9 | 2422.5 |
| | | | 86 | 0.7 | 475.0 | 8.7 |
| | | | 127 | 8.9 | 78.2 | 9.4 |
| | | | 170 | 133.2 | 55.6 | 12.9 |
| 10% CXB hydrogel | 480 mb; hyd; 27.8% cxbst; 3% SFf; 10% CXBf; 10% P188f | 5 mg | 14 | 310.9 | 811.1 | 489.9 |
| | | | 86 | 253.8 | 1203.3 | 4026.7 |
| | | | 127 | 8.3 | 47.2 | 22.9 |
| | | | 170 | 1.6 | 87.6 | 8.1 |
| CXB rods | 480 mb; 0.5 mm; 40% st; 100 mgsf; 200 mgcxb; lyo; 33.3% sf; 66.7% cxb | 0.7 mg | 14 | 4.6 | 27.5 | 8.9 |
| | | | 29 | 788.8 | 14.7 | 83.6 |
| | | | 58 | 1.7 | 21.1 | 99.5 |
| | | | 86 | 2.0 | 52.2 | 4.0 |
| | | | 126 | 2.0 | 11.3 | 5.2 |
| | | | 169 | 3.0 | 15.6 | 10.6 |

The administration of the silk fibroin compositions resulted in in vivo concentrations of CXB consistently above the $IC_{50}$ of celecoxib with its target protein, COX-2 (40 nM or 15 ng/mL). The administration of either the silk fibroin hydrogels or the rods resulted in a higher intraocular concentration of CXB near the ocular area of administration (e.g. the half of the eye in which the rod was positioned). The intraocular concentrations of CXB remained greater than the $IC_{50}$ of CXB over the course of the experiment. The silk fibroin hydrogels sustained intraocular concentrations of CXB greater than the estimated $EC_{80}$ (1-3 µM or 381-1143 ng/mL) for the first 86 days. About 3 months after hydrogel administration, the intraocular CXB concentration lowers, but it remains above the $IC_{50}$ for CXB for the remainder of the study. The silk rods delivered a lower, more consistent concentration of CXB over time in comparison with the hydrogels.

Regardless of proximity of the formulation to the area of the eye or the amount of time since injection, the silk fibroin hydrogel or rod compositions resulted in CXB concentrations at least 1.7-fold greater than the $IC_{50}$ in the vitreous humor and at least 4-fold greater than the $IC_{50}$ in the retina/choroid over the first 86 days. Over the course of 169 or 170 days, the silk fibroin rod or hydrogel compositions resulted in CXB concentrations at least 1.6-fold greater than the $IC_{50}$ in the vitreous humor and at least 4-fold greater than the $IC_{50}$ in the retina/choroid.

Over the first 86 days, administration of the hydrogels resulted in a concentration at least 250-fold greater than the $IC_{50}$ of celecoxib in the vitreous humor without the implant, at least 800-fold greater than the $IC_{50}$ of celecoxib in the vitreous humor with the implant, and at least 480-fold greater than the $IC_{50}$ of celecoxib in the retina/choroid. Over 170 days, administration of the hydrogels resulted in a concentration at least 1.6-fold greater than the $IC_{50}$ of celecoxib in the vitreous humor without the implant, at least 47-fold greater than the $IC_{50}$ of celecoxib in the vitreous humor with the implant, and at least 8-fold greater than the $IC_{50}$ of celecoxib in the retina/choroid over the course of the experiment.

Over the first 86 days, administration of the rods resulted in a concentration at least 1.7-fold greater than the $IC_{50}$ of celecoxib in the vitreous humor without the implant, at least 14-fold greater than the $IC_{50}$ of celecoxib in the vitreous humor with the implant, and at least 4-fold greater than the $IC_{50}$ of celecoxib in the retina/choroid. Over 169 days, administration of the rods resulted in a concentration at least 1.7-fold greater than the $IC_{50}$ of celecoxib in the vitreous humor without the implant, at least 11-fold greater than the $IC_{50}$ of celecoxib in the vitreous humor with the implant, and at least 4-fold greater than the $IC_{50}$ of celecoxib in the retina/choroid.

Both the hydrogel and the rod were able to deliver CXB at or above the $EC_{80}$, concentration of compound needed to elicit 80% of a complete response. The $EC_{80}$ was estimated to be 1-3 µM for CXB in this system. Hydrogel administration resulted in intraocular concentrations of CXB above the $EC_{80}$ for the first 86 days, but the intraocular concentration of CXB was at or below the efficacious range after 86 days. Rod administration resulted in intraocular concentrations at or near the efficacious range in the vitreous humor with the formulation for the first 86 days. The hydrogel platform was able to deliver CXB at concentrations at least 3 times the $EC_{80}$ for less than or equal to 3 months in all the ocular tissues.

Both the rod and hydrogel formulations showed residence in the intraocular space for at least 6 months. The results indicated that silk-fibroin hydrogels and silk-fibroin rod implants were both well-tolerated formulation options that maintained steady-state delivery of CXB to ocular tissues for at least 3-6 months. Even with the major differences in CXB dose (5 mg in the hydrogel; 700 μg in the rod), CXB levels were maintained in the back of the eye above the $IC_{50}$ for CXB to COX-2 over the course of the study. This indicated that the concentrations were in an efficacious range.

Example 19. Macromolecular Therapeutic Agent Storage and Stability by a Silk Composition Silk Fibroin Isolation and Hydrogel Formation Silk yarn is degummed at 100° C. for 120 minutes in 0.02 M sodium carbonate aqueous solution to remove sericin. 30 g of cut silk yarn is boiled in 1 L of deionized (DI) water with 0.02 M sodium carbonate for 80 minutes under stirring. Then the yarn is transferred to a new boiling 0.02 M sodium carbonate aqueous solution and boiled for additional 40 minutes under stirring. The fibroin is then placed in DI water at 60-70° C. for 20 minutes under stirring, and then rinsed with clean DI water. This is repeated three times. The fibroin is then placed in clean DI water and stirred for 20 minutes, then rinsed with clean DI water and repeated for a total of three 20 minute-rinse cycles. The fibroin is then dried overnight, weighed, and dissolved at 20% (w/v) in a 9.3 M aqueous solution of lithium bromide for 5 hours at 60° C. The resulting fibroin solution is dialyzed against water at 4° C. in a 50 kDa regenerated cellulose dialysis tubing for 48 hours with 6 water changes to remove the excess salt. The conductivity is recorded after each water change with a digital quality tester. When the conductivity is under 5 ppm the fibroin is ready.

The solution is centrifuged three times for 20 minutes each at 9,000 RPM and 4° C. to remove insoluble particles. The supernatant is collected, and samples of the supernatant are diluted at 1:20 and 1:40 in water. Standard samples are prepared for an A280 assay by diluting pre-measures fibroin solutions to 5, 2.5, 1.25, 0.625, 0.3125, and 0 mg/mL in water, for the generation of a standard curve. The silk concentration of the 1:20 and 1:40 diluted silk fibroin samples is measured against the standard curve using absorbance at 280 nm.

The fibroin solutions are diluted to a final concentration of 3% (w/v) in 10 mM phosphate buffer or TRIS buffer, pH 7.4. Some solutions of silk fibroin are also prepared with 0.5-5% (w/v) sucrose and/or 2-10 mM histidine buffer. The solutions are filtered through a 0.2 μm filter using a vacuum filter unit. Sucrose can be added to the solution prior to freezing to aid in reconstitution of the lyophilized silk fibroin after lyophilization. Then, 10 mL of each solution is aliquoted into 50 mL conical tubes, snap frozen in liquid nitrogen for 10 minutes, transferred for 20 minutes in –80° C., and lyophilized for 72 hours.

Therapeutic Agent Loading in Silk Fibroin Hydrogel

Lyophilized silk fibroin is dissolved with a solution of the therapeutic agent to obtain concentrations of 1.3, 3.6, 7.0, 13.0, and 23.0% (w/v) silk fibroin. A gelling agent (PEG400, glycerol, Poloxamer, etc.) is added to the therapeutic/silk solution to induce gel formation. The tube can be left at 4° C., room temperature (RT) or 37° C. overnight to induce gelation.

Stability of Therapeutic Agent

The effect of silk fibroin hydrogel on the stability of the therapeutic agent is evaluated by placing samples of the therapeutic loaded silk fibroin hydrogel at different temperatures (4° C., 25° C. or 37° C.). At weekly timepoints, the therapeutic agent is extracted from the formulation by placing a known mass of the formulation into a compatible buffer. The extracted solution is analyzed by using a stability indicating HPLC assay as well as a cell-based activity assay. The structural integrity of the formulation and/or the therapeutic agent is determined by using an HPLC assay and evaluating the presence of aggregation. The functional activity of the therapeutic is evaluated by using a cell-based assay.

In Vitro Release

An aliquot of the fibroin-therapeutic hydrogel is added to a 2-mL Eppendorf tube. 1.95 mL of release medium (PBS, pH 7.4) is added. The samples are incubated at 37° C. with gentle shaking. The release medium is changed after 24 hours and then approximately once daily for 7 days. The release medium is analyzed by HPLC to determine therapeutic concentration. A calibration curve is generated for the therapeutic agent by dissolving a known amount of the therapeutic agent in the release medium.

Example 20. Macromolecular Therapeutic Agent Storage and Stability by Silk Fibroin Solutions Lyophilized silk fibroin is dissolved in water to obtain concentrations of 1.3, 3.6, 7.0, 13.0, and 23.0% (w/v) silk fibroin. These silk fibroin solutions are used as stock solutions to prepare therapeutic solutions comprising 0.1%-30% silk fibroin and a therapeutic agent. The therapeutic solution is formulated with excipients and buffers including the silk fibroin solution.

The effect of the silk fibroin solutions on the stability of the therapeutic agent is evaluated by placing solutions of the therapeutic solutions containing silk fibroin at different temperatures (4° C., 25° C. or 37° C.). At weekly timepoints, the therapeutic solution is analyzed by using a stability indicating HPLC assay as well as a cell-based activity assay. The HPLC assay determines structural integrity of the formulation by evaluating the presence of aggregation. The functional activity of the therapeutic agent is evaluated by using a cell-based assay.

Example 21. Macromolecular Therapeutic Agent Lyophilization Stability by Silk Fibroin Lyophilized silk fibroin is dissolved in water to obtain concentrations of 1.3, 3.6, 7.0, 13.0, and 23.0% (w/v) silk fibroin. These silk fibroin solutions are used as stock solutions to prepare therapeutic solutions comprising 0.1%-30% silk fibroin and a therapeutic agent. The therapeutic agent is formulated with excipients and buffers including the silk fibroin solution. These solutions are then placed in glass vials, frozen and lyophilized.

The effect of silk fibroin solutions on the stability of the therapeutic agent through lyophilization is evaluated by placing the lyophilized vials of the therapeutic containing silk fibroin at different temperatures (4° C., 25° C. or 37° C.). At weekly timepoints, the therapeutic formulation is reconstituted. The reconstituted solution is analyzed by using a stability indicating HPLC assay as well as a cell-based activity assay. The HPLC assay determines the structural integrity of the formulation by evaluating the presence of aggregation. The functional activity of the therapeutic agent is evaluated by using a cell-based assay.

Example 22. Release Characteristics of Celecoxib from Silk Fibroin Hydrogels of Varying Silk Fibroin Molecular Weights Silk yarn was purchased from Jiangsu SOHO Silk and Textile Co. (Jiangsu, China). Lithium Bromide was purchased from Sigma-Aldrich (St. Louis, Mo.). Polysorbate-80 was purchased from Croda (Snaith, United Kingdom). The potassium phosphate monobasic and the potassium phosphate dibasic were purchased from Sigma Aldrich Fine Chemicals (St. Louis, Mo.). The glycerol, sodium carbonate, and sodium azide were purchased from Fisher Chemical (Waltham, Mass.). The celecoxib (CXB) was purchased from Cipla (Miami, Fla.).

Silk Fibroin Isolation

Silk yarn from SOHO was degummed at 100° C. for either 30, 60, 90, 120, or 480 minutes in 0.02 M sodium carbonate solution to remove sericin and modify fibroin molecular weight. The amount of boiling time was referred to as the "minute boil" or "mb". Longer boiling times produced silk fibroin with smaller molecular weights. 480 mb silk fibroin has an average molecular weight of between 30-60 kDa, 120 mb silk fibroin has an average molecular weight of between 100-300 kDa, and 90 mb silk fibroin has an average molecular weight of about 361 kDa. Fibroin was dried overnight, weighed, and dissolved at 20% (w/v) in 9.3 M lithium bromide solution for five hours at 60° C. The resulting solution was dialyzed against water in a 50 kDa regenerated cellulose membrane for 48 hours at 4° C. with six water changes. The resulting solution was centrifuged for 20 minutes at 9,000 RPM and 4° C. to remove insoluble particles. Solutions were diluted to a final concentration of 3% (w/v) in 10 mM phosphate buffer, pH 7.4, filtered through a 0.22 μm filter, frozen in liquid nitrogen, and lyophilized for at least 72 hours. Lyophilized silk fibroin was stored at −20° C. or less prior to use.

Hydrogel Preparation

Lyophilized silk-fibroin was reconstituted to a concentration of 6% (w/v) using a suspension of celecoxib. The silk/CXB suspension had a final concentration of 6% (w/v) silk-fibroin, 20% (w/v) CXB in suspension, 0.2% polysorbate-80, and 44 mM phosphate buffer. Silk/CXB and 80% glycerol in water solutions were then combined at a ratio of 1:1 and mixed until homogeneous. The final formulation for all hydrogels prepared was: 3% (w/v) silk-fibroin, 40% glycerol, 10% CXB, 0.1% tween-80, and 22 mM phosphate buffer, pH 7.4. Gels were incubated at 37° C. on an orbital mixer overnight to induce gelation, and the hydrogels were stored at 4° C. until use. The formulations tested were named by the method in which they were prepared. For example, in the sample named 480 mb; hyd; 3% SFf; 10% CXBf; 40% Glyc, "480 mb" refers to silk degummed with a 480-minute boil, "hyd" refers to the formulation of the sample as a hydrogel, "3% SFf" refers to a formulation with 3% (w/v) silk fibroin, "10% CXBf" refers to a formulation with 10% (w/v) celecoxib, and "40% Glyc" refers to a formulation with 40% (w/v) glycerol. Some samples were prepared with silk fibroin degummed with a 120, 90, 60, or 30-minute boil (120 mb, 90 mb, 60 mb, and 30 mb respectively). The formulations were listed in Table 40. In Table 40, "PS-80" is Polysorbate-80.

TABLE 40

FORMULATIONS OF SILK FIBROIN HYDROGELS PREPARED FROM SILK FIBROIN DEGUMMED WITH DIFFERENT BOILING TIMES FOR THE CUMULATIVE RELEASE EXPERIMENTS

| Sample name | Silk boiling time (mb) | Silk conc. (% w/v) | TPS-80 conc. (% w/v) | Phosphate Buffer (mM) | Glycerol conc. (% w/v) | CXB conc. (% w/v) | Actual CXB conc. ± Standard Deviation (% w/v) | Sample No. |
|---|---|---|---|---|---|---|---|---|
| 480 mb; hyd; 3% SFf; 10% CXBf; 40% Glycf | 480 | 3 | 0.1 | 22 | 40 | 10 | 10.92 ± 0.31 | 161-1 |
| 120 mb; hyd; 3% SFf; 10% CXBf; 40% Glycf | 120 | 3 | 0.1 | 22 | 40 | 10 | 9.78 ± 0.22 | 161-2 |
| 90 mb; hyd; 3% SFf; 10% CXBf; 40% Glycf | 90 | 3 | 0.1 | 22 | 40 | 10 | 9.27 ± 1.72 | 161-3 |
| 60 mb; hyd; 3% SFf; 10% CXBf; 40% Glycf | 60 | 3 | 0.1 | 22 | 40 | 10 | 9.19 ± 0.52 | 161-4 |
| 30 mb; hyd; 3% SFf; 10% CXBf; 40% Glycf | 30 | 3 | 0.1 | 22 | 40 | 10 | 9.34 ± 0.78 | 161-5 |
| Solution control | N/A | 0 | 0.1 | 22 | 40 | 10 | 11.68 ± 0.67 | 161-6 |

In Vitro Release of Celecoxib

In triplicate, 50 mg of each formulation was weighed into half of a #4 gelatin capsule. Capsules were placed into a 50 mL. conical tube containing 45 mL of release medium (lx phosphate buffered saline, 2% Polysorbate-80, and 0.05% sodium azide). The solubility of celecoxib in this release media is 850 μg/mL. 45 mL of this release media allows for 38 mg CXB solubility. This media ensured sink conditions (greater than or equal to 5 times CXB solubility) were maintained throughout the course of the study. The tubes were capped and incubated at 37° C. with shaking. 1 mL of the release media was collected from each sample at days 1, 4, 7, 10, 14 and 21 days and replaced with fresh media. At each timepoint, the tubes were stood on end for at least 30 minutes. to allow the formulation to settle prior to taking the sample. Release media was analyzed by HPLC-UV (Agilent 1290 Infinity) at 260 nm. Controls were prepared at Day 0 by weighing 50 mg of each formulation in triplicate in separate 20 mL. glass vials. Methanol was added to each sample to extract CXB. Samples were placed on a shaker at room temperature for 24 hrs. The supernatant was analyzed by HPLC-UV to determine CXB loading. The results of the release studies were displayed in Table 41A and Table 41B.

TABLE 41A

IN VITRO RELEASE KINETICS FOR SILK FIBROIN HYDROGELS WITH VARYING MOLECULAR WEIGHT SILK LOADED WITH CELECOXIB; AVERAGE CUMULATIVE PERCENTAGE (%) OF API RELEASED

| Sample No. | Day | | | | | | |
|---|---|---|---|---|---|---|---|
| | 0 | 1 | 3 | 7 | 14 | 21 | 28 |
| 161-1 | 0.0 | 69.6 | 93.0 | 89.1 | 91.6 | — | — |
| 161-2 | 0.0 | 26.9 | 49.0 | 66.8 | 82.2 | 91.9 | 86.4 |
| 161-3 | 0.0 | 28.9 | 54.6 | 74.2 | 90.1 | 100.3 | 94.1 |
| 161-4 | 0.0 | 27.5 | 51.3 | 67.0 | 81.6 | 89.0 | 83.8 |
| 161-5 | 0.0 | 47.7 | 71.7 | 78.1 | 86.3 | 91.7 | 86.4 |
| 161-6 | 0.0 | 70.9 | 95.1 | 93.7 | 93.0 | — | — |

TABLE 41B

STANDARD DEVIATION OF IN VITRO RELEASE KINETICS FOR SILK FIBROIN HYDROGELS WITH VARYING MOLECULAR WEIGHT SILK LOADED WITH CELECOXIB; IN TERMS OF AVERAGE CUMULATIVE PERCENTAGE (%) OF API RELEASED

| Sample No. | Day | | | | | | |
|---|---|---|---|---|---|---|---|
| | 0 | 1 | 3 | 7 | 14 | 21 | 28 |
| 161-1 | 0.0 | 7.2 | 1.8 | 3.3 | 7.0 | — | — |
| 161-2 | 0.0 | 2.2 | 1.2 | 2.0 | 1.3 | 2.8 | 2.6 |
| 161-3 | 0.0 | 2.0 | 0.5 | 3.3 | 4.5 | 5.7 | 5.5 |
| 161-4 | 0.0 | 1.8 | 2.6 | 3.9 | 5.1 | 6.1 | 5.8 |
| 161-5 | 0.0 | 21.9 | 12.1 | 6.0 | 4.6 | 6.5 | 6.2 |
| 161-6 | 0.0 | 5.6 | 4.6 | 4.3 | 5.5 | — | — |

The 480 mb hydrogels approached 100% CXB the quickest following a similar trajectory to the CXB suspension alone. This was most likely due to the formulation not completely gelling. When placed in release media it did not hold its shape and it dispersed as a suspension. Formulations prepared with the higher molecular weight range of silk-fibroin displayed similar release profiles following first-order release kinetics, with an initial burst of approximately 30% out to 21 days, with the exception of the hydrogel made with highest silk-fibroin molecular weight (30 mb). This formulation displayed a slightly higher burst than the others, but the release continued out to 21 days.

Example 23. Rheological Characteristics of Celecoxib-Containing Silk-Fibroin Hydrogels of Varying Silk Fibroin Molecular Weights Silk yarn was purchased from Jiangsu SOHO Silk and Textile Co. (Jiangsu, China). Lithium Bromide was purchased from Sigma-Aldrich (St. Louis, Mo.). Polysorbate-80 was purchased from Croda (Snaith, United Kingdom). The potassium phosphate monobasic and the potassium phosphate dibasic were purchased from Sigma Aldrich Fine Chemicals (St. Louis, Mo.). The glycerol, sodium carbonate, and sodium azide were purchased from Fisher Chemical (Waltham, Mass.). The celecoxib (CXB) was purchased from Cipla (Miami, Fla.).

Silk Fibroin Isolation

Silk yarn from SOHO was degummed at 100° C. for either 30, 60, 90, 120, or 480 minutes in 0.02 M sodium carbonate solution to remove sericin and modify fibroin molecular weight. The amount of boiling time was referred to as the "minute boil" or "mb". Longer boiling times produced silk fibroin with smaller molecular weights. 480 mb silk fibroin has an average molecular weight of between 30-60 kDa, 120 mb silk fibroin has an average molecular weight of between 100-300 kDa, and 90 mb silk fibroin has an average molecular weight of about 361 kDa. Fibroin was dried overnight, weighed, and dissolved at 20% (w/v) in 9.3 M lithium bromide solution for five hours at 60° C. The resulting solution was dialyzed against water in a 50 kDa regenerated cellulose membrane for 48 hours at 4° C. with six water changes. The resulting solution was centrifuged for 20 minutes at 9,000 RPM and 4° C. to remove insoluble particles. Solutions were diluted to a final concentration of 3% (w/v) in 10 mM phosphate buffer, pH 7.4, filtered through a 0.22 μm filter, frozen in liquid nitrogen, and lyophilized for at least 72 hours. Lyophilized silk fibroin was stored at −20° C. or less prior to use.

Hydrogel Preparation

Lyophilized silk-fibroin was reconstituted to a concentration of 6% (w/v) using a suspension of celecoxib. The silk/CXB suspension had a final concentration of 6% (w/v) silk-fibroin, 20% (w/v) CXB in suspension, 0.2% polysorbate-80, and 44 mM phosphate buffer. Silk/CXB and 80% glycerol in water solutions were then combined at a ratio of 1:1 and mixed until homogeneous. The final formulation for all hydrogels prepared was: 3% (w/v) silk-fibroin, 40% glycerol, 10% CXB, 0.1% polysorbate-80, and 22 mM phosphate buffer, pH 7.4. Gels were incubated at 37° C. on an orbital mixer overnight to induce gelation, and the hydrogels were stored at 4° C. until use. The formulations tested were named by the method in which they were prepared. For example, in the sample named 480 mb; hyd; 3% SFf; 10% CXBf; 40% Glyc, "480 mb" refers to silk degummed with a 480-minute boil, "hyd" refers to the formulation of the sample as a hydrogel, "3% SFf" refers to a formulation with 3% (w/v) silk fibroin, "10% CXBf" refers to a formulation with 10% (w/v) celecoxib, and "40% Glyc" refers to a formulation with 40% (w/v) glycerol. Some samples were prepared with silk fibroin degummed with a 120, 90, 60, or 30-minute boil (120 mb, 90 mb, 60 mb, and 30 mb respectively). The formulations were listed in Table 42.

TABLE 42

FORMULATIONS OF SILK FIBROIN HYDROGELS PREPARED FROM SILK FIBROIN DEGUMMED WITH DIFFERENT BOILING TIMES FOR THE RHEOLOGICAL EXPERIMENTS

| Sample name | Silk boiling time (mb) | Silk conc. (% w/v) | Polysorbate-80 conc. (% w/v) | Phosphate Buffer (mM) | Glycerol conc. (% w/v) | CXB conc. (% w/v) |
|---|---|---|---|---|---|---|
| 480 mb; hyd; 3% SFf; 10% CXBf; 40% Glyc | 480 | 3 | 0.1 | 22 | 40 | 10 |
| 120 mb; hyd; 3% SFf; 10% CXBf; 40% Glyc | 120 | 3 | 0.1 | 22 | 40 | 10 |
| 90 mb; hyd; 3% SFf; 10% CXBf; 40% Glyc | 90 | 3 | 0.1 | 22 | 40 | 10 |
| 60 mb; hyd; 3% SFf; 10% CXBf; 40% Glyc | 60 | 3 | 0.1 | 22 | 40 | 10 |
| 30 mb; hyd; 3% SFf; 10% CXBf; 40% Glyc | 30 | 3 | 0.1 | 22 | 40 | 10 |

Rheological Measurements of Silk Fibroin Formulations

The hydrogel samples were loaded onto a Peltier plate system held at 25° C. The geometry used was a 20 mm parallel plate with a gap of 1 mm and frequency at 1 Hz. Viscosity was measured during a time sweep at 1 s-1 over 135 seconds. The storage modulus (G'), the loss modulus (G"), and the phase angle were then measured during a time sweep over 145 seconds at 0.1% strain and 1 Hz. As seen in Table 43, the rheology showed a general increase in viscosity from silk fibroin prepared from a longer boiling time (480 mb) to silk fibroin prepared from a shorter boiling time (30 mb); therefore, the viscosity increased from low molecular weight silk-fibroin to high molecular weight silk-fibroin formulations. In Table 43, "Std. Dev." refers to standard deviation.

TABLE 43

RHEOLOGICAL PROPERTIES OF SILK FIBROIN HYDROGELS WITH CELECOXIB.

| Sample No. | Boil Time (mb) | Viscosity (Pa*s) | Viscosity Std. Dev. (Pa*s) | Phase Angle (°) | Phase Angle Std. Dev. (°) | G' (Pa) | G' Std. Dev. (Pa) | G" (Pa) | G" Std. Dev. (Pa) |
|---|---|---|---|---|---|---|---|---|---|
| P00161-01 | 480 | 6.56 | 1.67 | 9.60 | 2.97 | 76.98 | 8.43 | 12.91 | 3.85 |
| P00161-02 | 120 | 49.72 | 2.81 | 8.43 | 0.43 | 1148.30 | 93.06 | 169.69 | 8.63 |
| P00161-03 | 90 | 65.25 | 2.25 | 8.88 | 0.48 | 1652.94 | 134.85 | 257.58 | 13.09 |
| P00161-04 | 60 | 118.64 | 6.55 | 12.41 | 0.68 | 4279.45 | 276.60 | 939.41 | 45.63 |
| P00161-05 | 30 | 169.61 | 7.40 | 14.78 | 1.22 | 7820.86 | 539.69 | 2057.36 | 145.74 |

The viscosities ranged from 7 to 170 Pa s-1 for the range of molecular weights tested. The stiffness (as measured by G' and G", seen in Table 43) also showed an increase with increasing molecular weight of silk-fibroin, as defined by the minute boil. The phase angle, as seen in Table 43, increased slightly for the hydrogel formulations prepared from silk fibroin with a shorter boiling time. As the molecular weight of the silk-fibroin increased (marked by a lower degumming time) the hydrogel formulations were stiffer and much more viscous. These results displayed the range of properties the silk-fibroin hydrogel formulations could have. The formulations had also been used to analyze the release of CXB over time, and the physical characteristics of the hydrogels were able to be modified while only minimally affecting release kinetics.

Example 24. Rheology Studies of Silk Fibroin Hydrogels

Hydrogel samples were loaded into a Peltier plate system, with a 20 mm parallel plate geometry, at a temperature of 25° C. The gap was set to 1 mm, and the frequency was set to 1 Hz. Viscosity measurements were measured with a shear ramp was from 0.1 l/s to 1 l/s over 113 s with 11 samples, followed by a shear hold at 1 l/s for 180 s with 18 samples. Oscillatory measurements were measured with a strain ramp from 0.01 to 1% strain with a constant 1 Hz frequency over 173 s with 21 measurements and the G', G", and phase angle were averaged over the linear viscoelastic region (LVR). The viscosity was first studied as a function of silk fibroin concentration, as seen in Table 44. The viscosity of the silk fibroin hydrogels was studied for hydrogels with two different excipients. Silk fibroin hydrogels were studied with silk fibroin concentrations of 6%, 5%, 4%, 3%, and 2% (w/v) silk fibroin degummed with a 120-minute boil. The hydrogels were prepared with either 40% PEG300 or 40% glycerol, 0.2% polysorbate-80, 22 mM phosphate buffer, and 10% celecoxib (CXB). The components of the gel were mixed and allowed to gel at 37° C. with rotation.

TABLE 44

RHEOLOGICAL PROPERTIES OF SILK FIBROIN HYDROGELS
WITH VARYING CONCENTRATIONS OF SILK FIBROIN

| | | | | Average | | | | Standard Deviation of the Average | | | |
|---|---|---|---|---|---|---|---|---|---|---|---|
| Sample No. | Silk Fibroin % | Excip. | Excip. % | G' (Pa) | G" (Pa) | Phase Angle (°) | Visc. (Pa*s) | G' (Pa) | G" (Pa) | Phase Angle (°) | Visc. (Pa*s) |
| 130-01 | 6 | PEG300 | 40 | 71188 | 12346 | 10.13 | 1798 | 30242 | 4469 | 0.53 | 687 |
| 130-02 | 6 | Glycerol | 40 | 80647 | 12307 | 8.77 | 1722 | 46411 | 6745 | 0.39 | 957 |
| 130-03 | 5 | PEG300 | 40 | 33297 | 5859 | 10.04 | 717 | 8723 | 1426 | 0.27 | 184 |
| 130-04 | 5 | Glycerol | 40 | 33737 | 5054 | 8.54 | 726 | 12631 | 1873 | 0.16 | 275 |
| 130-05 | 4 | PEG300 | 40 | 21504 | 3845 | 10.24 | 364 | 8124 | 1409 | 0.48 | 142 |
| 130-06 | 4 | Glycerol | 40 | 18618 | 2677 | 8.21 | 379 | 6331 | 886 | 0.11 | 111 |
| 130-07 | 3 | PEG300 | 40 | 4968 | 996 | 11.52 | 57 | 440 | 101 | 2.12 | 1 |
| 130-08 | 3 | Glycerol | 40 | 7511 | 1046 | 7.95 | 161 | 2977 | 410 | 0.15 | 68 |
| 130-09 | 2 | PEG300 | 40 | 2484 | 473 | 11.05 | 34 | 1923 | 365 | 1.29 | 26 |
| 130-10 | 2 | Glycerol | 40 | 1814 | 257 | 8.24 | 31 | 1915 | 264 | 0.27 | 18 |

The viscosity of the hydrogels increased with the concentration of silk fibroin.

Example 25. Formulation and Release Characteristic of Rods of Increased Hydrophilicity SBPs were formulated as rods to determine whether soluble and/or bulky additives to silk fibroin rod formulations would increase API release. These additives were also included to enhance and increase the rate of in vivo degradation of silk fibroin rods. The silk fibroin was degummed for 480 minutes. The formulations tested were named by the method in which they were prepared. For example, in the sample named "480 mb; 0.5 mm; 20% st; 50mgsf; 200mgcxb; oven; 14.8% sf; 59.3% cxb; 25.9% sucrose/poly-20" refers to a silk fibroin rod prepared from silk degummed with a 480-minute boil (480 mb), an extrusion with a 0.5 mm diameter (0.5 mm), a preparation from a 20% stock solution of silk fibroin (20% st), a preparation from 50 mg of silk fibroin (50mgsf), a preparation from 200 mg of celecoxib (200mgcxb), oven drying (oven), a theoretical w/v percentage of 14.8% silk fibroin (14.8% sf), a theoretical w/v percentage of 59.3% celecoxib (59.3% cxb), and a theoretical w/v percentage of 25.9% other additives such as sucrose and polysorbate-20 (25.9% sucrose/poly-20). The samples tested were listed in Table 45. Other additives tested included polysorbate-80 (poly-80), trehalose, mannitol, PEG 2 kDa, hydroxyethylcellulose (HEC), carboxymethylcellulose (CMC), polyvinylpyrrolidone K-17 (K17), and polyvinylalcohol (PVA). The term theoretical loading percentage refers to the assumed percentage of a component incorporated in a substance or product. The product may be an SBP.

TABLE 45

FORMULATIONS OF SILK FIBROIN HYDROGELS PREPARED
WITH VARIOUS FILLERS TO ALTER HYDROPHILICITY

| Sample number | Formulation Description | Name | Theoretical dry CXB (mg) | Theoretical dry SF (mg) | Theoretical dry other (mg) |
|---|---|---|---|---|---|
| 222-01 | 40% SF; Control; Oven Dried | 480 mb; 0.5 mm; 40% st; 100 mgsf; 200 mgcxb; oven; 33.3% sf; 66.7% cxb | 200 | 100 | 0 |
| 222-03 | 20% SF; 70% Sucrose + 0.5% Polysorbate-20; Oven Dried | 480 mb; 0.5 mm; 20% st; 50 mgsf; 200 mgcxb; oven; 14.8% sf; 59.3% cxb; 25.9% sucrose/poly-20 | 200 | 50 | 87.5 |
| 222-05 | 20% SF; 70% Sucrose + 0.5% Polysorbate-80; Oven Dried | 480 mb; 0.5 mm; 20% st; 50 mgsf; 200 mgcxb; oven; 14.8% sf; 59.3% cxb; 25.9% sucrose/poly-80 | 200 | 50 | 87.5 |
| 222-09 | 20% SF; 70% Trehalose; Oven Dried | 480 mb; 0.5 mm; 20% st; 50 mgsf; 200 mgcxb; oven; 14.8% sf; 59.3% cxb; 25.9% trehalose | 200 | 50 | 87.5 |
| 222-11 | 20% SF; 70% Trehalose + 0.5% Polysorbate-80; Oven; Dried | 480 mb; 0.5 mm; 20% st; 50 mgsf; 200 mgcxb; oven; 14.8% sf; 59.3% cxb; 25.9% trehalose/poly-80 | 200 | 50 | 87.5 |
| 222-15 | 20% SF; 70% Mannitol + 0.5% Polysorbate-80; Oven Dried | 480 mb; 0.5 mm; 20% st; 50 mgsf; 200 mgcxb; oven; 14.8% sf; 59.3% cxb; 25.9% mannitol/poly-80 | 200 | 50 | 87.5 |

TABLE 45-continued

FORMULATIONS OF SILK FIBROIN HYDROGELS PREPARED
WITH VARIOUS FILLERS TO ALTER HYDROPHILICITY

| Sample number | Formulation Description | Name | Theoretical dry CXB (mg) | Theoretical dry SF (mg) | Theoretical dry other (mg) |
|---|---|---|---|---|---|
| 222-17 | 20% SF; 50% PEG 2 kDa; Oven Dried | 480 mb; 0.5 mm; 20% st; 50 mgsf; 200 mgcxb; oven; 50% 16.0% sf; 64.0% cxb; 20.0% PEG2 kDa | 200 | 50 | 62.5 |
| 222-19 | 20% SF; 5% HEC + 0.05% Polysorbate-20; Oven Dried | 480 mb; 0.5 mm; 20% st; 50 mgsf; 200 mgcxb; oven; 19.5% sf; 78.0% cxb; 2.4% hec/poly-20 | 200 | 50 | 6.25 |
| 222-21 | 20% SF; 5% CMC + 0.05% Polysorbate-20; Oven Dried | 480 mb; 0.5 mm; 20% st; 50 mgsf; 200 mgcxb; oven; 19.5% sf; 78.0% cxb; 2.4% cmc/poly-20 | 200 | 50 | 6.25 |
| 222-25 | 20% SF; 20% K17 + 0.05% Polysorbate-20; Oven Dried | 480 mb; 0.5 mm; 20% st; 50 mgsf; 200 mgcxb; oven; 18.2% sf; 72.7% cxb; 9.1% k17/poly-20 | 200 | 50 | 25 |
| 222-27 | 20% SF; 5% PVA + 0.05% Polysorbate-20; Oven Dried | 480 mb; 0.5 mm; 20% st; 50 mgsf; 200 mgcxb; oven; 19.5% sf; 78.0% cxb; 2.4% pva/poly-20 | 200 | 50 | 6.25 |

The density of the experimental loadings as well as the densities of the silk fibroin rods were also determined, as seen in Table 45. The differences in theoretical and experimental loadings of celecoxib were also determined as a percentage of the theoretical w/w loading of celecoxib. In Table 46, "Std. Dev." refers to standard deviation.

TABLE 46

EXPERIMENTAL LOADINGS AND DENSITIES OF SILK
FIBROIN RODS WITH INCREASED HYDROPHILICITY

| Sample number | Experimental % SF | Experimental % CXB | Std. Dev. of exp. % CXB | % Difference between theoretical and actual loading of CXB | Density (g/mL) | Std. Dev. of Density |
|---|---|---|---|---|---|---|
| 222-01 | 36.44 | 63.56 | 2.83 | −5% | 1.09 | 0.03 |
| 222-03 | 38.07 | 61.93 | 1.16 | 5% | 1.03 | 0.04 |
| 222-05 | 36.58 | 63.42 | 3.60 | 7% | 0.96 | 0.07 |
| 222-09 | 45.41 | 54.59 | 3.43 | −8% | 1.06 | 0.04 |
| 222-11 | 36.95 | 63.05 | 1.19 | 6% | 1.11 | 0.06 |
| 222-15 | 26.57 | 73.43 | 1.64 | 24% | 0.92 | 0.01 |
| 222-17 | 39.10 | 60.90 | 2.44 | −5% | 1.13 | 0.08 |
| 222-19 | 19.87 | 80.13 | 3.69 | 3% | 0.82 | 0.04 |
| 222-21 | 20.24 | 79.76 | 5.44 | 2% | 0.85 | 0.06 |
| 222-25 | 19.51 | 80.49 | 3.84 | 11% | 0.87 | 0.07 |
| 222-27 | 20.26 | 79.74 | 3.88 | 2% | 0.86 | 0.01 |

The silk fibroin rods were subject to in vitro release experiments to determine the release kinetics of celecoxib from these formulations. The silk fibroin rods were incubated in PBS with 0.6% polysorbate-80 and 0.05% sodium azide over the course of the experiment. The average cumulative release percentage of celecoxib over time was depicted in the release kinetics shown in Table 47A and Table 47B.

TABLE 47A

IN VITRO RELEASE KINETICS FOR HYDROPHILIC SILK FIBROIN RODS LOADED WITH CELECOXIB; AVERAGE CUMULATIVE PERCENTAGE (%) OF API RELEASED

| Day | 222-01 | 222-03 | 222-05 | 222-09 | 222-11 | 222-15 | 222-17 | 222-19 | 222-21 | 222-25 | 222-27 | CXB suspension |
|---|---|---|---|---|---|---|---|---|---|---|---|---|
| 0 | 0.0 | 0.0 | 0.0 | 0.0 | 0.0 | 0.0 | 0.0 | 0.0 | 0.0 | 0.0 | 0.0 | 0.0 |
| 1 | 12.7 | 18.7 | 17.1 | 21.4 | 18.1 | 16.1 | 20.1 | 21.2 | 16.4 | 18.6 | 20.5 | 106.8 |
| 4 | 31.9 | 44.4 | 47.7 | 50.7 | 44.6 | 45.6 | 48.3 | 55.4 | 44.4 | 53.0 | 49.5 | 110.1 |
| 7 | 46.3 | 60.8 | 63.0 | 64.4 | 60.3 | 61.8 | 67.3 | 71.4 | 57.7 | 67.7 | 60.4 | 91.6 |
| 14 | 55.0 | 70.2 | 74.5 | 77.0 | 72.7 | 75.3 | 80.1 | 82.9 | 70.7 | 82.6 | 74.8 | 87.7 |
| 21 | 63.3 | 78.6 | 92.0 | 86.7 | 82.5 | 85.2 | 92.2 | 81.7 | 85.2 | 85.0 | 84.7 | 86.5 |
| 28 | 81.5 | 93.5 | 91.7 | 94.5 | 99.2 | 99.0 | 100.9 | 96.3 | 97.6 | 98.8 | 93.7 | 90.4 |
| 35 | 83.5 | 91.4 | 88.8 | 91.2 | 94.7 | 94.4 | 97.1 | 88.5 | 92.1 | 89.1 | 89.3 | 83.3 |
| 42 | 88.6 | 90.3 | 88.7 | 91.4 | 92.5 | 95.0 | 97.2 | 89.0 | 92.0 | 92.4 | 87.6 | — |
| 49 | 92.1 | 91.3 | 89.2 | 92.5 | 95.0 | 95.1 | 99.3 | 88.9 | 92.7 | 87.8 | 87.7 | — |
| 56 | 93.6 | 92.2 | 89.8 | 93.9 | 96.4 | 96.6 | 99.1 | 90.6 | 93.5 | 94.7 | 89.7 | — |

TABLE 47B

STANDARD DEVIATION OF AVERAGE CUMULATIVE PERCENTAGE OF API RELEASED IN VITRO FOR HYDROPHILIC SILK FIBROIN RODS LOADED WITH CELECOXIB

| Day | 222-01 | 222-03 | 222-05 | 222-09 | 222-11 | 222-15 | 222-17 | 222-19 | 222-21 | 222-25 | 222-27 | CXB suspension |
|---|---|---|---|---|---|---|---|---|---|---|---|---|
| 0 | 0.0 | 0.0 | 0.0 | 0.0 | 0.0 | 0.0 | 0.0 | 0.0 | 0.0 | 0.0 | 0.0 | 0.0 |
| 1 | 0.9 | 0.7 | 0.4 | 2.7 | 1.6 | 0.7 | 1.6 | 1.8 | 1.0 | 0.5 | 3.6 | 1.0 |
| 4 | 2.6 | 1.3 | 3.0 | 3.6 | 4.3 | 1.9 | 4.0 | 2.8 | 2.6 | 1.9 | 2.4 | 1.4 |
| 7 | 5.5 | 3.2 | 1.3 | 3.5 | 7.1 | 0.8 | 4.8 | 4.8 | 4.8 | 4.6 | 4.0 | 6.5 |
| 14 | 3.0 | 2.3 | 1.5 | 1.4 | 8.1 | 2.2 | 3.3 | 5.7 | 3.4 | 3.5 | 1.3 | 3.7 |
| 21 | 2.9 | 2.5 | 18.4 | 6.1 | 10.7 | 0.8 | 2.1 | 6.7 | 9.1 | 1.5 | 5.2 | 14.6 |
| 28 | 3.5 | 1.2 | 2.6 | 0.2 | 10.4 | 5.7 | 5.8 | 3.2 | 3.5 | 3.1 | 2.8 | 15.5 |
| 35 | 2.4 | 2.4 | 1.8 | 0.8 | 9.7 | 4.5 | 5.6 | 7.5 | 3.7 | 6.1 | 0.2 | 16.9 |
| 42 | 3.8 | 1.8 | 2.4 | 0.0 | 14.2 | 4.3 | 6.5 | 7.4 | 3.5 | 2.3 | 2.8 | — |
| 49 | 3.9 | 2.3 | 1.6 | 0.5 | 9.5 | 4.7 | 6.3 | 7.8 | 2.5 | 8.7 | 3.3 | — |
| 56 | 2.9 | 2.3 | 1.7 | 0.2 | 10.8 | 4.8 | 6.2 | 7.8 | 3.1 | 2.3 | 2.6 | — |

Overall, formulations with additives, including sucrose, trehalose, mannitol, polysorbate-20, polysorbate-80, PEG 2 kDa, HEC, K17, CME, and PVA, showed increased API release during the initial burst as compared to silk fibroin rods without the additives. As used herein, the term "initial burst" refers to a rate of factor release from a source or depot over an initial release period (e.g., after administration or other placement, for example in solution during experimental analysis) that is higher than rates during one or more subsequent release periods. The initial burst was evaluated at 1 day for the silk fibroin rods. The silk fibroin rods with additives also demonstrated increased API release over the first 35 days of the experiment as compared to silk fibroin rods without the additives. These data suggested that additives to silk fibroin rods can be used to tune API release kinetics. The additives might also assist in rod degradation in vivo. The faster the drug is released from the formulation, the faster the majority of the surface area is exposed to the environment, and theoretically the faster the silk fibroin will degrade from enzymatic degradation. The control rod takes more time to disperse all of the API, and therefore will be around longer than rods that disperse API in less time.

Example 26. Analysis of Celecoxib Remaining in Silk Fibroin Rods after In Vivo Administration After the in vivo silk rods experiments, the silk fibroin rods were analyzed for the amount of celecoxib (CXB) that remained. At the desired timepoints of the in vivo experiments, New Zealand white rabbits were sacrificed, and their eyes were enucleated, snap frozen, and bisected. The formulation, hydrogel or implant (480 mb; 0.5 mm; 40% st; 100mgsf; 200mgcxb; lyo; 33.3% sf; 66.7% cxb) was removed from the eyes and collected for further studies. The vitreous containing the formulation was centrifuged at 10,000×g for 10 minutes. The resulting formulation pellet was frozen and lyophilized. Any remaining celecoxib was extracted from the formulations using acetonitrile and analyzed via HPLC-UV. Briefly, the formulation pellets were brought up in acetonitrile, and then vortexed, sonicated, and left on a shaker at room temperature for 24 to 48 hours. The supernatant was filtered through a 0.2 μm nylon syringe filter, diluted and then analyzed via HPLC-UV. The percentage of celecoxib remaining in the rod was studied as a function of time of in vivo study, as seen in Table 48.

TABLE 48

CELECOXIB REMAINING IN CXB LOADED SILK
RODS AFTER INTRAVITREAL INJECTION

| Sample | Sample Name | Day | Average % Remaining | St. Dev. (%) |
|---|---|---|---|---|
| Low CXB control | 1.4% CXB Suspension | 14 | 65.0 | 19.9 |
| | | 29 | 31.3 | 31.6 |
| | | 86 | 53.9 | 68.6 |
| High CXB control | 10% CXB Suspension | 14 | 0.4 | 0.6 |
| | | 86 | 88.8 | 3.6 |
| | | 127 | 139.2 | 39.6 |
| | | 170 | 87.0 | 0.6 |
| 10% CXB hydrogel | 480 mb; hyd; 27.8% cxbst; 3% SFf; 10% CXBf; 10% P188f | 14 | 100.3 | 20.2 |
| | | 86 | 49.9 | 17.2 |
| | | 127 | 87.0 | 22.5 |
| | | 170 | 81.6 | 7.9 |
| CXB rods | 480 mb; 0.5 mm; 40% st; 100 mgsf; 200 mgcxb; lyo; 33.3% sf; 66.7% cxb | 14 | 72.5 | 2.0 |
| | | 29 | 45.3 | 7.1 |
| | | 58 | 75.1 | 3.0 |
| | | 86 | 53.6 | 22.1 |
| | | 126 | 52.1 | 5.9 |
| | | 169 | 10.0 | 4.0 |

The concentration of celecoxib remaining in the rods decreased linearly as time passed. Extractions performed on the silk fibroin rods over the course of the study displayed a zero-order release of celecoxib in the vitreous. Fitting a curve to this linear regression demonstrated a good fit with the exception of the 1 month timepoint. The data demonstrated that approximately 10% of the loaded CXB still remained in the implant at 6 months. The in vivo half-life of release of the CXB from the rod implant, which represented the amount of time required for 50% of the celecoxib to be released from the silk fibroin rod, was estimated to be 3.5 months (about 85 days), with 90% CXB released by 6 months (169 days). Recoveries of the API from the hydrogel showed that there was still significant API remaining after completion of the study. The extractions of CXB from the rods and the hydrogels demonstrated that there was still sufficient CXB remaining to maintain steady-state delivery for at least 6 months with a single administration, since more than 50% of the celecoxib remained after 3 months of the experiment. Furthermore, the silk fibroin rods released CXB at a rate faster than that of the silk fibroin hydrogels in vivo.

Example 27. Histopathology Studies of Rabbit Eyes with Silk Rods Compared with Silk Hydrogels Eight formalin-fixed rabbit eyes were submitted to HistoTox Labs and processed into two blocks per sample. Eyes with gel formulations were collected at 203 days, and eyes with rod formulations were collected at 117 days. One slide per block was sectioned and stained with hematoxylin and eosin (H&E). Glass slides were evaluated by a board-certified veterinary pathologist using light microscopy. The presence of injected material was recorded, and histologic lesions were graded for severity (0=absent; 1=minimal; 2=mild; 3=moderate; 4=marked; 5=severe). The results of the experiment were summarized in Table 49. In Table 49, "P" refers to present and "NP" refers to not present.

TABLE 49

H&E GRADES OF THE RABBIT EYE HISTOPATHOLOGY DATA OF ANIMALS TREATED WITH SILK FIBROIN ROD AND HYDROGEL COMPOSITIONS

| Treatment | Sample | Block | Injected material, vitreous chamber | Infiltration, mononuclear cell/ multinucleated cell, injected material | Retinal distortion/ degeneration, focal |
|---|---|---|---|---|---|
| Silk-Fibroin Hydrogel | CCN-43L | 1 | NP | — | 0 |
| | | 2 | P (acellular aggregate) | 0 | 0 |
| | CCN-44L | 1 | NP | — | 0 |
| | | 2 | NP | — | 0 |
| | CCN-45L | 1 | NP | — | 0 |
| | | 2 | P (acellular aggregate) | 0 | 0 |
| Silk-Fibroin/ CXB Rod | CCN-86L | 1 | NP | — | 0 |
| | | 2 | P (rod) | 1 | 2 |
| | CCN-87L | 1 | P (rod) | 0 | 0 |
| | | 2 | P (rod) | 0 | 2 |
| | CCN-88L | 1 | NP | — | 0 |
| | | 2 | NP | — | 0 |
| Untreated | CCN-43R | 1 | NP | — | 0 |
| | | 2 | NP | — | 0 |
| | CCN-86R | 1 | NP | — | 0 |
| | | 2 | NP | — | 0 |

Injected material was visible in most injected (left) eyes. Injected silk fibroin hydrogel material was visible in two of three injected eyes; this material formed a mass up to 5 mm in diameter in the vitreous chamber, composed of pale amphophilic granular material surrounding 50-200 μm diameter pale basophilic structures with a more solid appearance. This material consistently lacked cellular infiltrates when captured. There were no other histologic findings in the silk fibroin hydrogel-injected eyes.

Injected material consistent with silk fibroin/celecoxib (CXB) rod was visible in two of the three injected eyes. This structure was present in the vitreous chamber, in close proximity to the retina; it was approximately 500 µm diameter, stained basophilic to amphophilic, and contained non-staining vacuoles or clefts. In one sample (CCN-86L, Block 1), the rod structure was surrounded and infiltrated by lymphocytes, macrophages, and multinucleated giant cells; however, in all other instances the rod was acellular. In two samples, the retina adjacent to the rod was focally distorted, with disorganized retinal layers and cell vacuolization. Given the proximity to the injected rod, this lesion was considered to be secondary to the injection procedure.

Example 28. Physical Properties of Silk Fibroin Hydrogels with Celecoxib for In Vivo Studies Silk fibroin hydrogels were prepared as described above. Briefly, lyophilized silk fibroin was reconstituted with an aqueous solution of sodium chloride, polysorbate-80, and phosphate buffer. The sodium chloride concentration was adjusted to ensure a final osmolarity of 280 mOsm. A suspension of celecoxib (CXB) was used to reconstitute silk fibroin in these hydrogel formulations. The silk fibroin was allowed to fully reconstitute prior to being drawn into a 6 mL syringe. Excipient solutions were prepared so that a 0.75:1 mix of silk-fibroin solution:excipient solution would result in the desired final formulations. The pH of polyethylene glycol (PEG) hydrogels was adjusted using hydrochloric acid to account for the changes in pH observed when mixing phosphate buffer and PEG. The excipient solutions were drawn up into a second 6 mL syringe. The solutions were mixed back and forth via a syringe connector until homogeneous. The resulting mixture was incubated at 37° C. overnight and aliquoted into 1 mL syringes prior to injection.

The formulations were prepared as described in Table 50. Multiple preparations of the same formulation may be examined. The samples in Table 50 were named by the process used to prepare and formulate each hydrogel. For example, the sample named "120 mb; hyd; 27.8% cxbst; 3% SFf; 10% CXBf; 10% P188f" refers to a formulation prepared from silk fibroin degummed with a 120-minute boil (120 mb), in a hydrogel format (hyd), from a stock of 27.8% w/v celecoxib (27.8% cxbst), with 3% w/v silk fibroin (3% SFf), with 10% w/v celecoxib (10% CXBf), and with 10% P188 (10% P188f). Longer boiling times (mb) produced silk fibroin with smaller molecular weights.

TABLE 50

PROPERTIES OF HYDROGEL FORMULATIONS WITH CELECOXIB

| Sample No. | 169-2 | 169-3 |
| --- | --- | --- |
| Sample name | 120 mb; hyd; 27.8% cxbst; 3% SFf; 10% CXBf; 10% P188f | 480 mb; hyd; 27.8% cxbst; 3% SFf; 10% CXBf; 10% P188f |
| Description | 10% CXB; 3% 120 mb Silk; 10% Poloxamer-188 | 10% CXB; 3% 480 mb Silk; 10% Poloxamer-188 |
| Average Actual CXB % | 9.61 | 9.77 |
| Average CXB dose (mg) | 4.8 | 4.9 |
| pH | 7.06 | 7.15 |
| Viscosity (Pa*s) | 76.44 | 113.16 |
| Phase Angle (°) | 5.35 | 8.68 |
| G' (Pa) | 4487.2 | 9117.6 |
| G" (Pa) | 418.9 | 1384.7 |
| Injection force (N) at 0.2 mL/minute | 8.1 | 9.9 |

Rheological Analysis of Hydrogel Formulations

The rheological properties of the hydrogel samples were analyzed. Using a Bholin CVOR 150 rheometer, 800 µL of each sample was directly deposited onto a Peltier Plate system using a 25 mm diameter parallel plate. The oscillation method kept strain, temperature, and frequency constant at 0.1%, 25° C., and 1 Hz respectively. A time sweep was used to measure the G', G", and phase angle values over 150 seconds. The viscoelastic method kept the shear rate, strain, and frequency constant at 1 l/s, 0.1%, and 1 Hz respectively. A time sweep then measured the viscosity over 60 seconds. This was performed in triplicate for each sample.

The results of the experiments were shown in Table 50. The hydrogel with lower molecular weight silk fibroin (480 mb) had a higher viscosity and phase angle than the hydrogel with higher molecular weight silk fibroin (120 mb). Indeed, the viscosity of sample 169-3 (480 mb; hyd; 27.8% cxbst; 3% SFf; 10% CXBf; 10% P188f) was measured at 113.16 Pa*s, approximately 1.5 times greater than the measured viscosity of sample 169-2 (120 mb; hyd; 27.8% cxbst; 3% SFf; 10% CXBf; 10% P188f) at 76.44 Pa*s. The phase angle of sample 169-3 (480 mb; hyd; 27.8% cxbst; 3% SFf; 10% CXBf; 10% P188f) was 8.68°, approximately 1.6 times the phase angle of sample 169-2 (120 mb; hyd; 27.8% cxbst; 3% SFf; 10% CXBf; 10% P188f) at 5.35°.

The hydrogel with lower molecular weight silk fibroin (480 mb) also had a higher shear storage modulus and shear loss modulus than the hydrogel with higher molecular weight silk fibroin (120 mb). As used herein, the term "shear storage modulus" or "G'" refers to the measure of a material's elasticity or reversible deformation as determined by the material's stored energy. As used herein, the term "shear loss modulus" or "G''" refers to the measure of a material's ability to dissipate energy, usually in the form of heat. Sample 169-3 (480 mb; hyd; 27.8% cxbst; 3% SFf; 10% CXBf; 10% P188f) had a G' value and a G" value of 9117.6 Pa and 1384.7 Pa respectively. Sample 169-2 (120 mb; hyd; 27.8% cxbst; 3% SFf; 10% CXBf; 10% P188f) had a G' value and a G" value of 4487.2 Pa and 418.9 Pa respectively. The measured G' for the lower molecular weight hydrogel was twofold greater than that of the higher molecular weight silk fibroin hydrogel, while the measured G" was at least threefold greater than that of the higher molecular weight silk fibroin hydrogel. Ultimately, the use of lower molecular weight silk fibroin produced thicker, more viscous gels.

Injection Forces

The force required to extrude the hydrogels was measured. Each hydrogel sample was mixed back and forth between two syringes to ensure homogeneity before being loaded into 1 mL syringe and capped with 27G, ½" needles. The syringes were inserted into a Mark-10 syringe compression fixture and the test stand was set to move the head down onto the syringe plunger and extrude the hydrogel at a rate of 0.5 in/min. This was estimated to be equivalent to 0.2 mL/min with this syringe configuration. The force gauge measured the force required to extrude the hydrogel with a maximum force set at 200 N. Data was collected over 60 seconds (20 points per second) and exported and graphed to find where the injectability force plateau. The average value was taken over this plateau region. Each sample was injected in triplicate and average force measurements were calculated. The average force measurements were listed in Table 50. The average force for extrusion was measured to be 9.9 N for sample 169-3 (480 mb; hyd; 27.8% cxbst; 3% SFf; 10% CXBf; 10% P188f) and 8.1 N for sample 169-2 (120 mb; hyd; 27.8% cxbst; 3% SFf; 10% CXBf; 10% P188f).

Preparation from the lower molecular weight silk fibroin resulted in a stiffer hydrogel that required a greater force for extrusion.

Example 29. Release of Protein Cargo from Silk Fibroin Hydrogels

Silk fibroin hydrogels were prepared from silk fibroin degummed with a 480 mb or a 120 mb. Sodium chloride was purchased from Chemsavers (Bluefield Va.). Polysorbate-80 was purchased from Croda (Snaith, United Kingdom). Phosphate buffered saline (10×PBS) was purchased from Gibco (USA). Sodium phosphate dibasic, sodium phosphate monobasic, human lysozyme, sucrose, Bovine Serum Albumin (BSA), trehalose, and poloxamer-188 (P188) were purchased from Sigma-Aldrich (St. Louis, Mo.). Sodium azide and glycerol were purchased from Fisher Chemical (Waltham, Mass.). Bevacizumab was purchased from Genentech Inc. (San Francisco, Calif.). Human immunoglobulin G (IgG) was purchased from Innovative Research (Novi, Mich.).

Silk Fibroin Hydrogel Preparation with Protein

To prepare the hydrogels with lysozyme, purified silk fibroin with a 480-minute boil or silk fibroin with a 120-minute boil were reconstituted to a concentration of 30% (w/v) with either water or lysozyme stock solution. The gelation excipient was mixed with these solutions to final formulation concentrations. The formulation was drawn into a syringe, capped, and left to gel at 4° C. overnight. Solutions that did not gel overnight were transferred to 37° C. for 3 hours to achieve gelling.

To prepare hydrogels with bovine serum albumin (BSA), 300 mg of purified silk fibroin with a 480-minute boil (mb) and silk fibroin degummed with a 120 mb was reconstituted with 0.7 mL of deionized water to make a final 30% (w/v) solution. BSA was dissolved with either polysorbate-80 (PS80) or poloxamer-188 (P188). Solutions were mixed to reach the desired final concentrations of fibroin/BSA/excipient. The resulting mixture was drawn into a 1 mL syringe, capped, and left to gel at 4° C. overnight. Solutions that did not gel overnight were transferred to 37° C. for 3 hours to achieve gelation.

To prepare hydrogels with bevacizumab, purified silk fibroin degummed with a 480-minute boil was reconstituted with sufficient deionized water to a concentration of 10% or 30% (w/v). Bevacizumab was lyophilized separately and re-dissolved in the silk solution. An 80% glycerol solution was mixed with the protein solution to obtain the final formulations. The resulting mixture was then drawn into a syringe, capped, and left to gel at 4° C. overnight. Solutions that did not gel were transferred to 37° C. for 3 hours to achieve gelling.

Purified 480 mb silk fibroin and 120 mb silk fibroin were reconstituted to 30% (w/v) with deionized water. IgG was dissolved with aqueous solutions of either polysorbate-80 (PS80) or P188. Solutions were mixed to reach the desired final concentrations of fibroin/IgG/excipient. The resulting mixture was drawn into a syringe, capped, and left to gel at 4° C. overnight. Solutions that did not gel overnight were transferred to 37° C. for 3 hours to achieve gelling.

The hydrogels prepared are described in Table 51. The samples were named for the process in which they were prepared. For example, the sample named "120 mb; hyd; 15% SFf; 2.5% bsaf; 10% P188f" refers to a sample prepared from silk fibroin degummed with a 120-minute boil (120 mb), a formulation as a hydrogel (hyd), a formulation with 15% w/v silk fibroin (15% SFf), a formulation with 2.5% w/v BSA (2.5% bsaf), and a formulation with 10% w/v P188 (10% P188f). Other potential components described included a formulation with lysozyme (% lysozymef), a preparation from silk fibroin degummed with a 480 mb (480 mb), a formulation with glycerol (% Glycf), a formulation with bevacizumab (% bevacizumabf), and a formulation with IgG (% iggf). Sample 203-03 (120 mb; hyd; 5% SFf; 2.5% lysozyme; 40% Glycf) did not form a gel. In Table 51, "Excip." refers to excipient. All IgG hydrogels contained 0.01% polysorbate-80. All lysozyme hydrogels contained 0.01% polysorbate-80. Bevacizumab hydrogels contained trace amounts of that buffer in which it is provided (trehalose, a sodium phosphate buffer, and polysorbate-20). All BSA hydrogels contained 0.1% polysorbate-80.

TABLE 51

PREPARATIONS OF SILK FIBROIN HYDROGELS AND CONTROLS WITH PROTEIN.

| Sample No. | Protein | [Protein] (%) | Silk Fibroin mb | [Silk fibroin] (%) | Excip. | [Excip.] (%) | Sample name | Mass (mg) |
|---|---|---|---|---|---|---|---|---|
| 203-01 | Lysozyme | 2.5 | 120 | 5 | P188 | 10 | 120 mb; hyd; 5% SFf; 2.5% lysozymef; 10% P188f | 145.37 182.93 202.12 |
| 203-02 | Lysozyme | 10 | 120 | 5 | P188 | 10 | 120 mb; hyd; 5% SFf; 10% lysozymef 10% P188f | 141.1 194.03 163.08 |
| 203-03 | Lysozyme | 2.5 | 120 | 5 | Glycerol | 40 | 120 mb; hyd; 5% SFf; 2.5% lysozymef; 40% Glycf | — — — |
| 203-04 | Lysozyme | 10 | 120 | 5 | Glycerol | 40 | 120 mb; hyd; 5% SFf; 10% lysozymef; 40% Glycf | 213.35 218.72 217.83 |
| 203-05 | Lysozyme | 2.5 | 120 | 15 | P188 | 10 | 120 mb; hyd; 15% SFf; 2.5% lysozymef; 10% P188f | 173.35 207.02 199.35 |

TABLE 51-continued

PREPARATIONS OF SILK FIBROIN HYDROGELS AND CONTROLS WITH PROTEIN.

| Sample No. | Protein | [Protein] (%) | Silk Fibroin mb | [Silk fibroin] (%) | Excip. | [Excip.] (%) | Sample name | Mass (mg) |
|---|---|---|---|---|---|---|---|---|
| 203-06 | Lysozyme | 10 | 120 | 15 | P188 | 10 | 120 mb; hyd; 15% SFf; 10% lysozymef; 10% P188f | 144.88 207.63 206.52 |
| 203-07 | Lysozyme | 2.5 | 120 | 15 | Glycerol | 40 | 120 mb; hyd; 15% SFf; 2.5% lysozymef; 40% Glycf | 223.87 205.3 218.84 |
| 203-08 | Lysozyme | 10 | 120 | 15 | Glycerol | 40 | 120 mb; hyd; 15% SFf; 10% lysozymef; 40% Glycf | 152.39 207.88 207.87 |
| 203-09 | Lysozyme | 2.5 | 480 | 5 | P188 | 10 | 480 mb; hyd; 5% SFf; 2.5% lysozymef; 10% P188f | 248.13 191.39 207.16 |
| 203-10 | Lysozyme | 2.5 | 480 | 5 | Glycerol | 40 | 480 mb; hyd; 5% SFf; 2.5% lysozymef; 40% Glycf | 209.86 231.13 231.01 |
| 203-11 | Lysozyme | 2.5 | 480 | 15 | P188 | 10 | 480 mb; hyd; 15% SFf; 2.5% lysozymef; 10% P188f | 222.07 210.8 234.87 |
| 203-12 | Lysozyme | 2.5 | 480 | 15 | Glycerol | 40 | 480 mb; hyd; 15% SFf; 2.5% lysozymef; 40% Glycf | 280.46 223.15 232.37 |
| 197-01 | BSA | 2.5 | 480 | 5 | P188 | 10 | 480 mb; hyd; 5% SFf; 2.5% bsaf; 10% P188f | 194.95 194.89 — |
| 197-02 | BSA | 2.5 | 480 | 15 | Pl88 | 10 | 480 mb; hyd; 15% SFf; 2.5% bsaf; 10% P188f | 231.42 226.19 277.73 |
| 197-03 | BSA | 2.5 | 120 | 5 | P188 | 10 | 120 mb; hyd; 5% SFf; 2.5% bsaf; 10% P188f | 203.5 234.64 227.49 |
| 197-04 | BSA | 2.5 | 120 | 15 | P188 | 10 | 120 mb; hyd; 15% SFf; 2.5% bsaf; 10% P188f | 252.32 200.16 217.13 |
| 197-05 | BSA | 2.5 | 120 | 5 | Glycerol | 40 | 120 mb; hyd; 5% SFf; 2.5% bsaf; 40% Glycf | 202.99 225.44 195.8 |
| 197-06 | BSA | 2.5 | 120 | 15 | Glycerol | 40 | 120 mb; hyd; 15% SFf; 2.5% bsaf; 40% Glycf | 338.31 206.25 214.3 |
| 187-2A | BSA | 2.5 | 480 | 5 | Glycerol | 40 | 480 mb; hyd; 5% SFf; 2.5% bsaf; 40% Glycf | 200.06 206.71 196.31 |
| 187-4A | BSA | 2.5 | 480 | 15 | Glycerol | 40 | 480 mb; hyd; 15% SFf; 2.5% bsaf; 40% Glycf | 204.86 207.03 196.56 |
| 201-01 | Bevacizumab | 2.5 | 480 | 5 | Glycerol | 40 | 480 mb; hyd; 5% SFf; 2.5% bevacizumabf; 40% Glycf | 204.8 216.91 224.1 |
| 201-02 | Bevacizumab | 2.5 | 480 | 15 | Glycerol | 40 | 480 mb; hyd; 15% SFf; 2.5% bevacizumabf; 40% Glycf | 222.22 225.4 228.86 |
| 201-03 | Bevacizumab | 2.5 | 120 | 5 | Glycerol | 40 | 120 mb; hyd; 5% SFf; 2.5% bevacizumabf; 40% Glycf | 209.93 190.21 226.91 |

TABLE 51-continued

PREPARATIONS OF SILK FIBROIN HYDROGELS AND CONTROLS WITH PROTEIN.

| Sample No. | Protein | [Protein] (%) | Silk Fibroin mb | [Silk fibroin] (%) | Excip. | [Excip.] (%) | Sample name | Mass (mg) |
|---|---|---|---|---|---|---|---|---|
| 193-01 | IgG | 2.5 | 480 | 5 | P188 | 10 | 480 mb; hyd; 5% SFf; 2.5% iggf; 10% P188f | 204.54 197.27 196.44 |
| 193-02 | IgG | 2.5 | 120 | 5 | P188 | 10 | 120 mb; hyd; 5% SFf; 2.5% iggf; 10% P188f | 192.16 191.09 223.79 |
| 193-03 | IgG | 2.5 | 480 | 5 | Glycerol | 40 | 480 mb; hyd; 5% SFf; 2.5% iggf; 40% Glycf | 201.41 220.71 205.86 |
| 193-04 | IgG | 2.5 | 120 | 5 | Glycerol | 40 | 120 mb; hyd; 5% SFf; 2.5% iggf; 40% Glycf | 194.62 195.54 221.22 |
| 193-05 | IgG | 2.5 | 480 | 15 | P188 | 10 | 480 mb; hyd; 15% SFf; 2.5% iggf; 10% P188f | 192.2 208.87 226.44 |
| 193-06 | IgG | 2.5 | 120 | 15 | P188 | 10 | 120 mb; hyd; 15% SFf; 2.5% iggf; 10% P188f | 211.77 211.43 242.67 |
| 193-07 | IgG | 2.5 | 480 | 15 | Glycerol | 40 | 480 mb; hyd; 15% SFf; 2.5% iggf; 40% Glycf | 228.47 211.99 241.57 |
| 193-08 | IgG | 2.5 | 120 | 15 | Glycerol | 40 | 120 mb; hyd; 15% SFf; 2.5% iggf; 40% Glycf | 190.38 215.59 200.78 |
| 1, 2-C | Control sample | N/A | 120 | 5 | P188 | 10 | 120 mb; hyd; 5% SFf; 10% P188f | 242.33 183.7 — |
| 3, 4-C | Control sample | N/A | 120 | 5 | Glycerol | 40 | 120 mb; hyd; 5% SFf; 40% Glycf | 205.27 204.63 — |
| 5, 6-C | Control sample | N/A | 120 | 15 | P188 | 10 | 120 mb; hyd; 15% SFf; 10% P188f | — — — |
| 7, 8-C | Control sample | N/A | 120 | 15 | Glycerol | 40 | 120 mb; hyd; 15% SFf; 40% Glycf | 177.8 229.1 — |
| 199-9 | BSA | 0.025 | N/A | N/A | Glycerol | 4 | 0.025% bsaf; 4% Glycf | — — |
| 199-10 | BSA | 0.025 | N/A | N/A | P188 | 1 | 0.025% bsaf; 1% P188f | — — |

In Vitro Release Profile of Silk Fibroin Hydrogels Formulated with Protein Apis and Other Excipients Protein loaded silk-fibroin hydrogels were weighed in triplicate (at approximately 200 mg) into 4 mL vials. 2 mL of release media were added (PBS, 0.01% polysorbate-80, 0.05% sodium azide). Samples were incubated with gentle shaking at 37° C. At 2 hours, 4 hours, 1, 2, 3, 7, 9, 10, 14, 21, and 28 days, 150 µL of release media was removed and replaced with 150 µL of fresh media. Control samples containing 2.5% lysozyme, 2.5% IgG, 2.5% bevacizumab, or 2.5% BSA with either 4% glycerol or 1% P188 were prepared to serve as a 100% drug release control. Controls with protein and gelling agent were utilized to assess the effects of the gelling agent on protein stability. Total protein released was quantified via size-exclusion chromatography using a Waters X-Bridge Protein BEH SEC, 200 Å, 3.5 µm column. An isocratic flow of mobile phase (100 mM sodium phosphate, 200 mM NaCl, pH 6.8) was run at 0.80 mL/min to elute protein. The HPLC system used was an Agilent 1290 with a PDA detector. Protein elution was monitored at 280 and 214 nm using a PDA detector. Cumulative % released was calculated using theoretical loading. Control sample 5,6-C was not tested because it was too stiff to get out of the syringe. The results of the cumulative release studies could be seen in Table 52A and Table 52B. The samples or readings denoted with "*" were completed in duplicate and samples or reading denoted with "**" were completed in singlicate.

TABLE 52A

IN VITRO RELEASE OF PROTEINS FROM SILK FIBROIN HYDROGELS; AVERAGE CUMULATIVE RELEASE PERCENTAGE (%) OF API RELEASED EACH DAY OF MEASUREMENT

| Protein | Sample No. | Day | | | | | | | | |
|---|---|---|---|---|---|---|---|---|---|---|
| | | 0 | 0.08 | 0.166 | 1 | 2 | 3 | 5 | 7 | 9 |
| Lysozyme | 203-1 | 0.0 | — | 84.575 | 71.01 | 95.24 | — | 96.25 | 121.36 | 108.19 |
| Lysozyme | 203-2 | 0.0 | — | 61.3 | 77.7 | 111.8 | — | 117.7 | 110.4 | 119.3 |
| Lysozyme | 203-4 | 0.0 | — | 60.0 | 65.6 | 97.6 | — | 95.5 | 88.6 | 95.8 |
| Lysozyme | 203-5 | 0.0 | — | 43.4 | 38.4 | 58.5 | — | 69.4 | 60.4 | 65.1 |
| Lysozyme | 203-6 | 0.0 | — | 76.4 | 79.8 | 110.8 | — | 110.9 | 107.9 | 120.8 |
| Lysozyme | 203-7 | 0.0 | — | 22.5 | 23.1 | 42.9 | — | 42.9 | 44.6 | 48.4 |
| Lysozyme | 203-8 | 0.0 | — | 32.4 | 73.1 | 80.4 | — | 85.7 | 82.9 | 89.7 |
| Lysozyme | 203-9 | 0.0 | 47.8 | — | 69.6 | 68.7 | 69.4 | — | 68.3 | — |
| Lysozyme | 203-10 | 0.0 | 83.1 | — | 74.0 | 81.8 | 82.7 | — | 83.0 | — |
| Lysozyme | 203-11 | 0.0 | 54.6 | — | 60.6 | 59.6 | 54.5** | — | 52.9 | — |
| Lysozyme | 203-12 | 0.0 | 25.3 | — | 24.4 | 20.7 | 20.4 | — | 19.5 | — |
| BSA | 197-1* | 0.0 | — | 66.0 | 131.9 | 109.1 | — | — | — | — |
| BSA | 197-2 | 0.0 | — | 90.4 | 123.2 | 105.3 | — | — | — | — |
| BSA | 197-3 | 0.0 | — | 73.0 | 122.9* | 89.7 | — | — | — | — |
| BSA | 197-4 | 0.0 | — | 96.2 | 136.9* | 108.4 | — | — | — | — |
| BSA | 197-5 | 0.0 | — | 77.6 | 121.6 | 116.9 | — | — | — | — |
| BSA | 197-6 | 0.0 | — | 94.3 | 103.2 | 86.6* | — | — | — | — |
| BSA | 187-2A | 0.0 | — | 52.6 | 74.6* | 75.7* | — | — | — | — |
| BSA | 187-4A | 0.0 | — | 70.8 | 69.1 | 68.0 | — | — | — | — |
| BSA | 199-9 | 0.0 | — | 107.9 | 118.9 | 119.7 | — | — | — | — |
| BSA | 199-10* | 0.0 | — | 107.4 | 124.8 | 125.6 | — | — | — | — |
| Bevacizumab | 201-1 | 0.0 | — | 36.8 | 46.6 | 48.6 | 46.7 | — | 43.4 | — |
| Bevacizumab | 201-2 | 0.0 | — | 39.1 | 45.7 | 43.7 | 36.7 | — | 31.5 | — |
| Bevacizumab | 201-3 | 0.0 | — | 46.4 | 72.5 | 63.1 | 57.0 | — | 66.6 | — |
| Bevacizumab | 201-5 | 0.0 | — | 89.9 | 108.8 | 89.2 | 83.4 | — | 86.6 | — |
| Bevacizumab | 201-6* | 0.0 | — | 90.0 | 103.8 | 92.4 | 88.9 | — | 92.7 | — |
| IgG | 193-01* | 0.0 | 24.1 | — | 35.6 | 30.4 | — | — | — | — |
| IgG | 193-02 | 0.0 | 9.8 | — | 13.8 | 12.7 | — | — | — | — |
| IgG | 193-03 | 0.0 | 56.1 | — | 70.3 | 59.1 | — | — | — | — |
| IgG | 193-04 | 0.0 | 50.4* | — | 62.5 | 50.7 | — | — | — | — |
| IgG | 193-05 | 0.0 | 40.0 | — | 46.7 | 45.3 | — | — | — | — |
| IgG | 193-06 | 0.0 | 29.0 | — | 28.5 | 27.3 | — | — | — | — |
| IgG | 193-07 | 0.0 | 43.0 | — | 42.0 | 38.1 | — | — | — | — |
| IgG | 193-08 | 0.0 | 61.1 | — | 44.9 | 43.2 | — | — | — | — |

TABLE 52B

STANDARD DEVIATIONS OF IN VITRO RELEASE OF PROTEINS FROM SILK FIBROIN HYDROGELS; STANDARD DEVIATIONS OF AVERAGE CUMULATIVE RELEASE PERCENTAGE (%) OF API RELEASED EACH DAY OF MEASUREMENT

| Protein | Sample No. | Day | | | | | | | | |
|---|---|---|---|---|---|---|---|---|---|---|
| | | 0 | 0.08 | 0.166 | 1 | 2 | 3 | 5 | 7 | 9 |
| Lysozyme | 203-1 | 0.0 | — | 16.6 | 15.4 | 20.9 | — | 22.3 | 9.0 | 22.6 |
| Lysozyme | 203-2 | 0.0 | — | 3.9 | 9.4 | 16.2 | — | 10.2 | 16.1 | 17.6 |
| Lysozyme | 203-4 | 0.0 | — | 4.3 | 8.2 | 6.8 | — | 8.8 | 7.1 | 7.7 |
| Lysozyme | 203-5 | 0.0 | — | 16.4 | 15.1 | 21.3 | — | 4.2 | 19.2 | 21.0 |
| Lysozyme | 203-6 | 0.0 | — | 16.7 | 15.7 | 23.2 | — | 29.3 | 24.4 | 30.5 |
| Lysozyme | 203-7 | 0.0 | — | 2.4 | 5.0 | 1.8 | — | 1.9 | 2.2 | 2.3 |
| Lysozyme | 203-8 | 0.0 | — | 29.1 | 21.9 | 5.7 | — | 4.8 | 5.9 | 6.0 |
| Lysozyme | 203-9 | 0.0 | 5.0 | — | 13.2 | 13.6 | 11.2 | — | 12.7 | — |
| Lysozyme | 203-10 | 0.0 | 0.3 | — | 9.7 | 5.6 | 0.4 | — | 1.2 | — |
| Lysozyme | 203-11 | 0.0 | 3.7 | — | 2.7 | 3.8 | 0.0** | — | 1.4 | — |
| Lysozyme | 203-12 | 0.0 | 1.2 | — | 1.2 | 2.2 | 0.6 | — | 0.8 | — |
| BSA | 197-1* | 0.0 | — | 1.7 | 0.4 | 0.4 | — | — | — | — |
| BSA | 197-2 | 0.0 | — | 10.0 | 25.2 | 7.6 | — | — | — | — |
| BSA | 197-3 | 0.0 | — | 16.3 | 13.2* | 28.6 | — | — | — | — |
| BSA | 197-4 | 0.0 | — | 10.3 | 18.3* | 14.2 | — | — | — | — |
| BSA | 197-5 | 0.0 | — | 8.4 | 2.0 | 28.4 | — | — | — | — |
| BSA | 197-6 | 0.0 | — | 15.3 | 14.1 | 28.4* | — | — | — | — |
| BSA | 187-2A | 0.0 | — | 1.9 | 1.9* | 0.5* | — | — | — | — |
| BSA | 187-4A | 0.0 | — | 6.7 | 7.4 | 7.5 | — | — | — | — |
| BSA | 199-9 | 0.0 | — | 3.5 | 2.1 | 1.7 | — | — | — | — |
| BSA | 199-10* | 0.0 | — | 3.7 | 3.4 | 3.6 | — | — | — | — |
| Bevacizumab | 201-1 | 0.0 | — | 0.9 | 0.3 | 0.6 | 0.8 | — | 0.9 | — |
| Bevacizumab | 201-2 | 0.0 | — | 0.9 | 1.0 | 1.3 | 2.7 | — | 1.3 | — |

TABLE 52B-continued

STANDARD DEVIATIONS OF IN VITRO RELEASE OF PROTEINS
FROM SILK FIBROIN HYDROGELS; STANDARD DEVIATIONS
OF AVERAGE CUMULATIVE RELEASE PERCENTAGE (%)
OF API RELEASED EACH DAY OF MEASUREMENT

| Protein | Sample No. | Day | | | | | | | | |
|---|---|---|---|---|---|---|---|---|---|---|
| | | 0 | 0.08 | 0.166 | 1 | 2 | 3 | 5 | 7 | 9 |
| Bevacizumab | 201-3 | 0.0 | — | 1.6 | 1.6 | 2.9 | 11.9 | — | 0.9 | — |
| Bevacizumab | 201-5 | 0.0 | — | 2.4 | 0.5 | 2.5 | 3.9 | — | 3.2 | — |
| Bevacizumab | 201-6* | 0.0 | — | 0.0 | 3.2 | 2.4 | 1.4 | — | 1.4 | — |
| IgG | 193-01* | 0.0 | 2.6 | — | 1.2 | 1.1 | — | — | — | — |
| IgG | 193-02 | 0.0 | 0.7 | — | 1.2 | 1.6 | — | — | — | — |
| IgG | 193-03 | 0.0 | 4.0 | — | 2.5 | 1.1 | — | — | — | — |
| IgG | 193-04 | 0.0 | 0.2 | — | 0.7 | 3.4 | — | — | — | — |
| IgG | 193-05 | 0.0 | 6.5 | — | 10.6 | 11.2 | — | — | — | — |
| IgG | 193-06 | 0.0 | 2.2 | — | 1.8 | 2.1 | — | — | — | — |
| IgG | 193-07 | 0.0 | 0.1 | — | 0.3 | 0.7 | — | — | — | — |
| IgG | 193-08 | 0.0 | 1.8 | — | 2.3 | 2.0 | — | — | — | — |

Lysozyme loading was used to modulate release kinetics. Formulations with lysozyme and P188 were analyzed first. Formulations prepared with P188 and 10% lysozyme loading and either 5% or 15% 120 mb silk fibroin day (203-2 and 203-6 respectively) reached nearly 80% release by 1 day. 120 mb silk fibroin hydrogel formulations with P188 showed silk fibroin concentration dependent API release. For example, sample 203-1 with 2.5% lysozyme and 5% 120 mb silk fibroin released 84.6% of the API in 4 hours. Increasing the silk fibroin concentration to 15% in sample 203-5 decreased the release at 4 hours to 43.4%, and caused the release to plateau at approximately 70% over 9 days.

In the hydrogels formulated with P188, the 5% 480 mb silk fibroin hydrogels with 2.5% lysozyme (203-9) showed lower burst and release when compared to the corresponding 120 mb silk fibroin hydrogels (203-1). The formulations with P188 and 480 mb silk fibroin also displayed a silk fibroin concentration dependence in release rate with silk fibroin concentration. This suggested that the release of lysozyme was related to the ratio of silk fibroin to lysozyme. The ratios of silk fibroin to lysozyme ranged from 0.5 to 6. In general, an increased ratio of silk fibroin to lysozyme reduced burst and release of the protein. Also, lower molecular weight silk fibroin may form a tighter hydrogel network, further reducing diffusion of the small lysozyme protein.

The release of lysozyme from silk hydrogels prepared with glycerol displayed similar trends to the those of the hydrogels prepared from P188. High loaded glycerol formulations (with 10% lysozyme) with 120 mb silk fibroin showed a high initial burst release dependent on silk fibroin concentration; higher concentrations of silk fibroin resulted in lower bursts of protein release. The formulation containing lower silk fibroin concentration (lower silk fibroin to lysozyme ratio) reached approximately 100% release at 2 days (sample 203-4), while the formulation containing higher concentration of silk fibroin plateaued at 80% and continued to release out to 9 days (sample 203-8). Increasing the silk fibroin to lysozyme ratio by reducing the lysozyme concentration from 10% to 2.5% reduced the initial burst (measured at 4 hours) from 32.4% in sample 203-8 to 22.5% in sample 203-7. This same effect can be seen with the 480 mb silk fibroin hydrogel formulations. Increasing the 480 mb silk fibroin concentration from 5% to 15%, while keeping the lysozyme loading constant at 2.5%, decreased the initial burst (measured at 2 hours) from 83.1% in sample 203-10 to 25.3% in sample 203-12. Lastly, hydrogels with glycerol and with the same silk fibroin to lysozyme ratio and different mb of silk fibroin showed similar release kinetics for the first day, however the 120 mb silk fibroin hydrogel (203-7) released at a faster rate over 9 days compared to the 480 mb silk fibroin hydrogel (203-12). The ratios of silk fibroin to lysozyme ranged from 0.5 to 6 for these hydrogels.

BSA loaded SF hydrogels showed very high burst and complete release of the protein within 1-3 days. BSA loaded silk fibroin hydrogels made with P188 as a gelling excipient reached complete release within 1 day. 4 hours into the experiment, cumulative release percentages ranged from approximately 66% to approximately 96%. The ratios of silk fibroin to BSA ranged from 2 to 6. Silk fibroin molecular weight or concentration, in the ranges tested, did not affect release kinetics of BSA in the hydrogel formulations with P188. The BSA control sample showed no reduction in concentration over the course of the study. In vitro release data for hydrogels prepared with glycerol showed that hydrogels made with 120 mb silk fibroin had a higher burst release and reached 100% release more quickly than 480 mb silk fibroin hydrogels. 480 mb silk fibroin hydrogels release approximately 65-80% of BSA by day 1, but the release then plateaus at day 2. Control BSA solution showed stability over the 2 days of release testing. This relationship between silk fibroin molecular weight and release of protein could represent a size dependent release mechanism. Protein release was diffusion based. Since there is minimal hydrolysis and no added enzymes, little to no degradation of the silk fibroin matrix occurs in vitro. Therefore, decreased release kinetics might be due to a tighter hydrogel network impeding the release of BSA. This effect was not observed with the P188 formulations. The hydrogel network might be different with the different gelling agents.

IgG release kinetics from silk fibroin hydrogel formulations with glycerol varied between 38.1% to 59.1% over two days, without significant release following measured cumulative API release at 2 hours. Hydrogels made with 5% silk fibroin (samples 193-03 and 193-04) released more protein by 2 days than those made with 15% silk fibroin (samples 193-07 and 193-08) regardless of the boiling time and molecular weight of the silk fibroin. This result indicated that the silk fibroin to IgG ratio could play a role in diffusion of protein from the silk fibroin formulation. Hydrogels prepared with 5% silk fibroin had a silk fibroin to IgG ratio of 2, while hydrogels prepared with 15% silk fibroin had a silk fibroin to IgG ratio of 6. Hydrogel formulations prepared with P188 demonstrated lower bursts and released less IgG (maximum release was 45.3%) than those made with glycerol (maximum release 59.1%). In general, by two days hydrogels made with 480 mb silk fibroin released more IgG than those made with 120 mb silk fibroin. Interestingly, 15% silk fibroin hydrogels made with P188 released more IgG than the corresponding hydrogels made with 5% silk fibroin, which was the opposite trend observed for the glycerol gels. A hazy precipitate also formed during formulation of the hydrogels with P188.

Bevacizumab release kinetics from silk fibroin hydrogel formulations all had similar characteristics. Hydrogels prepared with 5% silk fibroin had a silk fibroin to bevacizumab ratio of 2, while hydrogels prepared with 15% silk fibroin had a silk fibroin to bevacizumab ratio of 6. There was an initial burst phase, followed by a plateau. The burst release varied dependent upon molecular weight of the silk fibroin. 480 mb silk fibroin formulations showed lower initial bursts (measured at 4 hours) of approximately 40% while 120 mb silk fibroin formulations showed initial bursts (measured at 4 hours) of 46.4%. The difference increased at 1 day of release. The formulations with 480 mb silk fibroin (201-1 and 201-2) had released approximately 45% of the protein, while the formulation with 120 mb silk fibroin (201-3) had released 72.5% of its bevacizumab. The lower burst and lack of release with the 480 mb silk fibroin formulations could be due to a tighter silk network that formed with shorter silk fibroin proteins compared to the larger 120 mb silk fibroin hydrogels. There was no difference in release kinetics between formulations with 480 mb silk fibroin concentrations between 5 and 15%. The bevacizumab control displayed that the protein was stable in release media at 37° C. with only a 10% loss maintained over 7 days.

In general, silk fibroin hydrogels showed higher burst and faster release kinetics than the corresponding rod formulations. When compared to BSA, bevacizumab, and IgG hydrogel formulations, lysozyme (14.7 kDa) released faster than the much larger bevacizumab and IgG molecules (approximately 160 kDa) but more slowly than BSA. Bevacizumab loaded hydrogels containing glycerol released similar levels of protein (45%-70%) as IgG loaded hydrogels with glycerol. Both IgG and bevacizumab loaded hydrogels showed decreased release rate with increasing silk fibroin concentration. Given the similar size of these proteins (both approximately 150 kDa), it was possible that the release was controlled by diffusion through the silk fibroin network. BSA (66.5 kDa) and lysozyme (14.7 kDa) hydrogels released 100% of the protein by day 2, which suggested that smaller proteins diffused more quickly through the silk fibroin hydrogel network.

Example 30. Rheological Properties of Silk Fibroin Hydrogels with Celecoxib

The rheological properties of hydrogels loaded with celecoxib (CXB) were studied. The formulations were prepared as described for the cumulative release studies of celecoxib from silk fibroin hydrogels, seen in Table 53. To study the rheology, 600 μL of each hydrogel sample was loaded onto the Peltier plate of a Bholin CVOR 150 rheometer. Samples were analyzed at 25° C. using a 20 mm parallel plate and a gap of 1.0 mm. Oscillation parameters were set at a frequency of 1 Hz and 0.01% strain. Viscosity was measured at a shear rate of 1 l/s for 135 seconds, as seen in Table 53. Samples in Table 53 were named by the process used to prepare and formulate each hydrogel. For example, in the sample named 120 mb; hyd; 27.8% cxbst; 5% SFf; 10% CXBf; 40% PEG4kf, "120 mb" refers to silk degummed with a 120-minute boil, "hyd" refers to the formulation of the sample as a hydrogel, "27.8% cxbst" refers to a preparation from a stock solution of 27.8% of celecoxib, "5% SFf" refers to a formulation with 5% (w/v) silk fibroin, "10% CXBf" refers to a formulation with 10% (w/v) celecoxib, and "40% PEG4kf" refers to a formulation with 40% PEG 4 kDa. Some hydrogels were prepared with P188 (% P188f).

TABLE 53

RHEOLOGY DATA FOR HYDROGEL FORMULATIONS WITH CELECOXIB. STD. DEV. REFERS TO STANDARD DEVIATION.

| Sample No. | Sample name | Viscosity (Pas) | Viscosity Std. Dev. | Phase Angle (°) | Phase Angle Std. Dev. | G' (Pa) | G' Std. Dev. | G" (Pa) | G" Std. Dev. |
|---|---|---|---|---|---|---|---|---|---|
| 168-1 | 120 mb; hyd; 27.8% cxbst; 5% SFf; 10% CXBf; 40% PEG4kf | 964.19 | 182.55 | 10.80 | 0.54 | 31982 | 1516 | 6086 | 74 |
| 168-2 | 120 mb; hyd; 27.8% cxbst; 3% SFf; 10% CXBf; 40% PEG4kf | 324.48 | 50.86 | 9.86 | 1.65 | 7668 | 678 | 1316 | 82 |
| 168-3 | 120 mb; hyd; 27.8% cxbst; 5% SFf; 10% CXBf; 10% P188f | 484.94 | 13.86 | 8.32 | 2.72 | 30246 | 2656 | 4328 | 810 |
| 168-4 | 120 mb; hyd; 27.8% cxbst; 3% SFf; 10% CXBf; 10% P188f | 76.44 | 5.60 | 5.35 | 0.42 | 4487 | 274 | 419 | 22 |
| 168-5 | 480 mb; hyd; 27.8% cxbst; 5% SFf; 10% CXBf; 40% PEG4kf | 238.18 | 68.89 | 9.98 | 2.20 | 3545 | 497 | 609 | 57 |

TABLE 53-continued

RHEOLOGY DATA FOR HYDROGEL FORMULATIONS WITH CELECOXIB.
STD. DEV. REFERS TO STANDARD DEVIATION.

| Sample No. | Sample name | Viscosity (Pas) | Viscosity Std. Dev. | Phase Angle (°) | Phase Angle Std. Dev. | G' (Pa) | G' Std. Dev. | G" (Pa) | G" Std. Dev. |
|---|---|---|---|---|---|---|---|---|---|
| 168-6 | 480 mb; hyd; 27.8% cxbst; 3% SFf; 10% CXBf; 40% PEG4kf | 43.55 | 14.96 | 11.79 | 1.54 | 503 | 67 | 103 | 3 |
| 168-7 | 480 mb; hyd; 27.8% cxbst; 5% SFf; 10% CXBf; 10% P188f | 307.25 | 15.35 | 8.75 | 0.28 | 30825 | 1609 | 4737 | 153 |
| 168-8 | 480 mb; hyd; 27.8% cxbst; 3% SFf; 10% CXBf; 10% P188f | 113.16 | 9.29 | 8.68 | 0.93 | 9118 | 667 | 1385 | 94 |
| 168-9 | 480 mb; hyd; 27.8% cxbst; 2% SFf; 10% CXBf; 10% P188f | 59.72 | 5.47 | 8.14 | 0.53 | 3353 | 203 | 478 | 7 |

The viscosity of the silk fibroin hydrogels was directly related to both the concentration of silk fibroin and the molecular weight of the silk fibroin in the hydrogel. Higher concentrations of silk fibroin and/or the use of silk fibroin with a higher average molecular weight yielded higher viscosities in otherwise identical formulations. In formulations with 120 mb silk fibroin, the viscosity was lower for formulations with P188 instead of PEG 4 kDa. For formulations with 480 mb silk fibroin, the viscosity was higher for formulations with P188 instead of PEG 4 kDa. Formulations with P188 also had a smaller phase angle than the corresponding formulation with PEG 4 kDa. The concentration of silk fibroin in a hydrogel demonstrated a direct relationship with the stiffness of the hydrogel, as evidenced by the measured by the storage modulus (G') and the loss modulus (G"). Both the G' and G" values increased with increasing concentrations of silk fibroin.

Example 31. Injectability of Silk Fibroin Hydrogels with Celecoxib

The formulations were prepared as described for the cumulative release studies of celecoxib from silk fibroin hydrogels, seen in Table 54. The force required to extrude the hydrogels (injection force) was measured. Each hydrogel sample was mixed back and forth between two syringes to ensure homogeneity before being loaded into 1 mL syringe and capped with 27G, ½" needles. The syringes were inserted into a Mark-10 syringe compression fixture and the test stand was set to move the head down onto the syringe plunger and extrude the hydrogel at a rate of 0.5 in/min. This was estimated to be equivalent to 0.2 mL/min with this syringe configuration. The force gauge measured the force required to extrude the hydrogel with a maximum force set at 200 N. Data was collected over 60 seconds (20 points per second) and exported and graphed to find where the injectability force plateaued. The average value was taken over this plateau region. Each sample was injected in duplicate and average injection force measurements were calculated.

TABLE 54

ANALYSIS OF THE INJECTABILITY OF SILK FIBROIN
HYDROGEL FORMULATIONS WITH CELECOXIB

| | | Injection force (N) at 0.2 mL/minute | | | |
|---|---|---|---|---|---|
| Sample No. | Sample name | Average 1 | Average 2 | Overall Average | Standard Deviation |
| 168-1 | 120 mb; hyd; 27.8% cxbst; 5% SFf; 10% CXBf; 40% PEG4kf | 43.5 | 43.2 | 43.4 | 0.2 |
| 168-2 | 120 mb; hyd; 27.8% cxbst; 3% SFf; 10% CXBf; 40% PEG4kf | 19.6 | 20.4 | 20.0 | 0.6 |
| 168-3 | 120 mb; hyd; 27.8% cxbst; 5% SFf; 10% CXBf; 10% P188f | 16.5 | 15.2 | 15.9 | 0.9 |
| 168-4 | 120 mb; hyd; 27.8% cxbst; 3% SFf; 10% CXBf; 10% P188f | 7.3 | 8.9 | 8.1 | 1.2 |
| 168-5 | 480 mb; hyd; 27.8% cxbst; 5% SFf; 10% CXBf; 40% PEG4kf | 21.3 | 21.9 | 21.6 | 0.4 |
| 168-6 | 480 mb; hyd; 27.8% cxbst; 3% SFf; 10% CXBf; 40% PEG4kf | 9.6 | 9.6 | 9.6 | 0.0 |

TABLE 54-continued

ANALYSIS OF THE INJECTABILITY OF SILK FIBROIN
HYDROGEL FORMULATIONS WITH CELECOXIB

| Sample No. | Sample name | Injection force (N) at 0.2 mL/minute | | | |
|---|---|---|---|---|---|
| | | Average 1 | Average 2 | Overall Average | Standard Deviation |
| 168-7 | 480 mb; hyd; 27.8% cxbst; 5% SFf; 10% CXBf; 10% P188f | 16.1 | 16.9 | 16.5 | 0.5 |
| 168-8 | 480 mb; hyd; 27.8% cxbst; 3% SFf; 10% CXBf; 10% P188f | 9.4 | 10.3 | 9.9 | 0.7 |
| 168-9 | 480 mb; hyd; 27.8% cxbst; 2% SFf; 10% CXBf; 10% P188f | 6.0 | 6.4 | 6.2 | 0.3 |

The experimental results demonstrated a direct relationship between the concentration of silk fibroin in a hydrogel and the injection force the silk fibroin hydrogel required. Hydrogels with a higher concentration of silk fibroin (e.g. sample 168-1) required a larger injection force to extrude the hydrogel than the corresponding formulation with a lower concentration of silk fibroin (e.g. 168-2). In general, the hydrogels prepared with PEG 4 kDa required higher injection forces than the corresponding hydrogel with P188. In addition, the molecular weight of silk fibroin in the hydrogel was directly related to the injection force in the hydrogels prepared with PEG 4 kDa. The PEG 4 kDa hydrogels prepared from higher molecular weight silk fibroin (120 mb) demonstrated a higher injection force than the corresponding hydrogels prepared from comparatively lower molecular weight silk fibroin (480 mb).

Example 32. Effect of Select Excipients on Physical Properties of Hydrogels

The injectability experiment as described above was repeated to evaluate the effect of different excipients on injectability. Silk fibroin was degummed as described above, with a 120 mb. Glycerol was purchased from Fisher Chemical (Waltham, Mass.). Celecoxib (CXB) was purchased from Cipla, Miami Fla. Polysorbate-80 was purchased from Croda (Snaith UK). Potassium phosphate monobasic and potassium phosphate dibasic were purchased from Sigma Aldrich Fine Chemical (SAFC, St. Louis Mo.).

Preparation of Silk Fibroin Hydrogels

To prepare the hydrogels with glycerol, 300 mg of the 120 mb silk fibroin was dissolved in a 20% w/v stock suspension of dry heat treated (DHT) CXB with polysorbate-80 and phosphate buffer to prepare a silk/CXB suspension with either 7.1% (w/v) or 8.8% (w/v) silk fibroin. The suspensions with higher concentration of silk fibroin were used to generate the hydrogels with higher concentrations of silk fibroin. 2.835 mL of the resulting silk/CXB suspension was added to a 6 mL syringe. The silk/CXB suspension was then mixed with a second syringe containing 2.165 mL of a 92.4% w/v stock solution of glycerol via a B Braun fluid dispensing connector, back and forth until homogeneous (at least 25 times). The resulting mixture was then capped with a sterile syringe cap and incubated on a rotator overnight at 37° C. The syringes were stored at 4° C. until use.

To prepare the hydrogels with PEG400, 300 mg of the 120 mb silk fibroin was dissolved in a 20% w/v stock suspension of dry heat treated (DHT) CXB with polysorbate-80 and phosphate buffer to prepare a silk/CXB suspension with either 7.1% (w/v) or 8.8% (w/v) silk fibroin. The suspensions with higher concentration of silk fibroin were used to generate the hydrogels with higher concentrations of silk fibroin. 2.835 mL of the resulting silk/CXB suspension was added to a 6 mL syringe. The silk/CXB suspension was then mixed with a second syringe containing 2.165 mL of a 92.4% w/v stock solution of PEG400 via a B Braun fluid dispensing connector, back and forth until homogeneous (at least 25 times). The resulting mixture was then capped with a sterile syringe cap and incubated on a rotator overnight at 37° C. The syringes were stored at 4° C. until use.

The formulations were prepared as described in Table 55. The formulations tested were named by the method in which they were prepared. For example, in the sample named "120 mb; hyd; 20% cxbst; 4% SFf; 10% CXBf; 40% Glycf", "120 mb" refers to silk degummed with a 120-minute boil, "hyd" refers to the formulation of the sample as a hydrogel, "20% cxbst" refers to a preparation from a stock solution of 20% of celecoxib, "4% SFf" refers to a formulation with 4% (w/v) silk fibroin, "10% CXBf" refers to a formulation with 10% (w/v) celecoxib, and "40% Glycf" refers to a formulation with 40% glycerol. PEG400 was denoted in the hydrogels with "PEG400f".

TABLE 55

SILK FIBROIN HYDROGELS WITH PEG400
OR GLYCEROL AS EXCIPIENTS

| Sample No. | % Silk Fibroin | Excipient | % Excipient | Sample Name |
|---|---|---|---|---|
| 158-1 | 4 | Glycerol | 40 | 120 mb; hyd; 20% cxbst; 4% SFf; 10% CXBf; 40% Glycf |
| 158-2 | 4 | PEG400 | 40 | 120 mb; hyd; 20% cxbst; 4% SFf; 10% CXBf; 40% PEG400f |
| 158-3 | 5 | Glycerol | 40 | 120 mb; hyd; 20% cxbst; 5% SFf; 10% CXBf; 40% Glycf |
| 158-4 | 5 | PEG400 | 40 | 120 mb; hyd; 20% cxbst; 5% SFf; 10% CXBf; 40% PEG400f |

Injectability of Silk Fibroin Hydrogels with Select Excipients

The hydrogel samples were loaded into 1 mL syringes. The syringe was capped with a 27-gauge needle and loaded onto a Mark-10 syringe compression fixture. The test stand was set to extrude the hydrogel at a rate of 0.5 inches per minute, which was estimated to be equivalent to 0.2 mL/min. The force gauge then measured the force required to extrude the hydrogel at that rate, with a maximum force set at 200 N. The injection forces required to extrude the hydrogel at this rate were measured over 60 seconds, with 20 points per second. The data was then exported and graphed to find where the injectability plateaus. The average value was taken over this range. The results were presented in Table 56. The data showed that using PEG400 as an excipient led to approximately 25% greater resistance for injection than glycerol. The hydrogels with glycerol had lower injection forces than the corresponding hydrogel with PEG400 at all concentrations tested. It was also observed that hydrogels with 5% silk fibroin required higher injection forces than hydrogels with 4% silk fibroin, which was consistent with previous observations. All of the hydrogels created were within the acceptable injectability range.

TABLE 56

INJECTABILITY MEASUREMENTS WITH DIFFERENT EXCIPIENTS

| | | | | Replicate 1 | | Replicate 2 | | Overall | |
|---|---|---|---|---|---|---|---|---|---|
| Sample No. | % Silk Fibroin | Excipient | % Excipient | Average Force (N) | Standard Dev. | Average Force (N) | Standard Dev. | Average Force (N) | Standard Dev. |
| 158-1 | 4 | Glycerol | 40 | 7.95 | 0.17 | 8.12 | 0.26 | 8.03 | 0.12 |
| 158-2 | 4 | PEG400 | 40 | 9.85 | 0.12 | 10.53 | 0.15 | 10.19 | 0.48 |
| 158-3 | 5 | Glycerol | 40 | 14.57 | 0.23 | 14.59 | 0.28 | 14.58 | 0.01 |
| 158-4 | 5 | PEG400 | 40 | 18.97 | 0.34 | 18.51 | 0.13 | 18.74 | 0.33 |

Rheology of Silk Fibroin Hydrogels with Select Excipients

The hydrogel samples were loaded onto a Peltier plate system that kept the temperature at 25° C. The geometry used was a 20 mm parallel plate. The gap was set at 1 mm and the frequency at 1 Hz. Viscosity was taken during a time sweep at 1 1/s over 135 seconds. The experimental results were presented in Table 57. In hydrogels having the same silk fibroin concentration, using glycerol as an excipient created more viscous hydrogels than using PEG400. The effect was more prominent in hydrogels with 4% silk fibroin than 5%. The glycerol samples were generally stiffer than the PEG400 hydrogels at these two silk fibroin concentrations as measured by viscosity. However, the glycerol hydrogels also had lower injection forces at both concentrations. This difference indicated that either the glycerol has a positive effect on injectability, or PEG400 has a negative effect, or some combination thereof. The glycerol hydrogels could also exhibit more pronounced shear-thinning behavior than PEG400 hydrogels. This would account for the lower injection force when under greater shear stress. The more viscous samples were more likely to be the most cohesive hydrogels in vivo.

TABLE 57

VISCOSITY MEASUREMENTS WITH DIFFERENT EXCIPIENTS

| | | | | Replicate 1 | | Replicate 2 | | Overall | |
|---|---|---|---|---|---|---|---|---|---|
| | | | | Average | | Average | | | |
| Sample No. | % Silk Fibroin | Excipient | % Excipient | Viscosity (Pa*s) | Standard Dev. | Viscosity (Pa*s) | Standard Dev. | Average Force (N) | Standard Dev. |
| 158-1 | 4 | Glycerol | 40 | 103.97 | 2.43 | 138.58 | 158-1 | 4 | Glycerol |
| 158-2 | 4 | PEG 400 | 40 | 62.71 | 4.56 | 60.47 | 158-2 | 4 | PEG 400 |
| 158-3 | 5 | Glycerol | 40 | 231.07 | 15.85 | 281.12 | 158-3 | 5 | Glycerol |
| 158-4 | 5 | PEG 400 | 40 | 207.57 | 11.17 | 219.53 | 158-4 | 5 | PEG 400 |

The invention claimed is:

1. A method of making a pharmaceutical formulation, comprising dissolving degummed silk fibroin and a therapeutic agent in water to provide a solution, extruding the solution through a tube or a cannula to provide extruded rods comprising the silk fibroin and the therapeutic agent and having a uniform diameter of from about 0.1 mm to about 1.5 mm, incubating the extruded solution within the tube or cannula at 37° C. for 2 to 36 hours, and drying the extruded rods with the therapeutic agent to provide the pharmaceutical formulation.

2. The method of claim 1, wherein the silk fibroin rods have a length of 8 mm to 12 mm.

3. The method of claim 1, wherein the solution further comprises an excipient.

4. The method of claim 1, wherein drying comprises lyophilizing.

5. The method of claim 1, wherein the therapeutic agent is an ocular therapeutic agent.

6. The method of claim 1, further comprising preparing a pharmaceutical formulation comprising the extruded rods with the therapeutic agent and a pharmaceutically acceptable excipient.

7. The method of claim 6, wherein the silk fibroin rods have a density of 0.7 to 1.4 g/mL.

8. The method of claim 6, wherein the therapeutic agent is released over 7 days to one month.

9. The method of claim 6, wherein the pharmaceutical formulation comprises a ratio of a therapeutic agent concentration to a silk fibroin concentration of from about 0.01 to about 4.2.

10. The method of claim 6, wherein the at least one excipient is present at a concentration of from about 0.01% (w/v) to about 50% (w/v).

11. The method of claim 6, wherein the at least one excipient selected from the group consisting of lactose, sorbitol, sucrose, mannitol, lactose USP, partially pre-gelatinized maize starch, microcrystalline cellulose, phosphate salts, sodium chloride, hydrochloric acid, polysorbate 80, potassium phosphate monobasic, potassium phosphate dibasic, sodium phosphate dibasic, sodium phosphate monobasic, phosphate buffer, phosphate buffered saline, sodium hydroxide, dibasic calcium phosphate dehydrate, tartaric acid, citric acid, fumaric acid, succinic acid, malic acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose.

12. The method of claim 6, wherein the therapeutic agent is a therapeutic agent comprising a non-steroidal anti-inflammatory drug (NSAID).

13. The method of claim 12, wherein the NSAID comprises one or more of aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin.

14. The method of claim 1, wherein the degummed silk fibroin has a molecular weight of 1-25 kDa.

15. The method of claim 1, wherein the degummed silk fibroin has a molecular weight of 1-50 kDa.

\* \* \* \* \*